(12) United States Patent
Khairkhahan et al.

(10) Patent No.: US 12,419,747 B2
(45) Date of Patent: *Sep. 23, 2025

(54) DEVICE, SYSTEM, AND METHOD FOR TRANSCATHETER TREATMENT OF VALVULAR REGURGITATION

(71) Applicant: Polares Medical Inc., Palo Alto, CA (US)

(72) Inventors: Alexander K. Khairkhahan, Palo Alto, CA (US); Janine C. Robinson, Half Moon Bay, CA (US); Alan R. Klenk, San Jose, CA (US); Anuja Patel, Palo Alto, CA (US); Zaya Tun, Livermore, CA (US); Robert Quintos, Palo Alto, CA (US); Brett Snyder, Campbell, CA (US)

(73) Assignee: Polares Medical Inc., Palo Alto, CA (US)

( * ) Notice: Subject to any disclaimer, the term of this patent is extended or adjusted under 35 U.S.C. 154(b) by 191 days.

This patent is subject to a terminal disclaimer.

(21) Appl. No.: 18/343,337

(22) Filed: Jun. 28, 2023

(65) Prior Publication Data

US 2023/0404757 A1 Dec. 21, 2023

Related U.S. Application Data

(63) Continuation of application No. 16/918,295, filed on Jul. 1, 2020, which is a continuation of application
(Continued)

(51) Int. Cl.
*A61F 2/24* (2006.01)

(52) U.S. Cl.
CPC ............ *A61F 2/246* (2013.01); *A61F 2/2466* (2013.01); *A61F 2210/0014* (2013.01);
(Continued)

(58) Field of Classification Search
CPC ................... A61F 2/246; A61F 2/2466; A61F 2210/0014; A61F 2220/0016; A61F 2230/0006

See application file for complete search history.

(56) References Cited

U.S. PATENT DOCUMENTS

| 3,491,376 A | 1/1970 | Shiley |
| 3,503,079 A | 3/1970 | Smith |

(Continued)

FOREIGN PATENT DOCUMENTS

| CN | 102256568 | 12/2002 |
| CN | 1984621 | 6/2007 |

(Continued)

OTHER PUBLICATIONS

Office Action for JP 2021-212699 dated Sep. 19, 2023.
(Continued)

*Primary Examiner* — Suzette J Gherbi
(74) *Attorney, Agent, or Firm* — Knobbe, Martens, Olson & Bear, LLP

(57) ABSTRACT

The invention relates to a device for use in the transcatheter treatment of mitral valve regurgitation, specifically a coaptation assistance element for implantation across the valve; a system including the coaptation assistance element and anchors for implantation; a system including the coaptation assistance element and delivery catheter; and a method for transcatheter implantation of a coaptation element across a heart valve.

20 Claims, 76 Drawing Sheets

Related U.S. Application Data

No. 16/185,419, filed on Nov. 9, 2018, now Pat. No. 10,702,386, which is a continuation of application No. 15/918,988, filed on Mar. 12, 2018, now Pat. No. 10,123,874.

(60) Provisional application No. 62/470,684, filed on Mar. 13, 2017.

(52) U.S. Cl.
CPC ............. *A61F 2220/0016* (2013.01); *A61F 2220/0075* (2013.01); *A61F 2230/0006* (2013.01); *A61F 2230/0091* (2013.01); *A61F 2250/0018* (2013.01); *A61F 2250/0098* (2013.01)

(56) References Cited

U.S. PATENT DOCUMENTS

| | | |
|---|---|---|
| 3,656,185 A | 4/1972 | Carpentier |
| 3,671,979 A | 6/1972 | Moulopoulos |
| 3,874,388 A | 4/1975 | King et al. |
| 3,898,701 A | 8/1975 | La Russa |
| 3,938,197 A | 2/1976 | Milo |
| 4,007,743 A | 2/1977 | Blake |
| 4,011,601 A | 3/1977 | Clune et al. |
| 4,042,979 A | 8/1977 | Angell |
| 4,078,268 A | 3/1978 | Possis |
| 4,204,283 A | 5/1980 | Bellhouse et al. |
| 4,218,783 A | 8/1980 | Reul et al. |
| 4,261,342 A | 4/1981 | Aranguren Duo |
| 4,263,680 A | 4/1981 | Ruel et al. |
| 4,275,469 A | 6/1981 | Gabbay |
| RE31,040 E | 9/1982 | Possis |
| 4,352,211 A | 10/1982 | Parravicini |
| 4,488,318 A | 12/1984 | Kaster |
| 4,490,859 A | 1/1985 | Black et al. |
| 4,491,986 A | 1/1985 | Gabbay |
| 4,561,129 A | 12/1985 | Arpesella |
| 4,687,483 A | 8/1987 | Fisher et al. |
| 4,705,516 A | 11/1987 | Barone et al. |
| 4,759,758 A | 7/1988 | Gabbay |
| 4,790,843 A | 12/1988 | Carpentier et al. |
| 4,960,424 A | 10/1990 | Grooters |
| 4,994,077 A | 2/1991 | Dobben |
| 5,002,567 A | 3/1991 | Bona et al. |
| 5,078,737 A | 1/1992 | Bona et al. |
| 5,131,905 A | 7/1992 | Grooters |
| 5,197,980 A | 3/1993 | Gorshkov et al. |
| 5,217,484 A | 6/1993 | Marks |
| 5,258,023 A | 11/1993 | Reger |
| 5,332,402 A | 7/1994 | Teitelbaum |
| 5,344,442 A | 9/1994 | Deac |
| 5,370,662 A | 12/1994 | Stone et al. |
| 5,397,347 A | 3/1995 | Cuilleron et al. |
| 5,397,348 A | 3/1995 | Campbell et al. |
| 5,413,599 A | 5/1995 | Imachi et al. |
| 5,487,760 A | 1/1996 | Villafana |
| 5,500,015 A | 3/1996 | Deac |
| 5,522,886 A | 6/1996 | Milo |
| 5,554,186 A | 9/1996 | Guo et al. |
| 5,582,616 A | 12/1996 | Bolduc et al. |
| 5,593,435 A | 1/1997 | Carpentier et al. |
| 5,626,613 A | 5/1997 | Schmieding |
| 5,658,313 A | 8/1997 | Thal |
| 5,662,683 A | 9/1997 | Kay |
| 5,662,704 A | 9/1997 | Gross |
| 5,716,370 A | 2/1998 | Williamson, IV et al. |
| 5,733,331 A | 3/1998 | Peredo |
| 5,824,065 A | 10/1998 | Gross |
| 5,824,066 A | 10/1998 | Gross |
| 5,824,067 A | 10/1998 | Gross |
| 5,855,601 A | 1/1999 | Bessler et al. |
| 5,888,240 A | 3/1999 | Carpentier et al. |
| 5,957,949 A | 9/1999 | Leonhardt et al. |
| 6,007,577 A | 12/1999 | Vanney et al. |
| 6,024,096 A | 2/2000 | Buckberg |
| 6,042,607 A | 3/2000 | Williamson, IV et al. |
| 6,045,497 A | 4/2000 | Schweich et al. |
| 6,045,573 A | 4/2000 | Wenstrom |
| 6,063,114 A | 5/2000 | Nash et al. |
| 6,066,160 A | 5/2000 | Colvin et al. |
| 6,086,612 A | 7/2000 | Jansen |
| 6,113,631 A | 9/2000 | Jansen |
| 6,162,233 A | 12/2000 | Williamson, IV et al. |
| 6,217,610 B1 | 4/2001 | Carpentier et al. |
| 6,221,104 B1 | 4/2001 | Buckberg et al. |
| 6,250,308 B1 | 6/2001 | Cox |
| 6,264,602 B1 | 7/2001 | Mortier et al. |
| 6,287,339 B1 | 9/2001 | Vazquez et al. |
| 6,296,662 B1 | 10/2001 | Caffey |
| 6,299,637 B1 | 10/2001 | Shaolian et al. |
| 6,312,447 B1 | 11/2001 | Grimes |
| 6,312,464 B1 | 11/2001 | Navia |
| 6,332,893 B1 | 12/2001 | Mortier et al. |
| 6,358,277 B1 | 3/2002 | Duran |
| 6,383,147 B1 | 5/2002 | Stobie |
| 6,391,053 B1 | 5/2002 | Brendzel et al. |
| 6,391,054 B2 | 5/2002 | Carpentier et al. |
| 6,402,679 B1 | 6/2002 | Mortier et al. |
| 6,402,780 B2 | 6/2002 | Williamson, IV et al. |
| 6,409,758 B2 | 6/2002 | Stobie et al. |
| 6,419,695 B1 | 7/2002 | Gabbay |
| 6,439,237 B1 | 8/2002 | Buckberg et al. |
| 6,450,171 B1 | 9/2002 | Buckberg et al. |
| 6,451,024 B1 | 9/2002 | Thompson et al. |
| 6,454,799 B1 | 9/2002 | Schreck |
| 6,458,153 B1 | 10/2002 | Bailey et al. |
| 6,482,228 B1 | 11/2002 | Norred |
| 6,540,782 B1 | 4/2003 | Snyders |
| 6,544,167 B2 | 4/2003 | Buckberg et al. |
| 6,551,302 B1 | 4/2003 | Rosinko et al. |
| 6,565,603 B2 | 5/2003 | Cox |
| 6,569,198 B1 | 5/2003 | Wilson |
| 6,602,288 B1 | 8/2003 | Cosgrove et al. |
| 6,602,289 B1 | 8/2003 | Colvin et al. |
| 6,626,930 B1 | 9/2003 | Allen et al. |
| 6,629,534 B1 | 10/2003 | Goar et al. |
| 6,652,578 B2 | 11/2003 | Bailey et al. |
| 6,676,698 B2 | 1/2004 | McGuckin, Jr. et al. |
| 6,682,559 B2 | 1/2004 | Myers et al. |
| 6,702,852 B2 | 3/2004 | Stobie et al. |
| 6,719,790 B2 | 4/2004 | Brendzel et al. |
| 6,752,813 B2 | 6/2004 | Goldfarb et al. |
| 6,764,510 B2 | 7/2004 | Vidlund et al. |
| 6,780,200 B2 | 8/2004 | Jansen |
| 6,790,237 B2 | 9/2004 | Stinson |
| 6,797,002 B2 | 9/2004 | Spence et al. |
| 6,800,090 B2 | 10/2004 | Alferness et al. |
| 6,805,710 B2 | 10/2004 | Bolling et al. |
| 6,821,297 B2 | 11/2004 | Snyders |
| 6,837,247 B2 | 1/2005 | Buckberg et al. |
| 6,840,246 B2 | 1/2005 | Downing |
| 6,846,324 B2 | 1/2005 | Stobie |
| 6,869,444 B2 | 3/2005 | Gabbay |
| 6,908,478 B2 | 6/2005 | Alferness et al. |
| 6,911,043 B2 | 6/2005 | Myers et al. |
| 6,926,730 B1 | 8/2005 | Nguyen et al. |
| 6,966,925 B2 | 11/2005 | Stobie |
| 6,991,649 B2 | 1/2006 | Sievers |
| 6,997,950 B2 | 2/2006 | Chawla |
| 7,018,408 B2 | 3/2006 | Bailey et al. |
| 7,037,333 B2 | 5/2006 | Myers et al. |
| 7,048,754 B2 | 5/2006 | Martin et al. |
| 7,056,280 B2 | 6/2006 | Buckberg et al. |
| 7,070,618 B2 | 7/2006 | Streeter |
| 7,077,861 B2 | 7/2006 | Spence |
| 7,077,862 B2 | 7/2006 | Vidlund et al. |
| 7,083,628 B2 | 8/2006 | Bachman |
| 7,087,064 B1 | 8/2006 | Hyde |
| 7,112,207 B2 | 9/2006 | Allen et al. |
| 7,122,043 B2 | 10/2006 | Greenhalgh et al. |
| 7,160,322 B2 | 1/2007 | Gabbay |

(56) References Cited

U.S. PATENT DOCUMENTS

| | | |
|---|---|---|
| 7,166,126 B2 | 1/2007 | Spence et al. |
| 7,175,656 B2 | 2/2007 | Khairkhahan |
| 7,195,641 B2 | 3/2007 | Palmaz et al. |
| 7,217,284 B2 | 5/2007 | Houser et al. |
| 7,226,467 B2 | 6/2007 | Lucatero et al. |
| 7,275,546 B2 | 10/2007 | Buckberg et al. |
| 7,291,168 B2 | 11/2007 | Macoviak et al. |
| 7,294,148 B2 | 11/2007 | McCarthy |
| 7,296,577 B2 | 11/2007 | Taylor et al. |
| 7,316,706 B2 | 1/2008 | Bloom et al. |
| 7,320,704 B2 | 1/2008 | Lashinski et al. |
| 7,335,213 B1 | 2/2008 | Hyde et al. |
| 7,338,520 B2 | 3/2008 | Bailey et al. |
| 7,341,584 B1 | 3/2008 | Starkey |
| 7,357,814 B2 | 4/2008 | Gabbay |
| 7,374,572 B2 | 5/2008 | Gabbay |
| RE40,377 E | 6/2008 | Williamson, IV et al. |
| 7,381,220 B2 | 6/2008 | Macoviak et al. |
| 7,396,364 B2 | 7/2008 | Moaddeb et al. |
| 7,404,824 B1 | 7/2008 | Webler et al. |
| 7,435,257 B2 | 10/2008 | Lashinski et al. |
| 7,445,630 B2 | 11/2008 | Lashinski et al. |
| 7,455,689 B2 | 11/2008 | Johnson |
| 7,485,143 B2 | 2/2009 | Webler et al. |
| 7,510,573 B2 | 3/2009 | Gabbay |
| 7,510,576 B2 | 3/2009 | Langberg et al. |
| 7,527,646 B2 | 5/2009 | Rahdert et al. |
| 7,527,647 B2 | 5/2009 | Spence |
| 7,530,998 B1 | 5/2009 | Starkey |
| 7,534,259 B2 | 5/2009 | Lashinski et al. |
| 7,556,645 B2 | 7/2009 | Lashinski et al. |
| 7,559,936 B2 | 7/2009 | Levine |
| 7,563,267 B2 | 7/2009 | Goldfarb et al. |
| 7,563,273 B2 | 7/2009 | Goldfarb et al. |
| 7,591,847 B2 | 9/2009 | Navia et al. |
| 7,608,091 B2 | 10/2009 | Goldfarb et al. |
| 7,611,534 B2 | 11/2009 | Kapadia et al. |
| 7,621,948 B2 | 11/2009 | Herrmann et al. |
| 7,648,532 B2 | 1/2010 | Greenhalgh et al. |
| 7,655,015 B2 | 2/2010 | Goldfarb et al. |
| 7,658,762 B2 | 2/2010 | Lashinski et al. |
| 7,658,763 B2 | 2/2010 | Stobie |
| 7,666,224 B2 | 2/2010 | Vidlund et al. |
| 7,674,286 B2 | 3/2010 | Alfieri et al. |
| 7,678,145 B2 | 3/2010 | Vidlund et al. |
| 7,682,391 B2 | 3/2010 | Johnson |
| 7,691,144 B2 | 4/2010 | Chang et al. |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,736,388 B2 | 6/2010 | Goldfarb et al. |
| 7,740,638 B2 | 6/2010 | Hyde |
| 7,744,609 B2 | 6/2010 | Allen et al. |
| 7,753,923 B2 | 7/2010 | St. Goar et al. |
| 7,758,491 B2 | 7/2010 | Buckner et al. |
| 7,758,595 B2 | 7/2010 | Allen et al. |
| 7,776,084 B2 | 8/2010 | Johnson |
| 7,785,366 B2 | 8/2010 | Maurer et al. |
| 7,799,038 B2 | 9/2010 | Sogard et al. |
| 7,803,187 B2 | 9/2010 | Hauser |
| 7,819,915 B2 | 10/2010 | Stobie et al. |
| 7,846,203 B2 | 12/2010 | Cribier |
| 7,887,552 B2 | 2/2011 | Bachman |
| 7,901,454 B2 | 3/2011 | Kapadia et al. |
| 7,909,866 B2 | 3/2011 | Stobie |
| 7,914,576 B2 | 3/2011 | Navia et al. |
| 7,927,370 B2 | 4/2011 | Webler et al. |
| 7,935,144 B2 | 5/2011 | Robin et al. |
| 7,935,145 B2 | 5/2011 | Alfieri et al. |
| 7,938,827 B2 | 5/2011 | Hauck et al. |
| 7,942,928 B2 | 5/2011 | Webler et al. |
| 7,951,195 B2 | 5/2011 | Antonsson et al. |
| 7,951,196 B2 | 5/2011 | McCarthy |
| 7,955,385 B2 | 6/2011 | Crittenden |
| 7,959,673 B2 | 6/2011 | Carpentier et al. |
| 7,981,139 B2 | 7/2011 | Martin et al. |
| 7,988,725 B2 | 8/2011 | Gross et al. |
| 7,993,396 B2 | 8/2011 | McCarthy |
| 7,998,151 B2 | 8/2011 | St. Goar et al. |
| 8,012,201 B2 | 9/2011 | Lashinski et al. |
| 8,012,202 B2 | 9/2011 | Alameddine |
| 8,016,882 B2 | 9/2011 | Macoviak et al. |
| 8,029,518 B2 | 10/2011 | Goldfarb et al. |
| 8,052,751 B2 | 11/2011 | Aklog et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,092,525 B2 | 1/2012 | Eliasen et al. |
| 8,118,866 B2 | 2/2012 | Herrmann et al. |
| 8,128,691 B2 | 3/2012 | Keranen |
| 8,133,272 B2 | 3/2012 | Hyde |
| 8,142,494 B2 | 3/2012 | Rahdert et al. |
| 8,142,495 B2 | 3/2012 | Hasenkam et al. |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,207 B2 | 5/2012 | Machold et al. |
| 8,187,299 B2 | 5/2012 | Goldfarb et al. |
| 8,187,323 B2 | 5/2012 | Mortier et al. |
| 8,204,605 B2 | 6/2012 | Hastings et al. |
| 8,206,439 B2 | 6/2012 | Gomez Duran |
| 8,216,230 B2 | 7/2012 | Hauck et al. |
| 8,216,256 B2 | 7/2012 | Raschdorf, Jr. et al. |
| 8,216,302 B2 | 7/2012 | Wilson et al. |
| 8,216,303 B2 | 7/2012 | Navia |
| 8,221,493 B2 | 7/2012 | Boyle et al. |
| 8,226,711 B2 | 7/2012 | Mortier et al. |
| 8,241,304 B2 | 8/2012 | Bachman |
| 8,241,351 B2 | 8/2012 | Cabiri |
| 8,252,050 B2 | 8/2012 | Maisano |
| 8,252,051 B2 | 8/2012 | Chau et al. |
| 8,262,725 B2 | 9/2012 | Subramanian |
| 8,277,502 B2 | 10/2012 | Miller et al. |
| 8,287,591 B2 | 10/2012 | Keidar et al. |
| 8,292,884 B2 | 10/2012 | Levine et al. |
| 8,308,796 B2 | 11/2012 | Lashinski et al. |
| 8,323,336 B2 | 12/2012 | Hill et al. |
| 8,337,390 B2 | 12/2012 | Ferrazzi |
| 8,353,956 B2 | 1/2013 | Miller et al. |
| 8,361,086 B2 | 1/2013 | Allen et al. |
| 8,377,118 B2 | 2/2013 | Lashinski et al. |
| 8,382,796 B2 | 2/2013 | Blaeser et al. |
| 8,382,828 B2 | 2/2013 | Roberts |
| 8,382,829 B1 | 2/2013 | Call et al. |
| RE44,075 E | 3/2013 | Williamson, IV et al. |
| 8,398,708 B2 | 3/2013 | Meiri et al. |
| 8,408,214 B2 | 4/2013 | Spenser |
| 8,413,573 B2 | 4/2013 | Rebecchi |
| 8,414,644 B2 | 4/2013 | Quadri et al. |
| 8,449,606 B2 | 5/2013 | Eliasen et al. |
| 8,454,683 B2 | 6/2013 | Rafiee et al. |
| 8,470,028 B2 | 6/2013 | Thornton et al. |
| 8,500,800 B2 | 8/2013 | Maisano et al. |
| 8,506,624 B2 | 8/2013 | Vidlund et al. |
| 8,523,881 B2 | 9/2013 | Cabiri et al. |
| 8,545,553 B2 | 10/2013 | Zipory et al. |
| 8,608,797 B2 | 12/2013 | Gross et al. |
| 8,657,872 B2 | 2/2014 | Seguin |
| 8,690,939 B2 | 4/2014 | Miller et al. |
| 8,715,342 B2 | 5/2014 | Zipory et al. |
| 8,734,467 B2 | 5/2014 | Miller et al. |
| 8,784,483 B2 | 7/2014 | Navia |
| 8,790,394 B2 | 7/2014 | Miller et al. |
| 8,795,352 B2 | 8/2014 | O'Beirne et al. |
| 8,808,368 B2 | 8/2014 | Maisano et al. |
| 8,845,717 B2 | 9/2014 | Khairkhahan et al. |
| 8,858,623 B2 | 10/2014 | Miller et al. |
| 8,888,843 B2 | 11/2014 | Khairkhahan et al. |
| 8,888,844 B2 | 11/2014 | Eliasen et al. |
| 8,911,494 B2 | 12/2014 | Hammer et al. |
| 8,926,695 B2 | 1/2015 | Gross et al. |
| 8,926,696 B2 | 1/2015 | Cabiri et al. |
| 8,926,697 B2 | 1/2015 | Gross et al. |

(56) References Cited

U.S. PATENT DOCUMENTS

| | | |
|---|---|---|
| 8,940,042 B2 | 1/2015 | Miller et al. |
| 8,940,044 B2 | 1/2015 | Hammer et al. |
| 8,968,395 B2 | 3/2015 | Hauser et al. |
| 9,005,279 B2 | 4/2015 | Gabbay |
| 9,011,520 B2 | 4/2015 | Miller et al. |
| 9,011,530 B2 | 4/2015 | Reich et al. |
| 9,056,006 B2 | 6/2015 | Edelman et al. |
| 9,119,719 B2 | 9/2015 | Zipory et al. |
| 9,180,007 B2 | 11/2015 | Reich et al. |
| 9,192,472 B2 | 11/2015 | Gross et al. |
| 9,204,964 B2 | 12/2015 | Dahlgren et al. |
| 9,232,999 B2 | 1/2016 | Maurer et al. |
| 9,265,608 B2 | 2/2016 | Miller et al. |
| 9,277,994 B2 | 3/2016 | Miller et al. |
| 9,351,830 B2 | 5/2016 | Gross et al. |
| 9,414,921 B2 | 8/2016 | Miller et al. |
| 9,452,048 B2 | 9/2016 | O'beirne et al. |
| 9,474,606 B2 | 10/2016 | Zipory et al. |
| 9,526,613 B2 | 12/2016 | Gross et al. |
| 9,549,817 B2 | 1/2017 | Rafiee |
| 9,554,906 B2 | 1/2017 | Aklog et al. |
| 9,561,104 B2 | 2/2017 | Miller et al. |
| 9,592,118 B2 | 3/2017 | Khairkhahan et al. |
| 9,592,121 B1 * | 3/2017 | Khairkhahan ....... A61B 17/064 |
| 9,592,122 B2 | 3/2017 | Zipory et al. |
| 9,610,161 B2 | 4/2017 | Macoviak et al. |
| 9,610,162 B2 | 4/2017 | Zipory et al. |
| 9,610,163 B2 | 4/2017 | Khairkhahan et al. |
| 9,622,861 B2 | 4/2017 | Miller et al. |
| 9,636,224 B2 | 5/2017 | Zipory et al. |
| 9,662,209 B2 | 5/2017 | Gross et al. |
| 9,713,530 B2 | 7/2017 | Cabiri et al. |
| 9,724,192 B2 | 8/2017 | Sheps et al. |
| 9,730,793 B2 | 8/2017 | Reich et al. |
| 9,775,709 B2 | 10/2017 | Miller et al. |
| 9,814,572 B2 | 11/2017 | Edelman et al. |
| 9,872,769 B2 | 1/2018 | Gross et al. |
| 9,883,943 B2 | 2/2018 | Gross et al. |
| 9,918,840 B2 | 3/2018 | Reich et al. |
| 9,937,042 B2 | 4/2018 | Cabiri et al. |
| 9,949,828 B2 | 4/2018 | Sheps et al. |
| 9,968,452 B2 | 5/2018 | Sheps et al. |
| 9,968,454 B2 | 5/2018 | Reich et al. |
| 9,974,653 B2 | 5/2018 | Gross et al. |
| 10,028,832 B2 | 7/2018 | Quill et al. |
| 10,098,737 B2 | 10/2018 | Miller |
| 10,123,874 B2 * | 11/2018 | Khairkhahan ........ A61F 2/2466 |
| 10,130,472 B2 | 11/2018 | O'beirne et al. |
| 10,166,098 B2 | 1/2019 | Khairkhahan et al. |
| 10,195,030 B2 | 2/2019 | Gross et al. |
| 10,226,342 B2 | 3/2019 | Kutzik et al. |
| 10,251,635 B2 | 4/2019 | Khairkhahan et al. |
| 10,265,170 B2 | 4/2019 | Zipory et al. |
| 10,299,793 B2 | 5/2019 | Zipory et al. |
| 10,350,068 B2 | 7/2019 | Miller et al. |
| 10,357,366 B2 | 7/2019 | Gross et al. |
| 10,363,136 B2 | 7/2019 | Miller et al. |
| 10,363,137 B2 | 7/2019 | Gross et al. |
| 10,368,982 B2 | 8/2019 | Weber et al. |
| 10,376,266 B2 | 8/2019 | Herman et al. |
| 10,376,365 B2 | 8/2019 | Khairkhahan et al. |
| 10,383,726 B2 | 8/2019 | Kramer |
| 10,426,619 B2 | 10/2019 | Mohl |
| 10,433,955 B2 | 10/2019 | Edelman et al. |
| 10,449,046 B2 | 10/2019 | Rafiee |
| 10,449,049 B2 | 10/2019 | Li et al. |
| 10,449,333 B2 | 10/2019 | Hammer et al. |
| 10,470,882 B2 | 11/2019 | Gross et al. |
| 10,470,883 B2 | 11/2019 | Khairkhahan et al. |
| 10,478,303 B2 * | 11/2019 | Khairkhahan ........ A61F 2/2466 |
| 10,492,909 B2 | 12/2019 | Miller et al. |
| 10,500,048 B2 * | 12/2019 | Khairkhahan ....... A61B 17/068 |
| 10,512,542 B2 | 12/2019 | Khairkhahan et al. |
| 10,517,719 B2 | 12/2019 | Miller et al. |
| 10,543,088 B2 | 1/2020 | Lashinski |
| 10,548,729 B2 | 2/2020 | Zipory et al. |
| 10,548,731 B2 | 2/2020 | Lashinski et al. |
| 10,561,498 B2 | 2/2020 | Gross et al. |
| 10,568,738 B2 | 2/2020 | Sheps et al. |
| 10,583,009 B2 | 3/2020 | Hauser et al. |
| 10,610,360 B2 | 4/2020 | Reich et al. |
| 10,653,524 B2 | 5/2020 | Khairkhahan et al. |
| 10,702,386 B2 * | 7/2020 | Khairkhahan .......... A61F 2/246 |
| 10,751,180 B2 | 8/2020 | Schewel |
| 11,000,372 B2 | 5/2021 | Khairkhahan et al. |
| 11,026,791 B2 | 6/2021 | Genovese et al. |
| 11,076,957 B2 | 8/2021 | Mohl |
| 11,160,656 B2 | 11/2021 | Khairkhahan |
| 11,266,502 B1 * | 3/2022 | Wallace ................ A61F 2/2442 |
| 11,298,229 B2 | 4/2022 | Khairkhahan |
| 11,413,145 B2 | 8/2022 | Khairkhahan |
| 11,419,719 B2 | 8/2022 | Schewel et al. |
| 11,419,722 B2 | 8/2022 | Khairkhahan et al. |
| 11,426,279 B2 | 8/2022 | Khairkhahan et al. |
| 11,432,928 B2 | 9/2022 | Mohl |
| 11,464,634 B2 | 10/2022 | Khairkhahan et al. |
| 11,497,606 B2 | 11/2022 | Khairkhahan et al. |
| 11,504,237 B2 | 11/2022 | Gifford et al. |
| 11,534,302 B2 | 12/2022 | Khairkhahan et al. |
| 11,571,305 B2 | 2/2023 | Padala et al. |
| 11,622,759 B2 | 4/2023 | Khairkhahan et al. |
| 11,633,281 B2 | 4/2023 | Kappetein et al. |
| 11,648,119 B2 | 5/2023 | Khairkhahan et al. |
| 11,648,120 B2 | 5/2023 | Khairkhahan et al. |
| 11,672,659 B2 | 6/2023 | Khairkhahan et al. |
| 11,672,660 B2 | 6/2023 | Moh et al. |
| 11,678,986 B2 | 6/2023 | Khairkhahan et al. |
| 11,701,228 B2 | 7/2023 | Genovese et al. |
| 11,759,321 B2 | 9/2023 | Khairkhahan et al. |
| 11,883,291 B2 | 1/2024 | Gifford et al. |
| 11,974,921 B2 | 5/2024 | Khairkhahan et al. |
| 12,053,373 B2 | 8/2024 | McLean et al. |
| 12,109,116 B2 | 10/2024 | Khairkhahan et al. |
| 12,150,856 B2 | 11/2024 | Khairkhahan et al. |
| 12,251,308 B2 | 3/2025 | McLean et al. |
| 12,285,336 B2 | 4/2025 | Khairkhahan |
| 2001/0007956 A1 | 7/2001 | Letac et al. |
| 2001/0021872 A1 | 9/2001 | Bailey et al. |
| 2002/0029080 A1 | 3/2002 | Mortier et al. |
| 2002/0058995 A1 | 5/2002 | Stevens |
| 2002/0116024 A1 | 8/2002 | Goldberg et al. |
| 2002/0138135 A1 | 9/2002 | Duerig |
| 2002/0188301 A1 | 12/2002 | Dallara et al. |
| 2003/0023248 A1 | 1/2003 | Parodi |
| 2003/0100943 A1 | 5/2003 | Bolduc |
| 2003/0105474 A1 | 6/2003 | Bonutti |
| 2003/0135263 A1 | 7/2003 | Rourke et al. |
| 2003/0191497 A1 | 10/2003 | Cope |
| 2003/0199975 A1 | 10/2003 | Gabbay |
| 2004/0082956 A1 | 4/2004 | Baldwin et al. |
| 2004/0088047 A1 | 5/2004 | Spence et al. |
| 2004/0143323 A1 | 7/2004 | Chawla |
| 2004/0172046 A1 | 9/2004 | Hlavka et al. |
| 2004/0193217 A1 | 9/2004 | Lubbers et al. |
| 2004/0210307 A1 | 10/2004 | Khairkhahan |
| 2005/0004665 A1 | 1/2005 | Aklog |
| 2005/0004668 A1 | 1/2005 | Aklog et al. |
| 2005/0010287 A1 | 1/2005 | Macoviak et al. |
| 2005/0075727 A1 | 4/2005 | Wheatley et al. |
| 2005/0096740 A1 | 5/2005 | Langberg et al. |
| 2005/0107871 A1 | 5/2005 | Realyvasquez |
| 2005/0159810 A1 | 7/2005 | Filsoufi |
| 2005/0177180 A1 | 8/2005 | Kaganov et al. |
| 2005/0228495 A1 | 10/2005 | Macoviak |
| 2005/0261708 A1 | 11/2005 | Pasricha et al. |
| 2005/0267573 A9 | 12/2005 | Macoviak et al. |
| 2005/0283232 A1 | 12/2005 | Gabbay |
| 2006/0030885 A1 | 2/2006 | Hyde |
| 2006/0058871 A1 | 3/2006 | Zakay et al. |
| 2006/0122608 A1 | 6/2006 | Fallin et al. |
| 2006/0149368 A1 | 7/2006 | Spence |
| 2006/0190030 A1 | 8/2006 | To et al. |
| 2006/0252984 A1 | 11/2006 | Rahdert et al. |
| 2007/0005069 A1 | 1/2007 | Contiliano et al. |

(56) References Cited

U.S. PATENT DOCUMENTS

| | | |
|---|---|---|
| 2007/0049942 A1 | 3/2007 | Hindrichs et al. |
| 2007/0049970 A1 | 3/2007 | Belef et al. |
| 2007/0093890 A1 | 4/2007 | Eliasen et al. |
| 2007/0112352 A1 | 5/2007 | Sorensen et al. |
| 2007/0112425 A1 | 5/2007 | Schaller et al. |
| 2007/0118151 A1 | 5/2007 | Davidson |
| 2007/0129758 A1 | 6/2007 | Saadat |
| 2007/0149947 A1 | 6/2007 | Byrum |
| 2007/0185571 A1 | 8/2007 | Kapadia et al. |
| 2007/0233239 A1 | 10/2007 | Navia et al. |
| 2007/0239272 A1 | 10/2007 | Navia et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0250160 A1 | 10/2007 | Rafiee |
| 2007/0255399 A1 | 11/2007 | Eliasen et al. |
| 2007/0265658 A1 | 11/2007 | Nelson et al. |
| 2007/0265700 A1 | 11/2007 | Eliasen et al. |
| 2007/0265702 A1 | 11/2007 | Lattouf |
| 2007/0282375 A1 | 12/2007 | Hindrichs et al. |
| 2007/0293943 A1 | 12/2007 | Quinn |
| 2008/0065204 A1 | 3/2008 | Macoviak et al. |
| 2008/0109075 A1 | 5/2008 | Keranen |
| 2008/0125860 A1 | 5/2008 | Webler et al. |
| 2008/0125861 A1 | 5/2008 | Webler et al. |
| 2008/0195205 A1 | 8/2008 | Schwartz |
| 2008/0262609 A1 | 10/2008 | Gross et al. |
| 2008/0319541 A1 | 12/2008 | Filsoufi |
| 2009/0012354 A1 | 1/2009 | Wood |
| 2009/0088836 A1 | 4/2009 | Bishop et al. |
| 2009/0177277 A1 | 7/2009 | Milo |
| 2009/0234404 A1 | 9/2009 | Fitzgerald et al. |
| 2009/0259304 A1 | 10/2009 | O'Beirne et al. |
| 2009/0259307 A1 | 10/2009 | Gross et al. |
| 2009/0287304 A1 | 11/2009 | Dahlgren et al. |
| 2009/0326648 A1 | 12/2009 | Machold et al. |
| 2010/0010538 A1 | 1/2010 | Juravic et al. |
| 2010/0069954 A1 | 3/2010 | Blaeser et al. |
| 2010/0121435 A1 | 5/2010 | Subramanian et al. |
| 2010/0121437 A1 | 5/2010 | Subramanian et al. |
| 2010/0131057 A1 | 5/2010 | Subramanian et al. |
| 2010/0161043 A1 | 6/2010 | Maisano et al. |
| 2010/0161047 A1 | 6/2010 | Cabiri et al. |
| 2010/0249947 A1 | 9/2010 | Lesh et al. |
| 2010/0262233 A1 | 10/2010 | He |
| 2010/0280603 A1 | 11/2010 | Maisano et al. |
| 2010/0280604 A1 | 11/2010 | Zipory et al. |
| 2010/0280605 A1 | 11/2010 | Hammer |
| 2010/0280606 A1 | 11/2010 | Naor |
| 2010/0286767 A1 | 11/2010 | Zipory et al. |
| 2010/0298929 A1 | 11/2010 | Thornton et al. |
| 2010/0312333 A1 | 12/2010 | Navia et al. |
| 2011/0004299 A1 | 1/2011 | Navia et al. |
| 2011/0082538 A1 | 4/2011 | Dahlgren et al. |
| 2011/0106245 A1 | 5/2011 | Miller et al. |
| 2011/0106247 A1 | 5/2011 | Miller et al. |
| 2011/0137397 A1 | 6/2011 | Chau et al. |
| 2011/0166649 A1 | 7/2011 | Gross et al. |
| 2011/0184510 A1 | 7/2011 | Maisano et al. |
| 2011/0224785 A1 | 9/2011 | Hacohen |
| 2011/0238088 A1 | 9/2011 | Bolduc et al. |
| 2011/0282361 A1 | 11/2011 | Miller |
| 2011/0288635 A1 | 11/2011 | Miller et al. |
| 2011/0301698 A1 | 12/2011 | Miller et al. |
| 2011/0319989 A1 | 12/2011 | Lane et al. |
| 2011/0319990 A1 | 12/2011 | Macoviak et al. |
| 2012/0016468 A1 | 1/2012 | Robin et al. |
| 2012/0022557 A1 | 1/2012 | Cabiri et al. |
| 2012/0022644 A1 | 1/2012 | Reich et al. |
| 2012/0078360 A1 | 3/2012 | Rafiee |
| 2012/0136436 A1 | 5/2012 | Cabiri et al. |
| 2012/0165930 A1 | 6/2012 | Gifford et al. |
| 2012/0197388 A1 | 8/2012 | Khairkhahan et al. |
| 2012/0203336 A1 | 8/2012 | Annest |
| 2012/0245604 A1 | 9/2012 | Tegzes |
| 2012/0283757 A1 | 11/2012 | Miller et al. |
| 2012/0323316 A1 | 12/2012 | Chau et al. |
| 2012/0330410 A1 | 12/2012 | Hammer et al. |
| 2012/0330411 A1 | 12/2012 | Gross et al. |
| 2013/0023985 A1 | 1/2013 | Khairkhahan et al. |
| 2013/0096672 A1 | 4/2013 | Reich et al. |
| 2013/0116776 A1 | 5/2013 | Gross et al. |
| 2013/0116780 A1 | 5/2013 | Miller et al. |
| 2013/0131792 A1 | 5/2013 | Miller et al. |
| 2013/0190861 A1 | 7/2013 | Chau et al. |
| 2013/0190866 A1 | 7/2013 | Zipory et al. |
| 2013/0238024 A1 | 9/2013 | Taylor et al. |
| 2013/0282028 A1 | 10/2013 | Conklin et al. |
| 2013/0325110 A1 | 12/2013 | Khalil et al. |
| 2013/0338763 A1 | 12/2013 | Rowe et al. |
| 2014/0018906 A1 | 1/2014 | Rafiee |
| 2014/0025163 A1 | 1/2014 | Padala et al. |
| 2014/0039615 A1 | 2/2014 | Padala et al. |
| 2014/0067048 A1 | 3/2014 | Chau |
| 2014/0067054 A1 | 3/2014 | Chau et al. |
| 2014/0094903 A1 | 4/2014 | Miller et al. |
| 2014/0128965 A1 | 5/2014 | Rafiee |
| 2014/0142695 A1 | 5/2014 | Gross et al. |
| 2014/0148898 A1 | 5/2014 | Gross et al. |
| 2014/0222137 A1 | 8/2014 | Miller et al. |
| 2014/0243963 A1 | 8/2014 | Sheps et al. |
| 2014/0276648 A1 | 9/2014 | Hammer et al. |
| 2014/0277088 A1 | 9/2014 | Friedman |
| 2014/0309661 A1 | 10/2014 | Sheps et al. |
| 2014/0343668 A1 | 11/2014 | Zipory et al. |
| 2014/0358223 A1 | 12/2014 | Rafiee et al. |
| 2014/0379075 A1 | 12/2014 | Maurer et al. |
| 2015/0012087 A1 | 1/2015 | Miller et al. |
| 2015/0039083 A1 | 2/2015 | Rafiee et al. |
| 2015/0057682 A1 | 2/2015 | Kovach |
| 2015/0081014 A1 | 3/2015 | Gross et al. |
| 2015/0100116 A1 | 4/2015 | Mohl et al. |
| 2015/0105855 A1 | 4/2015 | Cabiri et al. |
| 2015/0112429 A1 | 4/2015 | Khairkhahan et al. |
| 2015/0112432 A1 | 4/2015 | Reich et al. |
| 2015/0119981 A1 | 4/2015 | Khairkhahan et al. |
| 2015/0164637 A1 | 6/2015 | Khairkhahan et al. |
| 2015/0182336 A1 | 7/2015 | Zipory et al. |
| 2015/0202043 A1 | 7/2015 | Zakai et al. |
| 2015/0230924 A1 | 8/2015 | Miller et al. |
| 2015/0257877 A1 | 9/2015 | Hernandez |
| 2015/0272586 A1 | 10/2015 | Herman et al. |
| 2015/0272734 A1 | 10/2015 | Sheps et al. |
| 2015/0297212 A1 | 10/2015 | Reich et al. |
| 2015/0366556 A1 | 12/2015 | Khairkhahan et al. |
| 2015/0366666 A1 | 12/2015 | Khairkhahan et al. |
| 2016/0008132 A1 | 1/2016 | Cabiri et al. |
| 2016/0030176 A1 | 2/2016 | Mohl et al. |
| 2016/0058557 A1 | 3/2016 | Reich et al. |
| 2016/0074164 A1 | 3/2016 | Naor |
| 2016/0089233 A1 | 3/2016 | Lee et al. |
| 2016/0106437 A1 | 4/2016 | Van Der Burg et al. |
| 2016/0113767 A1 | 4/2016 | Miller et al. |
| 2016/0157862 A1 | 6/2016 | Hernandez et al. |
| 2016/0158008 A1 | 6/2016 | Miller et al. |
| 2016/0262755 A1 | 9/2016 | Zipory et al. |
| 2016/0324639 A1 | 11/2016 | Nguyen et al. |
| 2016/0331523 A1 | 11/2016 | Chau et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0086975 A1 | 3/2017 | Gilmore et al. |
| 2017/0100249 A1 | 4/2017 | Miller et al. |
| 2017/0105839 A1 | 4/2017 | Subramanian et al. |
| 2017/0112618 A1 | 4/2017 | Li et al. |
| 2017/0135815 A1 | 5/2017 | Gross et al. |
| 2017/0135816 A1 | 5/2017 | Lashinski et al. |
| 2017/0189186 A1 | 7/2017 | Mohl |
| 2017/0196691 A1 | 7/2017 | Zipory et al. |
| 2017/0209270 A1 | 7/2017 | Miller et al. |
| 2017/0245993 A1 | 8/2017 | Gross et al. |
| 2017/0245994 A1 | 8/2017 | Khairkhahan et al. |
| 2017/0258588 A1 | 9/2017 | Zipory et al. |
| 2017/0258590 A1 | 9/2017 | Khairkhahan et al. |

(56) References Cited

U.S. PATENT DOCUMENTS

| | | |
|---|---|---|
| 2017/0265995 A1 | 9/2017 | Khairkhahan et al. |
| 2017/0296340 A1 | 10/2017 | Gross et al. |
| 2017/0325958 A1 | 11/2017 | Reich et al. |
| 2017/0325959 A1 | 11/2017 | Sheps et al. |
| 2017/0354500 A1 | 12/2017 | Martinez et al. |
| 2017/0367825 A1 | 12/2017 | Cabiri et al. |
| 2018/0008409 A1 | 1/2018 | Kutzik et al. |
| 2018/0014933 A1 | 1/2018 | Miller et al. |
| 2018/0014934 A1 | 1/2018 | Miller et al. |
| 2018/0049875 A1 | 2/2018 | Iflah et al. |
| 2018/0116797 A9 | 5/2018 | Miller et al. |
| 2018/0125657 A1 | 5/2018 | Dahlgren et al. |
| 2018/0228608 A1 | 8/2018 | Sheps et al. |
| 2018/0250133 A1 | 9/2018 | Reich et al. |
| 2018/0256318 A1 | 9/2018 | Khairkhahan |
| 2018/0256333 A1 | 9/2018 | Cabiri et al. |
| 2018/0256334 A1 | 9/2018 | Sheps et al. |
| 2018/0256865 A1 | 9/2018 | Finch et al. |
| 2018/0263776 A1 | 9/2018 | Gross et al. |
| 2018/0263777 A1 | 9/2018 | Gross et al. |
| 2018/0318080 A1 | 11/2018 | Quill et al. |
| 2018/0325670 A1 | 11/2018 | De Canniere |
| 2019/0008641 A1 | 1/2019 | Dahlgren et al. |
| 2019/0046318 A1 | 2/2019 | Miller et al. |
| 2019/0070004 A1 | 3/2019 | Ifah et al. |
| 2019/0076247 A1 | 3/2019 | Zeng |
| 2019/0076249 A1 | 3/2019 | Khairkhahan |
| 2019/0125325 A1 | 5/2019 | Sheps et al. |
| 2019/0133586 A1 | 5/2019 | Zipory et al. |
| 2019/0151090 A1 | 5/2019 | Gross et al. |
| 2019/0151093 A1 | 5/2019 | Keidar et al. |
| 2019/0159898 A1 | 5/2019 | Kutzik et al. |
| 2019/0167425 A1 | 6/2019 | Reich et al. |
| 2019/0175344 A1 | 6/2019 | Khairkhahan |
| 2019/0183644 A1 | 6/2019 | Hacohen |
| 2019/0201191 A1 | 7/2019 | McLean et al. |
| 2019/0216600 A1 | 7/2019 | Zipory et al. |
| 2019/0254821 A1 | 8/2019 | Rafiee et al. |
| 2019/0269512 A9 | 9/2019 | Lashinski |
| 2019/0269513 A9 | 9/2019 | Cabiri et al. |
| 2019/0274830 A1 | 9/2019 | Miller et al. |
| 2019/0282358 A1 | 9/2019 | Khairkhahan et al. |
| 2019/0282364 A1 | 9/2019 | Khairkhahan et al. |
| 2019/0290431 A1 | 9/2019 | Genovese et al. |
| 2019/0298332 A1 | 10/2019 | Khairkhahan et al. |
| 2019/0298522 A1 | 10/2019 | Subramanian et al. |
| 2019/0321049 A1 | 10/2019 | Herman et al. |
| 2019/0336288 A1 | 11/2019 | Gross et al. |
| 2019/0336289 A1 | 11/2019 | Miller et al. |
| 2019/0350703 A1 | 11/2019 | Weber et al. |
| 2019/0350705 A1 | 11/2019 | Schewel et al. |
| 2019/0374343 A1 | 12/2019 | Lashinski et al. |
| 2019/0374750 A1 | 12/2019 | Hammer et al. |
| 2019/0380834 A1 | 12/2019 | Rafiee |
| 2020/0015971 A1 | 1/2020 | Brauon et al. |
| 2020/0030097 A1 | 1/2020 | Khairkhahan et al. |
| 2020/0038186 A1 | 2/2020 | Gross et al. |
| 2020/0100899 A1 | 4/2020 | Miller et al. |
| 2020/0113685 A1 | 4/2020 | Miller et al. |
| 2020/0205966 A1 | 7/2020 | Khairkhahan et al. |
| 2020/0205975 A1 | 7/2020 | Khairkhahan |
| 2020/0205978 A1 | 7/2020 | Padala et al. |
| 2020/0205980 A1 | 7/2020 | Khairkhahan et al. |
| 2020/0214841 A1 | 7/2020 | Khairkhahan et al. |
| 2020/0222185 A1 | 7/2020 | Kappetein et al. |
| 2020/0275974 A1 | 9/2020 | Gifford et al. |
| 2020/0289265 A1 | 9/2020 | Gifford et al. |
| 2020/0330229 A1 | 10/2020 | Serraf et al. |
| 2020/0337843 A1 | 10/2020 | Khairkhahan et al. |
| 2020/0383776 A1 | 12/2020 | Schewel |
| 2020/0397567 A1 | 12/2020 | Khairkhahan et al. |
| 2021/0085462 A1 | 3/2021 | Gifford et al. |
| 2021/0196462 A1 | 7/2021 | Khairkhahan |
| 2021/0290390 A1 | 9/2021 | Genovese et al. |
| 2021/0298901 A1 | 9/2021 | Khairkhahan et al. |
| 2021/0346159 A1 | 11/2021 | Keränen |
| 2021/0353418 A1 | 11/2021 | Mohl |
| 2022/0000621 A1 | 1/2022 | Gifford et al. |
| 2022/0039944 A1 | 2/2022 | Khairkhahan |
| 2022/0039951 A1 | 2/2022 | Khairkhahan |
| 2022/0054269 A1 | 2/2022 | Khairkhahan |
| 2022/0079753 A1 | 3/2022 | Zimmerman et al. |
| 2022/0079755 A1 | 3/2022 | Zimmerman et al. |
| 2022/0096234 A1 | 3/2022 | Sorajja |
| 2022/0096236 A1 | 3/2022 | Guidotti et al. |
| 2022/0125579 A1 | 4/2022 | Mclean et al. |
| 2022/0160499 A1 | 5/2022 | Miyashiro et al. |
| 2022/0160508 A1 | 5/2022 | Miyashiro et al. |
| 2022/0183837 A1 | 6/2022 | Tuval et al. |
| 2022/0183839 A1 | 6/2022 | Khairkhahan |
| 2022/0192822 A1 | 6/2022 | McLean et al. |
| 2022/0233311 A1 | 7/2022 | Khairkhahan |
| 2022/0273433 A1 | 9/2022 | Kuck et al. |
| 2022/0296368 A1 | 9/2022 | Tuval et al. |
| 2022/0354637 A1 | 11/2022 | Khairkhahan |
| 2022/0354647 A1 | 11/2022 | Khairkhahan |
| 2022/0354648 A1 | 11/2022 | Khairkhahan |
| 2022/0362012 A1 | 11/2022 | Khairkhahan |
| 2022/0409372 A1 | 12/2022 | Khairkhahan |
| 2023/0040410 A1 | 2/2023 | Khairkhahan |
| 2023/0105858 A1 | 4/2023 | Khalil et al. |
| 2023/0107129 A1 | 4/2023 | Mohl |
| 2023/0132907 A1 | 5/2023 | McLean et al. |
| 2023/0138388 A1 | 5/2023 | Padala et al. |
| 2023/0142064 A1 | 5/2023 | Chau et al. |
| 2023/0147741 A1 | 5/2023 | Khairkhahan |
| 2023/0181313 A1 | 6/2023 | Mohl et al. |
| 2023/0248518 A1 | 8/2023 | Khairkhahan |
| 2023/0270549 A1 | 8/2023 | Guidotti et al. |
| 2023/0277169 A1 | 9/2023 | Khairkhahan |
| 2023/0293298 A1 | 9/2023 | Khairkhahan |
| 2023/0329865 A1 | 10/2023 | Kappetein et al. |
| 2023/0404757 A1 | 12/2023 | Khairkhahan |
| 2024/0016473 A1 | 1/2024 | Schewel et al. |
| 2024/0033083 A1 | 2/2024 | Khairkhahan |
| 2024/0041601 A1 | 2/2024 | Khairkhahan et al. |
| 2024/0341957 A1 | 10/2024 | Khairkhahan et al. |
| 2024/0366379 A1 | 11/2024 | Khairkhahan et al. |
| 2025/0041061 A1 | 2/2025 | Khairkhahan et al. |
| 2025/0099241 A1 | 3/2025 | Zimmerman et al. |
| 2025/0099247 A1 | 3/2025 | Khairkhahan et al. |

FOREIGN PATENT DOCUMENTS

| | | |
|---|---|---|
| CN | 101056596 | 10/2007 |
| CN | 101068508 | 11/2007 |
| CN | 101947146 | 1/2011 |
| CN | 102065777 | 5/2011 |
| CN | 102458309 | 5/2012 |
| CN | 102665612 | 9/2012 |
| CN | 102781790 | 11/2012 |
| CN | 102933175 | 2/2013 |
| CN | 202821715 | 3/2013 |
| CN | 103118602 | 5/2013 |
| CN | 103338726 | 10/2013 |
| CN | 104203158 | 12/2014 |
| CN | 102905648 | 1/2015 |
| CN | 104394803 | 3/2015 |
| CN | 104582637 | 4/2015 |
| CN | 105287050 | 2/2016 |
| CN | 105451688 | 3/2016 |
| EP | 1 294 310 | 3/2003 |
| EP | 1 959 865 | 8/2008 |
| EP | 2 410 948 | 2/2012 |
| EP | 1 796 597 | 1/2013 |
| EP | 2 661 239 | 11/2013 |
| EP | 2 667 824 | 12/2013 |
| EP | 2 995 279 | 3/2016 |
| EP | 3 160 396 | 5/2017 |
| EP | 3 167 846 | 5/2017 |
| EP | 3 372 198 | 9/2018 |
| EP | 3 658 075 | 6/2020 |
| EP | 3 768 195 | 1/2021 |
| EP | 3 852 681 | 7/2021 |

(56) References Cited

FOREIGN PATENT DOCUMENTS

| | | |
|---|---|---|
| EP | 3 880 124 | 9/2021 |
| EP | 3 911 272 | 11/2021 |
| EP | 3 912 595 | 11/2021 |
| EP | 4 171 443 | 5/2023 |
| JP | S54-088693 | 7/1979 |
| JP | 2005-535384 | 11/2005 |
| JP | 2006-528911 | 12/2006 |
| JP | 2007-518492 | 7/2007 |
| JP | 2008-517672 | 5/2008 |
| JP | 2010-511469 | 4/2010 |
| JP | 2012-511402 | 5/2012 |
| JP | 2012-520716 | 9/2012 |
| JP | 2014-510563 | 5/2014 |
| JP | 2014-231015 | 12/2014 |
| JP | 2015-523898 | 8/2016 |
| JP | 2016-533798 | 11/2016 |
| JP | 2017-18675 | 1/2017 |
| JP | 2020-127779 | 8/2020 |
| WO | WO 97/007744 | 3/1997 |
| WO | WO 99/53869 | 10/1998 |
| WO | WO 2004/014258 | 2/2004 |
| WO | WO 2004/100803 | 11/2004 |
| WO | WO 2004/103162 | 12/2004 |
| WO | WO 2005/069875 | 8/2005 |
| WO | WO 2006/032051 | 3/2006 |
| WO | WO 2006/041877 | 4/2006 |
| WO | WO 2006/086434 | 8/2006 |
| WO | WO 2007/062054 | 5/2007 |
| WO | WO 2007/135101 | 11/2007 |
| WO | WO 2007/140470 | 12/2007 |
| WO | WO 2008/068756 | 6/2008 |
| WO | WO 2008/141322 | 11/2008 |
| WO | WO 2010/106438 | 9/2010 |
| WO | WO 2011/037891 | 3/2011 |
| WO | WO 2011/047168 | 4/2011 |
| WO | WO 2012/061809 | 5/2012 |
| WO | WO 2012/092437 | 7/2012 |
| WO | WO 2012/102928 | 8/2012 |
| WO | WO 2013/059747 | 4/2013 |
| WO | WO 2013/131069 | 9/2013 |
| WO | WO 2013/173587 | 11/2013 |
| WO | WO 2013/178335 | 12/2013 |
| WO | WO 2013/192107 | 12/2013 |
| WO | WO 2014/181336 | 11/2014 |
| WO | WO 2014/207575 | 12/2014 |
| WO | WO 2015/020971 | 2/2015 |
| WO | WO 2015/052570 | 4/2015 |
| WO | WO 2015/061533 | 4/2015 |
| WO | WO 2015/195823 | 12/2015 |
| WO | WO 2015/200497 | 12/2015 |
| WO | WO 2016/059639 | 4/2016 |
| WO | WO 2016/178136 | 11/2016 |
| WO | WO 2016/183485 | 11/2016 |
| WO | WO 2017/079279 | 5/2017 |
| WO | WO 2017/136596 | 8/2017 |
| WO | WO 2018/169878 | 9/2018 |
| WO | WO 2018/169878 A1 | 9/2018 |
| WO | WO 2019/116322 | 6/2019 |
| WO | WO 2019/222694 | 11/2019 |
| WO | WO 2019/241777 | 12/2019 |
| WO | WO 2020/055811 | 3/2020 |
| WO | WO 2021/055983 | 3/2021 |
| WO | WO 2022/006087 | 1/2022 |
| WO | WO 2022/018494 | 1/2022 |
| WO | WO 2023/105334 | 6/2023 |
| WO | WO 2023/114289 | 6/2023 |
| WO | WO 2023/218127 | 11/2023 |

OTHER PUBLICATIONS

Office Action for CN 201980059862.2 dated Nov. 29, 2023.
Office Action for JP 2023-039771 dated Dec. 4, 2023.
Extended European Search Report, EP 20910735.8, dated Jan. 8, 2024.
Biocina et al., Mitral Valve Repair With The New Mitrofast® Repair System, Dubrava University Hospital, Zagreb, Crotia, Mitrofast Abstract European Soc CVS 55th Congress—May 11-14, 2006 Suppl 1 to vol. 5.
Biocina, The arteficial coaptation surface concept in mitral valve repair, University of Zagreb School of Medicine, Department of Cardiac Surgery, Savudrija Mitrofast 2010.
Chiam et al., Percutaneous Transcatheter Mitral Valve Repair, The American College of Cardiology Foundation, JACC: Cardiovascular Interventions, vol. 4 No. 1, Jan. 2011:1-13.
Jassar et al., Posterior Leaflet Augmentation in Ischemic Mitral Regurgitation Increases Leaflet Coaptation and Mobility, The Society of Thoracic Surgeons, Ann Thorac Surg 2012; 94:1438-45.
Langer et al., Posterior mitral leaflet extension: An adjunctive repair option for ischemic mitral regurgitation?, Surgery for Acquired Cardiovascular Disease, The Journal of Thoracic and Cardiovascular Surgery, Apr. 2006, downloaded Jun. 18, 2011.
Mohl et al., The Angel Valve Concept, Vienna University of Technology, Medical University of Vienna, Technology Offer, 1 page.
Mohl et al., An Innovative Concept For Transcatheter Treatment of Annular Dilatation and Restrictive Leaflet Motion in Mitral Insufficiency, Medical University of Vienna, 1 page.
Piemonte et al., Cardiovascular™: The Mitral Valve Spacer, Presented at Transcatheter Cardiovascular Therapeutics Conference—TCT Conference, Oct. 2008.
Rumel et al., The Correction of Mitral Insufficiency with a Trans-Valvular Polyvinyl Formalinized Plastic (Ivalon) Sponge Prosthesis: A Preliminary Report, American College of Chest Physicians, 1958;33;401-413, Dec. 2, 2010.
International Preliminary Report on Patentability for PCT/US2012/021744 mailed Aug. 8, 2013 in 15 pages.
International Search Report for Application No. PCT/US2013/046173 dated Oct. 4, 2013 in 15 pages.
International Search Report for Application No. PCT/US2014/061901 dated Jan. 26, 2015 in 14 pages.
International Search Report for Application No. PCT/US2015/036260 dated Oct. 1, 2015 in 20 pages.
International Search Report for Application No. PCT/US2015/037451 dated Oct. 6, 2015 in 12 pages.
International Search Report for Application No. PCT/US2016/060094 dated Feb. 9, 2017 in 8 pages.
International Search Report for Application No. PCT/US2018/022043 dated Jun. 25, 2018 in 13 pages.
Extended European Search Report, EP 12738989.8, dated May 24, 2016.
Office Action for EP 12738989.8 dated Mar. 3, 2017.
Office Action for EP 12738989.8 dated Sep. 19, 2017.
Extended European Search Report, EP 13806272.4, dated Nov. 11, 2015.
Extended European Search Report, EP 14856738.1, dated Jun. 7, 2017.
Extended European Search Report, EP 15809346.8, dated Feb. 13, 2018.
Extended European Search Report, EP 15812032.9, dated Oct. 18, 2017.
Extended European Search Report, EP 16862864.2, dated May 10, 2019.
Office Action for CA 2,825,520 dated Nov. 27, 2017.
Office Action for CA 2,825,520 dated Aug. 21, 2018.
Office Action for CA 2,877,344 dated Mar. 12, 2019.
Office Action for CA 2,877,344 dated Oct. 9, 2019.
Office Action for CA 2,877,344 dated Jul. 21, 2020.
Office Action for CN 201280006673.7 dated Dec. 10, 2014.
Office Action for CN 201280006673.7 dated Sep. 22, 2015.
Office Action for CN 201280006673.7 dated Feb. 1, 2016.
Office Action for CN 201380044122.4 dated Nov. 4, 2015.
Office Action for CN 201380044122.4 dated Aug. 24, 2016.
|Office Action for CN 201480070933.6 dated May 10, 2017.
Office Action for CN 201480070933.6 dated Dec. 25, 2017.
Office Action for CN 201480070933.6 dated Aug. 10, 2018.
Office Action for CN 201480070933.6 dated Apr. 17, 2019.
Office Action for CN 201580044329.0 dated Jan. 17, 2018.

(56) References Cited

OTHER PUBLICATIONS

Office Action for CN 201580044329.0 dated Jul. 29, 2019.
Office Action for CN 201580045375.2 dated Mar. 29, 2018.
Office Action for CN 201580045375.2 dated Nov. 12, 2018.
Office Action for CN 201680077877.8 dated Aug. 15, 2019.
Office Action for EP 15812032.9, dated Oct. 10, 2019.
Office Action for JP 2013-552015 dated Dec. 7, 2015.
Office Action for JP 2013-552015 dated Oct. 7, 2016.
Office Action for JP 2013-552015 dated Jun. 5, 2017.
Office Action for JP 2015-518499 dated Feb. 27, 2017.
Office Action for JP 2015-518499 dated Aug. 31, 2017.
Office Action for JP 2015-518499 dated Aug. 20, 2018.
Office Action for JP 2016-525999 dated Jul. 9, 2018.
Office Action for JP 2016-525999 dated Jun. 27, 2019.
Office Action for JP 2016-525999 dated Mar. 16, 2020.
Office Action for 2016-573983 dated Apr. 1, 2019.
Office Action for 2016-573983 dated Nov. 11, 2019.
Office Action for JP 2016-574967 dated May 7, 2019.
Office Action for JP 2016-574967 dated Dec. 26, 2019.
International Search Report for Application No. PCT/US2019/050331 dated Jan. 23, 2020 in 9 pages.
Office Action for CN 201580044329.0 dated Mar. 3, 2020.
Office Action for 2016-573983 dated May 11, 2020.
Office Action for CN 201580044329.0 dated Aug. 26, 2020.
Office Action for EP 15812032.9, dated Jul. 6, 2020.
Office Action for JP 2016-574967 dated Jun. 29, 2020.
Office Action for JP 2018-543021 dated Oct. 27, 2020.
Office Action for CA 2,877,344 dated Dec. 23, 2020.
Office Action for CA 2,934, 182 dated Dec. 9, 2020.
Office Action for JP 2020-082001 dated Mar. 29, 2021.
Extended European Search Report, EP 18768736.3, dated Oct. 9, 2020.
International Search Report for Application No. PCT/US2020/065261 dated Apr. 13, 2021 in 13 pages.
Office Action for CN 201880031519.2 dated May 19, 2021.
Office Action for EP 13806272.4, dated Mar. 23, 2021.
Office Action for EP 14856738.1, dated Apr. 23, 2021.
Office Action for JP 2020-085273 dated May 31, 2021.
Office Action for CA 2,934,182 dated Jun. 30, 2021.
Office Action for CA 2,958,065 dated Jul. 9, 2021.
Office Action for JP 2018-543021 dated Oct. 4, 2021.
Office Action for JP 2020-085273 dated Aug. 23, 2021.
Office Action for JP 2020-082001 dated Nov. 29, 2021.
Office Action for CA 2,934,182 dated Mar. 2, 2022.
Office Action for CA 2,958,065 dated Mar. 2, 2022.
Office Action for 2020-041944 dated Feb. 21, 2022.
Office Action for 2019-572351 dated Feb. 28, 2022.
International Search Report for Application No. PCT/US2021/016248 dated Mar. 29, 2022 in 15 pages.
Extended European Search Report, EP 19860754.1 dated Jun. 1, 2022.
International Search Report for Application No. PCT/US2022/071235 dated Jun. 27, 2022 in 13 pages.
Office Action for 2020-041944 dated Jul. 22, 2022.
Office Action for 2019-572351 dated Sep. 12, 2022.
Office Action for CN 202010539957.9 dated Nov. 3, 2022.
Office Action for JP 2021-212699 dated Dec. 6, 2022.
Office Action for JP 2021-153169 dated Dec. 26, 2022.
Office Action for CA 2,958,065 dated Nov. 18, 2022.
Office Action for JP 2021-176431 dated Jan. 6, 2023.
Office Action for 2020-041944 dated Feb. 13, 2023.
Office Action for CN 202010539957.9 dated Mar. 22, 2023.
Extended European Search Report, EP 22214458, dated Mar. 24, 2023.
Office Action for CA 3,004,418 dated Dec. 13, 2022.
Office Action for 2021-513859 dated Jun. 14, 2023.
Office Action for JP 2021-153169 dated Jul. 3, 2023.
Office Action for JP 2021-176431 dated Jul. 24, 2023.
Summons to attend oral proceedings, EP 15809346.8, dated Jun. 7, 2023.
Office Action for JP 2022-164138 dated Jul. 31, 2023.
Opposition to EP 3370650 filed Sep. 21, 2023.
Lasala, John M., and Jason H. Rogers. Interventional Procedures for Adult Structural Heart Disease. Elsevier/Saunders, 2014.
Hill, Arthur C et al. "Novel mitral repair device for the treatment of severe mitral regurgitation: preclinical ovine acute and chronic implantation model." Innovations (Philadelphia, Pa.) vol. 9,6 (2014): 432-8. doi: 10.1177/155698451400900607.
Iaizzo, Paul A. Handbook of Cardiac Anatomy, Physiology, and Devices. United States, Humana Press, 2009.
Sonne, Carolin et al. "Age and body surface area dependency of mitral valve and papillary apparatus parameters: assessment by real-time three-dimensional echocardiography." European journal of echocardiography: the journal of the Working Group on Echocardiography of the European Society of Cardiology vol. 10,2 (2009): 287-94. doi:10.1093/ejechocard/jen237.
Opposition to EP 3157469 filed Sep. 14, 2022.
International Search Report and Written Opinion for Application No. PCT/US2024/027244 dated Sep. 25, 2024 in 16 pages.
Summons to Attend Oral Proceedings, EP 13806272.4, dated Feb. 9, 2024.
Office Action for JP 2021-212699 dated Mar. 18, 2024.
Office Action for JP 2022-164138 dated Mar. 18, 2024.
Office Action for 2021-513859 dated Mar. 18, 2024.
Interlocutory Decision EP 15809346.8, dated Mar. 19, 2024.
Office Action for CN 202110375324.3 dated Apr. 30, 2024.
Office Action for CA 3,056,426 dated Feb. 16, 2024.
Office Action for EP19860754.1 dated May 29, 2024.
Office Action for 2023-213880 dated Jul. 16, 2024.
Invitation to Pay Additional Search Fees for PCT/US2024/027244 dated Jul. 30, 2024.
Office Action for JP 2023-039771 dated Aug. 13, 2024.
Extended European Search Report, EP21907438.2, dated Sep. 30, 2024.
Office Action for JP 2022-537714 dated Oct. 21, 2024.
Office Action for CN 202111212597.2 dated Jan. 8, 2025.
Office Action for 2023-213880 dated Jan. 15, 2025.
Office Action for JP 2023-039771 dated Mar. 11, 2025.
Office Action for CN 202080084279.X dated Mar. 15, 2025.
Office Action for CA 2,958,061 dated Apr. 9, 2025.

* cited by examiner

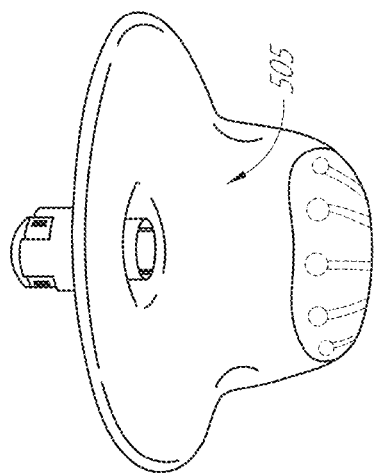
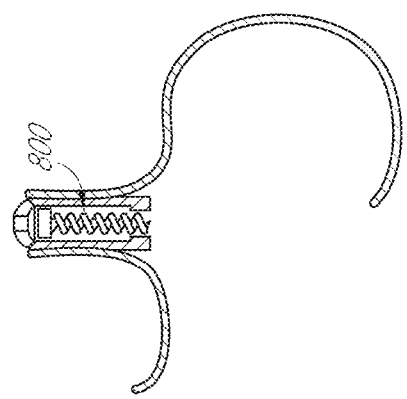
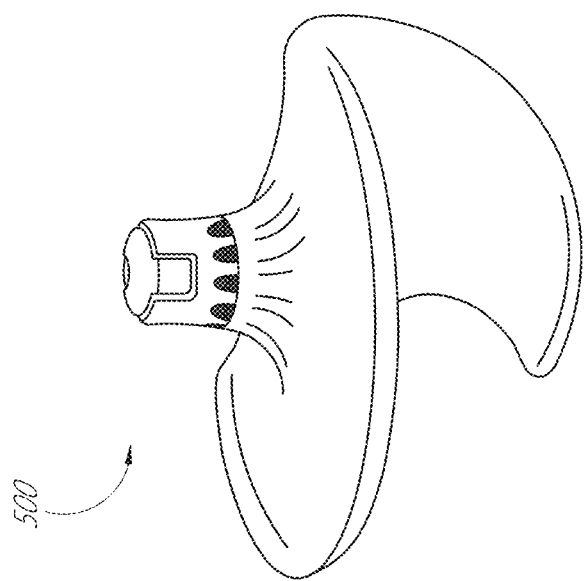
FIG. 5F
FIG. 5G
FIG. 5E

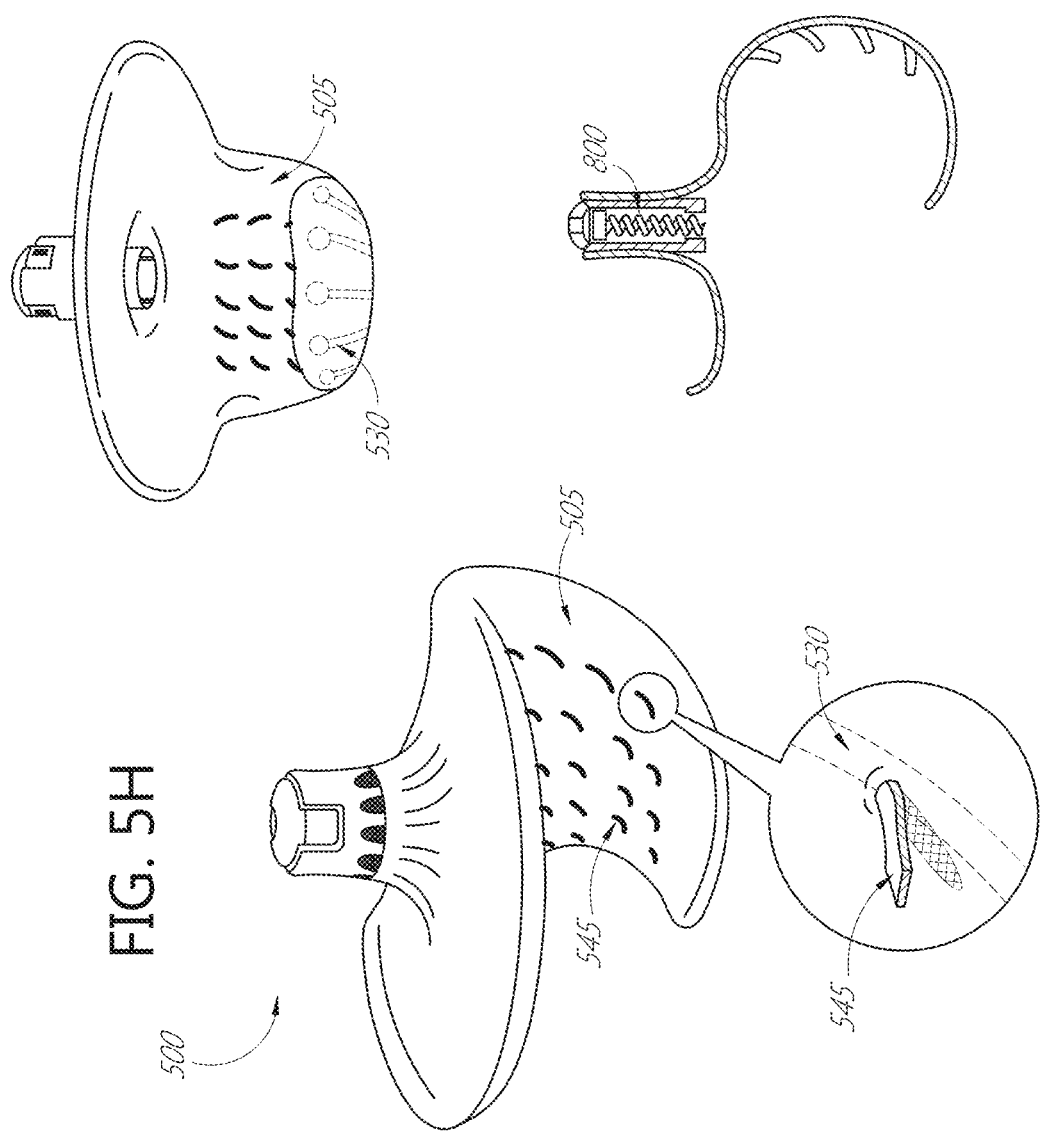

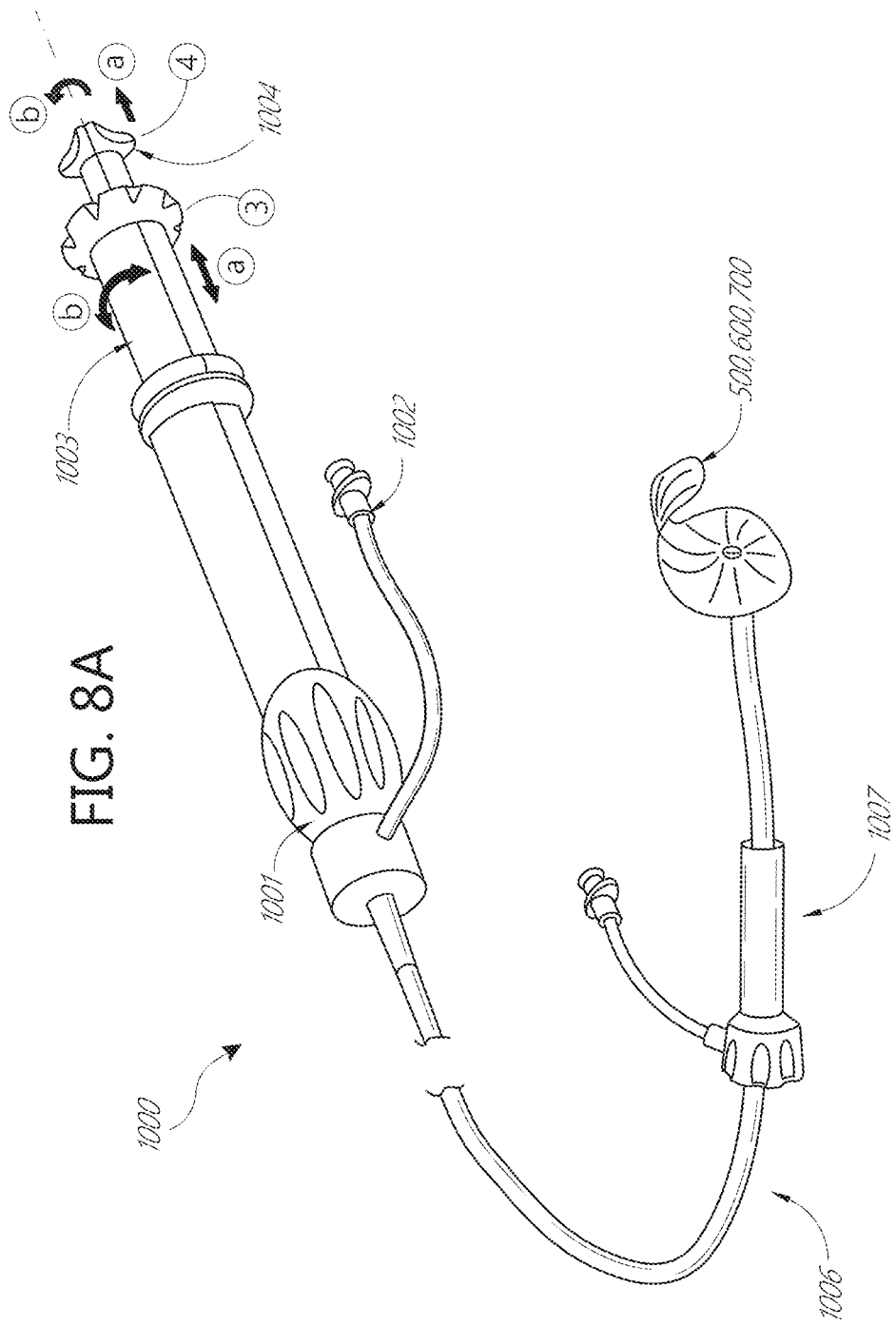

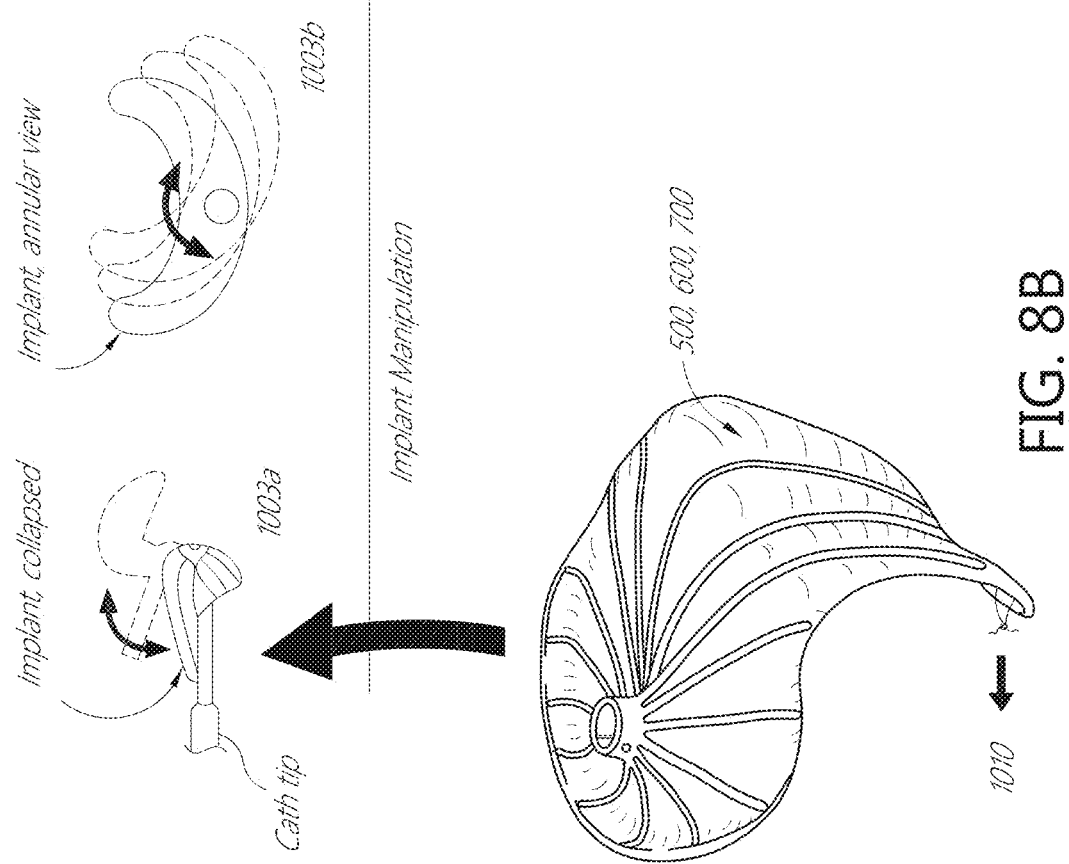

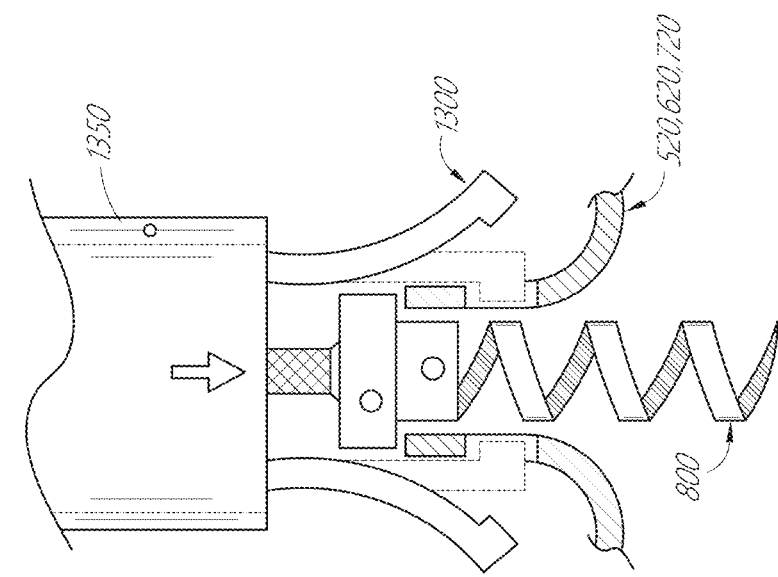
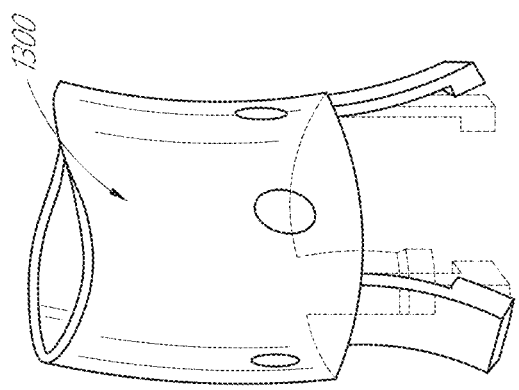
FIG. 8C

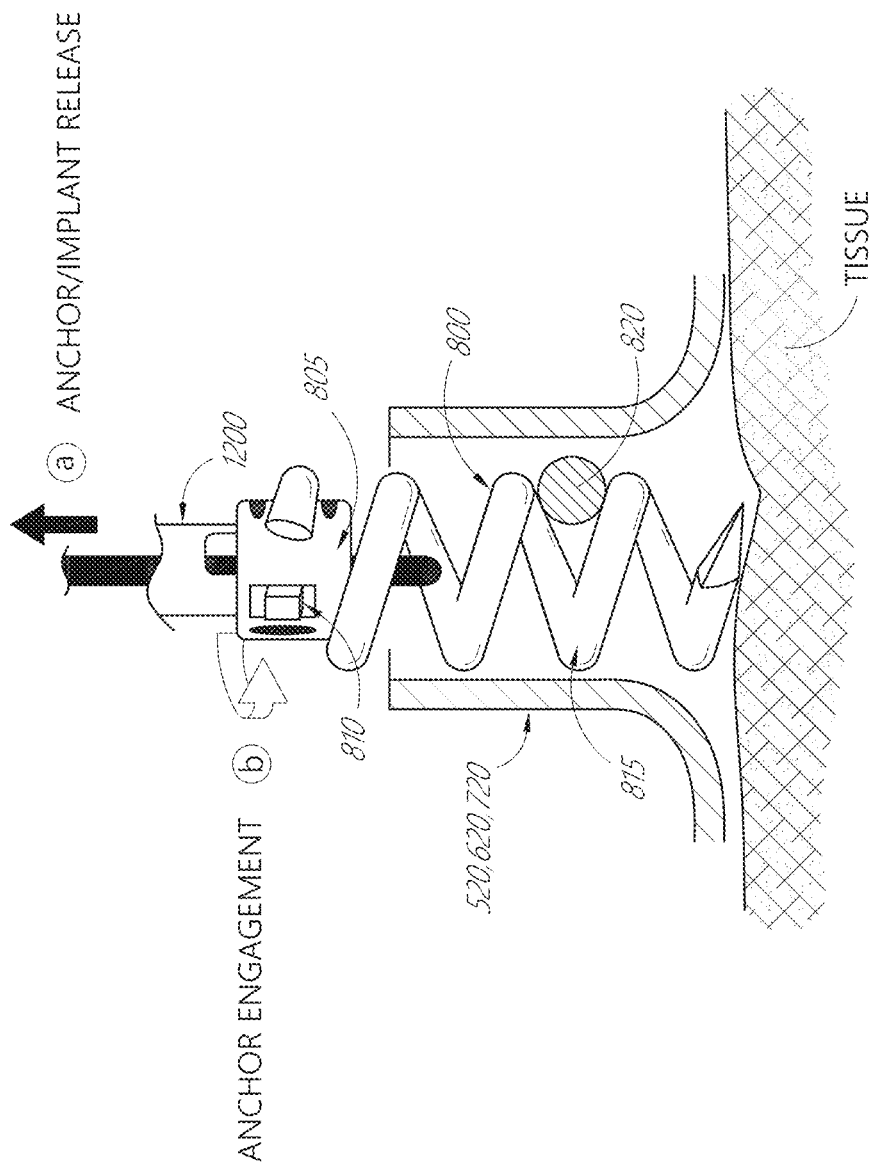

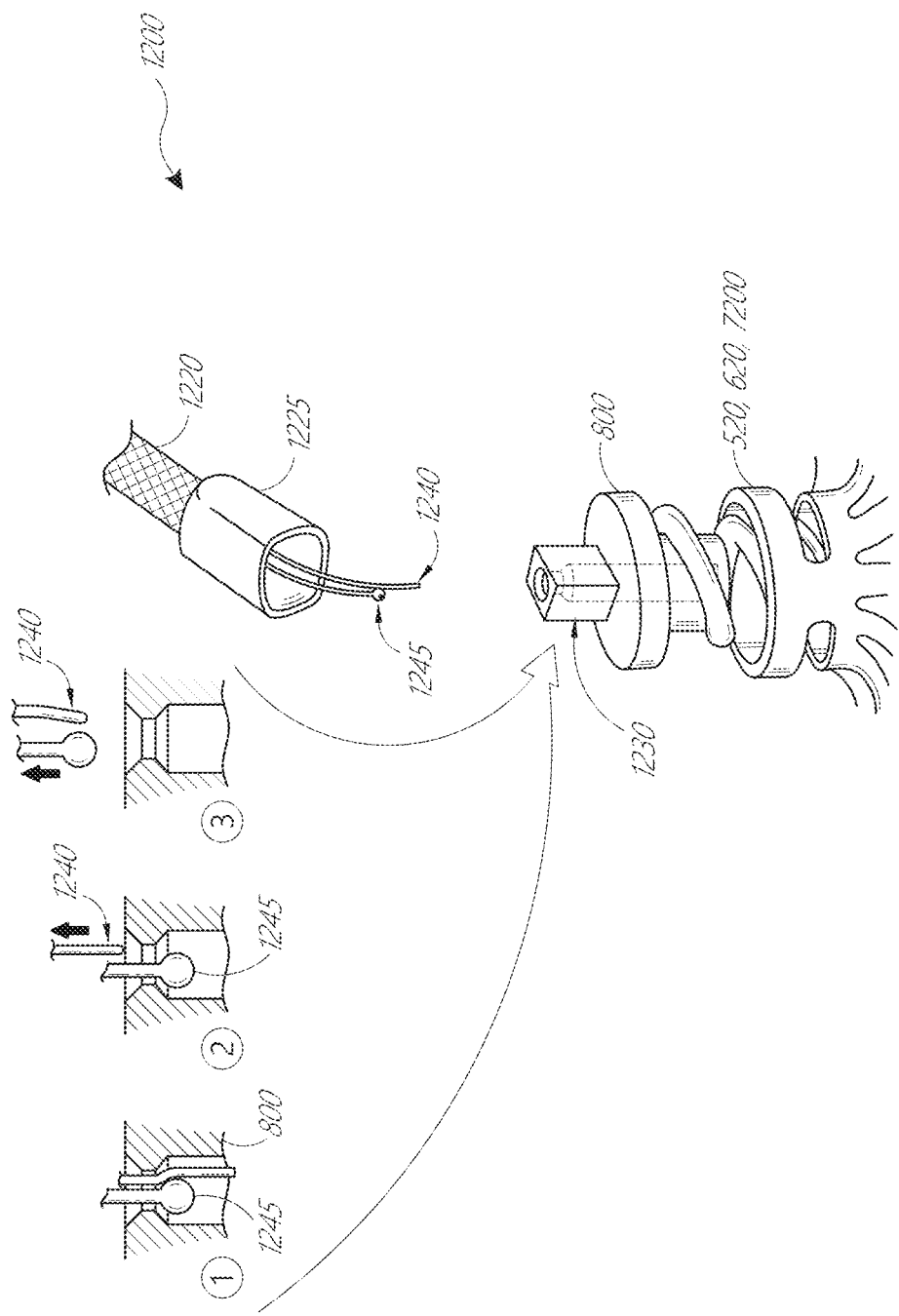

INITIAL IMPLANT ADVANCEMENT

PARTIAL IMPLANT OPENING & ADJUSTMENT

IMPLANT RECAPTURE

FULL IMPLANT OPENING - SECTIONED

SECONDARY ANCHOR PLACEMENT

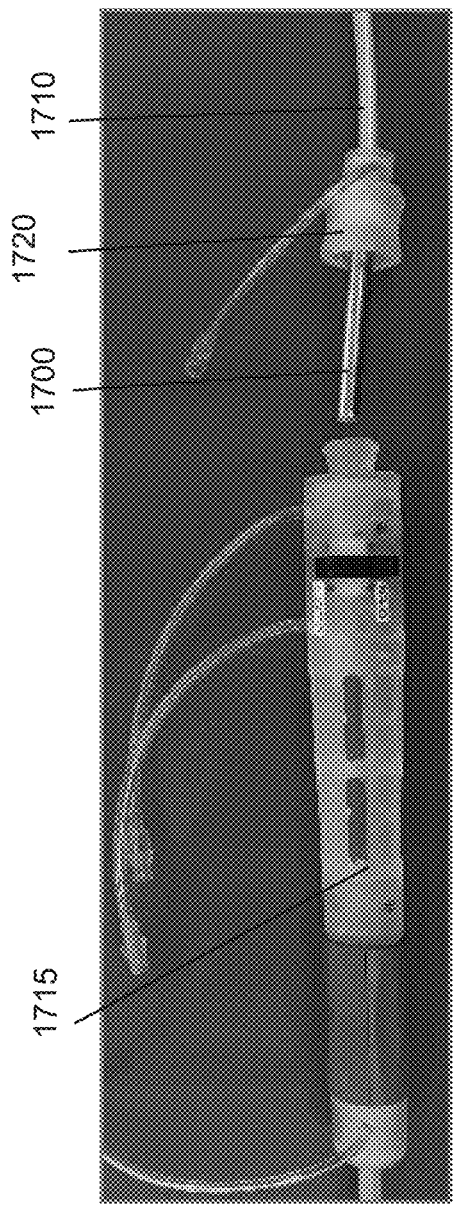
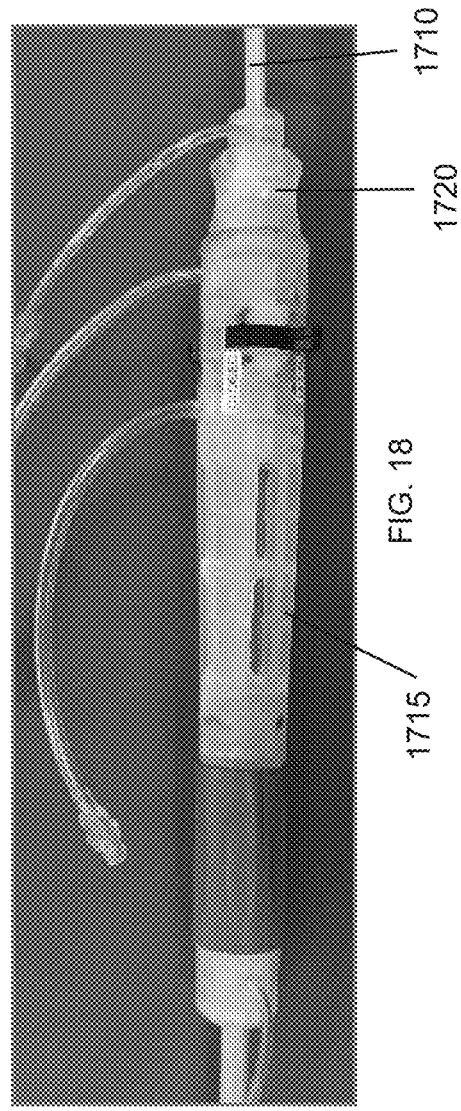
FIG. 17
FIG. 18

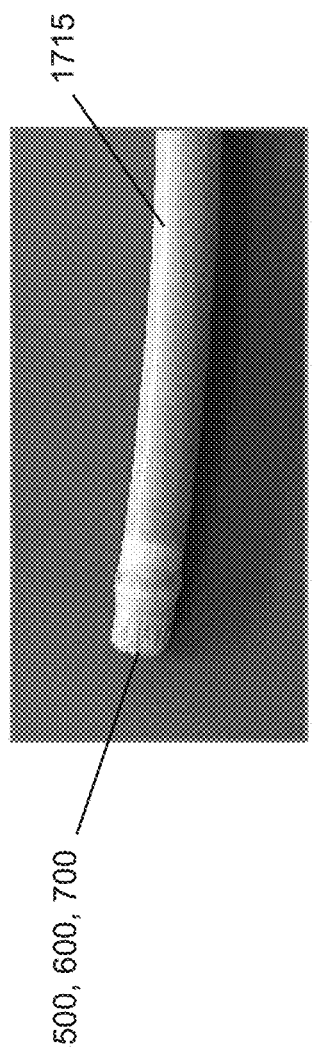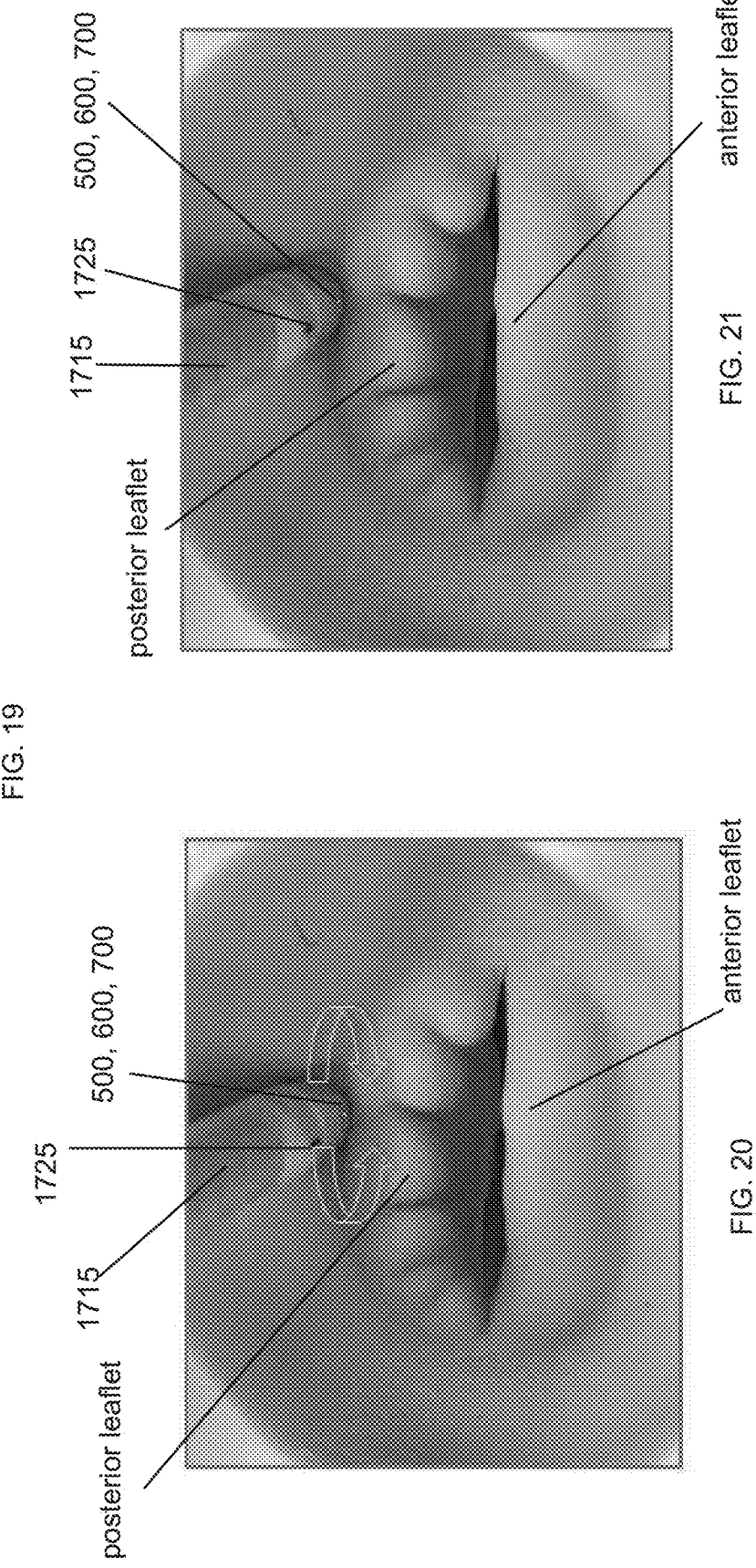
FIG. 19
FIG. 20
FIG. 21

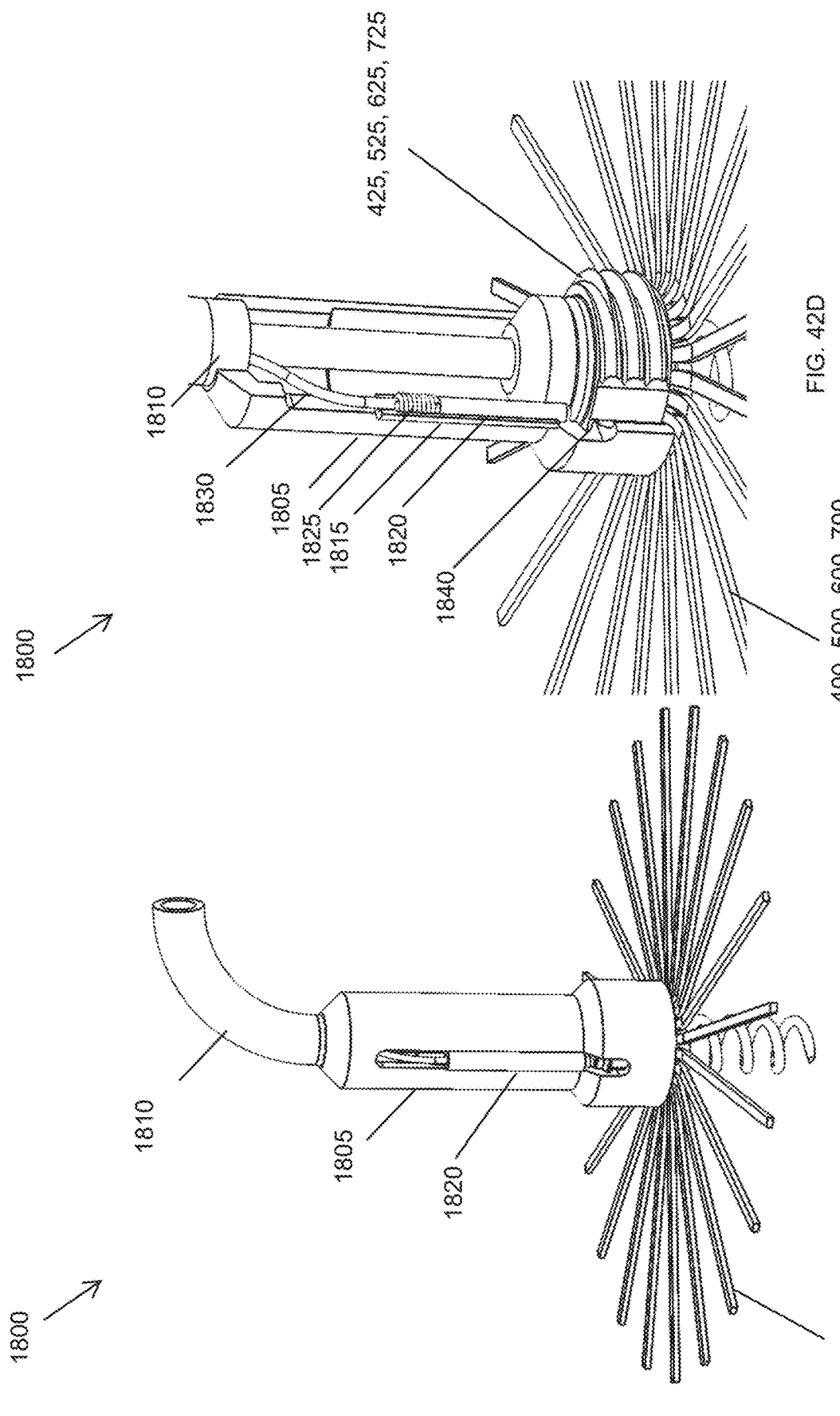

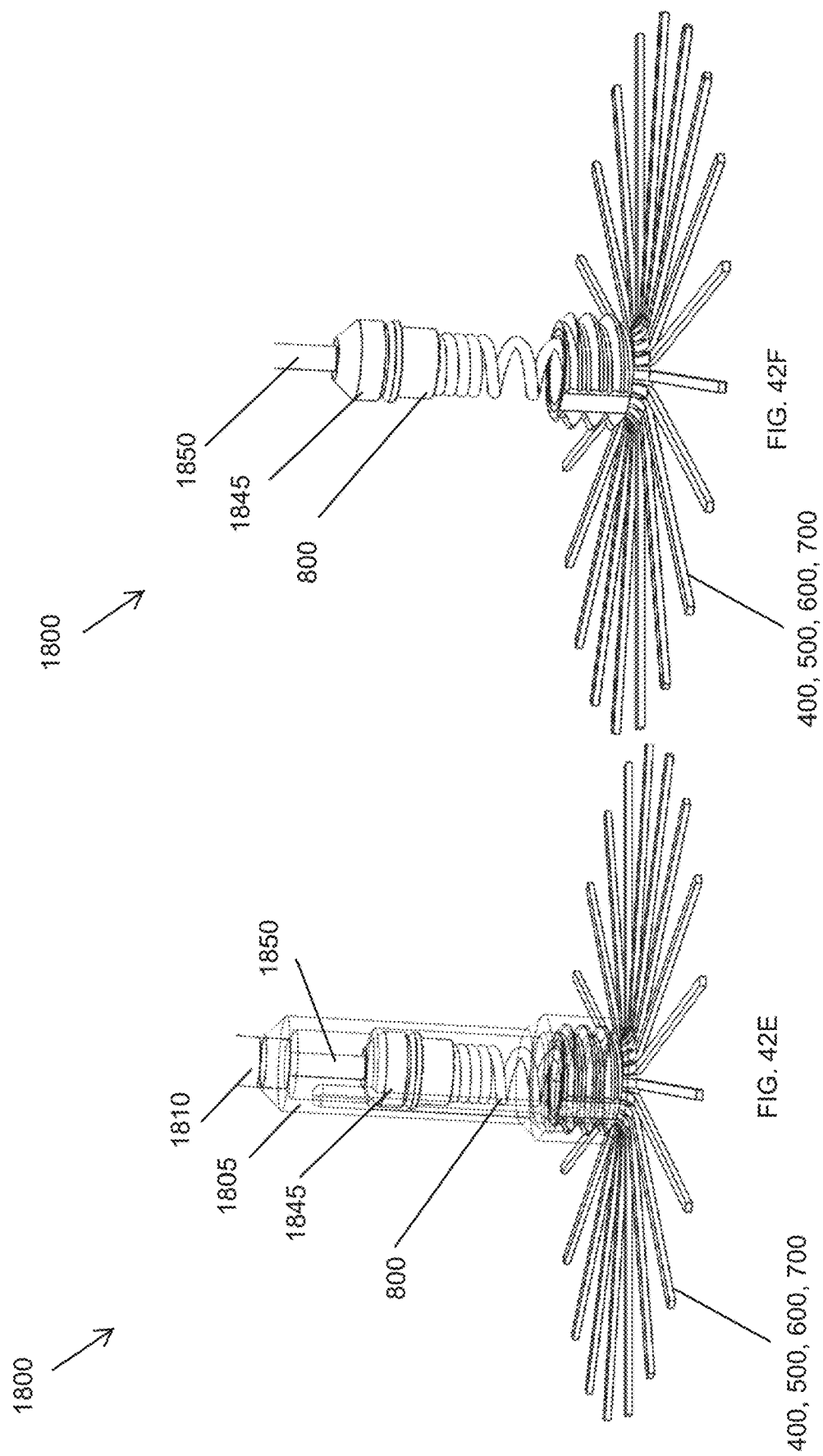

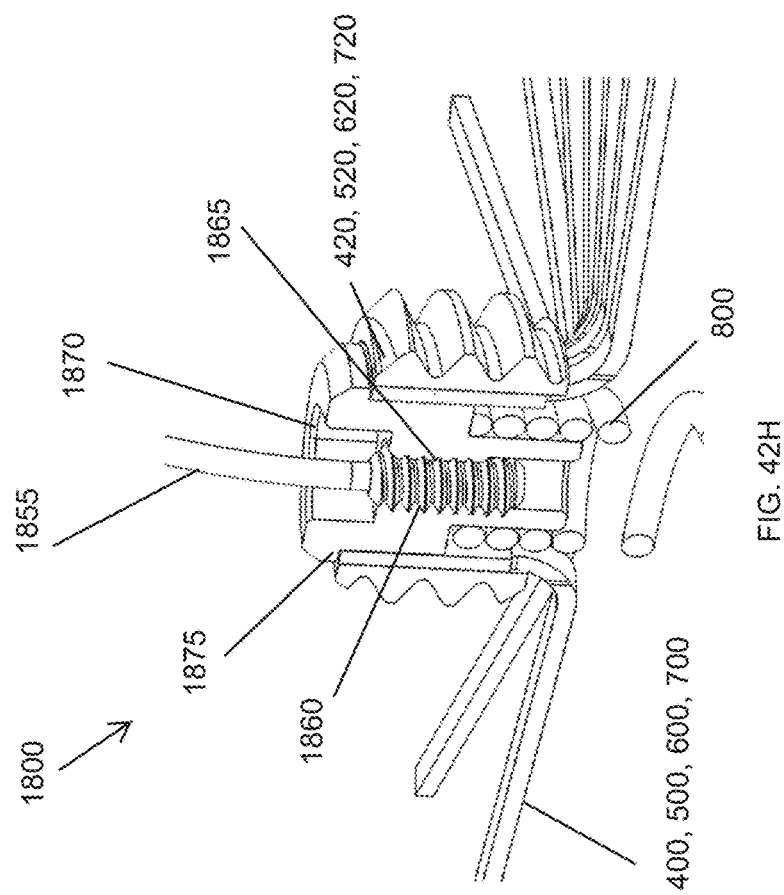
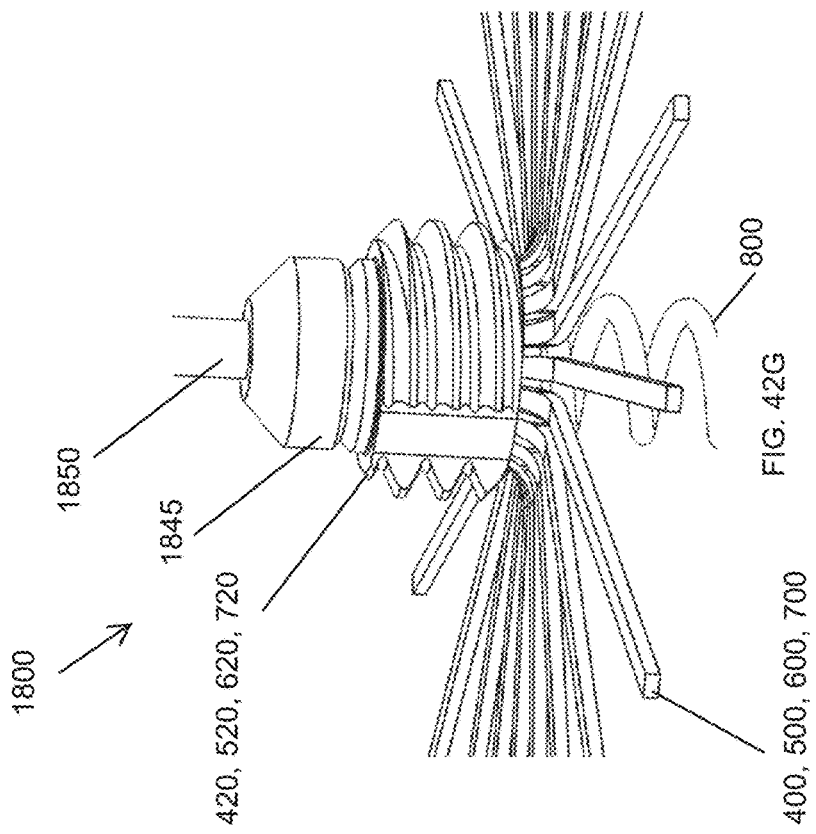
FIG. 42H
FIG. 42G

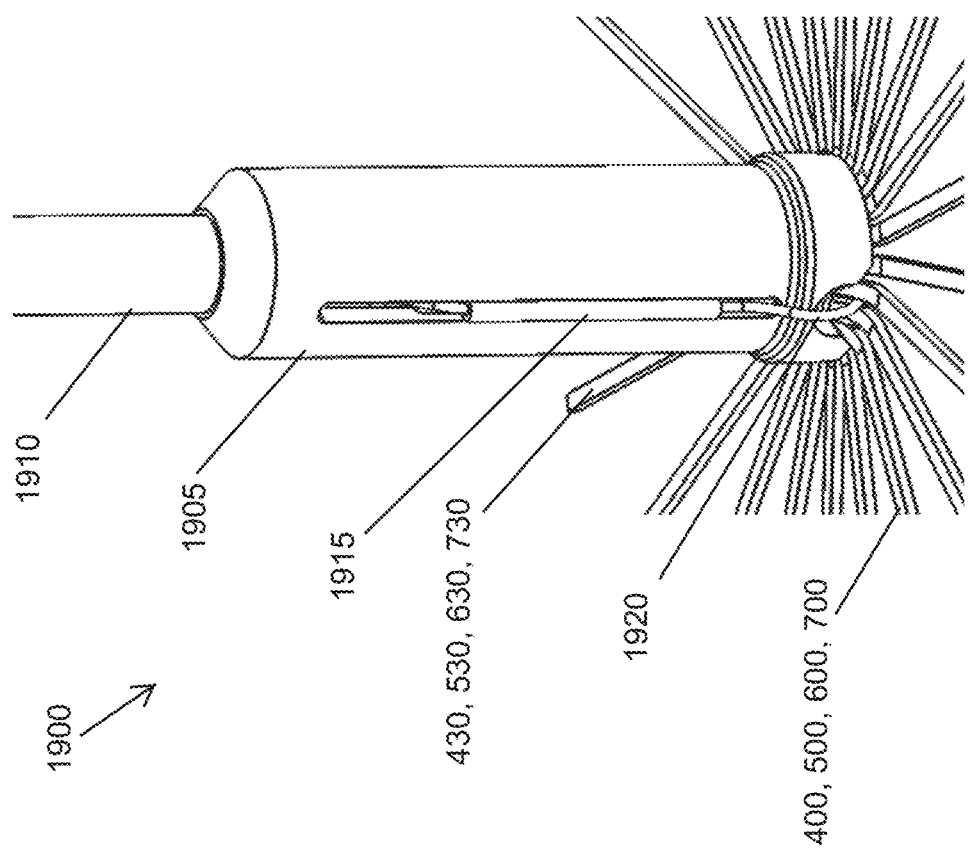

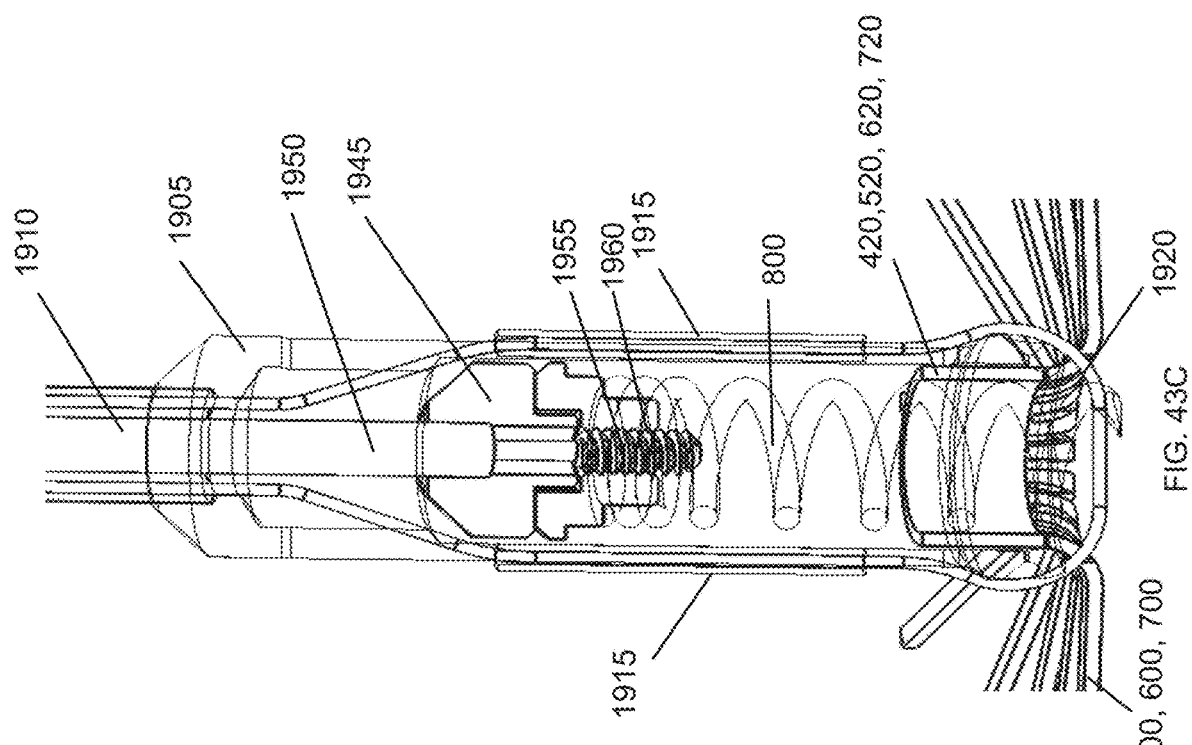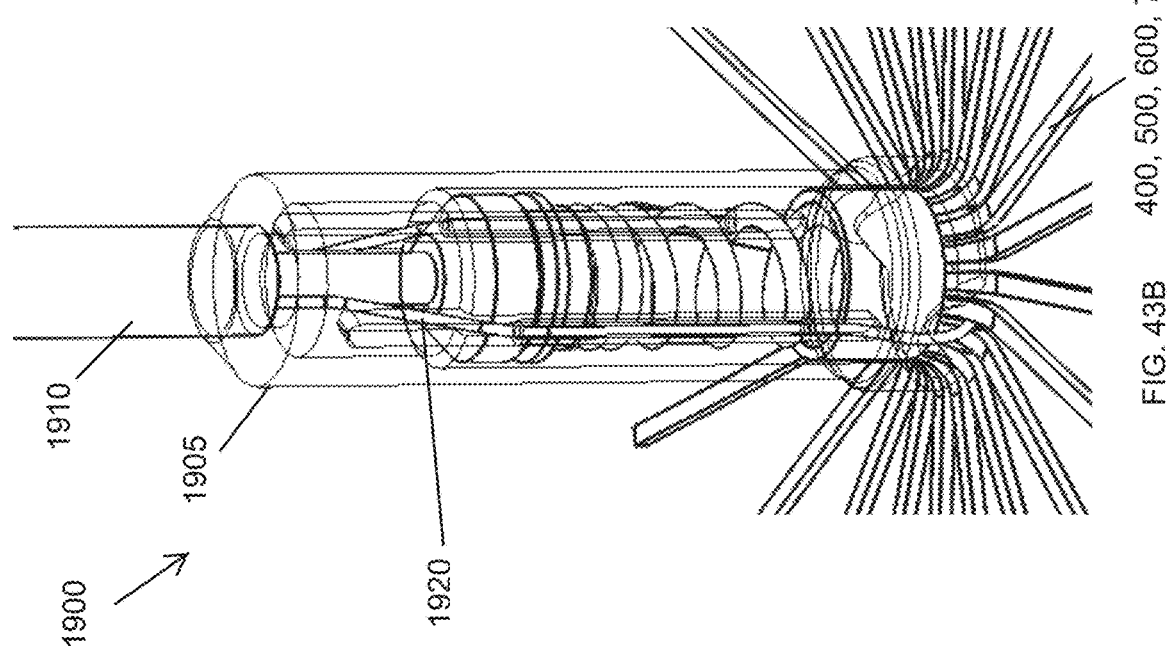

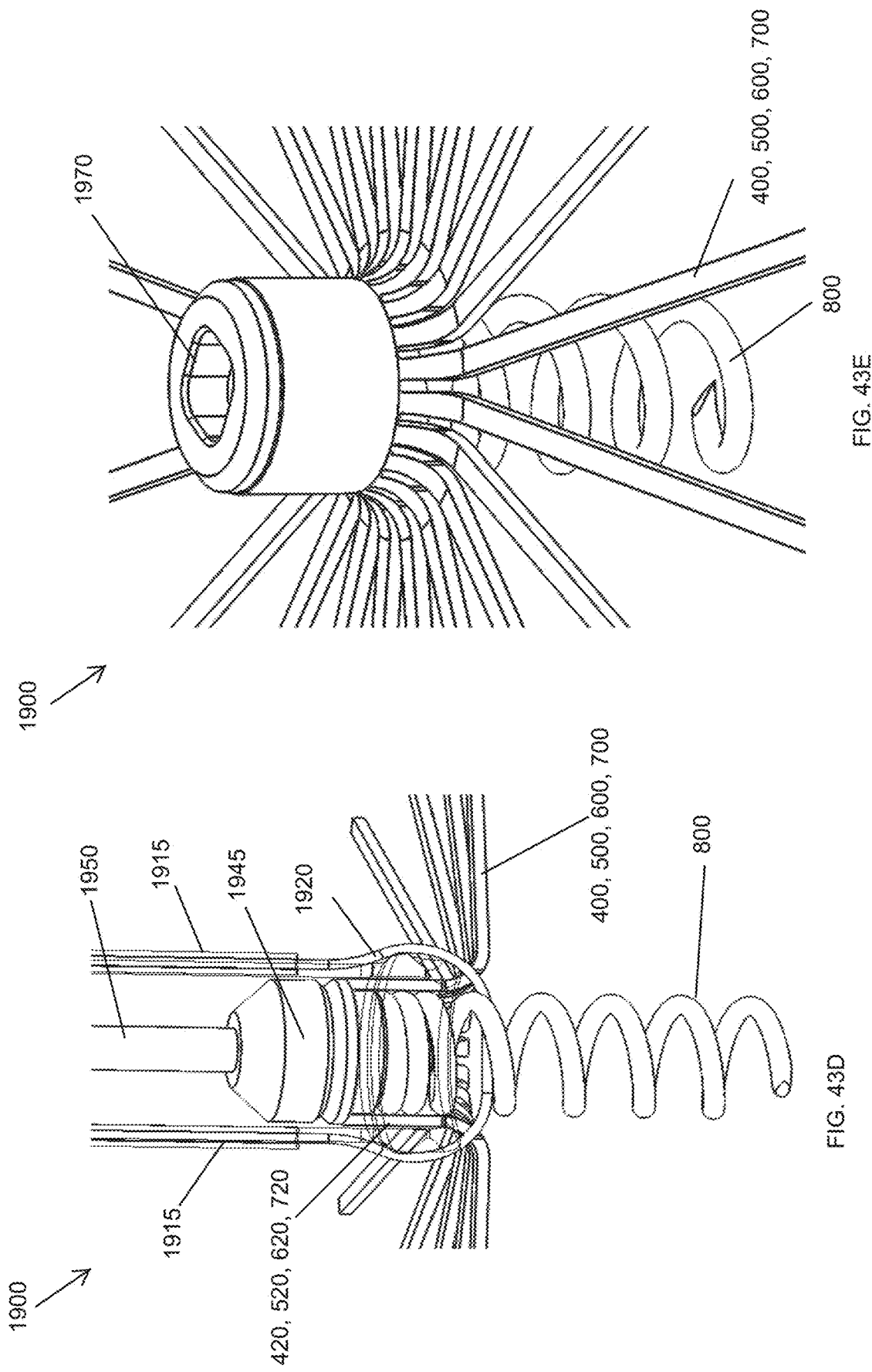

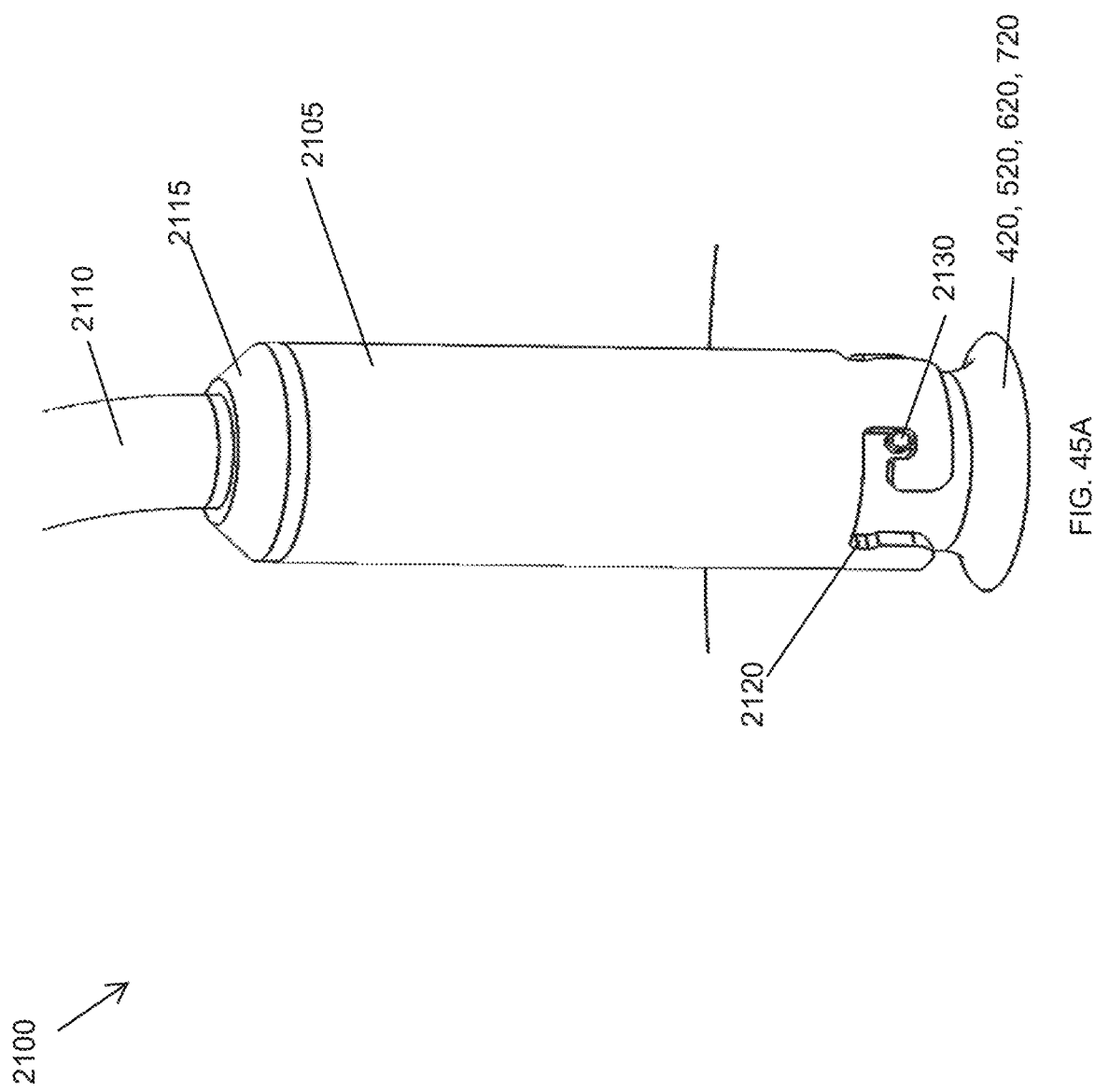

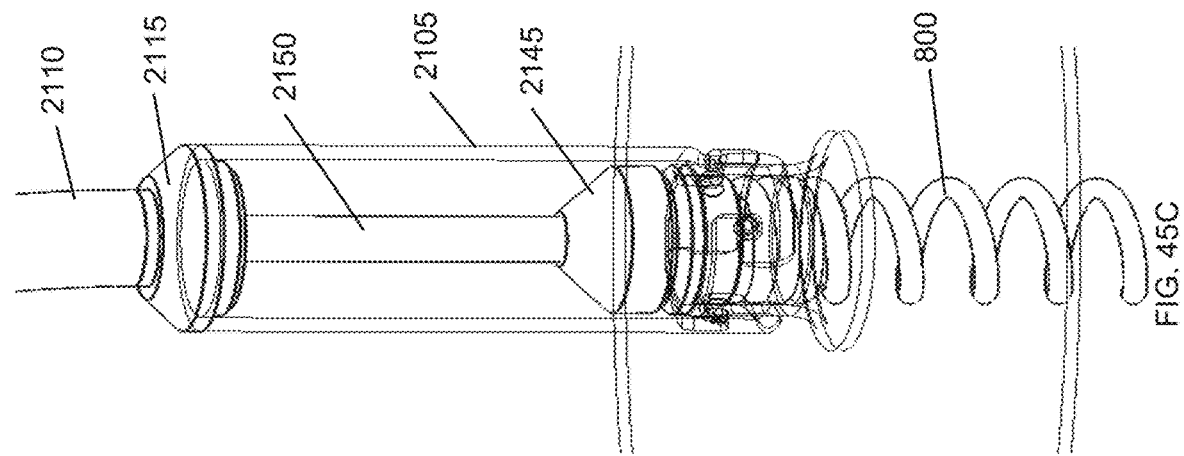
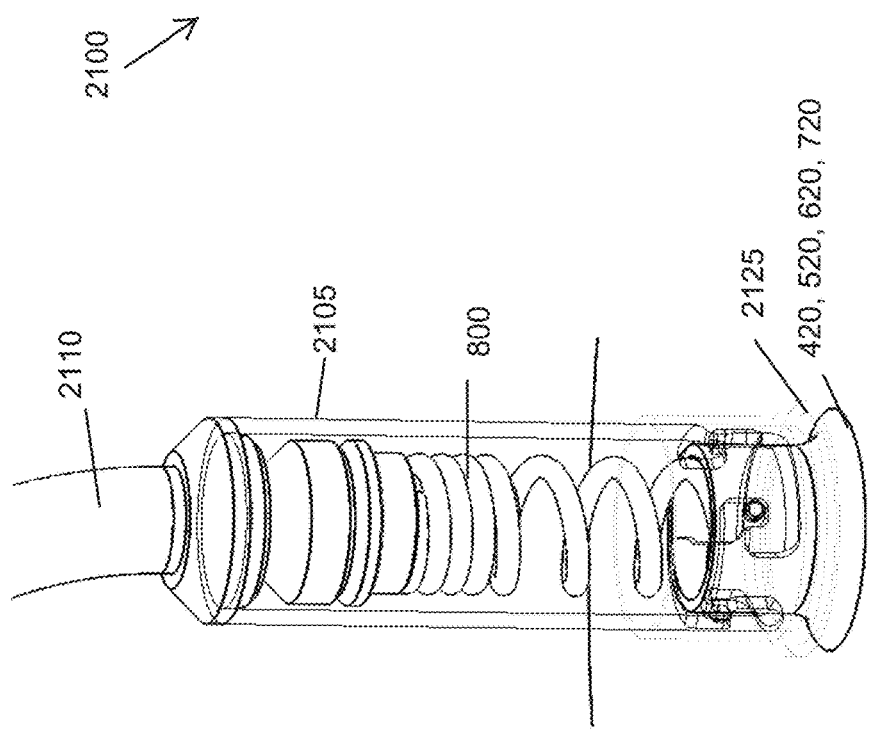

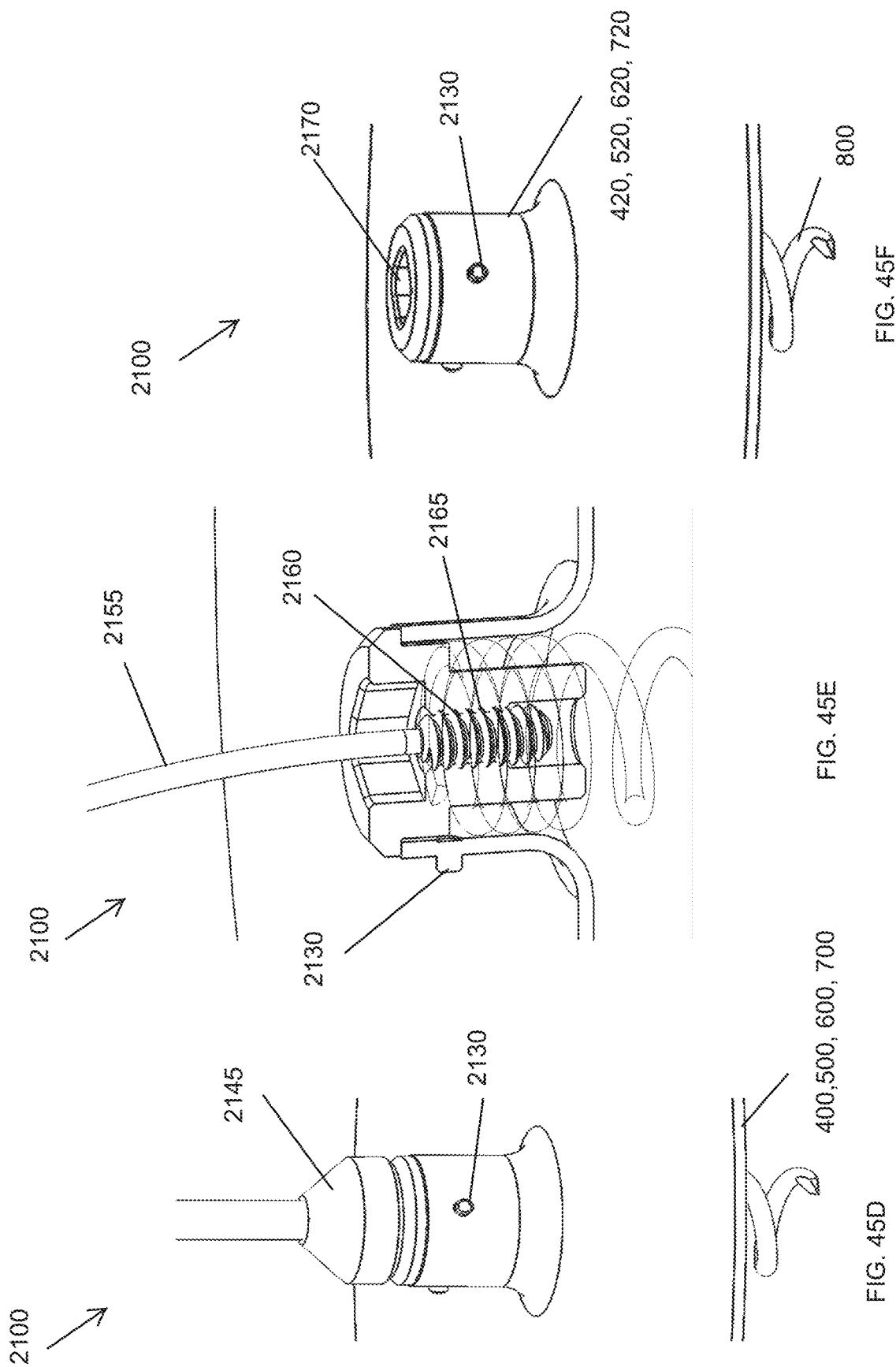

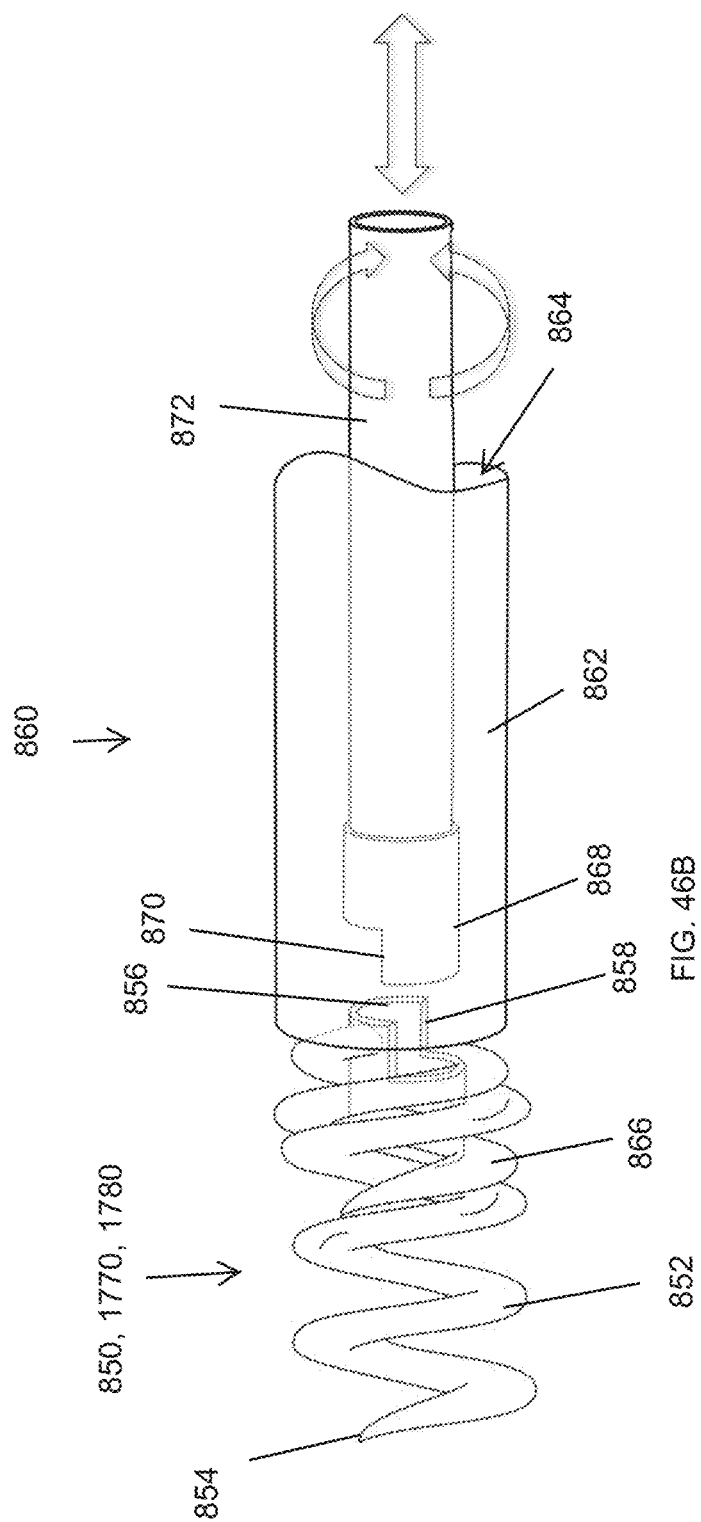

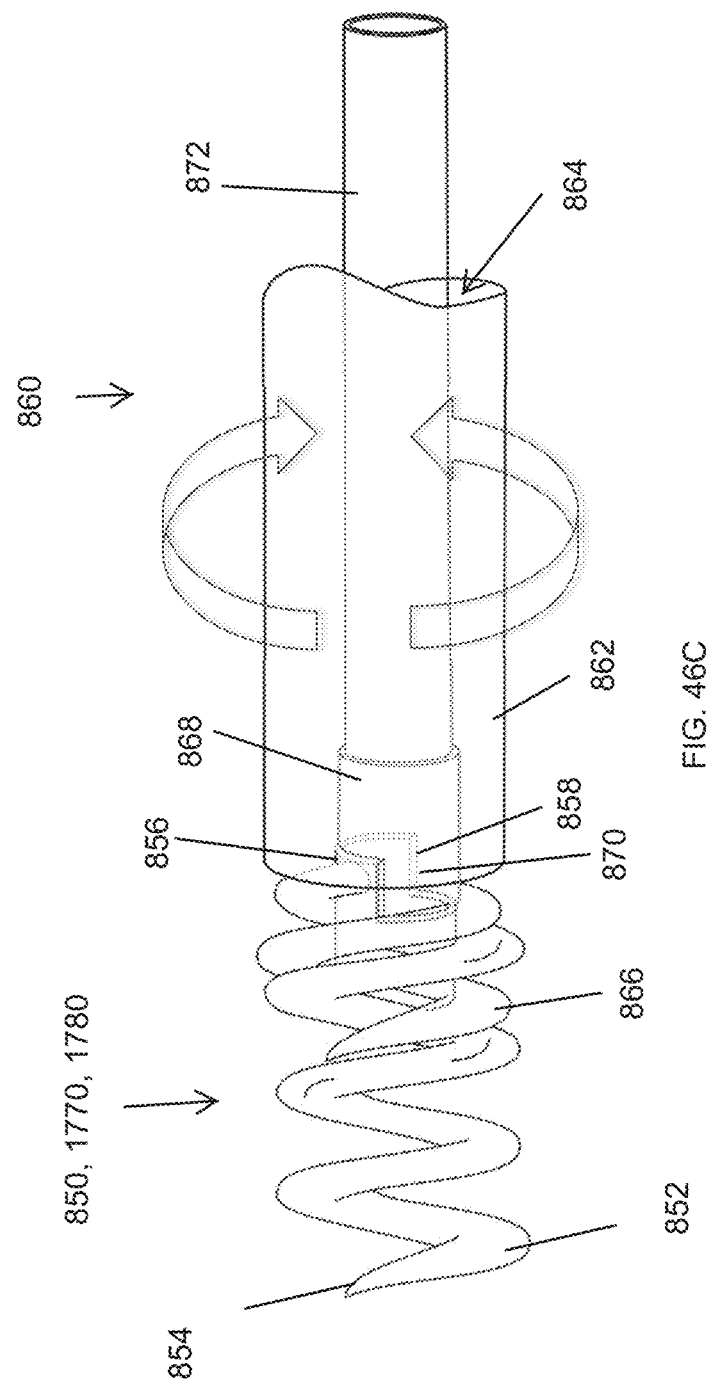

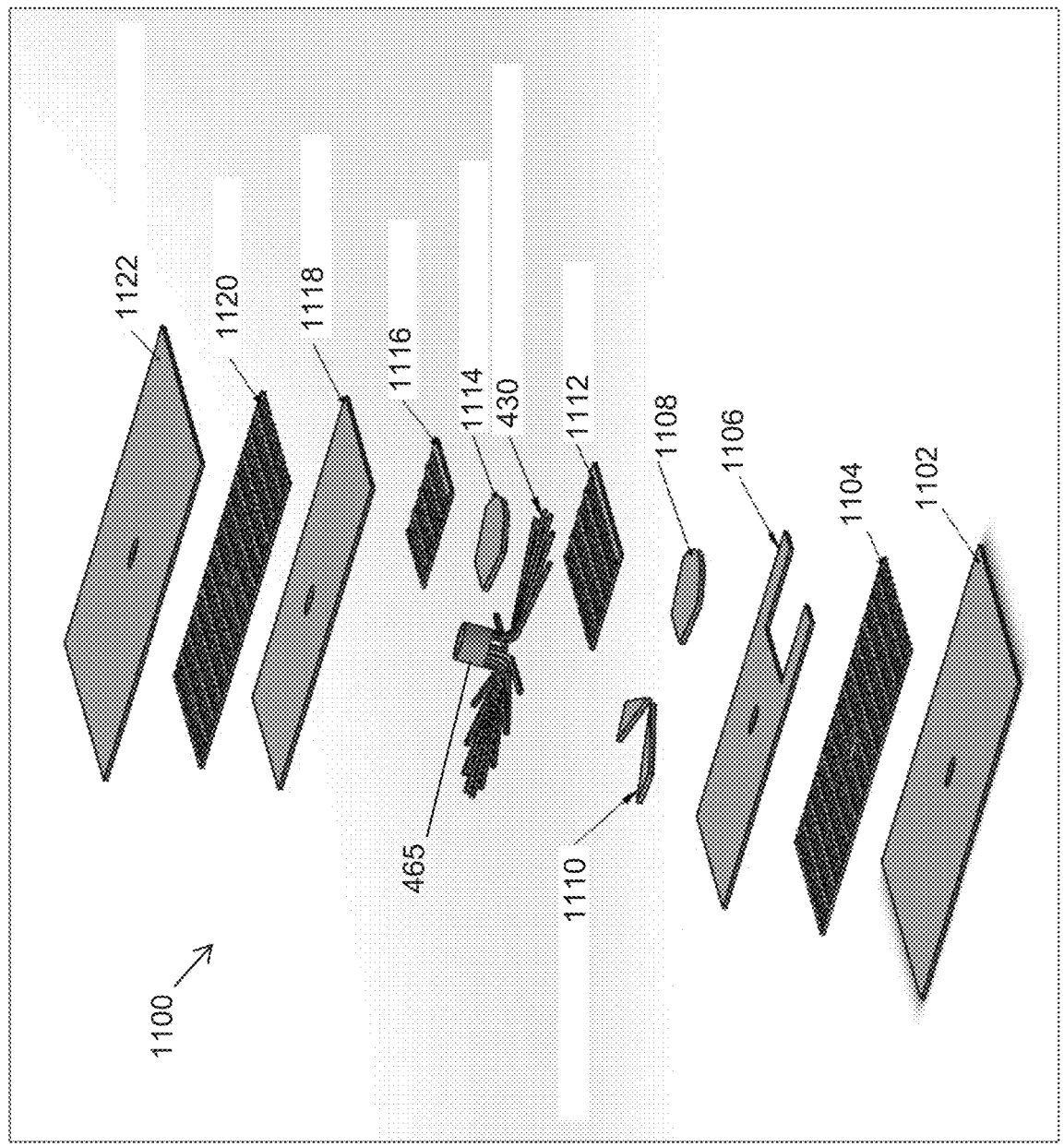

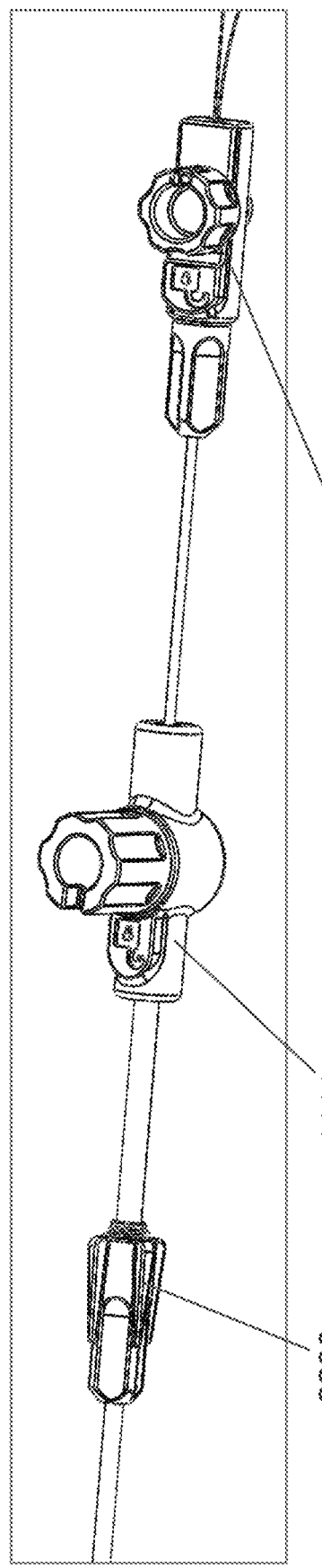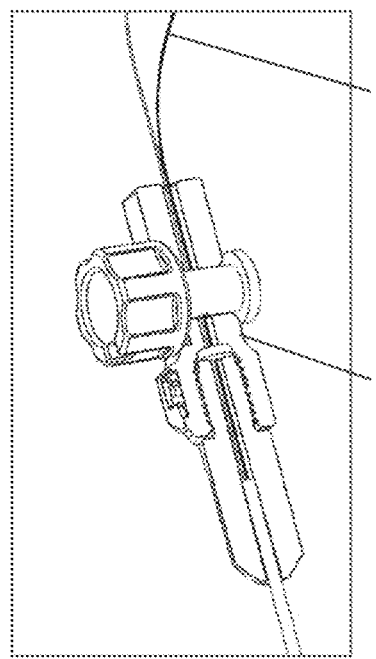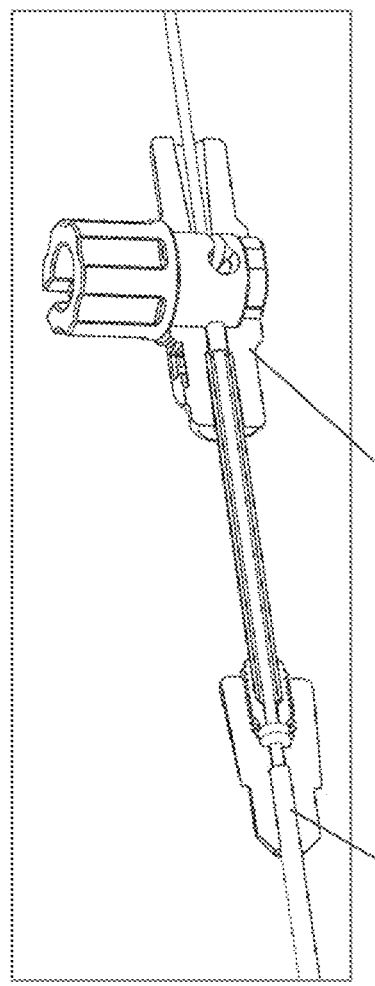
FIG. 55A
FIG. 55B
FIG. 55C

DEVICE, SYSTEM, AND METHOD FOR TRANSCATHETER TREATMENT OF VALVULAR REGURGITATION

CROSS-REFERENCE TO RELATED APPLICATIONS

The present application is a continuation of U.S. application Ser. No. 16/918,295, filed Jul. 1, 2020, which is a continuation of U.S. application Ser. No. 16/185,419, filed Nov. 9, 2018, which is a continuation of U.S. application Ser. No. 15/918,988, filed Mar. 12, 2018, which claims priority under 35 U.S.C. § 119(e) to U.S. Provisional Application No. 62/470,684, filed on Mar. 13, 2017, the disclosure of each is incorporated by reference herein in its entirety and made a part of the present specification.

BACKGROUND

Field

The present disclosure generally provides improved medical devices, systems, and methods, typically for treatment of heart valve disease and/or for altering characteristics of one or more valves of the body. Embodiments include implants for treatment of mitral valve regurgitation.

The human heart receives blood from the organs and tissues via the veins, pumps that blood through the lungs where the blood becomes enriched with oxygen, and propels the oxygenated blood out of the heart to the arteries so that the organ systems of the body can extract the oxygen for proper function. Deoxygenated blood flows back to the heart where it is once again pumped to the lungs.

The heart includes four chambers: the right atrium (RA), the right ventricle (RV), the left atrium (LA) and the left ventricle (LV). The pumping action of the left and right sides of the heart occurs generally in synchrony during the overall cardiac cycle.

The heart has four valves generally configured to selectively transmit blood flow in the correct direction during the cardiac cycle. The valves that separate the atria from the ventricles are referred to as the atrioventricular (or AV) valves. The AV valve between the left atrium and the left ventricle is the mitral valve. The AV valve between the right atrium and the right ventricle is the tricuspid valve. The pulmonary valve directs blood flow to the pulmonary artery and thence to the lungs; blood returns to the left atrium via the pulmonary veins. The aortic valve directs flow through the aorta and thence to the periphery. There are normally no direct connections between the ventricles or between the atria.

The mechanical heartbeat is triggered by an electrical impulse, which spreads throughout the cardiac tissue. Opening and closing of heart valves may occur primarily as a result of pressure differences between chambers, those pressures resulting from either passive filling or chamber contraction. For example, the opening and closing of the mitral valve may occur as a result of the pressure differences between the left atrium and the left ventricle.

At the beginning of ventricular filling (diastole) the aortic and pulmonary valves are closed to prevent back flow from the arteries into the ventricles. Shortly thereafter, the AV valves open to allow unimpeded flow from the atria into the corresponding ventricles. Shortly after ventricular systole (i.e., ventricular emptying) begins, the tricuspid and mitral valves normally shut, forming a seal, which prevents flow from the ventricles back into the corresponding atria.

Unfortunately, the AV valves may become damaged or may otherwise fail to function properly, resulting in improper closing. The AV valves are complex structures that generally include an annulus, leaflets, chordae and a support structure. Each atrium interfaces with its valve via an atrial vestibule. The mitral valve has two leaflets; the analogous structure of the tricuspid valve has three leaflets, and apposition or engagement of corresponding surfaces of leaflets against each other helps provide closure or sealing of the valve to prevent blood flowing in the wrong direction. Failure of the leaflets to seal during ventricular systole is known as malcoaptation, and may allow blood to flow backward through the valve (regurgitation). Heart valve regurgitation can have serious consequences to a patient, often resulting in cardiac failure, decreased blood flow, lower blood pressure, and/or a diminished flow of oxygen to the tissues of the body. Mitral regurgitation can also cause blood to flow back from the left atrium to the pulmonary veins, causing congestion. Severe valvular regurgitation, if untreated, can result in permanent disability or death.

Description of the Related Art

A variety of therapies have been applied for treatment of mitral valve regurgitation, and still other therapies may have been proposed but not yet actually used to treat patients. While several of the known therapies have been found to provide benefits for at least some patients, still further options would be desirable. For example, pharmacologic agents (such as diuretics and vasodilators) can be used with patients having mild mitral valve regurgitation to help reduce the amount of blood flowing back into the left atrium. However, medications can suffer from lack of patient compliance. A significant number of patients may occasionally (or even regularly) fail to take medications, despite the potential seriousness of chronic and/or progressively deteriorating mitral valve regurgitation. Pharmacological therapies of mitral valve regurgitation may also be inconvenient, are often ineffective (especially as the condition worsens), and can be associated with significant side effects (such as low blood pressure).

A variety of surgical options have also been proposed and/or employed for treatment of mitral valve regurgitation. For example, open-heart surgery can replace or repair a dysfunctional mitral valve. In annuloplasty ring repair, the posterior mitral annulus can be reduced in size along its circumference, optionally using sutures passed through a mechanical surgical annuloplasty sewing ring to provide coaptation. Open surgery might also seek to reshape the leaflets and/or otherwise modify the support structure. Regardless, open mitral valve surgery is generally a very invasive treatment carried out with the patient under general anesthesia while on a heart-lung machine and with the chest cut open. Complications can be common, and in light of the morbidity (and potentially mortality) of open-heart surgery, the timing becomes a challenge-sicker patients may be in greater need of the surgery, but less able to withstand the surgery. Successful open mitral valve surgical outcomes can also be quite dependent on surgical skill and experience.

Given the morbidity and mortality of open-heart surgery, innovators have sought less invasive surgical therapies. Procedures that are done with robots or through endoscopes are often still quite invasive, and can also be time consuming, expensive, and in at least some cases, quite dependent on the operator's skill. Imposing even less trauma on these sometimes frail patients would be desirable, as would be providing therapies that could be successfully implemented by a significant number of physicians using widely distributed skills. Toward that end, a number of purportedly less invasive technologies and approaches have been proposed. These include devices which seek to re-shape the mitral annulus from within the coronary sinus; devices that attempt to reshape the annulus by cinching either above to below the native annulus; devices to fuse the leaflets (imitating the Alfieri stitch); devices to re-shape the left ventricle, and the like.

Perhaps most widely known, a variety of mitral valve replacement implants have been developed, with these implants generally replacing (or displacing) the native leaflets and relying on surgically implanted structures to control the blood flow paths between the chambers of the heart. While these various approaches and tools have met with differing levels of acceptance, none has yet gained widespread recognition as an ideal therapy for most or all patients suffering from mitral valve regurgitation.

Because of the challenges and disadvantages of known minimally invasive mitral valve regurgitation therapies and implants, still further alternative treatments have been proposed. Some of the alternative proposals have called for an implanted structure to remain within the valve annulus throughout the heart beat cycle. One group of these proposals includes a cylindrical balloon or the like to remain implanted on a tether or rigid rod extending between the atrium and the ventricle through the valve opening. Another group relies on an arcuate ring structure or the like, often in combination with a buttress or structural cross-member extending across the valve so as to anchor the implant. Unfortunately, sealing between the native leaflets and the full perimeter of a balloon or other coaxial body may prove challenging, while the significant contraction around the native valve annulus during each heart beat may result in significant fatigue failure issues during long-term implantation if a buttress or anchor interconnecting cross member is allowed to flex. Moreover, the significant movement of the tissues of the valve may make accurate positioning of the implant challenging regardless of whether the implant is rigid or flexible.

In light of the above, it would be desirable to provide improved medical devices, systems, and methods. It would be particularly desirable to provide new techniques for treatment of mitral valve regurgitation and other heart valve diseases, and/or for altering characteristics of one or more of the other valves of the body. The need remains for a device which can directly enhance leaflet coaptation (rather than indirectly via annular or ventricular re-shaping) and which does not disrupt leaflet anatomy via fusion or otherwise, but which can be deployed simply and reliably, and without excessive cost or surgical time. It would be particularly beneficial if these new techniques could be implemented using a less-invasive approach, without stopping the heart or relying on a heart-lung machine for deployment, and without relying on exceptional skills of the operator to provide improved valve and/or heart function.

SUMMARY

The disclosure generally provides improved medical devices, systems, and methods. New coaptation assistance elements, systems, and methods for treatment of mitral valve regurgitation and other valve diseases are disclosed. The coaptation assistance element may remain within the blood flow path as the valve moves back and forth between an open-valve configuration and a closed valve configuration. The coaptation assistance elements may be relatively thin, elongate (along the blood flow path), and/or conformable structures which extend laterally across some, most, or all of the width of the valve opening, allowing coaptation between at least one of the native leaflets and the coaptation assistance element. The devices described herein can be used with any valve of the human body, including valves with two leaflets or three leaflets.

In some embodiments, an advantage is the ability to retrieve the coaptation assistance element. In some embodiments, the coaptation assistance element has a single anchor, which can engage or disengage tissue. In some embodiments, the anchor is captive within an annular hub of the coaptation assistance element. In some embodiments, the captive anchor is removed simultaneously with the removal of the coaptation assistance element. In some embodiments, the coaptation assistance element can include secondary anchors. In some embodiments, the coaptation assistance element can include passive anchors. In some embodiments, engagement of the anchor with the tissue positions one or more passive anchors into engagement with tissue. In some embodiments, an advantage is to retrieve the coaptation assistance element during a procedure. In some embodiments, the coaptation assistance element can be repositioned during a surgical procedure. In some embodiments, the coaptation assistance element can be removed from the patient during a subsequent surgical procedure. In some embodiments, the coaptation assistance element can be replaced by another device during a subsequent surgical procedure. In some embodiments, a single annular anchor facilitates the ability to retrieve the coaptation assistance element. In some embodiments, the location of the annular anchor facilitates the ability to retrieve the coaptation assistance element. In some embodiments, the ability to collapse the coaptation assistance element with the purse-string suture as described herein facilitates the ability to retrieve the coaptation assistance element.

In some embodiments, an advantage is the connection between the coaptation assistance element and the delivery catheter. In some embodiments, the coaptation assistance element includes an annular hub with features to engage the delivery catheter. In some embodiments, the coaptation assistance element and the delivery catheter are removably coupled such that the coaptation assistance element can be released from the delivery catheter during a procedure. In some embodiments, one or more secondary structures couples the coaptation assistance element and the delivery catheter after the coaptation assistance element is released from the delivery catheter. In some embodiments, the one or more secondary structures include the purse-string suture as descried herein. In some embodiments, the one or more secondary structures facilitate the collapse and/or expansion of the coaptation assistance element. In some embodiments, the coaptation assistance element and the delivery catheter are rotationally fixed relative to each other when coupled. In some embodiments, relative motion of the delivery catheter causes motion of the coaptation assistance element.

In some embodiments, an advantage is the coaptation assistance element can be delivered with a hub-leading orientation. In some methods of use, the annular hub can be moved into position relative to the anatomical structures. In some methods of use, the ventricular end of the coaptation assistance element can be retained within the delivery catheter until the annular hub is positioned. In some methods of use, once the annular hub and/or the annular anchor are engaged with the tissue, the coaptation assistance element can be expanded. In some methods of use, once the annular hub and/or the annular anchor are engaged with the tissue, the ventricular end of the coaptation assistance element can be positioned.

In some embodiments, an advantage is the coaptation assistance element can be delivered with a strut-leading orientation. In this method of use, one or more of the struts of the coaptation assistance element can be moved into position relative to the anatomical structures prior to the positioning of the annular hub. In some methods of use, the coaptation assistance element can be expanded or partially expanded prior to the engagement of the annular anchor. In some methods of use, the annular hub can be retained within the delivery catheter until one or more of the struts are positioned. In some methods of use, once the struts are positioned, the annular anchor can be engaged with the tissue.

In some embodiments, an advantage is the annular anchor can be rotated independently of the coaptation assistance element. As described herein, the coaptation assistance element is coupled to one portion of the delivery catheter. As described herein, the annular anchor is independently coupled to another portion of the delivery catheter, such as a driver disposed with the delivery catheter. The annular anchor can be rotated independently of the annular hub. The annular hub can remain stationary as the annular anchor is rotated to engage tissue. The annular anchor can be driven into the tissue while the delivery catheter retains the position of the annular hub.

In some embodiments, an advantage is the ability to collapse the coaptation assistance element. In some embodiments, the coaptation assistance element is fully collapsed. The fully collapsed configuration can be the insertion configuration or a low profile configuration. In some embodiments, the coaptation assistance element is partially collapsed. The partially collapsed configuration can be a partially deployed configuration. The partially collapsed configuration can allow the coaptation assistance element to be selectively deployed within the heart. The partially collapsed configuration can allow the coaptation assistance element to be moved into position within the heart. The configurations of the coaptation assistance element can be monitored such as by imaging to ensure proper deployment. In some embodiments, one or more purse-string sutures, or portions thereof, are tensioned to collapse or partially collapse the coaptation assistance element. In some embodiments, the partially collapsed configuration can allow rotation of the coaptation assistance element. In some embodiments, the fully collapsed configuration can allow rotation of the coaptation assistance element. In some embodiments, the coaptation assistance element can be rotated with a delivery catheter or portion thereof. In some embodiments, the coaptation assistance element can be rotated about a central location such as the annular hub.

In some embodiments, an advantage is the ability to expand the coaptation assistance element. In some embodiments, one or more purse-string sutures, or portions thereof, are released to expand the coaptation assistance element. In some embodiments, release of the purse-string suture allows one or more struts to assume a neutral configuration. In some embodiments, the release of the purse-string suture allows one or more struts to assume a pre-shaped curve. In some embodiments, the one or more struts comprise NiTi. In some embodiments, the purse-string suture can be repeatedly tensioned and/or released. In some embodiments, the purse-string suture is captive within the coaptation assistance element. In some embodiments, the purse-string suture is tensioned to remove the coaptation assistance element from a patient. In some embodiments, the purse-string suture is released to deploy the coaptation assistance element within the heart of a patient. In some embodiments, the purse-string suture can be selective deployed to expand a portion of coaptation assistance element while another portion of the coaptation assistance element remains collapsed or partially collapsed.

In some embodiments, an advantage is the ability to adjust the coaptation assistance element. In some embodiments, the coaptation assistance element can be held by a central location. In some embodiments, the central location is the anchor. In some embodiments, the central location is the hub. In some embodiments, the hub and/or the anchor are located generally near a mid-point of the diameter of the coaptation assistance element. In some embodiments, the hub and/or the anchor are generally located near a mid-point and/or central location of the annular portion of the coaptation assistance element. In some embodiments, the coaptation assistance element can be held at a neutral position. In some embodiments, the coaptation assistance element can be rotated by rotating a delivery catheter connected to the annular hub. In some embodiments, the coaptation assistance element can be moved longitudinally by corresponding longitudinal motion of a delivery catheter connected to the annular hub.

In some embodiments, an advantage is the coaptation assistance element can be retained by a delivery catheter after the coaptation assistance element is positioned. In some embodiments, the coaptation assistance element can be fully deployed within the mitral valve but still tethered to a delivery catheter. In some embodiments, the coaptation assistance element can be adjusted after the coaptation assistance element is fully deployed within the mitral valve. In some embodiments, the coaptation assistance element can be rotated about the hub after the coaptation assistance element is fully deployed. In some embodiments, the anchor can be disengaged and/or reengaged with the tissue after the coaptation assistance element is fully deployed. In some embodiments, the purse-string sutures can collapse and/or expand the coaptation assistance element or a portion thereof after the coaptation assistance element is fully deployed. In some embodiments, the coaptation assistance element can be recaptured after the coaptation assistance element is fully deployed. In some embodiments, the coaptation assistance element can be removed after the coaptation assistance element is fully deployed.

In some embodiments, an advantage is the coaptation assistance element does not require ventricular attachment. In some embodiments, the coaptation assistance element only requires annular attachment. In some embodiments, the coaptation assistance element only requires attachment of an annular anchor through an annular hub. In some embodiments, the coaptation assistance element only requires attachment of an annular anchor through an annular hub and annular barbs. In some embodiments, the coaptation assistance element only requires attachment of an annular anchor through an annular hub, annular barbs, and/or commissural barbs.

In some embodiments, an advantage is the radially extending frame. In some embodiments, the frame comprises an annular hub and one or more struts. In some embodiments, the struts extend radially from the annular hub. In some embodiments, the frame is constructed from a single, planar sheet of material. In some embodiments, the frame is precisely cut using water jet, laser etching or similar technology. In some embodiments, the frame is constructed by forming the annular hub with an edge of the frame. In some embodiments, the planar sheet of material is formed into a loop which becomes the annular hub. In some embodiments, the struts are bent to the desired configuration. In some embodiments, the struts are equally spaced about the circumference of the annular hub. In some embodiments, the struts are unequally spaced about the circumference of the annular hub. In some embodiments, the struts extending along a portion of the circumference of the annular hub are different than struts extending along another portion of the circumference of the annular hub. In some embodiments, one or more designated portions of the struts are designed to be placed near the annular region of the heart. In some embodiments, one or more designated portions of the struts are designed to be placed near the commissure region of the heart. In some embodiments, one or more designated portions of the struts are designed to be placed near the ventricular region of the heart. In some embodiments, the struts of the radially outward frame do not intersect. In some embodiments, the struts of the radially outward frame do not form a mesh. In some embodiments, the struts of the radially outward frame extend in a line from the hub to an edge of the coaptation assistance element. In some embodiments, the struts of the radially outward frame have a sharpened edge. In some embodiments, the sharpened edge extends in a straight line from the edge of the coaptation assistance element. In some embodiments, the sharpened edge is integrally formed in the strut. In some embodiments, a strut of the radially outward frame has one or more radii of curvature. In some embodiments, a strut of the radially outward frame can be concave or convex or both concave and convex along the length of the strut. In some embodiments, a strut of the radially outward frame has one or more inflection points.

In some embodiments, an advantage is the curvature of the frame. In some embodiments, the annular hub is radially extending. In some embodiments, the annular hub extends from the coaptation assistance element away from the annulus. In some embodiments, the annular hub extends from a surface of the coaptation assistance element above a planar surface of the struts. In some embodiments, an edge of the coaptation assistance element is curved. In some embodiments, one or more struts may curve laterally from the annular hub toward the superior edge. In some embodiments, the superior edge of the coaptation assistance element can curve upward from the annulus. In some embodiments, the superior edge of the coaptation assistance element can curve upward from the posterior leaflet. In some embodiments, the superior edge of the coaptation assistance element can curve downward toward the annulus. In some embodiments, the superior edge of the coaptation assistance element can curve downward toward the posterior leaflet. In some embodiments, one or more struts may curve laterally from the annular hub toward the inferior edge. In some embodiments, the inferior edge of the coaptation assistance element can curve away from the posterior leaflet. In some embodiments, the inferior edge of the coaptation assistance element can curve toward the posterior leaflet.

In some embodiments, a coaptation assistance element for treating mal-coaptation of a heart valve in provided. The heart valve has an annulus. The coaptation assistance element can include a body that includes an annular section and a coaptation section. In some embodiments, the annular section is configured to be implanted within a heart superior to a valve annulus. In some embodiments, the coaptation zone configured to be implanted within a heart and traversing a plane of the valve annulus. The coaptation assistance element can include a first coaptation surface, and an opposed second surface. In some embodiments, each surface is bounded by a first lateral edge, a second lateral edge, an inferior edge, and a superior edge. In some embodiments, the superior edge forms a lip and cupped downward toward the inferior edge or upward from the annular section. The coaptation assistance element can include a hub and an anchor coupled to the hub and carried by the annular section. In some embodiments, the anchor is selectively deployable at a first target location. The coaptation assistance element can include a plurality of struts extending radially outward from the hub. In some embodiments, the plurality of struts comprise at least a first strut residing within the annular section and a second strut extending from the annular section to the coaptation section, wherein the second strut has a total length that is longer than that of the first strut, such as, for example, a total length that is about, or at least about 110%, 120%, 130%, 140%, 150%, 160%, 170%, 180%, 190%, 200%, 225%, 250% or more of the total length of the first strut. In some embodiments, the total length of the second strut is between about 125% and about 300%, or between about 125% and 200% of the total length of the first strut.

In some embodiments, at least one strut of the plurality of struts has a sharpened tip configured to engage tissue. In some embodiments, the plurality of struts comprises Nitinol. In some embodiments, the anchor is helical-shaped. The coaptation assistance element can include one or more additional anchors. In some embodiments, the one or more additional anchors are active anchors. In some embodiments, the hub comprises a cross-pin configured to extend through a helix of the anchor. In some embodiments, the hub is configured to mate with a delivery catheter, wherein the delivery catheter is configured to position the hub near the first target location. In some embodiments, the delivery catheter is configured to rotate the anchor independently of the hub. The coaptation assistance element can include a radiopaque marker. The coaptation assistance element can include a plurality of radiopaque markers near the superior edge. In some embodiments, the superior edge forming a lip is cupped downward toward the inferior edge. In some embodiments, the superior edge forming a lip is cupped upward from the annular section. In some embodiments, the hub extends upward from the annular section. In some embodiments, the inferior edge curves backwards toward the hub.

In some embodiments, a method for treating mal-coaptation of a heart valve in a patient is provided. The heart valve has an annulus. The annulus further defines a valve plane, the valve plane separating an atrium proximally and a ventricle distally. The method can include coupling a delivery catheter to a hub of a coaptation assistance element. The method can include positioning the hub near the annulus. The method can include rotating an anchor through the hub and into heart tissue distal to the annulus. The method can include expanding the coaptation assistance element by allowing a plurality of struts to expand radially outward from the hub.

In some embodiments, the coaptation assist body is suspended such that the coaptation surface coapts with a first leaflet and a leaflet surface of the coaptation assist body overlays a second leaflet such that mal-coaptation is mitigated. The method can include engaging a sharpened end of a strut of the plurality of struts with heart tissue distal to the annulus. The method can include monitoring the position of the coaptation assistance element with one or more markers. The method can include monitoring the position of the coaptation assistance element with a plurality of markers near a superior edge of the coaptation assistance element. In some embodiments, a tip of the anchor is recessed in the hub during positioning the hub near the annulus.

In some embodiments, a coaptation assistance element for treating mal-coaptation of a heart valve of a heart is provided. The coaptation assistance element can include a first coaptation surface and an opposed second surface. The coaptation assistance element can include a first lateral edge, a second lateral edge, an inferior edge, and a superior edge. The coaptation assistance element can include a superior zone and an inferior zone. In some embodiments, the superior zone is configured to reside in the plane of an annulus of the heart valve. In some embodiments, the inferior zone comprises the first coaptation surface and the opposed second surface. In some embodiments, the inferior zone comprises a laminate layer such that a thickness of the inferior zone is greater than a thickness of a portion of the superior zone.

In some embodiments, the laminate layer comprises ePTFE. In some embodiments, the thickness of the inferior zone is at least about 25% thicker than the thickness of the portion of the superior zone. In some embodiments, the thickness of the inferior zone is at least about 50% thicker than the thickness of the portion of the superior zone. In some embodiments, the peripheral edge of the coaptation assistance element comprises a raised atraumatic edge surrounding only partially around the coaptation assistance element. In some embodiments, the peripheral edge of the coaptation assistance element comprises a raised atraumatic edge surrounding only the inferior zone of the coaptation assistance element. In some embodiments, the raised edge comprises a suture. In some embodiments, the peripheral edge of the coaptation assistance element comprises spaced apart barbs extending radially outwardly from the peripheral edge of only the superior zone of the coaptation assistance element. The coaptation assistance element can include a hub spaced inward from each of the first lateral edge, the second lateral edge, the inferior edge, and the superior edge. The coaptation assistance element can include an active anchor configured to couple to the hub and configured to be rotated relative to the hub to selectively deploy the active anchor at a first target location. The coaptation assistance element can include a plurality of struts spaced around the hub and extending outward from the hub, the plurality of struts comprising at least a first strut configured to be implanted within the heart and a second strut configured to be implanted within the heart such that the first coaptation surface coapts with a first leaflet of the heart valve and the opposed second surface overlays a second leaflet of the heart valve. In some embodiments, the coaptation assistance element comprises a layer of mesh.

In some embodiments, a coaptation assistance element delivery system for treating mal-coaptation of a heart valve is provided. In some embodiments, the heart valve has an annulus. The coaptation assistance element delivery system can include a coaptation assistance element comprising a first surface and an opposed second surface. In some embodiments, each surface bounded by a first lateral edge, a second lateral edge, an inferior edge, and a superior edge. The coaptation assistance element can include a hub. The coaptation assistance element delivery system can include a primary anchor disposed within a primary anchor housing. In some embodiments, the primary anchor is configured to extend through the hub to engage the annulus. The coaptation assistance element delivery system can include a release wire extending through the primary anchor housing and configured to be positioned adjacent to the annulus.

The coaptation assistance element delivery system can include a primary anchor driver disposed within the primary anchor housing. In some embodiments, the primary anchor driver is configured to rotate, but not translate, relative to the primary anchor housing. In some embodiments, the primary anchor driver comprises two extensions, wherein the two extensions are configured to engage a cross-bar of the primary anchor. The coaptation assistance element delivery system can include two release wires extending through the primary anchor housing. In some embodiments, the two release wires are configured to be positioned adjacent to the annulus, extending from the hub in opposite directions. In some embodiments, the two release wires cross. The coaptation assistance element delivery system can include a secondary anchor tether extending through the coaptation assistance element. In some embodiments, the secondary anchor tether extends around the release wire. The coaptation assistance element delivery system can include at least two secondary anchor tethers extending through the coaptation assistance element. In some embodiments, at least two secondary anchor tethers extend around the release wire. In some embodiments, at least one secondary anchor tether extends around the release wire and at least one secondary anchor tether extends around a second release wire. The coaptation assistance element delivery system can include a secondary anchor guide rail. In some embodiments, the secondary anchor guide rail is configured to lock a secondary anchor driver to a secondary anchor. In some embodiments, the secondary anchor guide rail is configured to prevent entanglement between a secondary anchor and an adjacent secondary anchor tether. In some embodiments, the secondary anchor guide rail is configured to slide along a secondary anchor tether to deliver a secondary anchor. The coaptation assistance element delivery system can include a secondary anchor driver. In some embodiments, the secondary anchor driver comprises at least one locking tab configured to engage a window of a secondary anchor. The coaptation assistance element delivery system can include a secondary anchor. In some embodiments, the secondary anchor is configured to be delivered by sliding the secondary anchor along a secondary anchor tether looped around the release wire. In some embodiments, the secondary anchor is configured to be rotated to engage the annulus. In some embodiments, the secondary anchor has a smaller diameter than the primary anchor. In some embodiments, the release wire is configured to be retracted after the primary anchor engages the annulus. In some embodiments, the release wire is configured to be retracted after the primary anchor and at least one secondary anchor engages the annulus. In some embodiments, the primary anchor housing is configured to be retracted after the release wire is retracted, wherein the primary anchor driver retracts with the primary anchor housing. In some embodiments, the trajectory of the primary anchor is through the hub. In some embodiments, a cross-pin of the hub is configured to couple the primary anchor to the coaptation assistance element. In some embodiments, at least one secondary anchor is configured to have two or more trajectories. In some embodiments, the trajectory of at least one secondary anchor is determined by the orientation of a respective secondary anchor guide rail. In some embodiments, the secondary anchor guide rail comprises a curved distal end, wherein the curved distal end defines the trajectory. The coaptation assistance element delivery system can include a proximal assembly configured to lock the position of a secondary anchor guide rail relative to a secondary anchor to prevent entanglement of a secondary anchor tether. The coaptation assistance element delivery system can include a proximal assembly configured to lock the position of a secondary anchor guide rail relative to a secondary anchor driver to facilitate coupling of the secondary anchor driver to a secondary anchor. The coaptation assistance element delivery system can include a proximal assembly configured to lock the position of a secondary anchor tether, wherein the secondary anchor tether is coupled to the release wire. The coaptation assistance element delivery system can include a proximal assembly configured to lock the position of a secondary anchor tether to apply tension to the secondary anchor tether to define a trajectory for a secondary anchor. The coaptation assistance element delivery system can include an anti-rotation feature. In some embodiments, a secondary anchor comprises the anti-rotation feature.

In some embodiments, a coaptation assistance element for treating mal-coaptation of a heart valve is provided. In some embodiments, the heart valve has an annulus. The coaptation assistance element can include a first surface and an opposed second surface, each surface bounded by a first lateral edge, a second lateral edge, an inferior edge, and a superior edge. The coaptation assistance element can include a hub. The coaptation assistance element can include a plurality of struts spaced around the hub and extending outward from the hub, the plurality of struts comprising at least a first strut configured to be implanted within a heart superior to a valve annulus and a second strut configured to be implanted within a heart and traversing a plane of the valve annulus.

In some embodiments, the coaptation assistance element comprises at least one layer of ePTFE. In some embodiments, the coaptation assistance element comprises at least one layer of mesh. In some embodiments, the coaptation assistance element comprises at least one layer of UHMWPE mesh. In some embodiments, the coaptation assistance element comprises at least one layer of fabric. In some embodiments, the coaptation assistance element comprises at least one layer of polyester fabric. In some embodiments, the first surface is reinforced. In some embodiments, the second surface is reinforced. In some embodiments, a ventricular surface is reinforced. In some embodiments, a coaptation surface is reinforced. In some embodiments, an anchor zone is reinforced. In some embodiments, at least one edge comprises a raised edge. In some embodiments, the coaptation assistance element is configured to minimize contact with a posterior leaflet. In some embodiments, the coaptation assistance element is configured to engage and embed within the annulus.

In some embodiments, a method of delivering a coaptation assistance element is provided. The method can include delivering a coaptation assistance element to a heart of a patient. In some embodiments, the coaptation assistance element is coupled to a coaptation assistance element delivery system. In some embodiments, the coaptation assistance element delivery system comprising a primary anchor disposed within a primary anchor housing. In some embodiments, the coaptation assistance element delivery system comprising at least one release wire. The method can include expanding the coaptation assistance element within the heart. The method can include anchoring the coaptation assistance element to an annulus of the heart valve by rotating the primary anchor.

The method can include rotating a primary anchor driver within the primary anchor housing. In some embodiments, the at least one release wire is coupled to the primary anchor housing and extends under the coaptation assistance element when the coaptation assistance element is expanded. In some embodiments, at least one secondary anchor tether extends through the coaptation assistance element when the coaptation assistance element is expanded. In some embodiments, at least one secondary anchor tether loops around the at least one release wire when the coaptation assistance element is expanded. In some embodiments, the coaptation assistance element is delivered in a low profile configuration. In some embodiments, the at least one release wire is configured to maintain the position of the primary anchor housing relative to the coaptation assistance element. In some embodiments, the at least one release wire is configured to maintain the position of at least one secondary anchor tether relative to the coaptation assistance element. In some embodiments, the coaptation assistance element is delivered via a delivery catheter. In some embodiments, a telescoping action is configured to position the coaptation assistance element relative to a location to engage the primary anchor with the annulus. The method can include rotating the primary anchor to engage the annulus. The method can include rotating a primary anchor driver within the primary anchor housing, wherein the primary anchor driver is configured to rotate by not translate relative to the primary anchor housing. The method can include sliding a secondary anchor assembly toward the annulus, along a secondary anchor tether. The method can include maintaining engagement between a secondary anchor driver and a secondary anchor with a secondary anchor guide rail. The method can include preventing entanglement between a secondary anchor and a secondary anchor tether with a secondary anchor guide rail. The method can include coupling a secondary anchor driver to a secondary anchor. The method can include partially retracting a secondary anchor guide rail before the secondary anchor engages tissue. The method can include retracting a secondary anchor guide rail after the secondary anchor engages tissue. The method can include retracting a secondary anchor driver after retracting a secondary anchor guide rail. The method can include retracting the at least one release wire.

In some embodiments, a coaptation assistance element for treating mal-coaptation of a heart valve is provided, the heart valve having an annulus. The coaptation assistance element can include a first coaptation surface and an opposed second surface, each surface bounded by a first lateral edge, a second lateral edge, an inferior edge, and a superior edge. The coaptation assistance element can include a hub. The coaptation assistance element can include an anchor coupled to the hub and configured to be rotated relative to the hub to selectively deploy the anchor at a first target location. The coaptation assistance element can include a plurality of struts spaced around the hub and extending outward from the hub. In some embodiments, the plurality of struts comprises at least a first strut configured to be implanted within a heart superior to a valve annulus and a second strut configured to be implanted within a heart and traversing a plane of the valve annulus.

In some embodiments, the second strut has a total length that is longer than that of the first strut. In some embodiments, the hub is spaced radially inward from each of the first lateral edge, the second lateral edge, the inferior edge, and the superior edge. In some embodiments, the plurality of struts are spaced circumferentially around the hub. In some embodiments, the superior edge forms a lip cupped downward toward the inferior edge or upward from the inferior edge. In some embodiments, at least one strut of the plurality of struts has a sharpened tip configured to engage tissue. In some embodiments, the plurality of struts comprise Nitinol. In some embodiments, the anchor is helical-shaped. The coaptation assistance element can include one or more additional anchors. In some embodiments, the one or more additional anchors are active anchors. In some embodiments, the hub comprises a cross-pin configured to extend through a helix of the anchor. In some embodiments, the hub is configured to mate with a delivery catheter, wherein the delivery catheter is configured to position the hub near the first target location. In some embodiments, the delivery catheter is configured to rotate the anchor independently of the hub. The coaptation assistance element can include a radiopaque marker. The coaptation assistance element can include a plurality of radiopaque markers near the superior edge. In some embodiments, the lip is cupped downward toward the inferior edge. In some embodiments, the lip is cupped upward from the inferior edge. In some embodiments, the hub extends upward from the first coaptation surface. In some embodiments, the inferior edge curves backwards toward the hub. In some embodiments, the hub is tubular. In some embodiments, the struts and the hub are integrally formed. In some embodiments, the coaptation assistance element is configured to be collapsed relative to the hub. In some embodiments, the active anchor is configured to be selectively coupled and decoupled from tissue.

In some embodiments, a coaptation assistance element for treating mal-coaptation of a heart valve is provided, the heart valve having an annulus. The coaptation assistance element can include a first coaptation surface and an opposed second surface. In some embodiments, each surface bounded by a first lateral edge, a second lateral edge, an inferior edge, and a superior edge. The coaptation assistance element can include a hub. The coaptation assistance element can include an anchor coupled to the hub. In some embodiments, the anchor is configured to be rotated in a first direction to selectively deploy the active anchor to engage tissue. In some embodiments, the active anchor is configured to be rotated in a second direction, opposite the first direction, to selectively disengage tissue. The coaptation assistance element can include a plurality of struts spaced around the hub. In some embodiments, the plurality of struts comprises at least a first strut configured to be implanted within a heart superior to a valve annulus and a second strut configured to be implanted within a heart and traversing a plane of the valve annulus.

In some embodiments, a coaptation assistance element for treating mal-coaptation of a heart valve is provided. In some embodiments, the heart valve has an annulus, an anterior leaflet, and a posterior leaflet. The coaptation assistance element can include a first coaptation surface and an opposed second surface. In some embodiments, each surface bounded by a first lateral edge, a second lateral edge, an inferior edge, and a superior edge. The coaptation assistance element can include a hub. The coaptation assistance element can include an anchor coupled to the hub and configured to be rotated relative to the hub to selectively deploy the anchor at a first target location. In some embodiments, the anchor is configured to be selectively deployed in the annulus. The coaptation assistance element can include a plurality of struts spaced around the hub. In some embodiments, the plurality of struts comprising at least a first strut configured to be implanted within a heart superior to a valve annulus and a second strut configured to be implanted within a heart and traversing a plane of the valve annulus.

BRIEF DESCRIPTION OF THE DRAWINGS

FIGS. 5E-5G illustrate the coaptation assistance element of FIG. 5A without annular anchor site.

FIGS. 5H-5J illustrate the coaptation assistance element of FIG. 5A with leaflet anchor sites.

FIG. 8A schematically illustrates an embodiment of control handle of a delivery system for a transcatheter technique.

FIG. 8B schematically illustrates a top view and a side view a coaptation assistance element coupled to the delivery system of FIG. 8A.

FIG. 8C schematically illustrates the connection between an annular hub of the coaptation assistance element and a tip of the delivery catheter.

FIG. 9A schematically illustrates the anchor manipulation of the delivery system of FIG. 8A.

FIGS. 9B-9E schematically illustrates embodiments of the connection between an annular anchor and a driver.

FIG. 17 illustrates a method for inserting an introducer.

FIG. 18 illustrates a method for connecting the introducer of FIG. 17 to a transseptal sheath.

FIG. 19 illustrates a method for advancing the transseptal sheath of FIG. 18.

FIG. 20 illustrates a method for positioning the transseptal sheath of FIG. 19.

FIG. 21 illustrates a method for delivering an anchor.

FIG. 29 illustrates the anchored implant with guidewires.

FIG. 30 illustrates the anchored implant.

FIGS. 42A-42I illustrate an embodiment of an implant delivery system.

FIGS. 43A-43E illustrate an embodiment of an implant delivery system.

FIGS. 45A-45K illustrate an embodiment of an implant delivery system.

FIGS. 46A-46C illustrate an embodiment of an anchor delivery system.

FIG. 48 illustrates an embodiment of implant construction.

FIGS. 55A-55C illustrate an embodiment of a proximal assembly.

DETAILED DESCRIPTION

Figure 1A:
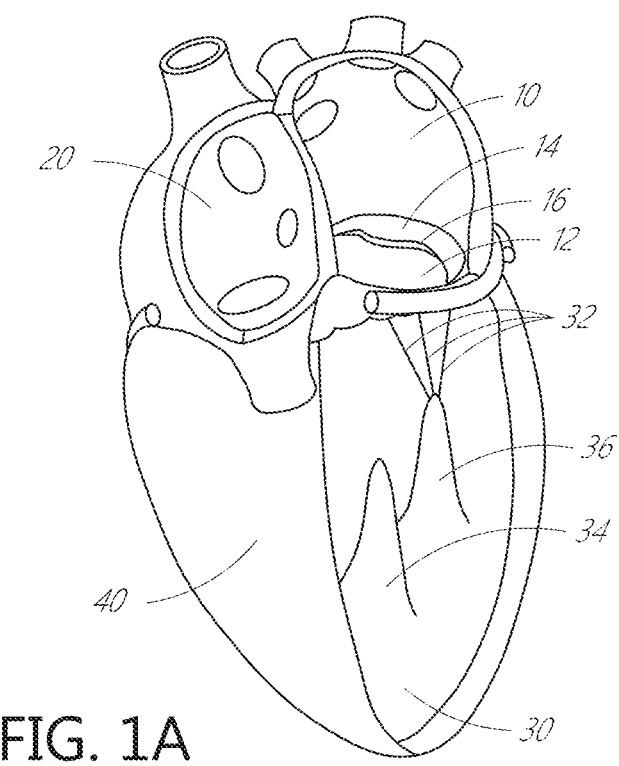
FIGS. 1A-1F schematically illustrate some of the tissues of the heart and mitral valve, as described in the Background section and below, and which may interact with the implants and systems described herein.
Figure 1B:
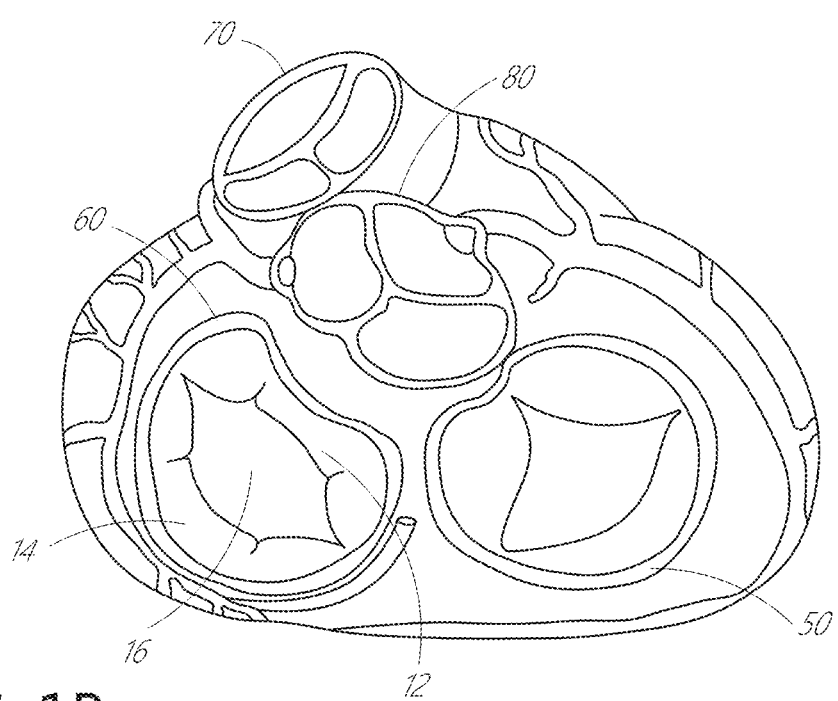
Figure 1C:
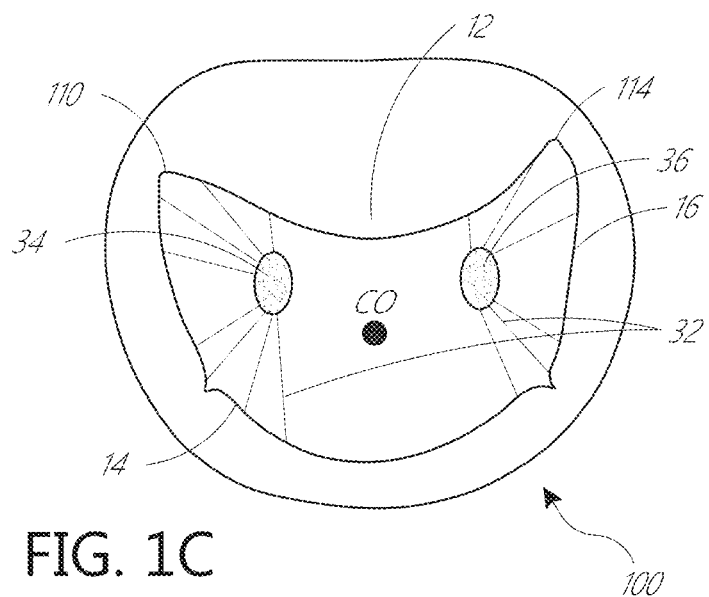
Figure 1D:
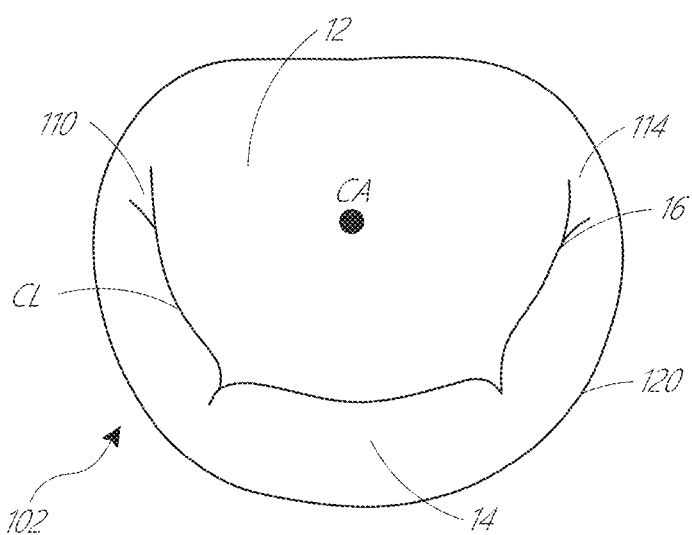

The present invention, in some embodiments, generally provides improved medical devices, systems, and methods, often for treatment of mitral valve regurgitation and other valve diseases including tricuspid regurgitation. While the description that follows includes reference to the anterior leaflet in a valve with two leaflets such as the mitral valve, it is understood that "anterior leaflet" could refer to one or more leaflets in valve with multiple leaflets. For example, the tricuspid valve has 3 leaflets so the "anterior" could refer to one or two of the medial, lateral, and posterior leaflets. The coaptation assistance elements described herein will generally include a coaptation assist body (sometimes referred to herein as a valve body) which is generally along the blood flow path as the leaflets of the valve move back and forth between an open-valve configuration (with the anterior leaflet separated from valve body) and a closed-valve configuration (with the anterior leaflet engaging opposed surfaces of the valve body). The valve body will be disposed between the native leaflets to close the gap caused by mal-coaptation of the native leaflets by providing a surface for at least one of the native leaflets to coapt against, while effectively replacing a second native leaflet in the area of the valve which, were it functioning normally, it would occlude during systole. The gaps may be lateral (such as may be caused by a dilated left ventricle and/or mitral valve annulus) and/or axial (such as where one leaflet prolapses or is pushed by fluid pressure beyond the annulus when the valve should close). In some embodiments, the coaptation assist elements may completely assist one, two, or more valve leaflets, or in some embodiments partially assist a valve leaflet, for example, covering only one or more of the A1, A2, and/or A3 scallops of the anterior leaflet, and/or one or more of the P1, P2, and/or P3 scallops of the posterior leaflet.

Among other uses, the coaptation assistance elements, and methods described herein may be configured for treating functional and/or degenerative mitral valve regurgitation (MR) by creating an artificial or new coaptation zone within which at least one of the native mitral valve leaflets can seal. The structures and methods herein will largely be tailored to this application, though alternative embodiments might be configured for use in other valves of the heart and/or body, including the tricuspid valve, valves of the peripheral vasculature, the inferior vena cava, or the like.

Referring to FIGS. 1A-1D, the four chambers of the heart are shown, the left atrium 10, right atrium 20, left ventricle 30, and right ventricle 40. The mitral valve 60 is disposed between the left atrium 10 and left ventricle 30. Also shown are the tricuspid valve 50 which separates the right atrium 20 and right ventricle 40, the aortic valve 80, and the pulmonary valve 70. The mitral valve 60 is composed of two leaflets, the anterior leaflet 12 and posterior leaflet 14. In a healthy heart, the two leaflets appose during systole at the coaptation zone 16.

Figure 1E:
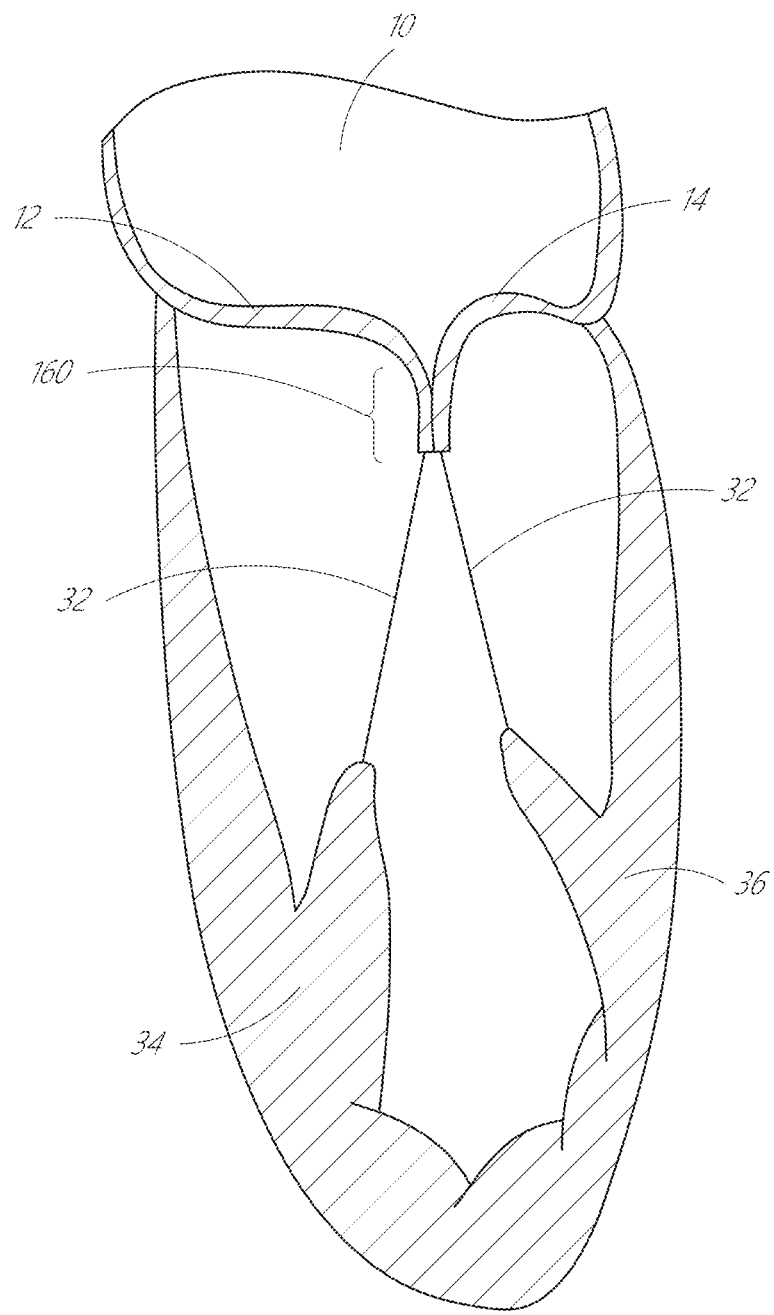

The fibrous annulus 120, part of the cardiac skeleton, provides attachment for the two leaflets of the mitral valve, referred to as the anterior leaflet 12 and the posterior leaflet 14. The leaflets are axially supported by attachment to the chordae tendinae 32. The chordae, in turn, attach to one or both of the papillary muscles 34, 36 of the left ventricle. In a healthy heart, the chordae support structures tether the mitral valve leaflets, allowing the leaflets to open easily during diastole but to resist the high pressure developed during ventricular systole. In addition to the tethering effect of the support structure, the shape and tissue consistency of the leaflets helps promote an effective seal or coaptation. The leading edges of the anterior and posterior leaflet come together along a funnel-shaped zone of coaptation 16, with a lateral cross-section 160 of the three-dimensional coaptation zone (CZ) being shown schematically in FIG. 1E.

Figure 1F:
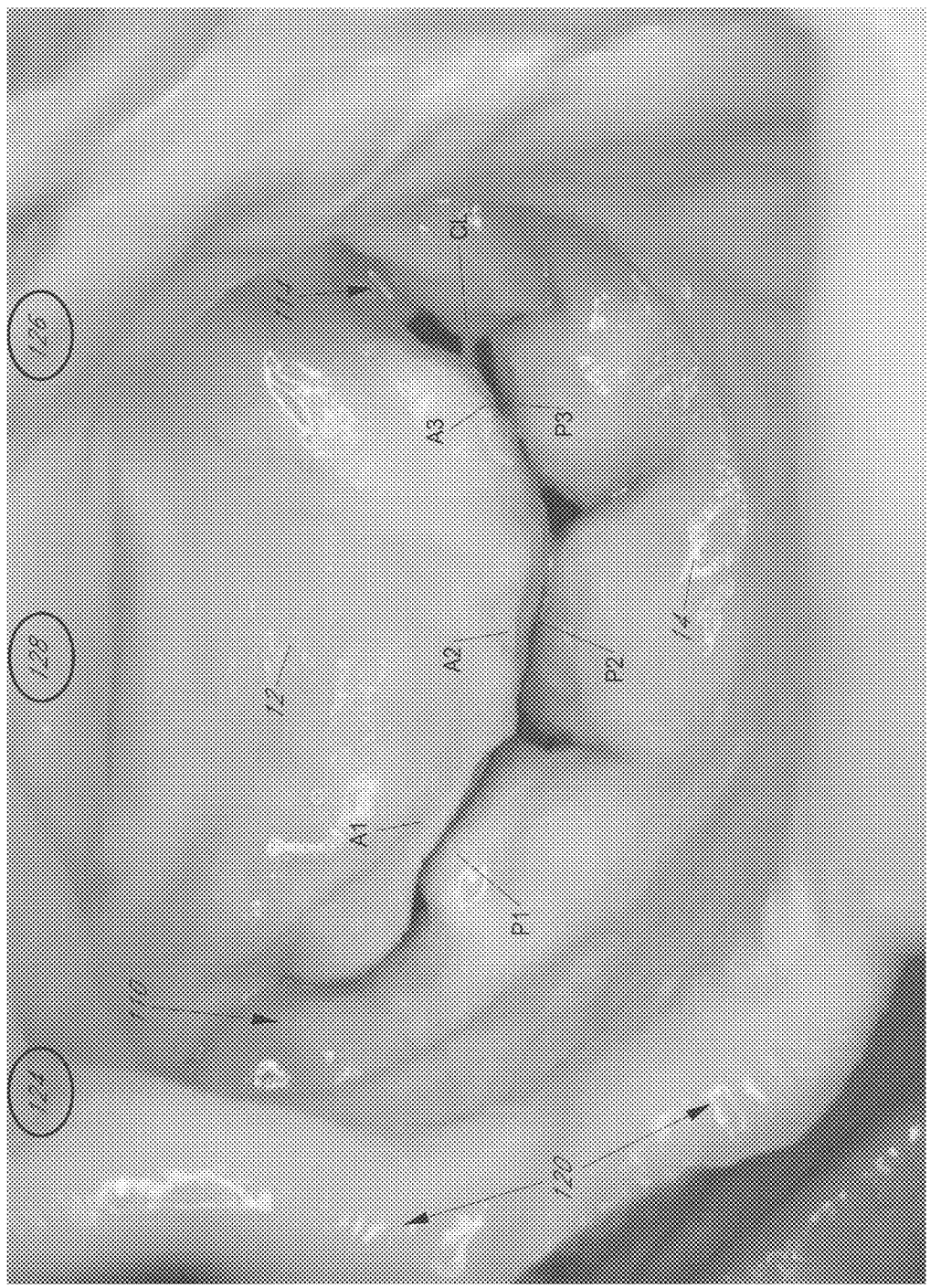

The anterior and posterior mitral leaflets are dissimilarly shaped. The anterior leaflet is more firmly attached to the annulus overlying the central fibrous body (cardiac skeleton), and is somewhat stiffer than the posterior leaflet, which is attached to the more mobile posterior mitral annulus. Approximately 80 percent of the closing area is the anterior leaflet. Adjacent to the commissures 110, 114, on or anterior to the annulus 120, lie the left (lateral) 124 and right (septal) 126 fibrous trigones which are formed where the mitral annulus is fused with the base of the non-coronary cusp of the aorta (FIG. 1F). The fibrous trigones 124, 126 form the septal and lateral extents of the central fibrous body 128. The fibrous trigones 124, 126 may have an advantage, in some embodiments, as providing a firm zone for stable engagement with one or more annular or atrial anchors. The coaptation zone CL between the leaflets 12, 14 is not a simple line, but rather a curved funnel-shaped surface interface. The first 110 (lateral or left) and second 114 (septal or right) commissures are where the anterior leaflet 12 meets the posterior leaflet 14 at the annulus 120. As seen most clearly in the axial views from the atrium of FIGS. 1C, 1D, and 1F, an axial cross-section of the coaptation zone generally shows the curved line CL that is separated from a centroid of the annulus CA as well as from the opening through the valve during diastole CO. In addition, the leaflet edges are scalloped, more so for the posterior versus the anterior leaflet. Mal-coaptation can occur between one or more of these A-P (anterior-posterior) segment pairs A1/P1, A2/P2, and A3/P3, so that mal-coaptation characteristics may vary along the curve of the coaptation zone CL.

Figure 2B:
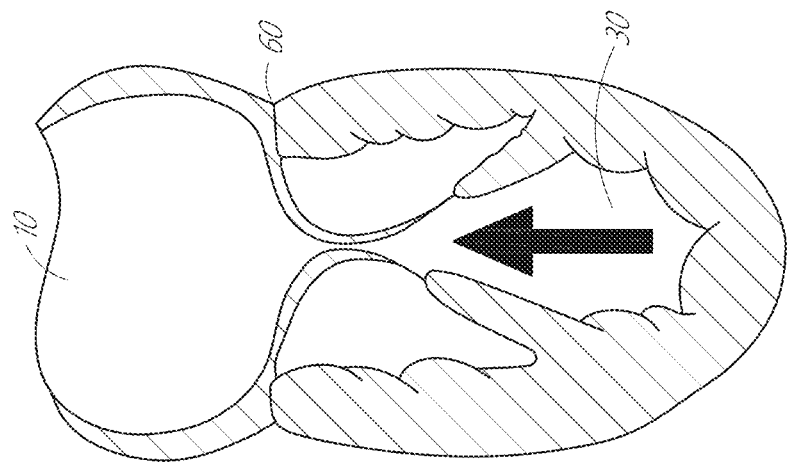
FIG. 2B illustrates a simplified cross-section of a heart, schematically showing mitral valve function during systole.
Figure 2A:
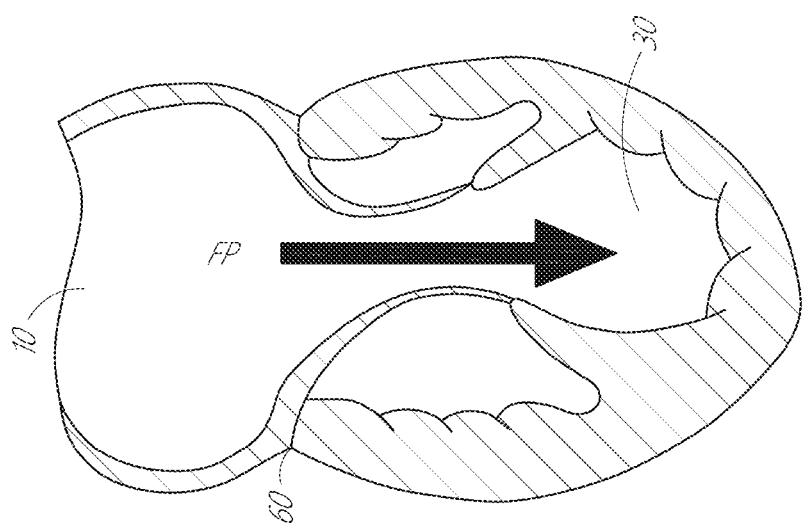
FIG. 2A illustrates a simplified cross-section of a heart, schematically showing mitral valve function during diastole.

Referring now to FIG. 2A, a properly functioning mitral valve 60 of a heart is open during diastole to allow blood to flow along a flow path FP from the left atrium toward the left ventricle 30 and thereby fill the left ventricle. As shown in FIG. 2B, the functioning mitral valve 60 closes and effectively seals the left ventricle 30 from the left atrium 10 during systole, first passively then actively by increase in ventricular pressure, thereby allowing contraction of the heart tissue surrounding the left ventricle to advance blood throughout the vasculature.

Referring to FIGS. 3A-3B and 4A-4B, there are several conditions or disease states in which the leaflet edges of the mitral valve fail to oppose sufficiently and thereby allow blood to regurgitate in systole from the ventricle into the atrium. Regardless of the specific etiology of a particular patient, failure of the leaflets to seal during ventricular systole is known as mal-coaptation and gives rise to mitral regurgitation.

Figure 3A:
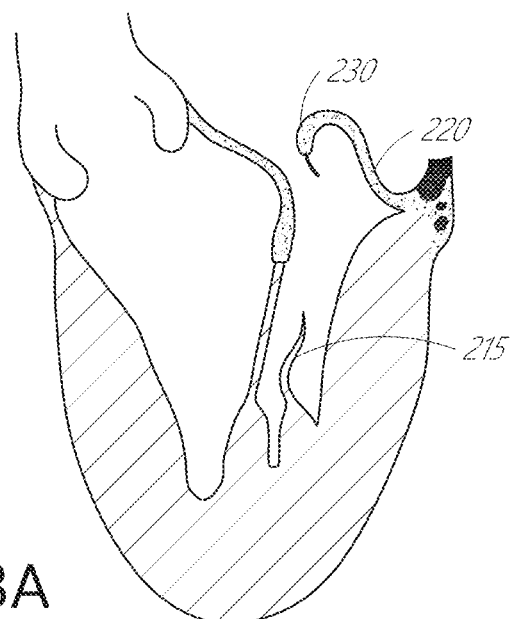
FIGS. 3A-3B illustrate a simplified cross-section of a heart, schematically showing mitral valve regurgitation during systole in the setting of mal-coaptation of the mitral valve leaflets.

Generally, mal-coaptation can result from either excessive tethering by the support structures of one or both leaflets, or from excessive stretching or tearing of the support structures. Other, less common causes include infection of the heart valve, congenital abnormalities, and trauma. Valve malfunction can result from the chordae tendinae becoming stretched, known as mitral valve prolapse, and in some cases tearing of the chordae 215 or papillary muscle, known as a flail leaflet 220, as shown in FIG. 3A. Or if the leaflet tissue itself is redundant, the valves may prolapse so that the level of coaptation occurs higher into the atrium, opening the valve higher in the atrium during ventricular systole 230. Either one of the leaflets can undergo prolapse or become flail. This condition is sometimes known as degenerative mitral valve regurgitation.

Figure 3B:
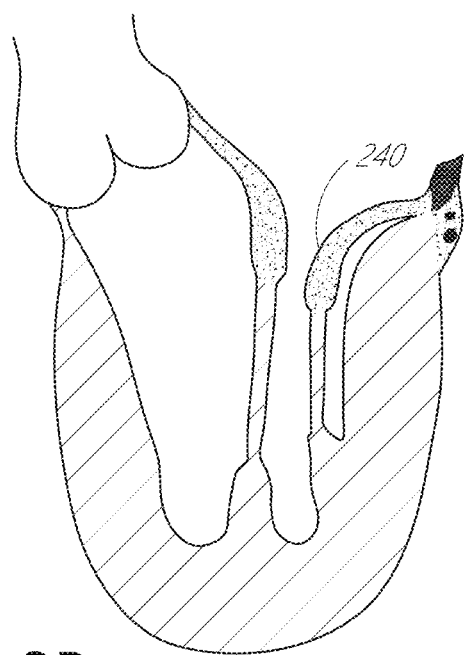

In excessive tethering, as shown in FIG. 3B, the leaflets of a normally structured valve may not function properly because of enlargement of or shape change in the valve annulus: so-called annular dilation 240. Such functional mitral regurgitation generally results from heart muscle failure and concomitant ventricular dilation. And the excessive volume load resulting from functional mitral regurgitation can itself exacerbate heart failure, ventricular and annular dilation, thus worsening mitral regurgitation.

Figure 4A:
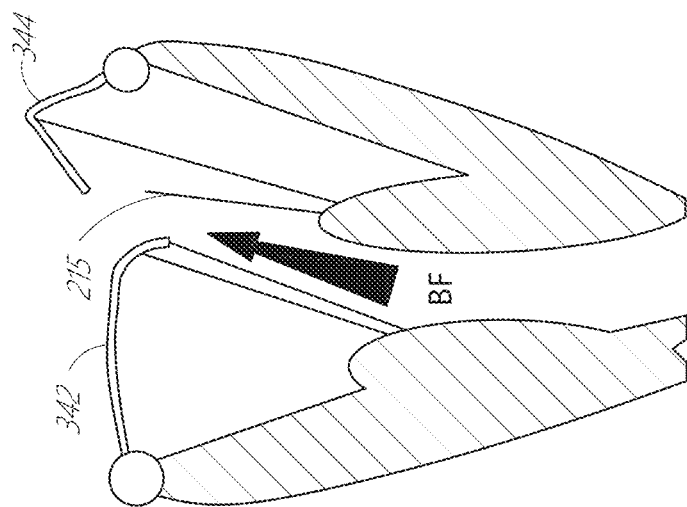
FIG. 4A illustrates a stylized cross section of a heart, showing mitral valve mal-coaptation in the setting of functional mitral valve regurgitation.
Figure 4B:
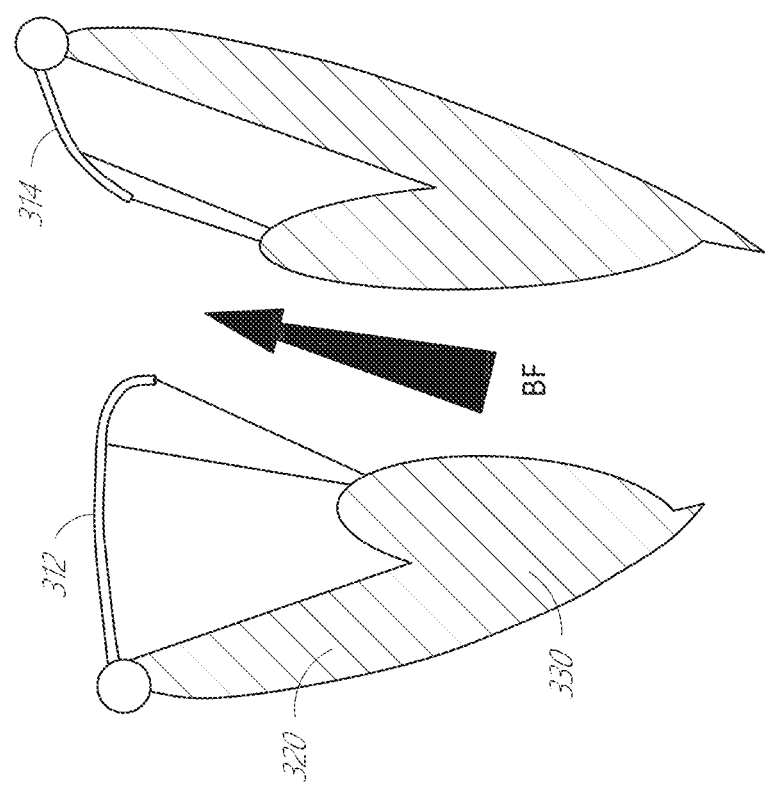
FIG. 4B illustrates a stylized cross section of a heart, showing mitral valve mal-coaptation in the setting of degenerative mitral valve regurgitation.

FIG. 4A-4B illustrate the backflow BF of blood during systole in functional mitral valve regurgitation (FIG. 4A) and degenerative mitral valve regurgitation (FIG. 4B). The increased size of the annulus in FIG. 4A, coupled with increased tethering due to hypertrophy of the ventricle 320 and papillary muscle 330, prevents the anterior leaflet 312 and posterior leaflet 314 from apposing, thereby preventing coaptation. In FIG. 4B, the tearing of the chordae 215 causes prolapse of the posterior leaflet 344 upward into the left atrium, which prevents apposition against the anterior leaflet 342. In either situation, the result is backflow of blood into the atrium, which decreases the effectiveness of left ventricle compression.

Further description of coaptation assistance elements, tools, anchors, features, systems, and methods, which can be utilized in conjunction with the disclosure herein, can be found in the following applications, each of which is incorporated by reference in their entirety: U.S. patent application Ser. No. 13/099,532, filed May 3, 2011; U.S. patent application Ser. No. 13/531,407, filed Jun. 22, 2012; U.S. patent application Ser. No. 14/313,975, filed Jun. 24, 2014; U.S. patent application Ser. No. 14/742,199, filed Jun. 17, 2015; U.S. patent application Ser. No. 14/749,344, filed Jun. 24, 2015; and U.S. patent application Ser. No. 10/419,706, filed Apr. 18, 2003.

In some embodiments, the coaptation assistance elements described herein may be deployed to overlie the posterior leaflet, the chordae and papillary muscle. In some embodiments, the coaptation assistance element attaches superiorly to the posterior aspect of the annulus and inferiorly to the posterior aspect of the left ventricle via annular anchor and/or ventricular anchor. In other embodiments, more than one annular anchor and/or more than one ventricular anchor may be used to attach the coaptation assistance element. In some elements, the one or more annular anchors may be replaced by or supplemented with one or more atrial or commissural anchors, which can be annular in some embodiments. The coaptation assistance element may attach to the superior surface of the posterior annulus, the posterior atrial wall, or the annulus itself. A coaptation zone has been established between the coaptation assistance element and the native anterior leaflet. Similar coaptation assistance elements can be used in both functional and degenerative mitral valve regurgitation because the failure of leaflet coaptation occurs in both, regardless of the mechanism behind the dysfunction. In some embodiments, differently sized coaptation assistance elements can be placed such that the native anterior leaflet apposes the coaptation element at the appropriately established coaptation point, blocking flow of blood during contraction of the ventricle.

A variety of sizes of coaptation assistance elements may be provided, with differing dimensions configured to fit varying anatomies. For example, there may be a height, which measures from the superior annular attachment site to the inferior-most edge of the coaptation assistance element in a plane basically perpendicular to the plane defined by the annulus of the valve, a depth between the coaptation point and the superior attachment site, and a projection between the posterior wall at the level of the coaptation point and the coaptation point. There is also a medial-lateral diameter of the coaptation assistance element, typically larger in functional MR. During diastole, the coaptation assistance element may stay in substantially the same position, while movement of the native anterior leaflet opens the valve, permitting flow of blood from the left atrium to the left ventricle with minimal restriction. In some embodiments, the surface of the coaptation assistance element may balloon or stretch upwards during ventricular systole, while the anchors remain unmoved. This may be advantageous as enhancing the seal between the anterior or coaptation surface of the element and the native leaflet at the coaptation zone during systole. During diastole, the surface may return to an initial position in which it lies more anteriorly, toward the anterior leaflet. This may provide an improved blood flow path between the atrium and ventricle during diastole, improving outflow from the atrium past the coaptation assist element.

In some methods of use, the native posterior leaflet is left in position, and the coaptation assistance element is attached superiorly to the posterior annulus or adjacent atrial wall. Many possible alternate embodiments may have differing attachment mechanisms. In other methods of use, the posterior leaflet is not present, having been removed surgically or the result of disease. In some methods of use, the native leaflet attaches to the posterior surface of the coaptation assistance element. In some methods of use, the coaptation assistance element may attach to the anterior surface of the posterior leaflet, rather than the annulus or atrial wall. These are some examples of variations, but still others are contemplated. In some methods of use, an anchoring structure (not shown) could pass from the coaptation assistance element, through the atrial wall into the coronary sinus, wherein the anchoring structure attaches to a mating structure in the coronary sinus. In some methods of use, the anchoring structure, which could be a mechanical structure or a simple suture, can pass through the atrial wall and be anchored by a knot or mechanical element, such as a clip, on the epicardial surface of the heart. Similarly, attachment inferiorly may be to the ventricular muscle, through the apex into the epicardium or pericardium and secured from outside, or at other attachment sites using alternative attachment means.

The coaptation assistance element described herein may exhibit a number of desirable characteristics. Some embodiments need not rely on reshaping of the mitral annulus (such as by thermal shrinking of annular tissue, implantation of an annular ring prosthesis, and/or placement of a cinching mechanism either above or beneath the valve plane, or in the coronary sinus or related blood vessels). Advantageously, they also need not disrupt the leaflet structure or rely on locking together or fusing of the mitral leaflets. Many embodiments can avoid reliance on ventricular reshaping, and after implantation represent passive implanted devices with limited excursion which may result in very long fatigue life. Thus, the coaptation assistance element can be secured across a posterior leaflet while otherwise leaving native heart (e.g., ventricular, mitral annulus, etc.) anatomy intact.

Mitigation of mitral valve mal-coaptation may be effective irrespective of which leaflet segment(s) exhibit mal-coaptation. The treatments described herein will make use of coaptation assistance elements that are repositionable during the procedure, and even removable after complete deployment and/or tissue response begins or is completed, often without damaging the valve structure. Nonetheless, the coaptation assistance element described herein may be combined with one or more therapies that do rely on one or more of the attributes described above as being obviated. The coaptation assistance element can exhibit benign tissue healing and rapid endothelialization which inhibits migration, thromboembolism, infection, and/or erosion. In some cases, the coaptation assistance element will exhibit no endothelialization but its surface will remain inert, which can also inhibit migration, thromboembolism, infection and/or erosion.

Figure 5A:
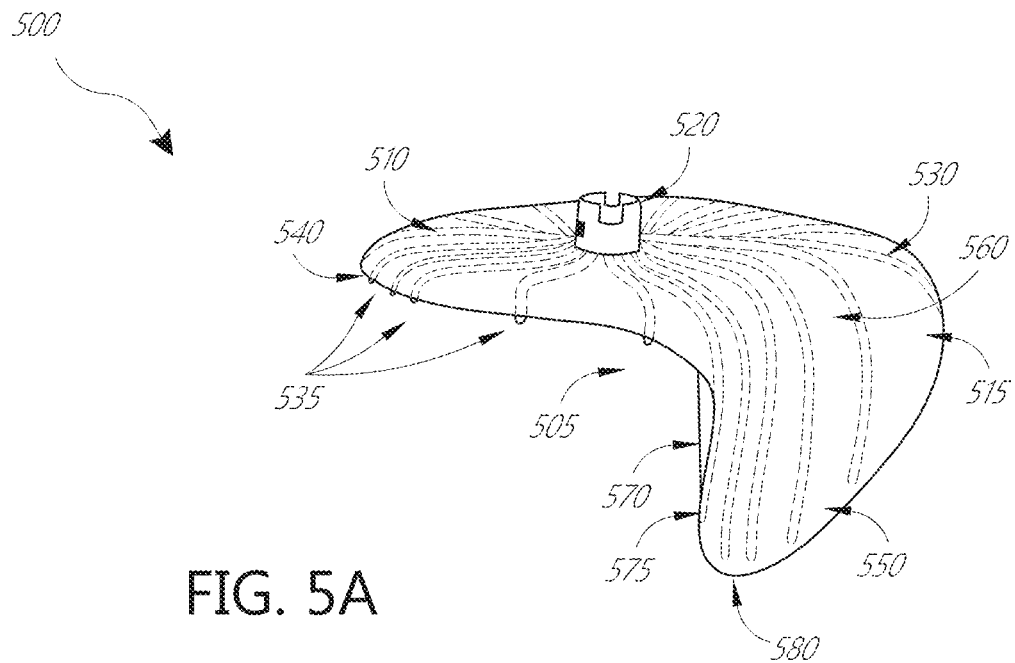
FIG. 5A illustrates a perspective view of an embodiment of a coaptation assistance element.
Figure 5B:
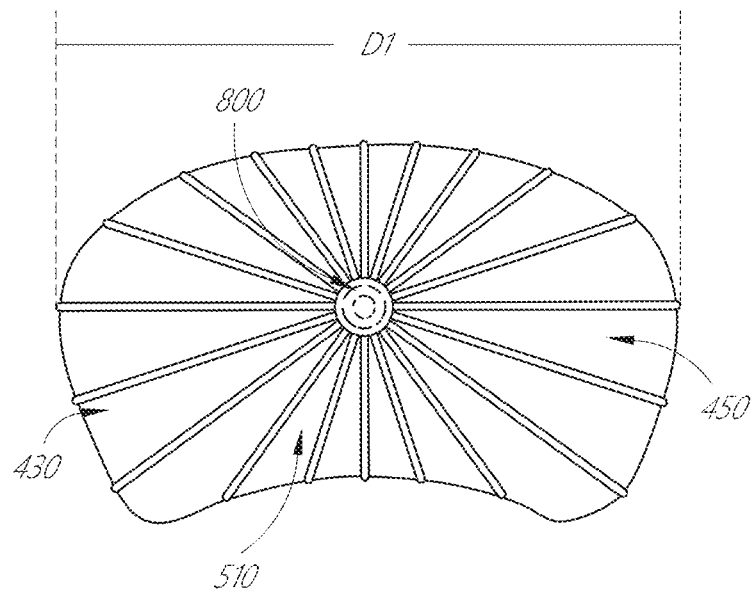
FIG. 5B illustrates the top view of the coaptation assistance element of FIG. 5A.
Figure 6:
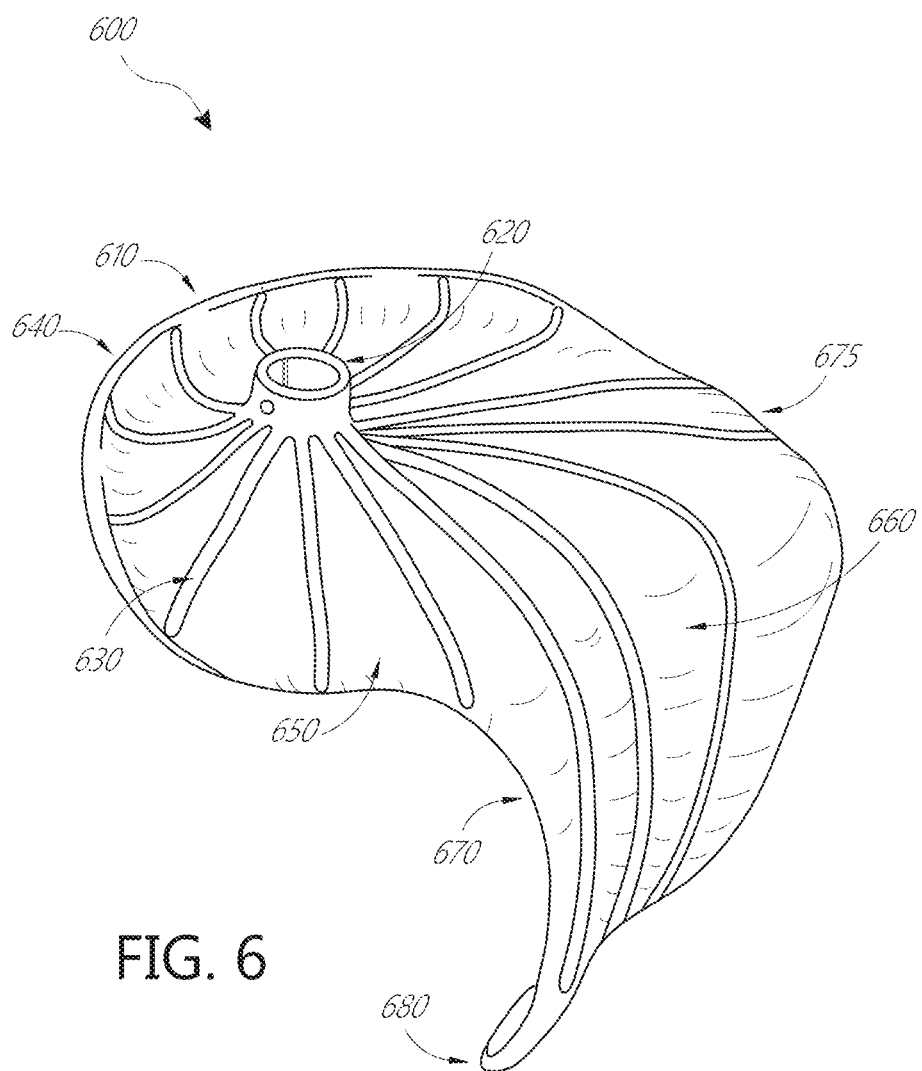
FIG. 6 illustrates a perspective view of an embodiment of a coaptation assistance element.

FIGS. 5A-5B show two views of an embodiment of a coaptation assistance element 500. The coaptation assistance element 500 can include a first surface 505 disposed toward a mal-coapting native leaflet, in the instance of a mitral valve, the posterior leaflet and a second surface 515 which may be disposed toward the anterior leaflet. The second surface 515 can include a coaptation surface 560. The superior edge 540 of the coaptation assistance element 500 may be curved to match the general shape of the annulus or adjoining atrial wall, as described herein. The superior edge 540 can be curved downward, toward the posterior leaflet, as shown in FIG. 5A, or curved upward, toward the atrial wall to match the general shape of the left atrial wall, as shown in FIG. 6 and described herein.

The coaptation assistance element 500 can have a geometry which permits it to traverse the valve between attachment sites in the atrium and ventricle. In some embodiments, the attachment sites are only in the atrium. In some embodiments, the attachment sites are only near the annulus and the commissures of the valve. The coaptation assistance element 500 can be unattached near the inferior edge 580. The coaptation assistance element 500 does not require ventricular attachment. In some embodiments, the geometry of the coaptation assistance element 500 helps to maintain the position of the coaptation assistance element 500 within the valve. In some embodiments, the coaptation assistance element 500 is curved to cup the posterior leaflet. In some embodiments, the coaptation assistance element 500 is curved backwards toward the superior edge 540. The coaptation assistance element 500 may provide the coaptation surface 560 for the anterior leaflet to coapt against. FIGS. 5A and 5B illustrate that geometry.

In some methods of use, the posterior leaflet can be left intact. The coaptation assistance element 500 may attach to the atrium or annulus such that it effectively seals off the posterior leaflet. In some methods of use, the posterior leaflet can be removed. The coaptation assistance element 500 may, in the instance that the leaflet is or has been removed, replace the posterior leaflet. In some embodiments, the coaptation assistance element 500 only requires annular attachment. In some embodiments, the coaptation assistance element 500 only requires attachment at a single point. The single point may be a central location of the coaptation assistance element 500, for instance, a centrally-located hub. In some embodiments, the coaptation assistance element 500 may attach to the atrium or annulus along an edge. In some embodiments, the coaptation assistance element 500 may attach to the atrium or annulus at a location separated from the edge of the coaptation assistance element 500, for instance, at a centrally-located hub.

The coaptation assistance element 500 can include an annular hub 520 engaging an annular anchor 800. The annular anchor 800 may be engaged at a proximal end by a driver, described herein. The annular anchor 800 can include a sharpened tip to engage tissue. In some methods of use, the tip of the annular anchor 800 is within the annular hub 520 during delivery of the coaptation assistance element 500. In some methods of use, the tip of the annular anchor 800 is above the annular section 510 during delivery. The tip of the annular anchor 800 can remain recessed within the annular hub 520 until the annular anchor 800 is rotated to engage tissue. In some embodiments, the coaptation assistance element 500 can be assembled extra-corporeally, engaging the annular anchor 800 to the coaptation assistance element 500 via the annular hub 520 and the drivers to the annular anchor 800. The drivers can then be withdrawn into a delivery catheter, with the coaptation assistance element 500 in a collapsed position. The drivers may be separately manipulated by the operator to place the annular anchor 800 in the appropriate position. Alternatively, the annular anchor 800 may be engaged to the coaptation assistance element 500 and/or the driver sequentially, either before or after deployment through the delivery catheter. The coaptation assistance element 500 after placement can entirely cover the posterior leaflet so that the coaptation assistance element 500 coapts with the anterior leaflet during systole and, with the native anterior leaflet, maintains the valve seal at the annular ring.

In some embodiments, the annular anchor 800 is an active anchor. The user can selectively engage or disengage the annular anchor 800 from tissue. Unlike barbs or other passive anchors, an active anchor can be activated such as by rotation in order to engage tissue. The annular anchor 800 allows placement of the coaptation assistance element 500 prior to engagement of the annular anchor 800. The coaptation assistance element 500 can make contact with the tissue without any adhesion of the annular anchor 800. In some embodiments, the annular anchor 800 and corresponding hub 520 are centrally located on the coaptation assistance element 500. The annular anchor 800 and corresponding hub 520 are spaced apart from any edge of the coaptation assistance element 500. The location of the annular anchor 800 and corresponding hub 520 can be at a neutral center to prevent swinging of the coaptation assistance element 500 when the coaptation assistance element 500 is held by the annular hub 520. The corresponding hub 520 provides a convenient location to hold and move the coaptation assistance element 500.

The annular hub 520 may have a built-in or coupled annular anchor 800. In some embodiments, the annular anchor 800 can be retained by a cross-pin, described herein, within the annular hub 520. The cross-pin may pass through the helical structure of the annular anchor 800 to prevent dislodgement of the annular anchor 800 from the annular hub 520 by a blunt force. The annular anchor 800 may comprise a helix rotatable with respect to the annular hub 520. In some embodiments, other anchors may be used. The annular anchor 800 may be in the form of a tether or other attachment means extending from the coaptation assistance element 500 thru the ventricle septum to the right ventricle. The annular anchor 800 may be in the form of a tether or other attachment means extending thru the apex into the epicardium or pericardium. The annular anchor 800 may be secured from outside the heart in and combined endo/epi procedure. When helical anchors are used, they may comprise bio-inert materials such as Platinum/Ir, a Nitinol alloy, and/or stainless steel.

In some embodiments, the coaptation assistance element 500 can include a single central annular anchor 800 inside the annular hub 520. The coaptation assistance element 500 can be delivered percutaneously as described herein by attachment of a delivery catheter to the annular hub 520. The coaptation assistance element 500 can be configured for adjustable positioning by removing and reattachment of the annular anchor 800. The coaptation assistance element 500 can be recapturable by removal of the annular anchor 800 and withdrawal of the coaptation assistance element 500. The coaptation assistance element 500, may also include secondary anchors including commissural anchors, ventricular anchor, annular anchors, barbs, tethers or any other known fixation device.

As may be seen in FIGS. 5A-5B, the coaptation assistance element 500 can include a plurality of struts 530. In some embodiments, one or more of the struts 530 have one end terminating at the hub 520 and the other end extending radially outwardly toward one of the superior edge 540, the lateral edges 570 and 575, and the inferior edge 580 of the coaptation assistance element 500. The struts 530 may extend outward in various directions from the hub 520, and can be spaced apart from adjacent struts 530 at regular or irregular intervals. In some embodiments, adjacent struts 530 extend outward from the hub at an angle of between about 5 degrees and about 45 degrees, between about 10 degrees and about 30 degrees, or about 5, 10, 15, 20, 25, or 30 degrees with respect to an adjacent strut 530. The struts 530 may be arranged generally parallel to the longitudinal axis of the coaptation assistance element 500 to assist in maintaining the shape of the coaptation assistance element 500 upon placement. The struts 530 may allow the coaptation assistance element 500 to assume a reduced configuration for deployment through a catheter. In some embodiments, the struts 530 that form a portion of the coaptation zone of the implant 500 have a maximum length that is greater than struts 530 that only form a portion of the annular zone of the implant. In some embodiments, the struts 530 that form a portion of the coaptation zone of the implant can be, for example, at least about 10%, 20%, 30%, 40%, 50%, 75%, 100%, 125%, or 150% longer than the struts 530 that form a portion of the annular zone of the implant.

FIG. 5A shows a view of the coaptation assistance element 500 with an annular anchor site 535. The annular anchor site 535 can be a portion of the struts 530. The annular anchor site 535 is shown extending downward from the coaptation assistance element 500 in FIG. 5A. In other embodiments, the annular anchor site 535 may extend in other directions from the coaptation assistance element 500 to engage tissue. In some embodiments, the annular anchor site 535 comprises one or more barbs having a sharpened tip. The annular anchor site 535 may be a passive anchor.

In some embodiments, the coaptation assistance element 500 can include one or more retractable barbs. For instance, the barbs can be retracted during delivery of the coaptation assistance element 500. For instance, the barbs can be advanced after the coaptation assistance element 500 is positioned relative to the anatomical structures. In some embodiments, the barbs are actively retracted and/or advanced. For instance, the delivery catheter described herein can include a mechanism coupled to the barbs designed to retract and/or advance the barbs. In other embodiments, the barbs are passively advanced and/or retracted. In some embodiments, the coaptation assistance element 500 is delivered with the barbs in a retracted state. In some embodiments, the barbs can be covered by the valve body covering as described herein. In some embodiments, the interface between the tissue and the valve body covering pushes back the valve body covering and exposes the barbs. In some embodiments, the tissue dissolves and/or absorbs a portion of the valve body covering and exposes the barbs. In some embodiments, the motion of the purse-string suture, described herein, advances the barbs. In some embodiments, the motion of the purse-string suture causes motion of the valve body covering to expose the barbs. Other configurations are contemplated.

The annular anchor site 535 may define a diameter D1 shown in FIG. 5B, which may in some embodiments correspond to the distance between the medial and lateral commissures of the native valve or the intracommissural distance (ICD). D1 may range between 20-60 mm with, in some embodiments, a preferred length between 35-45 mm, as corresponding most closely to the widest range of human mitral ICD. In some embodiments, D1 may be the distance from the right to left fibrous trigones.

The coaptation assistance element 500 can include a generally annular section 510. The annular section 510 can be positioned above the native leaflets when the coaptation assistance element 500 is deployed. In some embodiments, the annular section 510 may be curved toward the annulus or curved away from the annulus. The annular section 510 can be concave. In other embodiments, the annular section 510 may be substantially flat with respect to the annulus. One or more of the struts 530 may curve laterally from the hub 520 toward the superior edge 540 to assist in maintaining the shape of the annular section 510 of the coaptation assistance element 500 upon deployment. The coaptation assistance element 500 can curve downward from the hub 520 toward the annular anchor site 535. In some embodiments, the coaptation assistance element 500 does not rest against the posterior leaflet. In some embodiments, the annular anchor site 535 is the only point of contact between the posterior annulus of the mitral valve and the coaptation assistance element 500. The superior edge 540 can include an annular radius of curvature. The annular curve radius can curve toward the annulus. The annular curve radius can curve toward the coaptation surface 560. In some embodiments, the annular curve radius can be between 0 mm-5 mm, 5 mm-10 mm, 10 mm-15 mm, 15 mm-20 mm, 20 mm-25 mm, 25 mm-30 mm, etc.

The struts 530 may be composed of a radio-opaque material. In some embodiments, the struts 530 are composed of resiliently deformable materials such as a shape memory metal, e.g., Nitinol or a shape memory polymer. In some embodiments, the material is Elgiloy. In other embodiments, the struts 530 may be composed of other materials to include stainless steel, polypropylene, high density polyethylene (PE), Dacron, acellular collagen matrix such as SIS, or other plastics, etc. In other embodiments, the struts 530 may be a combination such as a high density PE sheath around a core of ePTFE, Dacron, and/or polypropylene. The struts 530 may have a circular cross section, an oval cross section, or be ribbon-like. In some embodiments, the struts 530 are coiled springs or zig-zag shaped. The struts 530 may have a constant stiffness. In some embodiments, one or more struts 530 can have differing stiffness along the length of the one or more struts 530. The struts 530 may be stiffer at the annular end than at the ventricular end of the coaptation assistance element 500. The struts 530 may be less stiff at the annular end than at the ventricular end of the coaptation assistance element 500. The struts 530 may be stiffer at a midpoint, for instance at an inflection point or curve. The struts 530, along with one or more other support structures, can form a frame. In some embodiments, one or more support structures may be provided which run parallel to the superior edge 540 of the coaptation assistance element 500 and assist in maintaining the shape of the superior edge 540. The struts 530 and/or other support structures of the frame can be laser-cut from a Nitinol tube in some embodiments.

The coaptation assistance element body covering 550 may be comprised of a material such as ePTFE. Other materials for the coaptation assistance element body covering 550 include polyester, polyurethane foam, polycarbonate foam, biologic tissue such as porcine pericardium, processed bovine pericardium, pleura, peritoneum, silicone, Dacron, acellular collagen matrix, etc. In some embodiments, the coaptation assistance element body covering 550 can include a foam material surrounded by ePTFE. Use of sponge or foam material enhances the capability of having the coaptation assistance element 500 to fold to a small enough diameter to pass through a catheter. In some embodiments, the coaptation assistance element body covering 550 has no pores. In other embodiments, the coaptation assistance element body covering 550 may have micropores to enhance endothelialization and cellular attachment. The coaptation assistance element body covering 550 may also incorporate a radiopaque material or an echo-enhancement material for better visualization. Any support structures of the coaptation assistance element 500 including the struts 530 or support interface including the hub 520 may be coated with radio-opaque materials such as gold or platinum or impregnated with barium. The coaptation surface 560 may be coated with an echo enhancement material. The coaptation assistance element body covering 550 may be coated with a material to inhibit thrombosis, such as heparin bonding or quinoline and quinoxaline compounds, or with a material to accelerate endothelialization, or with antibiotic to inhibit infection. In some embodiments, the purse-string suture 1010 described herein can incorporate a radiopaque material or an echo-enhancement material for better visualization.

In some embodiments, the struts 530 may be sandwiched between layers of coaptation assistance element body covering 550. The coaptation assistance element body covering 550 may be composed of the same material on the first surface 505 and the second surface 515. The coaptation assistance element body covering 550 may be composed of different materials on the first surface 505, or a portion thereof, and the second surface 515, or a portion thereof. In some embodiments, the struts 530 may be attached to or embedded in the first surface 505 or the second surface 515 of a single layer of coaptation assistance element body covering 550. In some embodiments, the struts 530 may be "stitched" through the coaptation assistance element body covering 550. The annular anchor site 535 can be exposed ends of the struts 530 from the coaptation assistance element body covering 550.

The coaptation assistance element 500 can include a purse-string suture 1010. The purse-string suture 1010 can extend along a portion of the coaptation assistance element 500. The purse-string suture 1010 can extend along the superior edge 540, or a portion thereof. The purse-string suture 1010 can extend along the lateral edge 570, or a portion thereof. The purse-string suture 1010 can extend along the lateral edge 575, or a portion thereof. The purse-string suture 1010 can extend along the inferior edge 580, or a portion thereof. The purse-string suture 1010 can extend along a perimeter, or a portion thereof, of the coaptation assistance element 500. The purse-string suture 1010 can extend along one or more struts 530. The purse-string suture 1010 can extend in a linear path, a non-linear path, a curve, a semi-circle or any open or closed shape.

In some embodiments, the purse-string suture 1010 may be sandwiched between layers of valve body covering 550. For instance, the purse-string suture 1010 can be disposed in a lumen between layers of coaptation assistance element body covering 550. In some embodiments, the purse-string suture 1010 may be attached to or embedded in the first surface 505 or the second surface 515 of a single layer of valve body covering 550. In some embodiments, the purse-string suture 1010 may be "stitched" through the coaptation assistance element body covering 550. The purse-string suture 1010 can pass from the first surface 505 to the second surface 515 and back to the first surface 505. The purse-string suture 1010 can include one or more exposed ends from the coaptation assistance element body covering 550. In embodiments where the purse-string suture 1010 is a loop, the purse-string suture can include one or more exposed sections of the loop from the valve body covering.

The coaptation assistance element 500 may be collapsed by tightening the purse-string suture 1010. The coaptation assistance element 500 may be expanded by loosening the purse-string suture 1010. The one or more exposed ends or loops can be manipulated by a delivery catheter or other tool to tighten or loosen the purse-string suture 1010. The ability to collapse or expand the coaptation assistance element 500 may be beneficial for recapture of the coaptation assistance element 500 and/or repositioning of the coaptation assistance element 500.

The coaptation assistance element 500 may be rotated by tightening one or more purse-string suture 1010 and/or loosening one or more purse-string suture 1010. For instance, tightening one or more purse-string suture 1010 on the lateral edge 570 and/or loosening one or more purse-string suture 1010 on the lateral edge 575 may cause the coaptation assistance element 500 to rotate. One or more purse-string sutures 1010 may be coupled to the coaptation assistance element 500 to enable multi-directional rotation.

The coaptation assistance element 500 may be expanded by loosening the purse-string suture 1010. The one or more exposed ends or loops can be manipulated by a delivery catheter or other tool to tighten or loosen the purse-string suture 1010. The ability to collapse or expand the coaptation assistance element 500 may be beneficial for recapture of the coaptation assistance element 500 and/or repositioning of the coaptation assistance element 500.

The coaptation surface 560 of the coaptation assistance element 500 may be adjusted by motion of the purse-string suture 1010. The one or more exposed ends or loops can be manipulated by a delivery catheter or other tool to tighten or loosen the purse-string suture 1010 to change the curvature of the coaptation surface 560 in situ. The ability to adjust the curvature of the coaptation assistance element 500 may be beneficial to conform to the geometry of heart including the geometry of the anterior leaflet.

The annular dimension of the coaptation assistance element 500 may be adjusted by motion of the purse-string suture 1010. The one or more exposed ends or loops can be manipulated by a delivery catheter or other tool to tighten or loosen the purse-string suture 1010 to change one or more dimensions of the coaptation assistance element 500 in situ. The ability to adjust dimensions of the coaptation assistance element 500 may be beneficial to conform to the geometry of the heart.

The coaptation assistance element 500 can include one or more purse-string sutures 1010. In some embodiments, the coaptation assistance element 500 includes one purse-string suture, two purse-string sutures, three purse-string sutures, four purse-string sutures, five purse-string sutures, six purse-string suture, seven purse-string sutures, eight purse-string sutures, nine purse-string sutures, ten purse-string sutures, etc. For instance, a purse-string suture 1010 can extend along each edge of the coaptation assistance element 500. When multiple purse-string sutures are provided, the purse-string sutures 1010 can act together to change the configuration of the coaptation assistance element 500. When multiple purse-string sutures are provided, the purse-string sutures 1010 can act independently to change the configuration of the coaptation assistance element 500.

FIG. 5A further illustrates a coaptation element height, corresponding to the distance between the inferior edge 580 and the annular hub 520 as measured perpendicular to the plane defined by the annulus of the valve. Coaptation element height of some embodiments may be 10-80 mm, with some embodiments ranging between 40-55 mm. The coaptation element height can be between 10-20 mm, 20-30 mm, 30-40 mm, 40-50 mm, 50-60 mm, 60-70 mm, 70-80 mm, etc.

FIG. 5A illustrates the generally triangular shape of coaptation assistance element 500, such that the coaptation assistance element 500 has a superior edge 540, lateral edges 570 and 575, and inferior edge 580. In some embodiments, the superior edge 540 has a length greater than that of inferior edge 580, such that the transverse distance between lateral edges 570 and 575 generally decreases from superior to inferior on the coaptation assistance element 500. For example, the length of the superior edge 540 may be in the range of 15-50 mm, or 25-35 mm, while the length of the inferior edge 580 may be in the range of 1-15 mm, or 2-6 mm.

The annular hub 520 may be a hub, an eyelet, or any other tether site known in the art. In some embodiments, the annular hub 520 is located at a midpoint of the distance D1. In some embodiments, the annular hub 520 is located at a neutral center to prevent swinging of the coaptation assistance element 500 when the coaptation assistance element 500 is held by the annular hub 520. In other embodiments, the annular hub 520 is located at one of the commissures. While only one annular anchor 800 is shown, in other embodiments, two or more annular hubs 520 may be provided.

In some embodiments, the struts 530 can comprise NiTi tubing. In some embodiments, the struts 530 can be laser cut from the tubing. In some embodiments, the frame including one or more struts 530 and/or one or more support structures can be laser cut from a single piece of material. In some embodiments, the frame including one or more struts 530, the annular hub 520, and/or one or more support structures can be integrally formed. In some embodiments, the coaptation assistance element body covering 550 comprises ePTFE lamination. The lamination can surround one or more of the struts 530 and/or one or more support structures (e.g., one side, two sides, first side 505, second side 515). The struts 530 and/or one or more support structures can be encased by two or more layers of lamination. The perimeter of the annular section 510 of the coaptation assistance element 500 can be cupped down. The perimeter of the annular section 510 of the coaptation assistance element 500 can be cupped up. The perimeter of the annular section 510 of the coaptation assistance element 500 can include secondary anchors such as the annular anchor site 535.

In some embodiments, the annular anchor 800 and the annular hub 520 form a single central anchor system. In some embodiments, the coaptation assistance element 500 is affixed to the tissue by only one annular anchor 800 which passes through the hub 520. In other embodiments, additional fixation is included. In some embodiments, the coaptation assistance element 500 is affixed to the tissue by the one anchor 800 which passes through the hub 520 and the annular anchor site 535 as described herein. The system can include features to allow rotational adjustment of the coaptation assistance element 500. For instance, the hub 520 and/or the annular anchor 800 can be coupled to the delivery catheter to allow the transmission of axial movement and/or torque. The coaptation assistance element 500 can be immovably grasped by a delivery catheter such that rotation of a feature of the delivery catheter, such as a handle, causes rotation of the coaptation assistance element 500. The coaptation assistance element 500 can be immovably grasped by a delivery catheter such that axial movement of a feature of the delivery catheter, such as a drive shaft, causes axial movement of the coaptation assistance element 500.

In some embodiments, the hub 520 is located at a neutral position on the coaptation assistance element 500. The neutral position can be a central location on the annular section 510. The neutral position can be between the lateral edges 505, 515. The neutral position can be between the superior edge 540 and the cooptation surface 560. The neutral position can enhance stability of the coaptation assistance element 500 when the coaptation assistance element 500 is grasped at a single location such as the hub 520 and/or the annular anchor 800. The neutral position can be aligned with a structure of the mitral valve. The neutral position can be aligned along the coaptation zone.

In some embodiments, the coaptation assistance element 500 is delivered percutaneously as described herein. In some embodiments, the coaptation assistance element 500 is adjustable via a delivery catheter. For instance, the coaptation assistance element 500 can be expanded and/or collapsed by the delivery catheter. For instance, the coaptation assistance element 500 can be rotated about a fixed position of the annular hub 520. For instance, the coaptation assistance element 500 can be recapturable. For instance, the coaptation assistance element 500 can be engaged and reengaged by the delivery catheter. For instance, the annular anchor 800 can be disengaged from the tissue and the delivery catheter can recapture the coaptation assistance element 500.

Figure 5C:
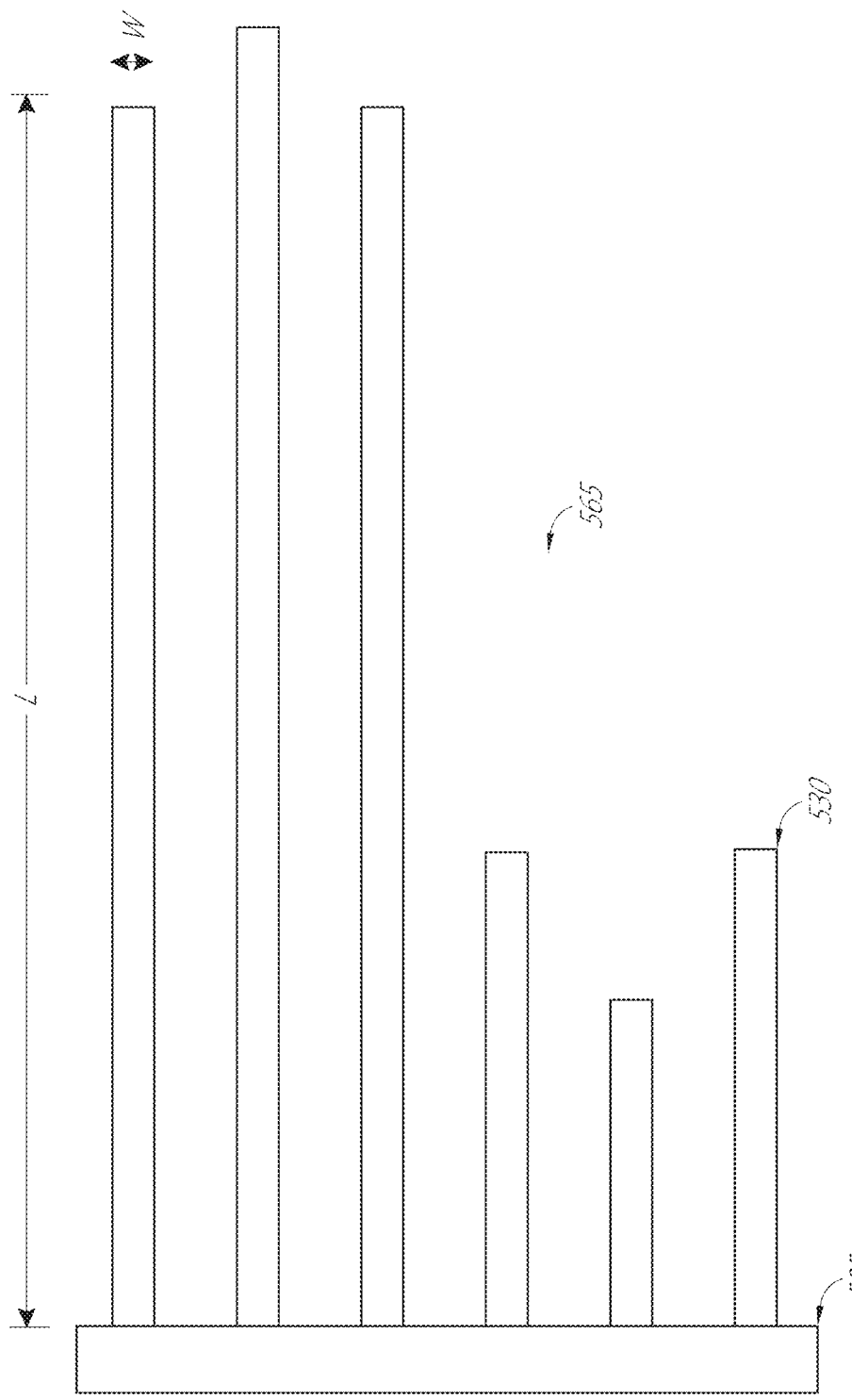
FIGS. 5C-5D illustrates an embodiment of the struts of a coaptation assistance element.
Figure 5D:
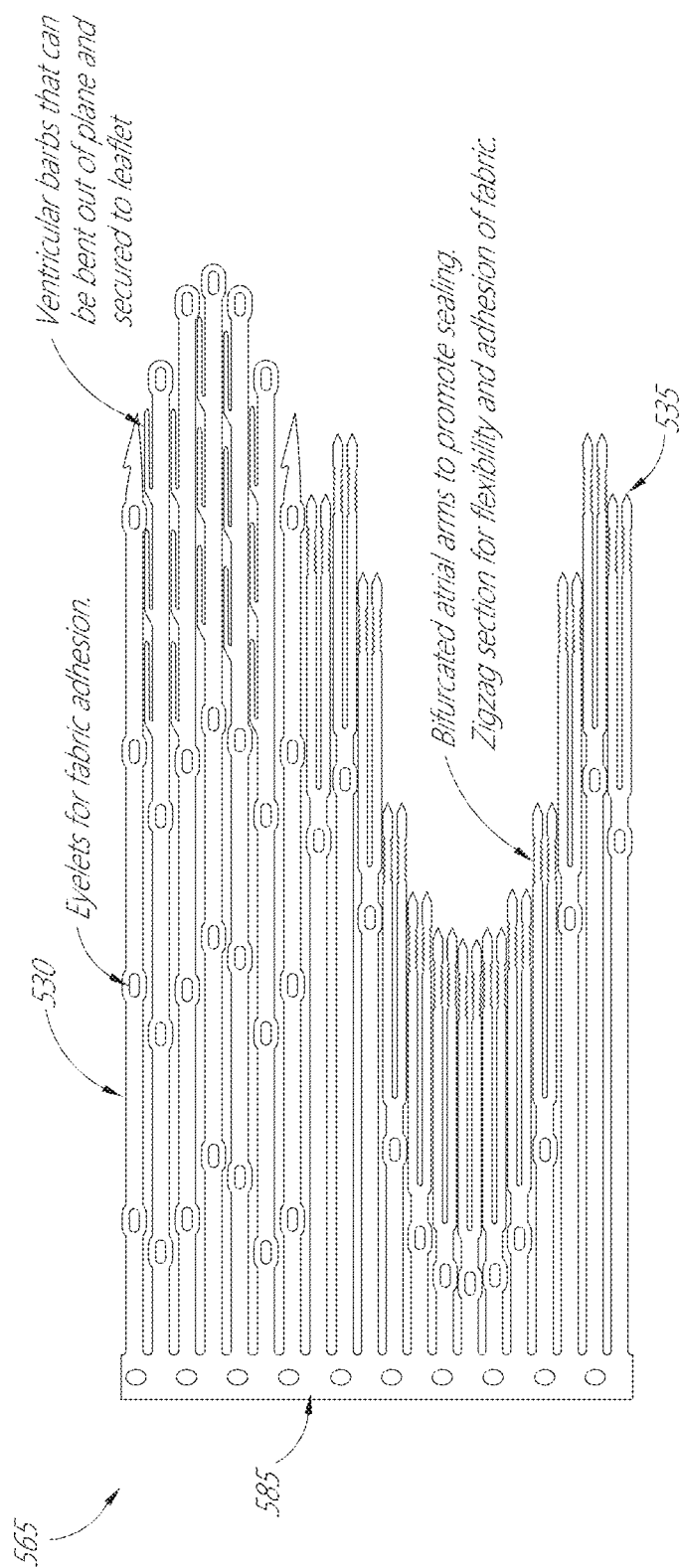

FIGS. 5C-5D illustrate embodiments of a frame 565 of the coaptation assistance element 500. These figures illustrated the flattened patterns of the frame 565 prior to bending and/or shape setting. In some embodiments, the frame 565 is cut from a tubular stock. In other embodiments, the frame 565 is cut from flat stock such as a flat sheet of material. The frame 565 including portions thereof can be laser cut. The frame 565 can include one or more struts 530. In the embodiment shown in FIG. 5D, the frame 565 includes twenty struts 530 but other configurations are contemplated (e.g., one strut, two struts, three struts, four struts, five struts, between five and ten struts, between ten and fifteen struts, between fifteen and twenty struts, between twenty and twenty-five struts, between twenty-five and thirty struts, between two and thirty struts, between five and thirty struts, etc.). In some embodiments, the frame 565 can include about, at least about, or no more than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more struts, or a range incorporating any two of the aforementioned values. In some embodiments, the length of the struts extending to the superior upwardly or downwardly cupping lip are shorter than, such as less than about 80%, 70%, 60%, 50%, 40%, 30%, 20%, or less than the longest inferior-extending strut.

In some embodiments, one, two, or more struts 530 are coupled to a backing 585. In some embodiments, the backing 585 is transverse to the direction of the struts 530. In the illustrated embodiment, the backing 585 is vertical or generally vertical and the struts 530 are horizontal or generally horizontal. In some embodiments, the backing 585 is the annular hub 520. For instance, the two ends of the backing 585 can be joined using methods known in the art to form the annular hub 520. The two ends are joined, for instance, if the frame 565 is cut from flat stock. In other embodiments, the frame 565 is formed from tubular stock. The backing 585 can be a portion of uncut tubular stock. The two ends of the backing 585 may not need to be joined if the frame 565 is formed from tubular stock. The uncut tubular stock can form the annular hub 520. The patters of the frame 565 as shown in FIG. 5D can be cut from tubular stock, thereby eliminating the need to join the two ends of the backing. Other modes of manufacturing are contemplated to form the frame 565. In other embodiments, the backing 585 forms at least a portion of the annular hub 520. In some embodiments, the backing 585 surrounds at least a portion of the annular hub 520. In some methods of manufacturing, the backing 585 can be formed into a shape of a circle. In some methods of manufacturing, the struts 530 extend radially outward from the backing 585 once the backing 585 is shaped into a circle. The backing 585 can include one or more openings designed to accept a cross-pin, as disclosed herein. In some methods of manufacturing, the backing 585 is removed.

Referring to FIGS. 5A and 5C, a plurality of struts 530 can extend from the annular hub 520 to the inferior end 580. In some embodiments, these struts 530 are longer than other struts 530 of the frame 565. In some embodiments, the struts 530 might include an anchor or barb that interacts with the subvalvular structure, including the ventricular wall. In some embodiments, these struts engage the posterior leaflet or another anatomical structure. In some embodiments, the ventricular anchoring is passive.

Referring to FIG. 5A-5D, a plurality of struts 530 can extend from the annular hub 520 to the superior end 540. In some embodiments, these struts 530 are shorter than other struts 530 of the frame 565. In some embodiments, these struts 530 form an atrial anchor and/or the annular anchor site 535 described herein. In some embodiments, these struts engage the annulus or another anatomical structure. In some embodiments, the annular anchoring is passive.

Referring to FIGS. 5A and 5D, a plurality of struts 530 can extend from the annular hub 520 to the lateral edges 570 and 575. In some embodiments, these struts 530 have a mid-length between the ventricular struts and the atrial struts. In some embodiments, these struts engage the commissures or another anatomical structure. In some embodiments, the commissural anchoring is passive.

The struts 530 can have a variety of lengths based on the desired shape of the coaptation assistance element 500. As shown in FIGS. 5C-5D, two or more struts 530 have a different length. As shown in FIGS. 5C-5D, two or more struts 530 have the same length. FIG. 5C shows a schematic model of the frame 565. One or more of the top three struts can form the coaptation surface 560 and extend to the inferior edge. One or more of the bottom three struts can form the annular portion and extend to the superior edge. The struts 530 can be laser-cut from a tube. The length can be measured from the annular hub 520 to an edge of the coaptation assistance element 500. The range of the strut length can be 1 mm to 50 mm. The range of the strut length can be 5 mm to 35 mm for the annular portion 510. The strut length can be about 15 mm for the annular portion 510. The range of the strut length can be 20 mm to 35 mm for the coaptation surface 560. The strut length can be about 30 mm for the coaptation surface 560. Other configurations of the range of strut length are contemplated e.g., 5 mm to 45 mm, 10 mm to 40 mm, 15 mm to 35 mm, about 5 mm, about 10 mm, about 15 mm, about 20 mm, about 25 mm, about 30 mm, about 35 mm, about 40 mm, about 45 mm, about 50 mm, about 55 mm, about 60 mm, 1 mm to 10 mm, 5 mm to 15 mm, 10 mm to 20 mm, 15 mm to 25 mm, 20 mm to 30 mm, 25 mm to 35 mm, 30 mm to 40 mm, etc.

The width can be measured perpendicular to the strut length. The range of the strut width can be 0.1 mm to 2 mm. One or more struts can have an outer diameter or width of about 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, less than 0.5 mm, less than 1 mm, less than 1.5 mm, less than 2 mm, etc. One or more struts 530 can have a varying width along the strut length. In some embodiment, one or more struts 530 taper near an edge of the coaptation assistance element 500. In some embodiments, one or more struts 530 taper near the annular hub 520. The one or more struts 530 can include a reduced diameter or taper at the connection between the one or more struts 530 the annular hub 520. The taper near the annular hub 520 can aid in collapsing the coaptation assistance element 500. The taper near the annular hub 520 can facilitate insertion of the coaptation assistance element 500 into the delivery catheter. The taper can reduce stress and/or strain in the strut 530 during collapse. In some embodiments, the taper can aid in longer fatigue life. In some embodiments, one or more struts 530 include a varying width taper. The width of the strut 530 can vary along the length of the strut 530. One or more struts 530 can include eyelets along the length of the strut 530. In some embodiments, the eyelets can reduce stress of the struts 530. In some embodiments, the eyelets can facilitate adhesion between the strut 530 and the valve body covering 550.

The thickness can be measured perpendicular to the strut length and strut width. The thickness can be determined by the thickness of the material of the frame, as described herein. The range of the strut thickness can be 0.2 mm to 0.5 mm. One or more struts can have a thickness of about 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, less than 0.5 mm, less than 1 mm, less than 1.5 mm, less than 2 mm, etc.

One or more the struts 530 can include barbs. In some embodiments, the barbs can be configured for placement near the ventricular end of the coaptation assistance element 500. In some embodiments, the barbs can be bent out of the plane of the strut 530. In some embodiments, the barb can have a bayonet configuration. In some embodiments, the barbs can have a sharped tip. In some embodiments, one or more struts 530 can be bifurcated. In some embodiments, one or more struts 530 can include one or more zigzag sections. In some embodiments, the zigzag section reduces stress and/or increases flexibility of the strut 530. In some embodiments, the zigzag section facilitates adhesion between the strut 530 and the coaptation assistance element body covering 550.

In some embodiments, one or more struts 530 can include supplemental barbs. In some embodiments, the supplemental barbs can be bent out of the plane of the strut 530. In some embodiments, one or more portions of the strut length are bent out of the plane of the strut. For instance, a portion of the strut can be twisted or bent during manufacturing. In some embodiments, the portion that is bent out of plane is shaped to engage tissue. In some embodiments, one or more struts 530 can include increased widths to compensate for electropolishing or other post manufacturing processes. In some embodiments, the backing 585 can include one or more features to engage the delivery catheter described herein. In some embodiments, the backing 585 can include one or more notches designed to interface with a locking tab or other feature of the delivery catheter as described herein. In some embodiments, one or more struts 530 can include a greater width than other struts 530. In some embodiments, the frame 565 includes two or more struts 530 that have a greater width than other struts 530. The two or more struts 530 can facilitate visualization of the coaptation assistance element 500. In some embodiments, the two or more struts 530 that have a greater width are designed to be placed near the commissures when the coaptation assistance element 500 is deployed. In some embodiments, one or more struts 530 can have smaller width compared with one or more other struts. In some embodiments, each strut 530 has the same width near the annular hub 520. The backing 585 can be modified to interface with the delivery catheter, as described herein. The backing 585 can be designed to allow independent rotation of the anchor 800 within the hub of the coaptation assistance element 500.

FIGS. 5E, 5F, and 5G show an embodiment of the coaptation assistance element 500 without barbs. FIG. 5E shows a schematic perspective view of the coaptation assistance element 500. FIG. 5F shows a schematic perspective view of the first surface 505 disposed toward a mal-coapting native leaflet. FIG. 5G shows a schematic cross-sectional view including the anchor 800.

FIGS. 5H, 5I, and 5J show an embodiment of the coaptation assistance element 500 with leaflet anchor sites 545. As shown in FIG. 5A, the annular anchor sites 535 such as barbs can extend along an edge of the coaptation assistance element 500. FIGS. 5H, 5I, and 5J show an embodiment of the coaptation assistance element 500 with leaflet anchor sites 545 extending from the first surface 505 disposed toward a mal-coapting native leaflet.

FIG. 5H shows a schematic perspective view of the coaptation assistance element 500 including an enlarged section showing the leaflet anchor sites 545. FIG. 5I shows a schematic perspective view of the first surface 505 disposed toward a mal-coapting native leaflet. FIG. 5J shows a schematic cross-sectional view including the anchor 800.

In some embodiments, the leaflet anchor sites 545 comprise one or more barbs having a sharpened tip. The leaflet anchor sites 545 may be a passive anchor. In some embodiments, the coaptation assistance element 500 can include one or more retractable barbs. For instance, the leaflet anchor sites 545 can be retracted during delivery of the coaptation assistance element 500. For instance, the leaflet anchor sites 545 can be advanced after the coaptation assistance element 500 is positioned relative to the anatomical structures. In some embodiments, the leaflet anchor sites 545 are actively retracted and/or advanced. For instance, the delivery catheter described herein can include a mechanism coupled to the leaflet anchor sites 545 designed to retract and/or advance the barbs. In other embodiments, the leaflet anchor sites 545 are passively advanced and/or retracted. In some embodiments, the leaflet anchor sites 545 can be covered by the valve body covering as described herein. In some embodiments, the interface between the tissue and the valve body covering pushes back the valve body covering and exposes the leaflet anchor sites 545. In some embodiments, the tissue dissolves and/or absorbs a portion of the valve body covering and exposes the leaflet anchor sites 545. In some embodiments, the motion of the purse-string suture, described herein, advances the leaflet anchor sites 545. In some embodiments, the motion of the purse-string suture causes motion of the valve body covering to expose the leaflet anchor sites 545. Other configurations are contemplated.

One or more struts 530 may have one or more barbs along the length of the strut 530. In the illustrated embodiment, five struts 530 each have four leaflet anchor sites 545 along the length of the struts. Other configurations are contemplated varying the number of struts 530 (e.g., one strut, two struts, three struts, four struts, five struts, six struts, seven struts, eight struts, nine struts, ten struts, etc.) and varying the number of leaflet anchor sites 545 per strut 530 (e.g., one barb, two barbs, three barbs, four barbs, five barbs, six barbs, seven barbs, eight barbs, nine barbs, ten barbs, etc.). One or more struts 530 can have the same number of leaflet anchor sites 545. Two or more struts 530 can have a different number of leaflet anchor sites 545. The leaflet anchor sites 545 can be disposed to engage the posterior leaflet.

In some embodiments, the struts 530 may be sandwiched between layers of valve body covering 550. In some embodiments, the struts 530 may be attached to or embedded in the first surface 505 or the second surface 515 of a single layer of valve body covering 550. In some embodiments, the struts 530 may be "stitched" through the valve body covering 550. The first surface 505 can include one or more openings for the leaflet anchor sites 545. In other embodiments, the leaflet anchor sites 545 can push through the valve body covering 550. The leaflet anchor sites 545 can have a pre-set curve which can exert a force on the first surface 505. The leaflet anchor sites 545 can be sharpened to cut through the valve body covering 550.

The frame 565 can have many advantages. The frame 565 can be formed from a flattened pattern. The frame 565 can include an edge which forms the annular hub 520. The edge can include a longitudinal strip or backing 585. One or more struts 530 can extend from the backing 585. In the illustrated embodiment of FIGS. 5C and 5D, the one or more struts 530 are perpendicular to the longitudinal strip. The struts 530 are generally parallel. In some embodiments, the struts 530 are generally perpendicular to the backing 585 that forms the annular hub 520. In some embodiments, the struts 530 form an angle with the backing 585. For instance, the longitudinal axis of the struts 530 can form an acute angle with the backing 585. The angle can aid in the collapse of the struts 530 into the delivery catheter.

The frame 565 can be constructed from a single, planar sheet of material. The frame 565 can be precisely cut using water jet, laser etching or similar technology. The details of the struts 530, including barbs, can be machined into the struts 530. The frame 565 can be bent and/or shape set to achieve the desired geometry. In some embodiments, the backing 585 is folded to form a loop. The frame 565 can be rolled into a tubular shape. The backing 585 can be welded or otherwise secured. The backing 565 when secured end to end to form a loop can be considered the annular hub 520.

The struts 530 are bent to the desired configuration. The struts 530 can form one or more curves. The struts 530 can have one or more inflection points. The struts 530 can have concave portions and/or convex portions. One or more struts 530 can include a radially outward flare beginning at an inflection point. In some embodiments, the superior edge 540 is curved upward away from the inferior edge 580. In some embodiments, the superior edge 540 is curved downward toward the inferior edge 580. In some embodiments, one or more struts 530 can be substantially flat. The struts 530 near the commissures can be substantially flat. In some embodiments, the inferior edge 580 is curved backward toward the superior edge 540. In some embodiments, the inferior edge 580 is curved forward away from the superior edge 540.

The struts 530 can be equally spaced about the circumference of the annular hub 520. The struts 530 can be unequally spaced about the circumference of the annular hub 520. The struts 530 extending along a portion of the circumference of the annular hub 520 are different than struts extending along another portion of the circumference of the annular hub 520. One or more designated portions of the struts 530 can be designed to be placed near the annular region of the heart. One or more designated portions of the struts 530 can be designed to be placed near the commissure region of the heart. One or more designated portions of the struts 530 can be designed to be placed near the ventricular region of the heart. The geometry of the radially extending struts 530 can be shaped to match the geometry of the patient. In some embodiments, the geometry is patient specific. The operator can shape one or more struts 530 based on the geometry of the heart. The operator can modify the shape of one or more struts 530 based on the geometry of the patient.

Figure 5K:
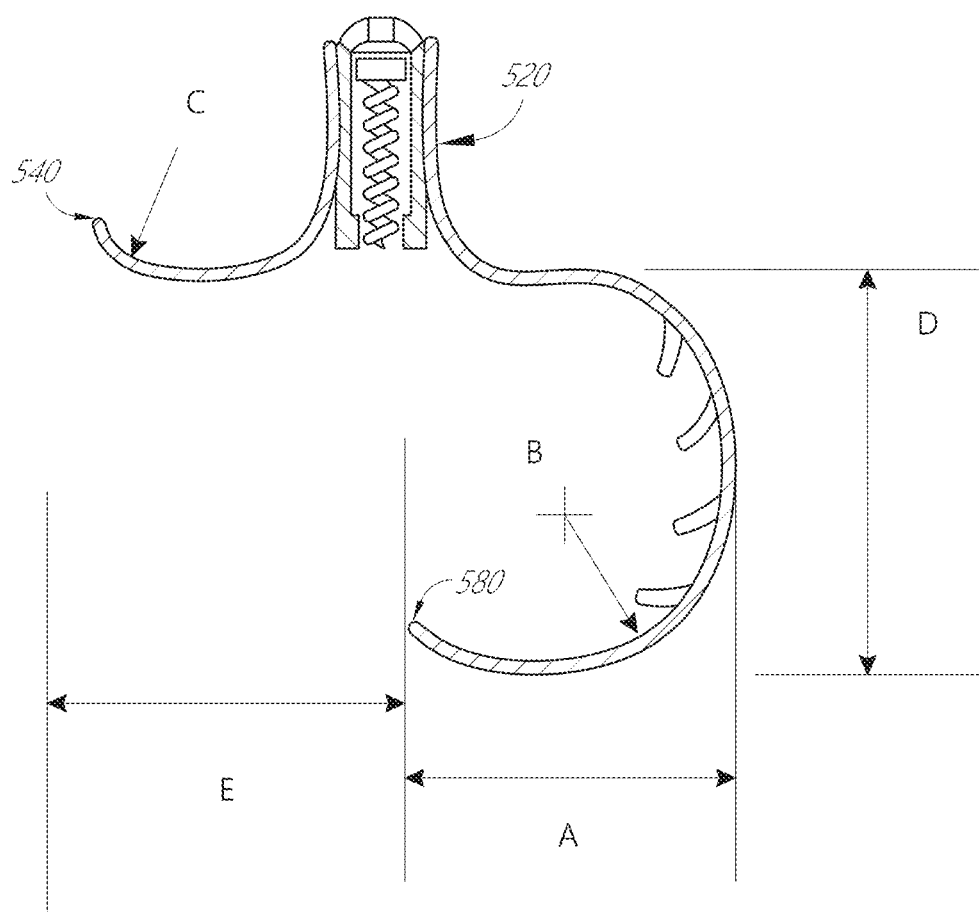
FIG. 5K illustrates dimensions of the coaptation assistance element of FIG. 5A.

FIG. 5K illustrates dimensions of the coaptation assistance element 500. The coaptation assistance element 500 can include a dimension A. The dimension A can be a linear projected dimension or posterior projection. In some embodiments, the range of dimension A can be 1 mm to 40 mm. In some embodiments, the range of dimension A can be 4 mm to 24 mm. Other configurations of the range of dimension A are contemplated e.g., 5 mm to 35 mm, 10 mm to 30 mm, 15 mm to 25 mm, about 1 mm, about 2 mm, about 3 mm, about 4 mm, about 5 mm, about 6 mm, about 7 mm, about 8 mm, about 9 mm, about 10 mm, 1 mm to 10 mm, 5 mm to 15 mm, 10 mm to 20 mm, 15 mm to 25 mm, 20 mm to 30 mm, 25 mm to 35 mm, 30 mm to 40 mm, etc. The dimension A can be 0 mm if no posterior projection, for instance if the coaptation assistance element 500 is straight.

The coaptation assistance element 500 can include a dimension B. In some embodiments, the dimension B can be a radius of curvature. The radius of curvature can be concave or convex, as described herein. In some embodiments, the range of dimension B can be 1/16 inch to 1/2 inch. In some embodiments, the range of dimension B can be 1.5 mm to 13 mm. In some embodiments, the range of dimension B can be 1/4 inch to 3/8 inch. In some embodiments, the range of dimension B can be 6 mm to 9.5 mm. In some embodiments, the range of dimension B can be 1 mm to 15 mm. Other configurations of the range of dimension B are contemplated e.g., 2 mm to 14 mm, 3 mm to 13 mm, 4 mm to 12 mm, 5 mm to 11 mm, 6 mm to 10 mm, 7 mm to 9 mm, about 1 mm, about 2 mm, about 3 mm, about 4 mm, about 5 mm, about 6 mm, about 7 mm, about 8 mm, about 9 mm, about 10 mm, 1 mm to 10 mm, 5 mm to 15 mm, 10 mm to 20 mm, etc. The dimension B can be 0 mm if no curvature, for instance if the coaptation assistance element 500 is straight.

The coaptation assistance element 500 can include a dimension C. In some embodiments, the dimension C can be a radius of curvature near the superior edge 540. In some embodiments, the range of dimension C can be 1 mm to 10 mm. In some embodiments, the range of dimension C can be 1 mm to 5 mm. Other configurations of the range of dimension C are contemplated e.g., 2 mm to 9 mm, 3 mm to 8 mm, 4 mm to 7 mm, 5 mm to 6 mm, about 1 mm, about 2 mm, about 3 mm, about 4 mm, about 5 mm, about 6 mm, about 7 mm, about 8 mm, about 9 mm, about 10 mm, 1 mm to 15 mm, 5 mm to 10 mm, 3 mm to 9 mm, etc. The dimension C can be 0 mm if no curvature, for instance if the coaptation assistance element 500 is straight.

The coaptation assistance element 500 can include a dimension D. The dimension D can be a coaptation element height. The dimension D can correspond to the distance between the inferior edge 580 and the atrial anchor site or annular hub 520 as measured perpendicular to the plane defined by the annulus of the valve. In some embodiments, the range of dimension D can be 10 mm to 80 mm. In some embodiments, the range of dimension D can be 40 mm to 55 mm. Other configurations of the range of dimension D are contemplated e.g., 5 mm to 105 mm, 10 mm to 100 mm, 15 mm to 95 mm, 20 mm to 90 mm, 25 mm to 85 mm, 30 mm to 80 mm, 35 mm to 75 mm, 40 mm to 70 mm, 45 mm to 65 mm, 50 mm to 60 mm, about 10 mm, about 20 mm, about 30 mm, about 40 mm, about 50 mm, about 60 mm, about 70 mm, about 80 mm, about 90 mm, about 100 mm, 10 mm to 50 mm, 20 mm to 60 mm, 30 mm to 70 mm, 40 mm to 80 mm, 50 mm to 90 mm, 60 mm to 100 mm, 70 mm to 110 mm, etc.

The coaptation assistance element 500 can include a dimension E. The dimension E can be a linear projected dimension or anterior projection. In some embodiments, the range of dimension E can be 2 mm to 20 mm. In some embodiments, the range of dimension E can be 5 mm to 10 mm. Other configurations of the range of dimension E are contemplated e.g., 0 mm to 25 mm, 5 mm to 20 mm, 10 mm to 15 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, 1 mm to 10 mm, 5 mm to 15 mm, 10 mm to 20 mm, 15 mm to 25 mm, 20 mm to 30 mm, 25 mm to 35 mm, 30 mm to 40 mm, etc. The dimension E can be 0 mm if no anterior projection.

The struts 530 of the coaptation assistance element 500 can form a posterior curve of the coaptation surface 560. The posterior bend can have a bend length of the distal 30-100% of the strut. In some embodiments, the posterior bend can have a bend length of at least the distal 40% of the strut. The angle of the posterior bend can be in the range of 0 degrees to 90 degrees with respect to the longitudinal axis of the coaptation assistance element 500. In some embodiments, the angle of the posterior bend can be in the range 45 degrees to 90 degrees.

FIG. 6 illustrates an embodiment of a coaptation assistance element 600. The coaptation assistance element 600 can be similar to the coaptation assistance element 500, and include any features of the coaptation assistance element 500 described herein, with certain additional features described below.

The coaptation assistance element 600 can include an annular hub 620 engaging an annular anchor (not shown). The annular hub 620 may have a built-in or coupled annular anchor, such as annular anchor 800 described herein. The annular anchor may include a helix rotatable with respect to the annular hub 620. In some embodiments, the coaptation assistance element 600 can include a single annular anchor inside the annular hub 620. The coaptation assistance element 600 can be delivered percutaneously as described herein by attachment of a delivery catheter to the annular hub 620.

As may be seen in FIG. 6, the coaptation assistance element 600 can include struts 630. In some embodiments, one, two, or more struts 630 have one end terminating at the annular hub 620 and the other end extending radially outwardly toward the superior edge 640, the lateral edges 670 and 675, and the inferior edge 680 of the coaptation assistance element 600. The struts 630 may extend outward from the hub 620. The struts 630 may be arranged generally parallel to the longitudinal axis of the coaptation assistance element 600 to assist in maintaining the shape of the coaptation assistance element 600 upon placement. The struts 630 may allow the coaptation assistance element 600 to assume a reduced configuration for deployment through a catheter.

The coaptation assistance element 600 can include an annular section 610. The annular section 610 can be positioned above the annulus of the native leaflet when the coaptation assistance element 600 is deployed and form a lip as shown. In some embodiments, the annular section 610 may be may be curved upwardly, e.g., away from the annulus and in a direction substantially opposite from, and substantially parallel to the coaptation surface 660, and form the superior-most portion of the coaptation assist element 600 when implanted. The annular section 610 can be convex. In other embodiments, the annular section 610 may be may be substantially flat with respect to the annulus. One or more of the struts 630 may curve laterally from the annular hub 620 toward the superior edge 640 to assist in maintaining the shape of the annular section 610 of the coaptation assistance element 600 upon deployment. The coaptation assistance element 600 can curve upward from the annular hub 620. In some embodiments, the superior edge 640 does not rest against the posterior leaflet. The superior edge 640 can include an annular radius of curvature. The annular curve radius can curve away from the annulus. The annular curve radius can curve toward the coaptation surface 660. In some embodiments, the annular curve radius can be between 0 mm-5 mm, 5 mm-10 mm, 10 mm-15 mm, 15 mm-20 mm, 20 mm-25 mm, 25 mm-30 mm, etc., or ranges incorporating any two of the previous values. The coaptation assistance element body covering 650 may be similar to the coaptation assistance element body covering 550 described herein.

In some embodiments, the perimeter of the annular section 610 is cupped upward and in a direction substantially opposite to the longitudinal axis of the coaptation surface 660. In some embodiments, the coaptation assistance element 600 includes annular anchor site similar to annular anchor site 535. In other embodiments, the coaptation assistance element 600 does not include annular anchor site as shown in FIG. 6.

FIGS. 7A-7E illustrate an embodiment of a coaptation assistance element 700. The coaptation assistance element 700 can be similar to the coaptation assistance elements 500 or 600, and can include any feature described herein, with certain elements described below.

Figure 7A:
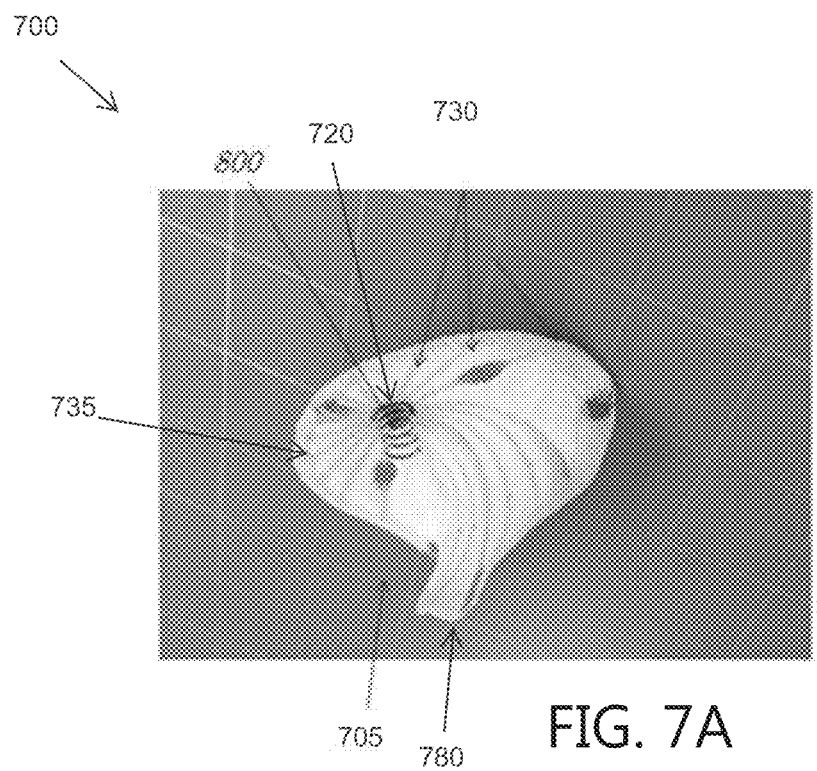
FIG. 7A illustrates a perspective view of an embodiment of a coaptation assistance element showing a first surface disposed toward a mal-coapting native leaflet.
Figure 7B:
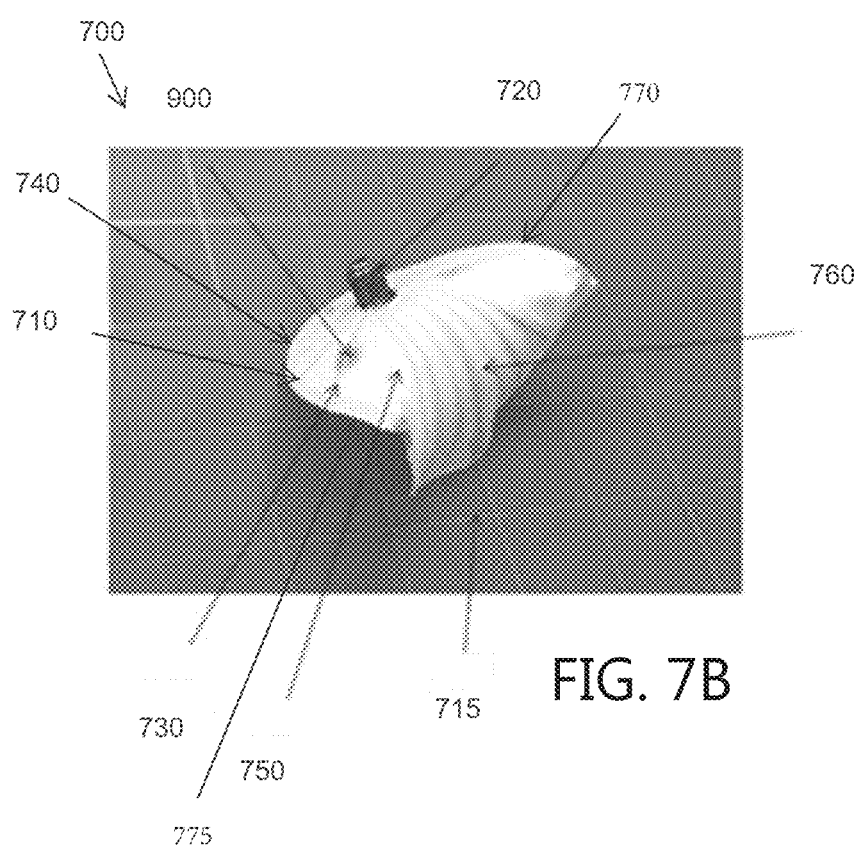
FIG. 7B illustrates another perspective view of the coaptation assistance element of FIG. 7A showing a second surface which can include a coaptation surface.
Figure 7C:
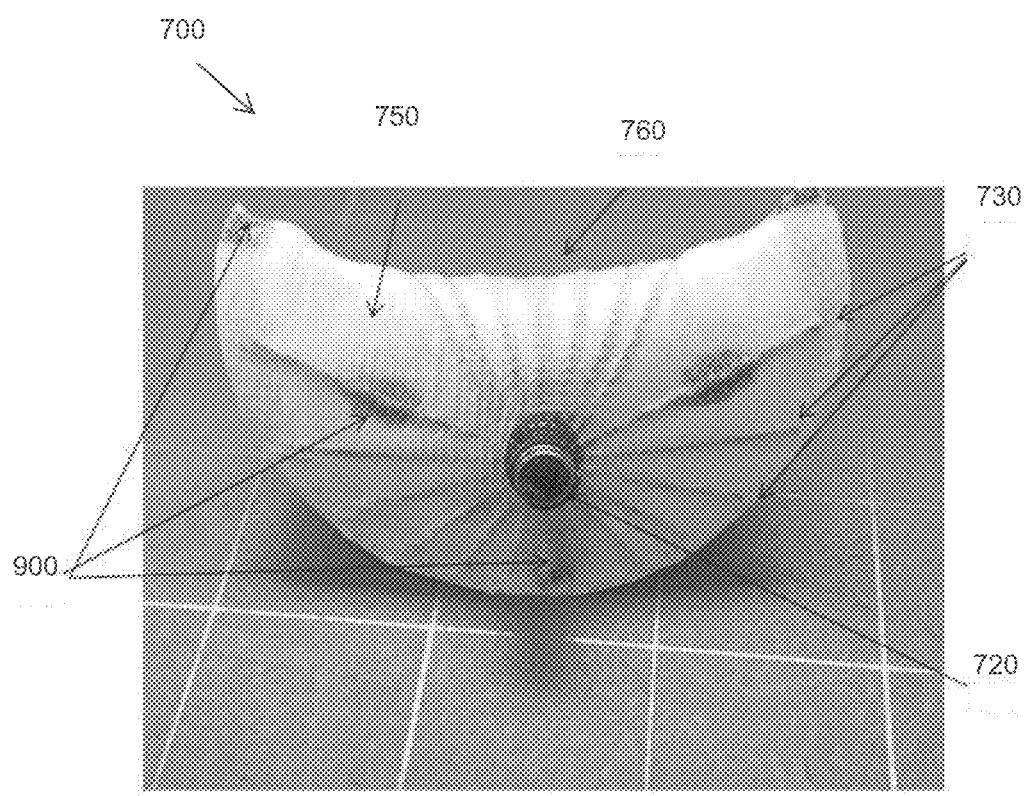
FIG. 7C illustrates a top view of the coaptation assistance element of FIG. 7A.

The coaptation assistance element 700 can include a first surface 705 and a second surface 715. FIG. 7A illustrates a perspective view of the first surface 705 or inferior surface disposed toward a mal-coapting native leaflet, in the instance of a mitral valve, the posterior leaflet. FIG. 7B illustrates a perspective view of the second surface 715 or superior surface which may be disposed toward the anterior leaflet. The second surface 715 can include a coaptation surface 760. The superior edge 740 of the coaptation assistance element 700 may be curved to match the general shape of the annulus or adjoining atrial wall. The superior edge 740 can be curved downward, toward the posterior leaflet, as shown in FIG. 7B. FIG. 7C illustrates a top view of the coaptation assistance element 700.

FIGS. 7A-7C show a view of the coaptation assistance element 700 with an annular hub 720. The coaptation assistance element 700 can include the annular hub 720 designed to engage the annular anchor 800. The annular anchor 800 may be engaged at a proximal end by a driver, described herein. The annular hub 720 may have a built-in or coupled annular anchor 800. The annular anchor 800 may comprise a helix rotatable with respect to the annular hub 720. The coaptation assistance element 700 can be delivered percutaneously as described herein by attachment of a delivery catheter to the annular hub 720.

As may be seen in FIGS. 7A-7C, the coaptation assistance element 700 can include struts 730. In some embodiments, one or more struts 730 have one end terminating at the annular hub 720 and the other end extending radially outwardly toward the superior edge 740, the lateral edges 770 and 775, and the inferior edge 780 of the coaptation assistance element 700 shown in FIG. 7B. The annular anchor site 735 is shown extending downward from the body of the coaptation assistance element 700 in FIG. 7B. The annular anchor 800 can be an active anchor. The annular anchor sites 735 can be a passive anchor, such as barbs. The annular anchor sites 735 can be at the distal ends of one or more struts 730.

The annular section 710 can be positioned above the native leaflets when the coaptation assistance element 700 is deployed. In some embodiments, the annular section 710 may be may be curved toward the annulus or atrial wall. One or more of the struts 730 may curve laterally from the hub 720 toward the superior edge 740 to assist in maintaining the shape of the annular section 710 of the coaptation assistance element 700 upon deployment. The coaptation assistance element 700 can curve downward from the annular hub 720 toward the annular anchor site 735. The annular section 710 can be concave. In some embodiments, one or more support structures may be provided which run parallel to the superior edge 740 of the coaptation assistance element 700 and assist in maintaining the shape of the superior edge 740. The struts 730 and/or other support structures of the frame can be laser-cut from a Nitinol tube in some embodiments. The valve body covering 750 may be comprised of a material as described herein.

In some embodiments, the coaptation assistance element 700 includes an active anchor such as annular anchor 800. In some embodiments, the coaptation assistance element 700 includes a passive anchor such as annular anchor site 735. The annular anchor site 735 can include barbs at the tip of one or more struts 730.

The coaptation assistance element 700, as well as any coaptation assistance element 500, 600 described herein, can include one or more markers 900. The marker 900 can be positioned on any portion of the coaptation assistance element 500, 600, 700 or any element thereof, such as the struts 530, 630, 730, the annular hub 520, 620, 720, the purse-string suture 1010, and/or the annular anchor sites 535, 735. In some embodiments, the marker 900 is positioned on the annular anchor 800. In other embodiments, the marker 900 is integrally formed with the coaptation assistance element 500, 600, 700 or the annular anchor 800. A plurality of markers 900 can be arranged in specific patterns, on the coaptation assistance element, to provide a fluoroscopic visual aid for the operator to accurately orient and position the coaptation assistance element 500, 600, 700 and/or the annular anchor 800 within the heart of a patient.

In some embodiments, the markers 900 may be radio-opaque or they may be covered by a radio graphic marker. During the process of delivery of the coaptation assistance element 500, 600, 700 and/or the annular anchor 800, the markers 900 may be visualized if a fluoroscope is used. The marker 900 can help position the coaptation assistance element 500, 600, 700 and/or the annular anchor 800 within the heart of a patient. In some embodiments, torque can be applied to the annular anchor 800 such that the annular anchor 800 is driven into the tissue. To provide feedback whether the annular anchor 800 is secured appropriately, fluoroscopic markers 900 may be present on the annular anchor 800. The markers may be located at the proximal end. These markers 900 may inform the medical team about how far the annular anchor 800 may have travelled towards the annular hub 520, 620, 720 and may be informative about when the annular anchor 800 is securely in place. In some embodiments, to ensure that appropriate torque is applied, the torque level at a handle may spike as the annular anchor 800 bottoms out on the annular hub 520, 620, 720. The systems described herein can include one or more markers 900 (e.g., one, two, three, four, five, six, seven, eight, nine, ten, more than one, more than two, more than three, more than four, etc.). The systems described herein can include two or more different markers 900. The different markers can indicate different components of the system, different portions of the coaptation assistance element 500, 600, 700 or positioning points such as the most proximal point, most distal point, midline, etc.

Figure 7D:
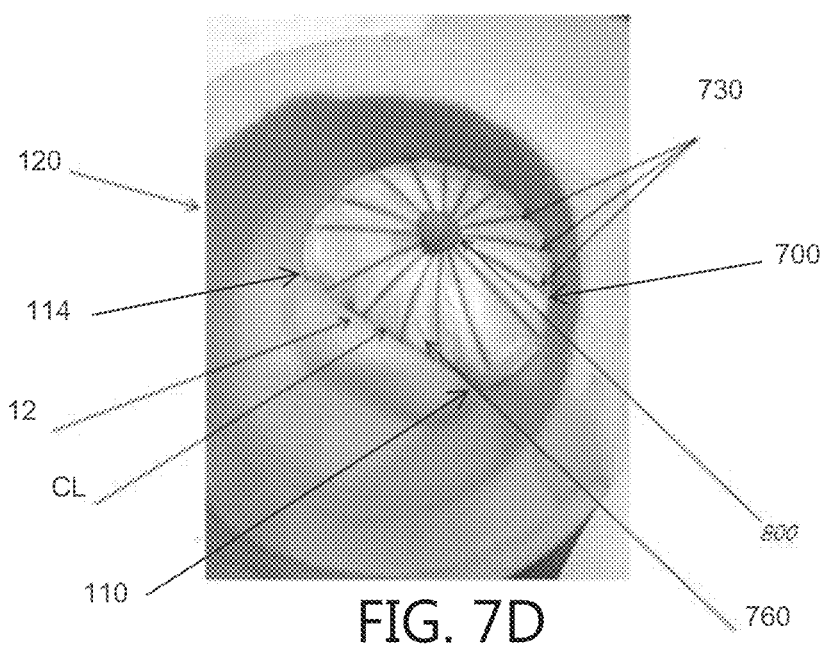
FIG. 7D illustrates the coaptation assistance element of FIG. 7A implanted within a model of a mitral valve.
Figure 7E:
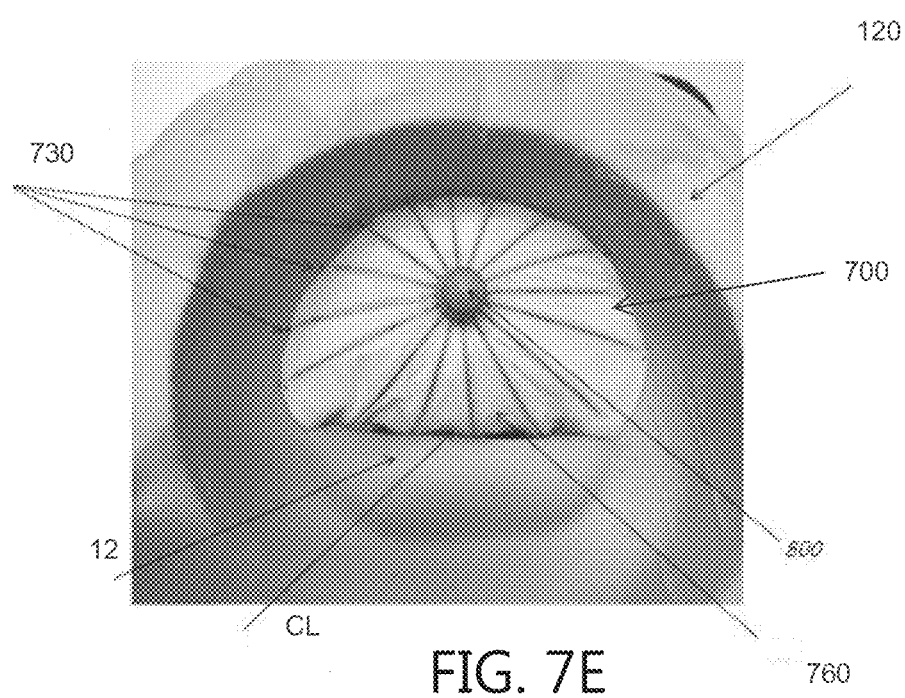
FIG. 7E illustrates a top view of the coaptation assistance element of FIG. 7A implanted within a model of a mitral valve.

FIGS. 7D-7E illustrate an embodiment of the coaptation assistance element 700 deployed within the heart mitral valve model. Referring back to FIG. 1F, the coaptation zone CL between the leaflets is not a simple line, but rather a curved funnel-shaped surface interface as shown in FIG. 7C. The first 110 (Anterio-lateral or left) and second 114 (Posterio-medial or right) commissures are where the anterior leaflet 12 meets the posterior leaflet at the coaptation zone, which form the coaptation line (CL). As seen most clearly in the axial views from the atrium of FIG. 7D, an axial cross-section of the coaptation zone generally shows the curved line CL that is separated from a centroid of the annulus as well as from the opening through the valve during diastole. In addition, the leaflet edges are scalloped, more so for the posterior versus the anterior leaflet. Mal-coaptation can occur between one or more of these A-P (anterior-posterior) segment pairs A1/P1, A2/P2, and A3/P3, so that mal-coaptation characteristics may vary along the curve of the coaptation zone CL, as shown in FIG. 1F.

In some embodiments, the coaptation assistance element 700 is placed over the posterior leaflet to create a new surface onto which the native leaflet, here the anterior leaflet, can coapt. The mitral valve is shown with the anterior leaflet 12. The zone of coaptation occurs between the anterior leaflet 12 and the coaptation surface 760 of the coaptation assistance element 700.

Referring now to FIG. 8A, aspects of the delivery catheter 1000 are illustrated. The delivery catheter 1000 can include a control handle. The delivery catheter 1000 can include a tip deflection control 1001. The tip deflection control 1001 can allow a distal portion of the delivery catheter 1000 to deflect. This may be advantageous to place the coaptation assistance element 500, 600, 700 within the mitral valve. The delivery catheter 1000 can be inserted into a transseptal sheath (not shown). The transseptal sheath allows the introduction of the delivery catheter into the left atrium. The delivery catheter 1000 may further include one or more ports 1002, such as a flush, irrigation and/or aspiration port to remove the air from the system and allow injection of fluids such as saline or contrast media to the site of implantation. The catheter 1000 can include a catheter shaft 1006. The catheter 1000 can include an implant inserter 1007.

The delivery catheter 1000 may include an implant control knob 1003. The implant control knob 1003 can control the movements of the coaptation assistance element 500, 600, 700. The implant control knob 1003 may enable the collapse of the coaptation assistance element 500, 600, 700. The implant control knob 1003 may enable the expansion of the coaptation assistance element 500, 600, 700. The arrow 1003a indicates the direction of movement of the implant control knob 1003 for the coaptation assistance element 500, 600, 700 to be collapsed by the delivery catheter 1000 and/or expanded by the delivery catheter 1000. The implant control knob 1003 may enable the rotation of the coaptation assistance element 500, 600, 700. The arrow 1003b indicates the direction of movement of the implant control knob 1003 for the coaptation assistance element 500, 600, 700 to be rotated.

The implant control knob 1003 can be internally connected to the coaptation assistance element 500, 600, 700 to allow the transmission of axial movement and/or torque. For instance, the implant control knob 1003 of the delivery catheter 1000 can be coupled to the annular hub 520, 620, 720 For instance, the implant control knob 1003 can be connected to one or more purse-string suture 1010 which may control the deployment of the coaptation assistance element 500, 600, 700. The purse-string suture 1010 may facilitate the collapse and/or expansion of the coaptation assistance element 500, 600, 700 as described herein. The purse-string suture 1010 may facilitate the rotation of the coaptation assistance element 500, 600, 700 as described herein. In some embodiments, the delivery catheter 1000 releasably engages coaptation assistance element 500, 600, 700 such that axial movement and torque can be transmitted from the delivery catheter 1000 to the coaptation assistance element 500, 600, 700

In some embodiments, a tip 1300 of the delivery catheter 1000 is releasably coupled to the annular hub 520, 620, 720 For instance, the tip 1300 of the delivery catheter 1000 can lock onto the annular hub 520, 620, 720 such that movement of the delivery catheter 1000 causes movement of the coaptation assistance element 500, 600, 700. In some embodiments, the system includes a release mechanism between the delivery catheter 1000 and the annular hub 520, 620, 720.

The annular hub 520, 620, 720 may have features, which can lock with the tip 1300 of the delivery catheter 1000. Referring back to FIGS. 5A-7E, the annular hub 520, 620, 720 can include one or more features to engage a portion of the delivery catheter 1000. The feature can include one or more notches in the hub 520 of the Implant as shown in FIG. 5A. The feature can include an internal lip as shown in FIG. 9A. The feature can include windows accessible from the outside of the hub 520, 620, 720, as shown in FIG. 8C. The feature can include any structure or mechanism capable of coupling the annular hub 520, 620, 720 and a portion of the delivery catheter 1000. In some embodiments, the annular hub 520, 620, 720 and the delivery catheter 1000 are coupled via a screw mechanism. For instance, the annular hub 520, 620, 720 can include a female thread and the distal end of the delivery catheter 1000 can include a male thread. In some embodiments, the annular hub 520, 620, 720 and the delivery catheter 1000 are coupled via a noose and pin configuration. For instance, the annular hub 520, 620, 720 can include a pin such as an outwardly extending pin and the distal end of the delivery catheter 1000 can include a loop or noose designed to be tightened around the pin. Other configurations are contemplated.

FIG. 8B shows the coaptation assistance element 500, 600, 700 coupled to the delivery catheter 1000. The coaptation assistance element 500, 600, 700 can be collapsed as shown or expanded as shown by the dashed lines by movement along arrow 1003a. The coaptation assistance element 500, 600, 700 can be rotated as shown by the dashed lines by movement along arrow 1003b.

Referring to FIG. 8C, the delivery catheter 1000 can include the tip 1300. The distal end of the tip 1300 can include distal locking tabs. In some embodiments, the tip 1300 includes a plurality of pre-bent or shape-set locking tabs. In some embodiments, the tip includes two locking tabs, three locking tabs, four locking tabs, five locking tabs, a plurality of locking tabs, a multitude of locking tabs, etc. This "AT-lock" (axial-torsional lock) can include nitinol locking tabs on the tip 1300. In some embodiments, the locking tabs of the tip 1300 can be actuated by a sheath 1350. In some embodiments, the sheath 1350 is hollow to allow movement of other components such as the driver described herein. The movement sheath 1350 can force the locking tabs inward into engagement with the annular hub 520, 620, 720. In some embodiments, the locking tabs of the tip 1300 engage a feature such as a window or lip of the annular hub 520, 620, 720. In some embodiments, movement of the sheath 1350 in the opposite direction can cause the release of the annular hub 520, 620, 720 from the tip. In other embodiments, the locking tabs of the tip 1300 can be actuated by a central pin inserted within tip 1300 (not shown). In some embodiments, the central pin is hollow to allow movement of other components such as the driver described herein. The movement of the central pin can force the locking tabs outward into engagement with the annular hub 520, 620, 720.

In some embodiments, the distal end of the tip 1300 can be actuated to lock the delivery catheter 1000 to the annular hub 520, 620, 720. In some embodiments, the distal end of the tip 1300 can be actuated to unlock the delivery catheter 1000 from the annular hub 520, 620, 720. As described herein, secondary structures such as the purse-string sutures may remain coupled to the coaptation assistance element 500, 600, 700 after the annular hub 520, 620, 720 is released from the tip 1300. In some embodiments, when the delivery catheter 1000 is unlocked, one or more secondary structures such as the purse-string sutures described herein can retain a relative position between the delivery catheter 1000 and the annular hub 520, 620, 720. During a procedure, the tip 1300 may be repeatedly locked and unlocked.

Referring back to FIG. 8A, the delivery catheter 1000 can include the anchor control knob 1004. In some embodiments, the anchor control knob 1004 can enable the release of the annular anchor 800 and/or the coaptation assistance element 500, 600, 700. In some embodiments, the anchor control knob 1004 can enable the engagement of the annular anchor 800 for instance to rotate the annular anchor 800 and/or to axially move the annular anchor 800. In some embodiments, the anchor control knob 1004 can enable the disengagement of the annular anchor 800. In some embodiments, the anchor control knob 1004 can control a driver 1200 configured to apply torque. In some embodiments, the anchor control knob 1004 can control a driver 1200 configured to apply tension and/or release the coaptation assistance element 500, 600, 700. In some embodiments, the anchor control knob 1004 can control a driver 1200 configured to apply tension and torque.

The anchor control knob 1004 of the delivery catheter 1000 may be coupled to the annular anchor 800 to allow transmission of torque to the annular anchor 800. The anchor control knob 1004 may enable simple manipulation of the torque or position of the annular anchor 800. The arrow 1004a indicates the direction of movement of the anchor control knob 1004 for the annular anchor 800 to be engaged or disengaged. For instance, moving the anchor control knob 1004 toward the annular anchor 800 may engage a driver 1200 with the annular anchor 800. The arrow 1004b indicates the direction of movement of the anchor control knob 1004 for the transmission of torque to the annular anchor 800. In some embodiments, the arrow 1004b indicates the direction to release the annular anchor 800. For instance, the further application of torque may twist the driver 1200 out of engagement with the annular anchor 800.

An embodiment of an annular anchor 800 is illustrated in detail in FIG. 9A. Other components of the delivery catheter 1000 are not shown in FIG. 9A, such as the component which engages the annular hub 520, 620, 720. The annular anchor 800 may be coupled to the driver 1200 in various ways, as described herein. The annular anchor 800 may be coupled to the coaptation assistance element 500, 600, 700 in various ways. In some embodiments, the annular hub 520, 620, 720 may have a cross-pin 820. The cross-pin 820 can provide a site about which a helical structure 815 of the annular anchor 800 may wrap around as shown. The annular anchor 800 can have a shoulder 805. The shoulder 805 may fit around the outside of a driver 1200 of the delivery catheter 1000.

In some embodiments, the driver 1200 is releasably coupled to the annular anchor 800. The driver 1200 can be coupled and/or controlled by the anchor control knob 1004 described herein. One or more drivers 1200 can deliver torque to drive the annular anchor 800 into tissue. One or more drivers 1200 can deliver tension to hold and/or release the annular anchor 800. In some embodiments, a single driver 1200 delivers torque and tension. In other embodiments, two or more drivers 1200 deliver torque and tension. For instance, the driver 1200 can lock onto the annular anchor 800 such that movement of the driver 1200 causes movement of the annular anchor 800. In some embodiments, the system includes a release mechanism between the driver 1200 and the annular anchor 800. In some embodiments, the distal end of the driver 1200 can be actuated to lock the driver 1200 to the annular anchor 800. In some embodiments, the distal end of the driver 1200 can be actuated to unlock the driver 1200 from the annular anchor 800. In some embodiments, when the driver 1200 is unlocked, one or more secondary structures such as the purse-string sutures can retain a relative position between the delivery catheter 1000 and the annular anchor 800. During a procedure, the driver 1200 may be repeatedly locked and unlocked.

Figure 9B:
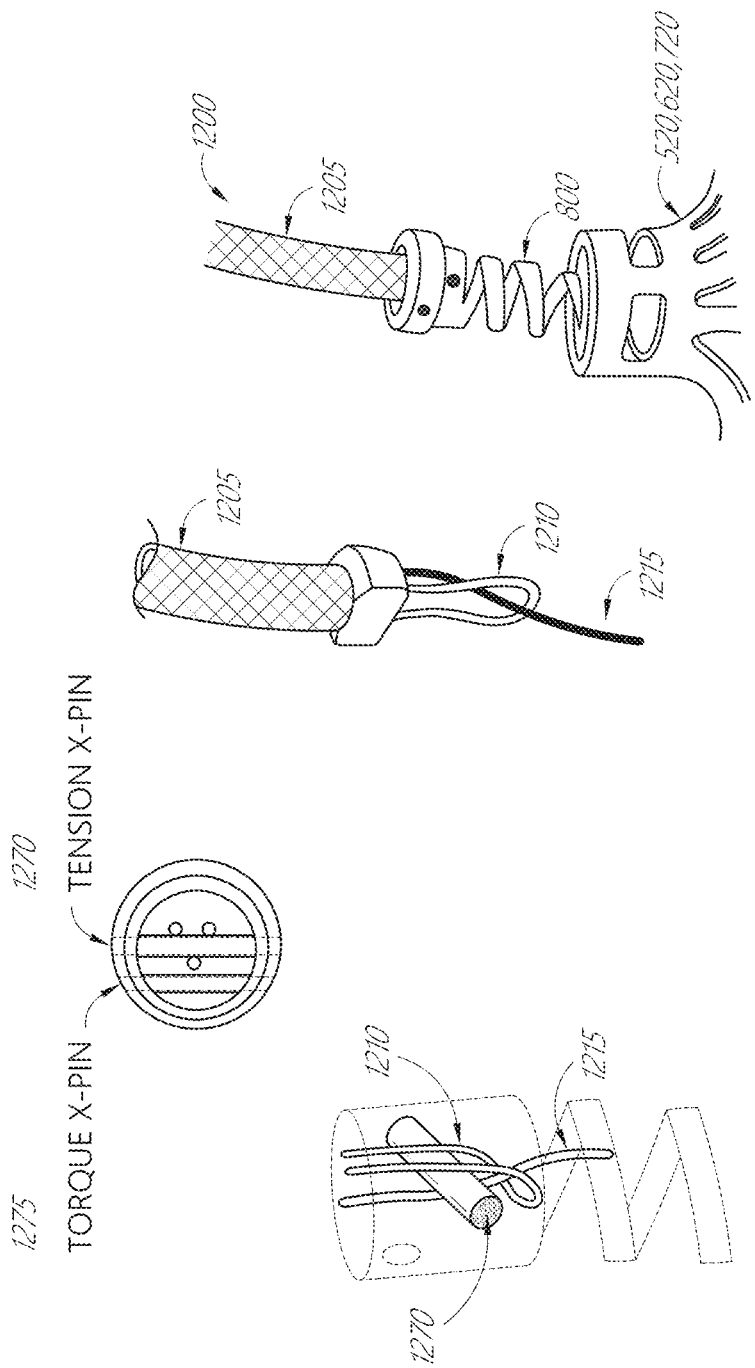

FIG. 9B illustrates an embodiment of a driver 1200. The driver 1200 can include a torque shaft 1205. The torque shaft 1205 can include a loop 1210. The loop 1210 can engage a pin 1215 extending and looping around the tension cross-pin 1270 and through the anchor 800. The rotation of the torque shaft 1205 can cause a torque to be applied to a torque cross-pin 1275, thereby causing rotation of the annular anchor 800. In some embodiments, the annular anchor 800 can include a torque cross-pin and a tension cross-pin. Another driver (not shown) can apply a torque to the tension cross-pin to apply tension to the annular anchor 800. One or more drivers 1200 can engage the annular anchor 800 to deliver torque. One or more drivers 1200 can engage the annular anchor 800 to deliver tension. In some embodiments, delivery of the annular anchor 800 is independent of rotation of the coaptation assistance element 500, 600, 700.

Figure 9C:
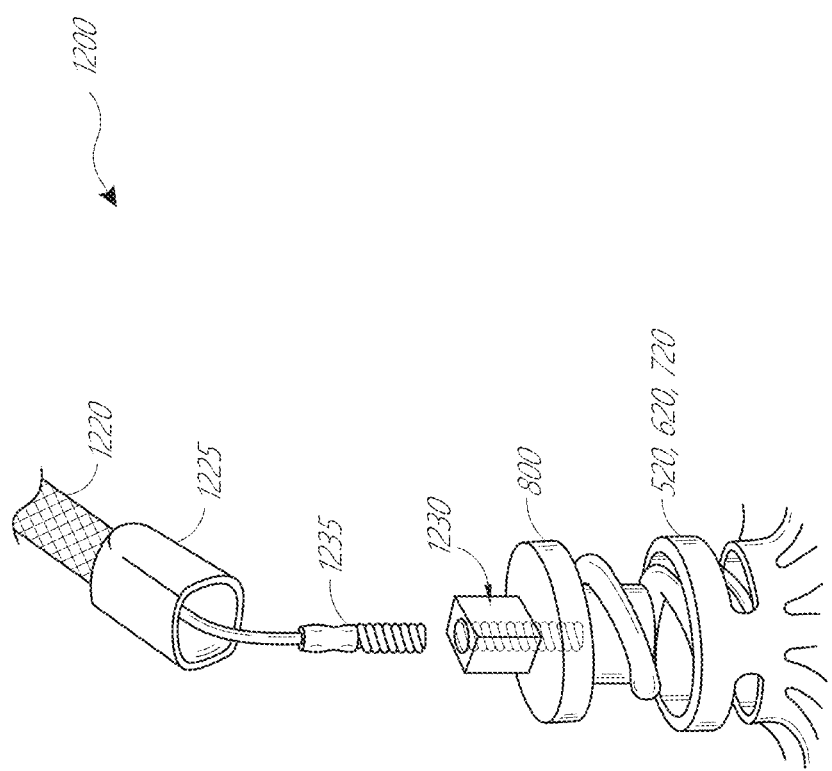

FIG. 9C illustrates an embodiment of a driver 1200. The driver 1200 can include a torque shaft 1220. The torque shaft 1220 can include an anchor docking cap 1225. The anchor docking cap 1225 can engage the annular anchor 800 in a single orientation or one of a plurality of orientations. In some embodiments, the annular anchor 800 includes a protrusion 1230 and the anchor docking cap 1225 is designed to accept the protrusion 1230. In other embodiments, the annular anchor 800 includes a recess (not shown) to accept a mating protrusion on the anchor docking cap 1225 (not shown). The rotation of the torque shaft 1220 can cause a torque to be applied to the annular anchor 800. Another driver 1235 can apply tension to the annular anchor 800. In some embodiments, the driver 1235 can include a release screw. In other embodiments, the loop and pin release mechanism described in FIG. 9B may be used. The release screw can be rotated to release the annular anchor 800. One or more drivers 1200 can engage the annular anchor 800 to deliver torque. One or more drivers 1200 can engage the annular anchor 800 to deliver tension.

Figure 9E:
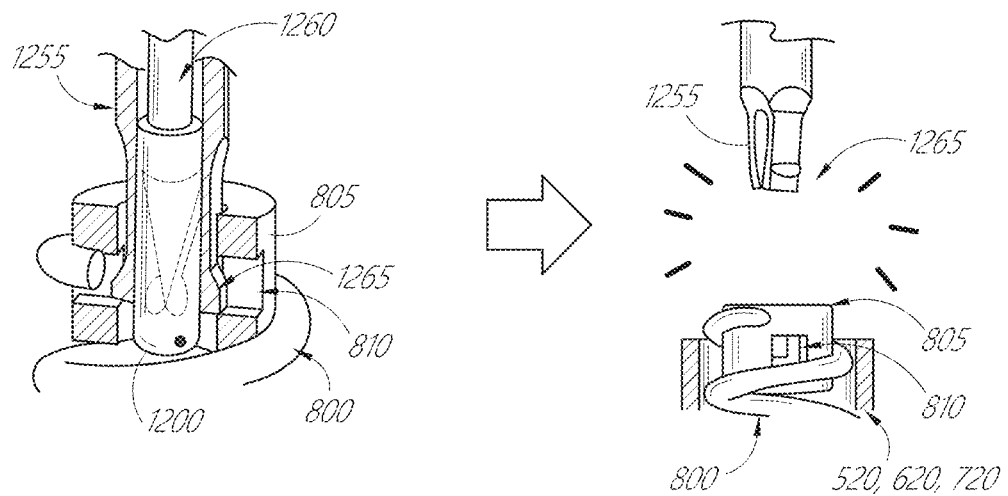

FIG. 9D illustrates an embodiment of a driver 1200 and the annular anchor 800. The driver 1200 can include a torque shaft 1220. The torque shaft 1220 can include an anchor docking cap 1225. In some embodiments, the annular anchor 800 includes a protrusion 1230 and the anchor docking cap 1225 is designed to accept the protrusion 1230. In other embodiments, the annular anchor 800 includes a recess (not shown) to accept a mating protrusion on the anchor docking cap 1225 (not shown). Two or more wires 1240, 1245 can apply tension to the annular anchor 800. In some embodiments, the wire 1240 acts as a pin, and the wire 1245 terminates in a ball. In a retained state, the wires 1240, 1245 are both positioned within an opening in the annular anchor 800. The opening is too small to allow the pin and ball end of wires 1240, 1245 to pass side by side. In some methods of use, the wire 1240 is retracted first. The retraction of the wire 1240 yields sufficient room to allow retraction of the wire 1245. The wires 1240, 1245 can be actuated to release the annular anchor 800. One or more drivers 1200 can engage the annular anchor 800 to deliver torque. One or more drivers 1200 can engage the annular anchor 800 to deliver tension FIG. 9E illustrates an embodiment of the driver 1200. The driver 1200 can include a torque shaft 1255. The shoulder 805 may have features such as windows 810 which can lock with one or more distal locking tabs 1265 of the torque shaft 1255. The distal locking tabs 1265 may include nitinol material such as a Shape-set NiTi clip. The distal locking tabs 1265 may be pushed outward into the windows 810 by a driver 1260. The driver 1260 acts as a release mechanism. The longitudinal movement of the driver 1260 toward the annular anchor 800 may push the distal locking tabs 1265 outward toward the windows 810. The longitudinal movement of the driver 1260 away from the annular anchor 800 may allow the distal locking tabs 1265 to regain a neutral configuration and disengage from the windows 810. The distal locking tabs 1265 engaged with the windows 810 of the annular anchor 800 can allow the transmission of axial movement between the torque shaft 1255 and the annular anchor 800. The distal locking tabs 1265 engaged with the windows 810 of the annular anchor 800 can allow the transmission of torque between the torque shaft 1255 and the annular anchor 800. In embodiments where the annular anchor 800 is built-in or captured by the annular hub 520, 620, 720, the distal locking tabs 1265 engaged with the windows 810 can allow the transmission of axial movement between the delivery catheter and the coaptation assistance element 500, 600, 700.

In some embodiments, an advantage is the annular anchor 800 can be rotated independently of the coaptation assistance element 500, 600, 700. As described herein, the coaptation assistance element 500, 600, 700 is coupled to the delivery catheter 1000. As described herein, the annular anchor 800 is independently coupled to the driver 1200. The annular anchor 800 can be rotated independently of the annular hub 520, 620, 720. The annular hub 520, 620, 720 can remain stationary as the annular anchor 800 is rotated to engage tissue.

In some methods, the annular anchor 800 can be preloaded onto the coaptation assistance element 500, 600, 700 and coupled to the driver 1200 during the process of mounting the coaptation assistance element 500, 600, 700 onto the delivery catheter 1000. This can occur before the coaptation assistance element 500, 600, 700 is pulled into an implant sheath and/or another portion of the delivery catheter 1000 and is being readied for insertion into the femoral vein. As disclosed herein, torque can be applied such that the annular anchor 800 is driven into the tissue. In some embodiments, to ensure that appropriate torque is applied, the torque level at the handle may spike as the annular anchor 800 bottoms out on the annular hub 520, 620, 720. This increased torque level may be felt at the handle providing feedback that appropriate torque has been applied. In other embodiments, radiopaque markings may aid in visually determining the level of anchor engagement within tissue. In some embodiments, the markings can be located on the annular anchor 800 and/or the coaptation assistance element 500, 600, 700.

FIGS. 10-15 show various methods, which may be performed during a method of use of the coaptation assistance element 500, 600, 700. The method may include collapsing the coaptation assistance element 500, 600, 700. The method may include of coupling the coaptation assistance element 500, 600, 700 to the delivery catheter 1000. The method may include coupling the locking tabs 1265 with the annular anchor 800 and/or the coaptation assistance element 500, 600, 700. The method can include any step disclosed herein for manufacturing the coaptation assistance element 500, 600, 700.

In some embodiments, an advantage is the coaptation assistance element 500, 600, 700 can be delivered with a hub-leading orientation. In this method of use, the annular hub 520, 620, 720 can be moved into position relative to the anatomical structures prior to another portion of the coaptation assistance element 500, 600, 700. In some methods of use, the ventricular end of the coaptation assistance element 500, 600, 700 can be retained within the delivery catheter 1000 until the annular hub 520, 620, 720 is positioned. In some methods of use, once the annular hub 520,620, 720 and/or the annular anchor 800 are engaged with the tissue, the coaptation assistance element 500, 600, 700 can be expanded. In some methods of use, once the annular hub 520, 620, 720 and/or the annular anchor 800 are engaged with the tissue, the ventricular end of the coaptation assistance element 500, 600, 700 can be positioned.

In some embodiments, an advantage is the coaptation assistance element 500, 600, 700 can be delivered with a strut-leading orientation. In this method of use, one or more of the struts 530, 630, 730 of the coaptation assistance element 500, 600, 700 can be moved into position relative to the anatomical structures prior to another portion of the coaptation assistance element 500, 600, 700. In some methods of use, the coaptation assistance element 500, 600, 700 can be expanded or partially expanded prior to the positioning of the annular hub 520, 620, 720. In some methods of use, the annular hub 520, 620, 720 can be retained within the delivery catheter until one or more of the struts 530, 630, 730 are positioned. In some methods of use, once the struts 530, 630, 730 are positioned, the annular anchor 800 is engaged with the tissue.

Figure 10:
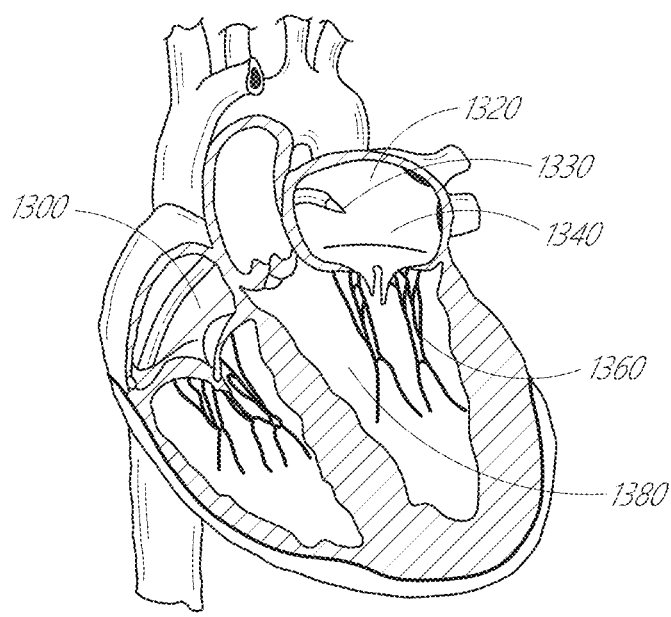
FIG. 10 schematically illustrates a method for a transcatheter technique showing transseptal crossing.

FIG. 10 illustrates an embodiment of transseptal crossing. The method may include femoral vein access. Access may be gained through a vessel such as the femoral vein in order to reach a chamber of the heart such as the right atrium 1300. The left ventricle 1380 and its papillary muscles are also shown 1360. The method may include transseptal puncture and crossing with standard transseptal kit 1330 to the left atrium 1320. The method may include exchanging for custom transseptal sheath and delivery catheter 1000, as described herein. A transseptal puncture kit may be exchanged for a transseptal sheath and dilator, and the dilator may be exchanged for an implant delivery catheter which may be as disclosed herein and in U.S. Pat. No. 8,888,843 to Khairkhahan et al., incorporated by reference in its entirety. The method may include removing a dilator. The method may include advancing the delivery catheter 1000. However, other approaches such as transapical, transatrial, femoral artery, brachial artery, and the like are also within the scope of the invention.

Figure 11:
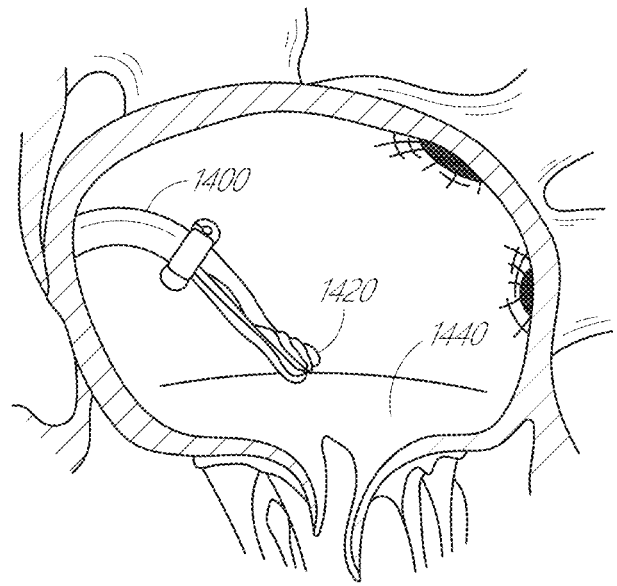
FIG. 11 schematically illustrates a method for a transcatheter technique showing initial coaptation assistance element advancement.

FIG. 11 illustrates initial advancement of the coaptation assistance element 500, 600, 700. The method may include advancing the coaptation assistance element 500, 600, 700 inside the retrieval sheath. The retrieval sheath can include a tip having a plurality of petals radiating from a central hub 1420. The retrieval sheath may be positioned within a transseptal sheath 1400. The mitral valve is show at the base of the left atrium 1440. The method may include advancing the annular section 510, 610, 710 toward the annulus before advancing the coaptation surface 560, 660, 760 toward the annulus. The method may include deploying the ventricular end or inferior surface 580 after deploying the annular portion 510.

Figure 12:
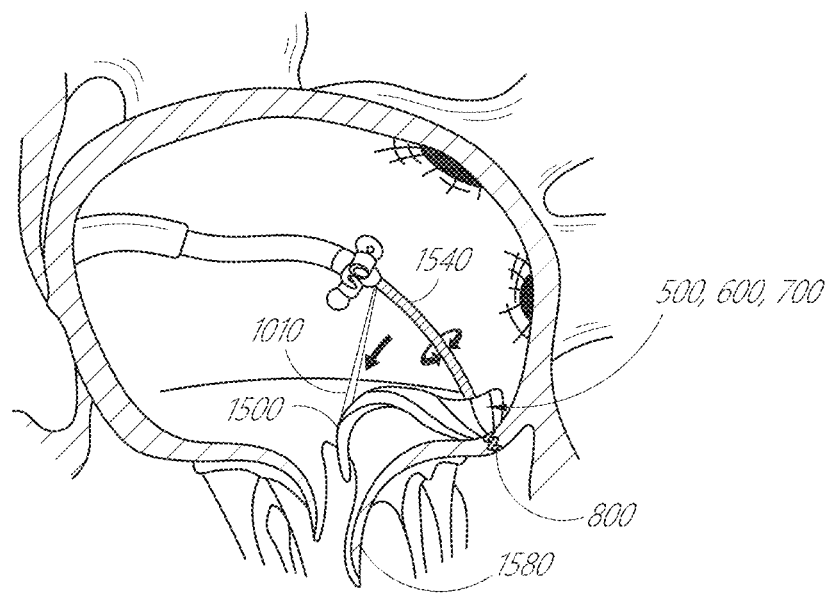
FIG. 12 schematically illustrates a method for a transcatheter technique showing partial coaptation assistance element opening.

FIG. 12 illustrates partial deployment of the coaptation assistance element 500, 600, 700. The coaptation assistance element 500, 600, 700 may be advanced in proximity to the target location under imaging guidance such as ultrasound or fluoroscopy. The annular anchor 800 coupled with the coaptation assistance element 500, 600, 700 is engaged in tissue. An anchor torque shaft 1540 may be rotated internally and independent of the rotation of an implant torque shaft (not shown). Controlled release of a purse-string suture 1010 around the perimeter of the coaptation assistance element 500, 600, 700 may cause the coaptation assistance element 500, 600, 700 to expand. Prior to full expansion of the coaptation assistance element 500, 600, 700, rotational adjustment of the coaptation assistance element 500, 600, 700 may be performed to align the interior (ventricular) section of the coaptation assistance element 500, 600, 700 with a valve opening 1580.

The method may include advancing the coaptation assistance element 500, 600, 700 toward a target location. The method may include advancing the annular hub 520, 620, 720 toward a target location. The method may include advancing the annular anchor 800, which is coupled to the annular hub 520, 620, 720, toward a target location. The method may include echo or fluoroscopic guidance of the annular anchor 800, the hub 520, 620, 720, and/or the coaptation assistance element 500, 600, 700. The method may include engaging the annular anchor 800 in tissue. The method may include rotating the anchor control knob 1004 to rotate the annular anchor 800. The method may include the independent rotation of the annular anchor 800 from the hub 520, 620, 720. The method may include holding the hub 520, 620, 720 stationary during rotation of the annular anchor 800. The method may include controlled release of the purse-string suture 1010. The release may cause the coaptation assistance element 500, 600, 700 to expand. The purse-string suture 1010 may be disposed within the coaptation assistance element 500, 600, 700 and/or along a perimeter of the coaptation assistance element 500, 600, 700. The purse-string suture 1010 can facilitate the collapse and/or expansion of the coaptation assistance element 500, 600, 700. The method may include rotational adjustment of the coaptation assistance element 500, 600, 700 to align an inferior edge 580, 680, 780 or ventricular section of the coaptation assistance element 500, 600, 700 with the valve opening. The method may include rotational adjustment of the coaptation assistance element 500, 600, 700 to align an inferior edge 580, 680, 780 or ventricular section around the posterior leaflet.

Figure 13:
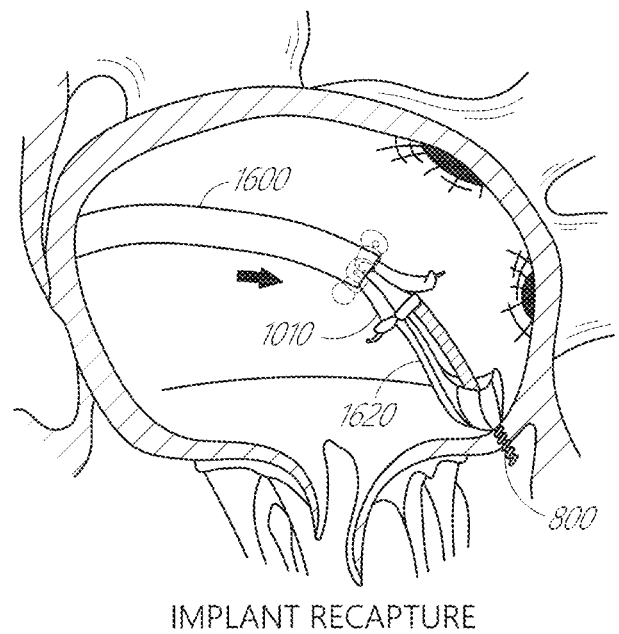
FIG. 13 schematically illustrates a method for a transcatheter technique showing coaptation assistance element collapsing.

FIG. 13 illustrates recapture of the coaptation assistance element 500, 600, 700. The coaptation assistance element 500, 600, 700 may be recaptured by tightening a purse-string suture 1010 around a portion of the perimeter 1620 of the coaptation assistance element 500, 600, 700 to collapse the coaptation assistance element 500, 600, 700. The perimeter can include any edge, any combination of edges, or all of the edges described herein. A recapture sheath and transseptal sheath 1600 may be advanced over the collapsed coaptation assistance element 500, 600, 700. Recapture sheath petals that radiate from a central hub may roll over the coaptation assistance element 500, 600, 700 allowing the coaptation assistance element 500, 600, 700 to be retracted into the transseptal sheath. The annular anchor 800 may be unscrewed or otherwise released, and the system may be removed. The prolapsed or partially encapsulated coaptation assistance element 500, 600, 700 by the recapture sheath petals can be another mode of delivery. The encapsulated-first delivery mode can be in contrast to the hub-first and the strut-delivery modes described herein.

In some methods, recapture is an optional method. The method may include tightening of the purse-string suture 1010. This tightening may collapse the coaptation assistance element 500, 600, 700. The method may include advancing the recapture sheath and/or the transseptal sheath over the collapsed coaptation assistance element 500, 600, 700. The recapture sheath can fold outward to roll over the coaptation assistance element 500, 600, 700. The method may include retracting the coaptation assistance element 500, 600, 700 into the transseptal sheath. The method may include rotating the annular anchor 800 to disengage tissue. The method may include removing the coaptation assistance element 500, 600, 700 and the annular anchor 800.

Figure 14:
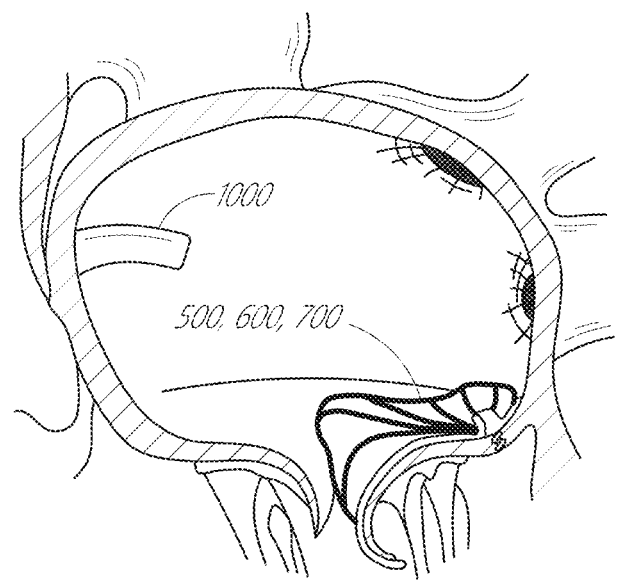
FIG. 14 schematically illustrates a method for a transcatheter technique showing a cross-sectional view of the coaptation assistance element.

FIG. 14 illustrates a cross-section view of the deployed coaptation assistance element 500, 600, 700. The method may include releasing of the coaptation assistance element 500, 600, 700. The method may include retraction of the delivery catheter 1000.

Figure 15:
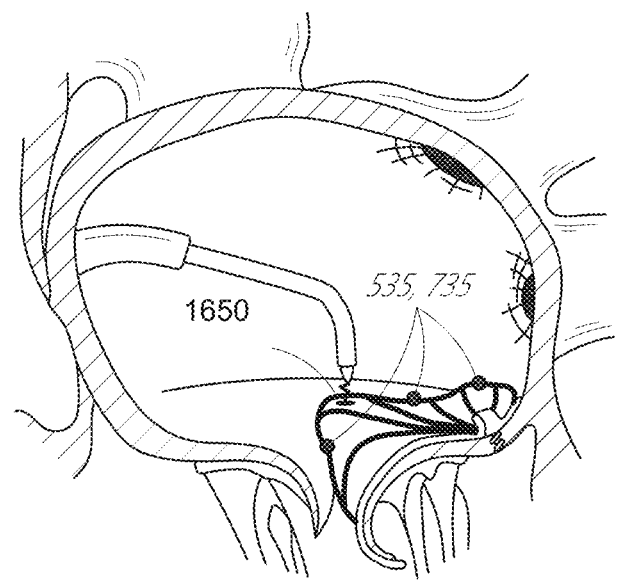
FIG. 15 schematically illustrates a method for a transcatheter technique showing secondary anchor placement.

FIG. 15 illustrates deployment of secondary anchors. In some methods, deployment of secondary anchors is an optional method. The method may include engaging annular attachment sites 535, 735 to the annulus. The method may include engaging ventricular anchors. The method may include engaging commissural anchors 1650. The method may include deploying markers on strategic locations on the coaptation assistance element 500, 600, 700 and/or the annular anchor 800. The method may include detecting markers, such as detecting radiopaque markers. The method may include facilitating the placement of anchor 800 under fluoroscopy. The method may include locating radiopaque markers along the perimeter of the coaptation assistance element 500, 600, 700 to indicate the shape of coaptation assistance element 500, 600, 700.

In some embodiments, the manufacturer provides instructions for use of the system including one or more of the steps disclose herein, or any step previously described or inherent in the drawings.

FIGS. 16-30 show various methods, which may be performed during a method of use of the coaptation assistance element 500, 600, 700. The method can include any step disclosed herein, according to some embodiments of the invention. The method can include any step disclosed herein for manufacturing and/or deploying the coaptation assistance element 500, 600, 700. The method can include collapsing the coaptation assistance element 500, 600, 700.

Figure 16:
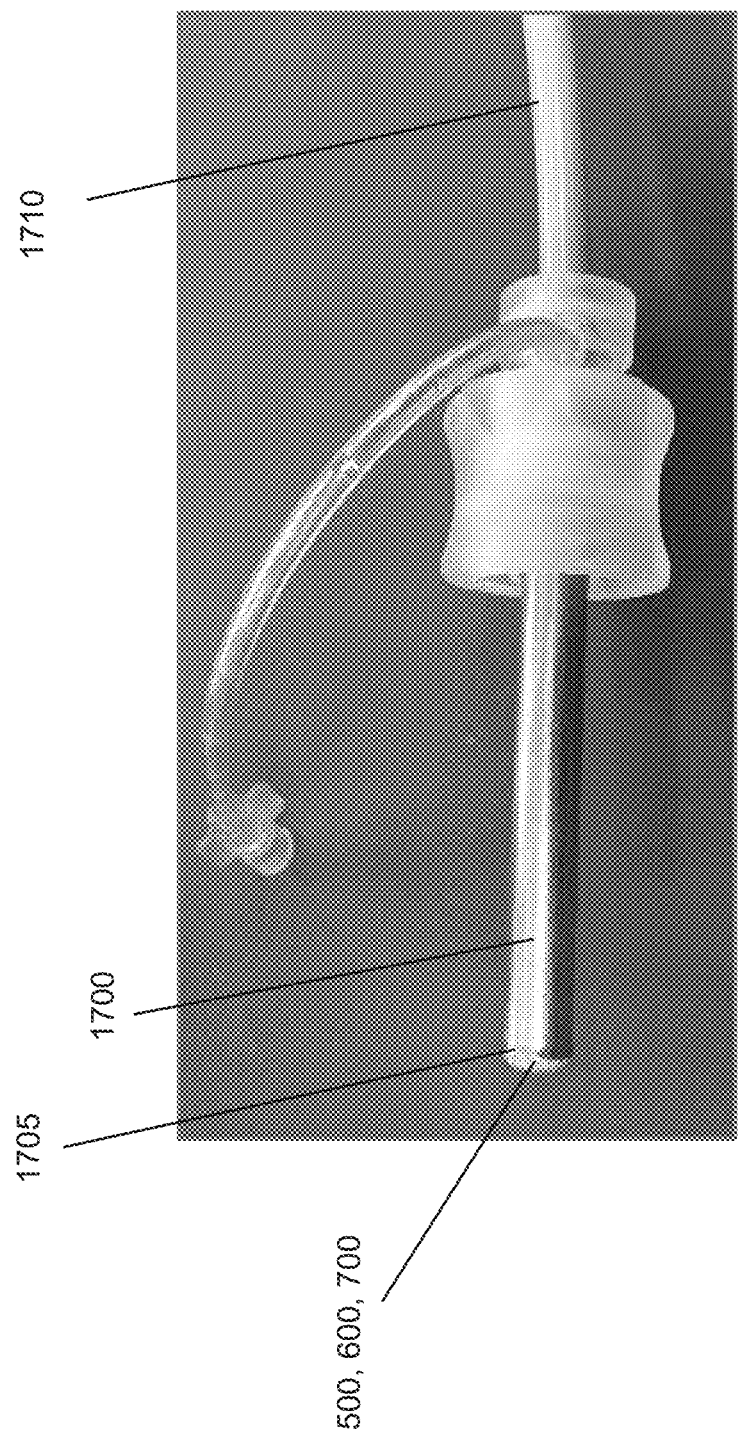
FIG. 16 illustrates a method for implant delivery showing loading of an implant.

FIG. 16 illustrates a method for implant delivery showing loading of the coaptation assistance element 500, 600, 700. The coaptation assistance element 500, 600, 700 can be collapsed, as described herein. The collapsed coaptation assistance element 500, 600, 700 can be loaded into a transseptal sheath introducer 1700. The transseptal sheath introducer 1700 can include a sheath having a lumen to accommodate the collapsed coaptation assistance element 500, 600, 700. The collapsed coaptation assistance element 500, 600, 700 can be inverted within the transseptal sheath introducer 1700. The annular hub 520, 620, 720 can be positioned near the edge 1705 of the transseptal sheath introducer 1700. The transseptal sheath introducer 1700 can include a multilumen catheter 1710 connected to the coaptation assistance element 500, 600, 700. The method can include loading of the coaptation assistance element 500, 600, 700 into the transseptal sheath introducer 1700.

FIG. 17 illustrates a method for inserting the transseptal sheath introducer 1700 into a transseptal sheath 1715. The transseptal sheath introducer 1700 can include the multilumen catheter 1710. The multilumen catheter 1710 and/or the transseptal sheath introducer 1700 can include a hub 1720. The hub 1720 can connect with the transseptal sheath 1715. The proximal end of the transseptal sheath 1715 is shown in FIG. 17. In FIG. 17, the transseptal sheath introducer 1700 is not connected to the transseptal sheath 1715. In FIG. 18, the transseptal sheath introducer 1700 is connected to the transseptal sheath 1715. The method can include connecting the transseptal sheath introducer 1700 to the transseptal sheath 1715. The method can include connecting an assembly comprising the coaptation assistance element 500, 600, 700 to the transseptal sheath 1715.

FIG. 19 illustrates a method for advancing the transseptal sheath introducer 1700. The transseptal sheath introducer 1700 can be advanced to the distal end of the transseptal sheath 1715. The coaptation assistance element 500, 600, 700 can be advanced through the transseptal sheath 1715. The collapsed coaptation assistance element 500, 600, 700 can be inverted while advancing through the transseptal sheath 1715. In FIG. 19, the coaptation assistance element 500, 600, 700 is at the distal end of the transseptal sheath 1715.

FIG. 20 illustrates a method for positioning the transseptal sheath 1715. The coaptation assistance element 500, 600, 700 can be located at the distal end of the transseptal sheath

1715 during positioning. The transseptal sheath 1715 can be positioned in the annulus. The transseptal sheath 1715 can be positioned over the posterior leaflet. The transseptal sheath 1715 can be centered over P2 described herein. The method can include locating the coaptation assistance element 500, 600, 700 to the posterior leaflet. The method can include locating the coaptation assistance element 500, 600, 700 centered over P2. The method can include locating the coaptation assistance element 500, 600, 700 in the annulus. The transseptal sheath 1715 can be rotated as shown by the arrows. The transseptal sheath 1715 can position the coaptation assistance element 500, 600, 700 by rotating. The transseptal sheath 1715 can correct atrial/ventricle orientation. The transseptal sheath 1715 can include one or more markings/indicia 1725. The markings 1725 can enable a user to guide the rotation of the transseptal sheath 1715. The markings 1725 can enable a user to provide correct orientation of an annulus portion of the coaptation assistance element 500, 600, 700. The markings 1725 can enable a user to provide correct orientation of a ventricle portion of the coaptation assistance element 500, 600, 700. In some embodiments, the marking 1725 can include a radiopaque marker. FIG. 20 shows the coaptation assistance element 500, 600, 700 and the transseptal sheath 1715 centered over P2 in the annulus of a mitral valve. FIG. 20 shows rotation of the coaptation assistance element 500, 600, 700 and the transseptal sheath 1715.

FIG. 21 illustrates a method for delivering the anchor 800. The anchor 800 can include any of the features of the anchors described herein. The anchor 800 can be considered a P2 anchor based on the location of the anchor 800 after deployment. The anchor 800 can extend through the annular hub 520, 620, 720 as described herein. The method can include delivering in the anchor 800 while the coaptation assistance element 500, 600, 700 is within the transseptal sheath 1715. In some embodiments, the anchor 800 is coupled to the annular hub 520, 620, 720 of the coaptation assistance element 500, 600, 700 before loading into the transseptal sheath 1715. In some embodiments, the anchor 800 is coupled to the annular hub 520, 620, 720 of the coaptation assistance element 500, 600, 700 while within the transseptal sheath 1715. In some embodiments, the anchor 800 is coupled to the annular hub 520, 620, 720 of the coaptation assistance element 500, 600, 700 after the transseptal sheath 1715 is positioned within the annulus. The method can include delivering the anchor 800 while the coaptation assistance element 500, 600, 700 is within the transseptal sheath 1715. The coaptation assistance element 500, 600, 700 can be centered over P2 in the annulus during delivery of the anchor 800. The anchor 800 can be inserted by rotating the anchor 800 into the tissue of the annulus, as described herein.

Figure 22B:
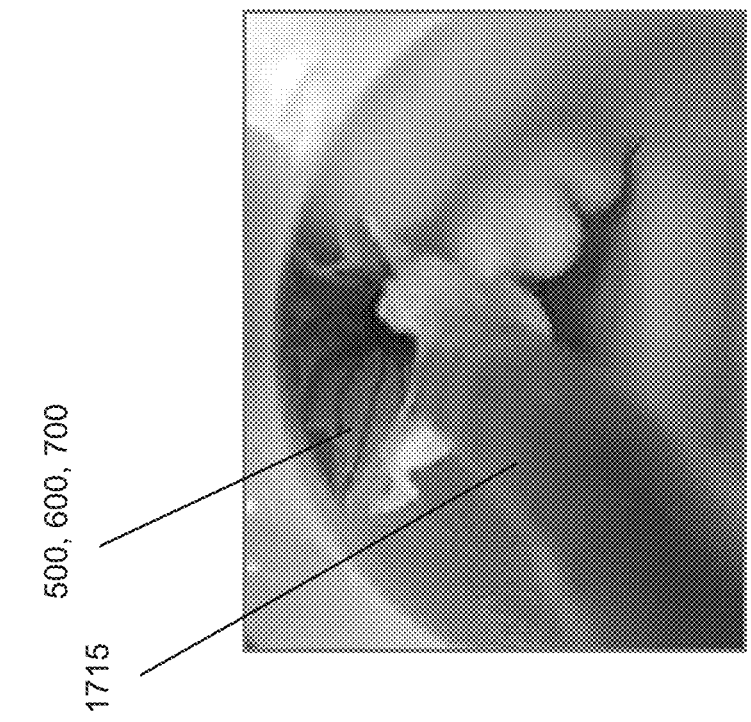
FIGS. 22A-22D illustrate a method for deploying the implant.
Figure 22A:
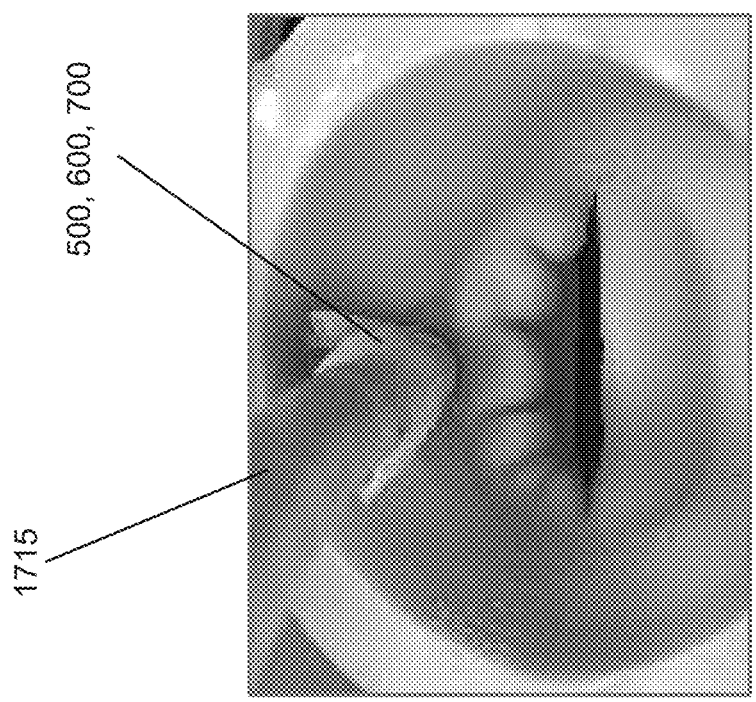

FIGS. 22A-22D illustrate a method for deploying the coaptation assistance element 500, 600, 700. The coaptation assistance element 500, 600, 700 can be deployed by retracting the transseptal sheath 1715. The transseptal sheath 1715 can be retracted by moving the transseptal sheath 1715 proximally from the anchor 800. The coaptation assistance element 500, 600, 700 can be inverted within the transseptal sheath 1715. In some embodiments, the annular portion near the annular hub 520, 620, 70 of the coaptation assistance element 500, 600, 700 can be deployed first as shown in FIG. 22A. In some embodiments, the ventricular portion of the coaptation assistance element 500, 600, 700 can be deployed next as shown in FIG. 22B. The coaptation assistance element 500, 600, 700 can be inverted such that the ventricular portion extends proximally from the annular portion.

Figure 22D:
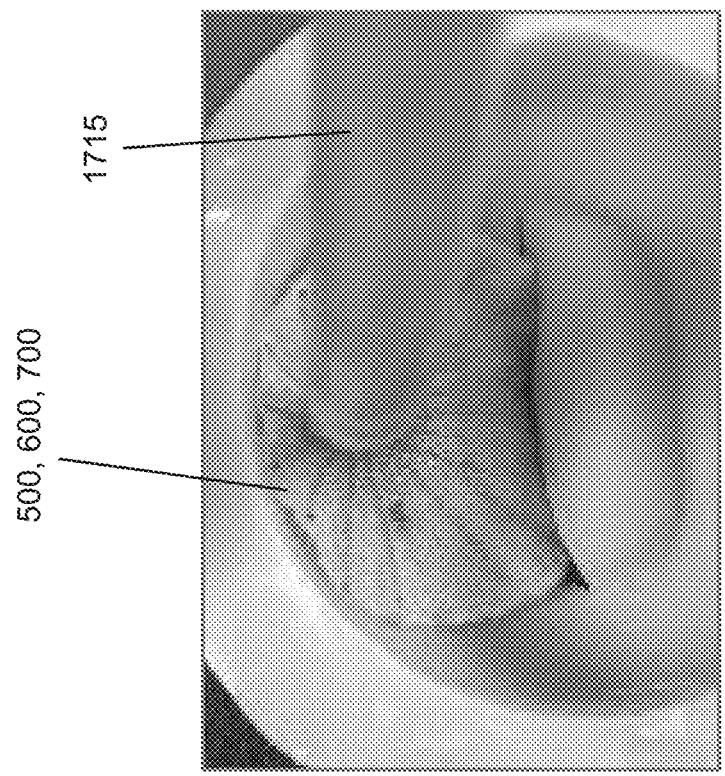
Figure 22C:
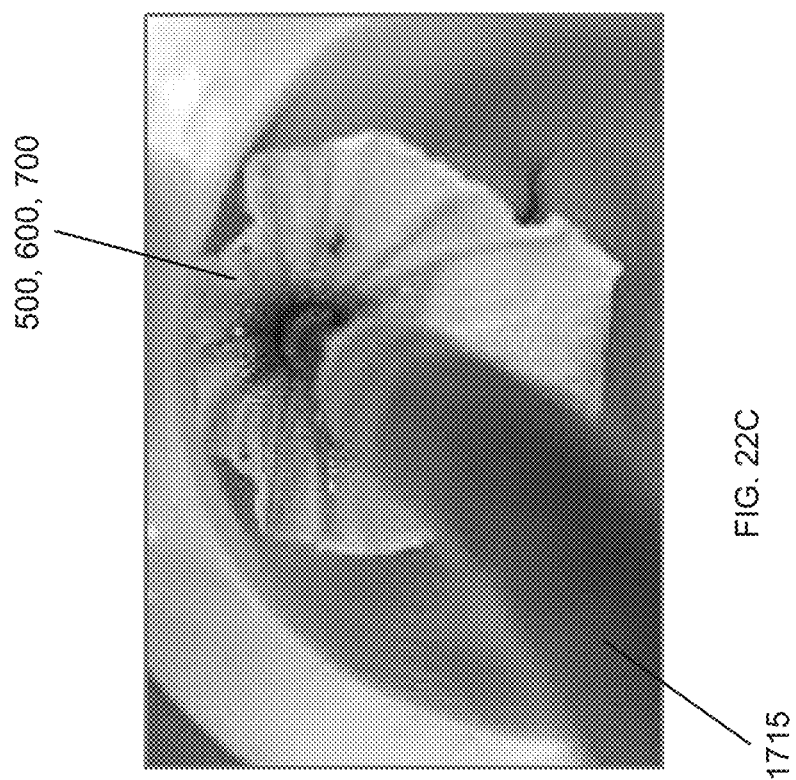

In some embodiments, the coaptation assistance element 500, 600, 700 can expand outward from P2 as the coaptation assistance element 500, 600, 700 is deployed as shown in FIG. 22C. The coaptation assistance element 500, 600, 700 can be inverted such that the ventricular portion extends proximally from the annular portion. The coaptation assistance element 500, 600, 700 can be inverted such that the ventricular portion extends toward the transseptal sheath 1715.

In some embodiments, the coaptation assistance element 500, 600, 700 can be folded back as shown in FIG. 22D. The coaptation assistance element 500, 600, 700 can be reversed from the initially deployed configuration such that the ventricular portion extends distally from the annular portion. The coaptation assistance element 500, 600, 700 can be positioned such that the ventricular portion extends away from the transseptal sheath 1715. The method can include deploying the coaptation assistance element 500, 600, 700 by retracting the transseptal sheath 1715. FIGS. 22A-22D show deployment of the coaptation assistance element 500, 600, 700.

FIGS. 23-30 illustrate deploying one or more secondary anchors 850. The secondary anchor 850 can include any of the features of the anchor 800. The secondary anchor 850 can comprise a helix or helical structure. The secondary anchor 850 can be designed to engage the tissue of heart, such as the tissue of the annulus. The secondary anchor 850 can comprise bio-inert materials such as Platinum/Ir, a Nitinol alloy, and/or stainless steel.

Figure 23:
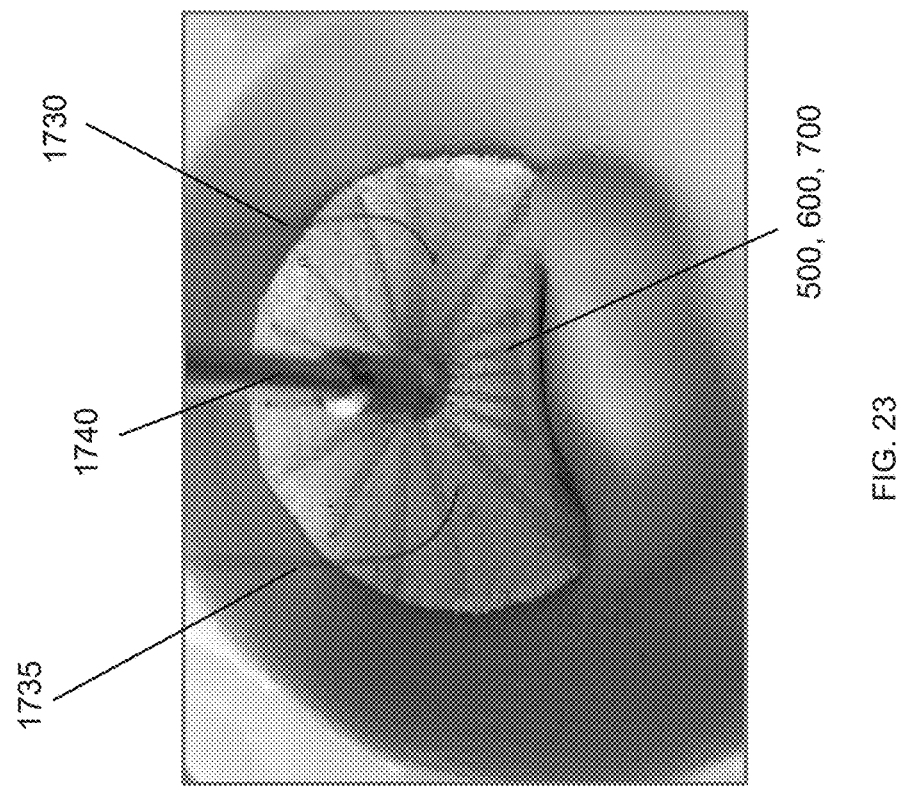
FIG. 23 illustrates a method for utilizing one or more secondary anchor guidewires.

FIG. 23 illustrates a method for utilizing one or more secondary anchor guidewires. The coaptation assistance element 500, 600, 700 can include one or more secondary anchor guidewires. In the illustrated embodiment, the coaptation assistance element 500, 600, 700 can include the first guidewire 1730 and the second guidewire 1735. In some embodiments, the coaptation assistance element 500, 600, 700 can include any number of secondary anchor guidewires (e.g., about or at least about one, two, three, four, five, etc.). In some embodiments, the number of secondary anchor guidewires corresponds to (equals) the number of secondary anchors (e.g., one guidewire for one secondary anchor, two guidewires for two secondary anchors, etc.). FIG. 23 illustrates an embodiment of a docking tube 1740. The docking tube 1740 can include any of the features described herein, including those shown in FIGS. 42A-45K.

FIG. 23 illustrates a tether mode. The tether mode can correspond to one or more methods to evaluate the coaptation assistance element 500, 600, 700. The tether mode can correspond to one or more methods to evaluate the function of the coaptation assistance element 500, 600, 700 without one or more delivery systems. In some embodiments, the tether mode can correspond to one or more methods to evaluate the function of the coaptation assistance element 500, 600, 700 without the transseptal sheath 1715. The tether mode can evaluate function without the bulk of the delivery system attached. FIG. 23 shows the deployed coaptation assistance element 500, 600, 700. FIG. 23 shows the coaptation assistance element 500, 600, 700 going to tether mode by retracting an implant shaft. FIG. 23 shows the coaptation assistance element 500, 600, 700 going to tether mode by retracting the transseptal sheath 1715.

Figure 24:
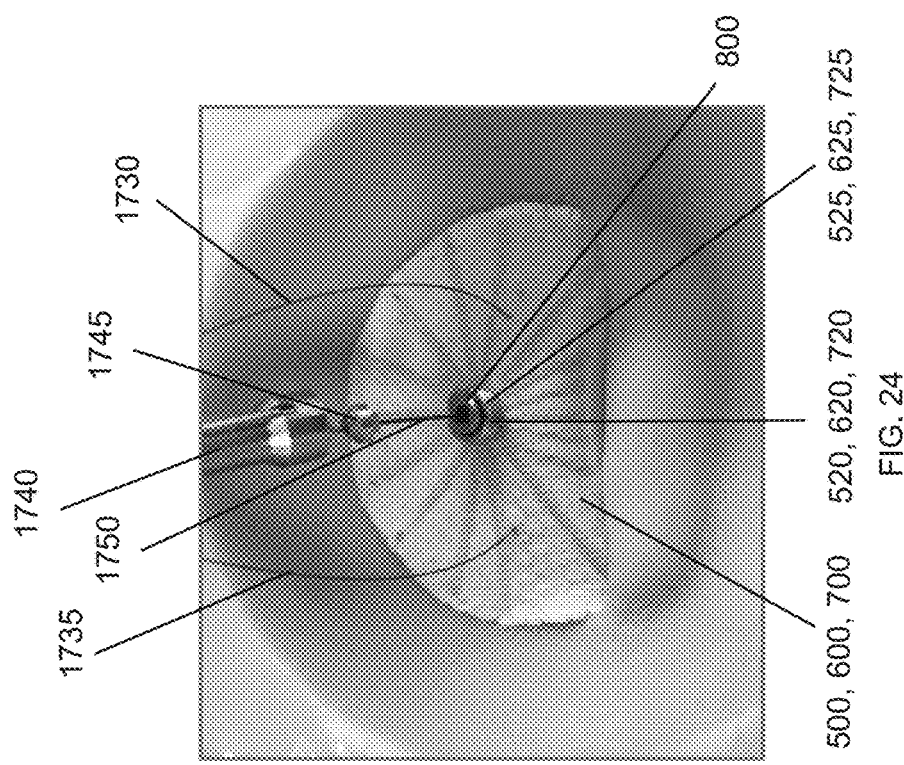
FIG. 24 illustrates a method for removing an anchor driver.

FIG. 24 illustrates a method involving the docking tube 1740. The docking tube 1740 can include internal threads. The docking tube 1740 can include an internally threaded DS hub for coupling to an externally threaded portion 525, 625, 725 of the annular hub 520, 620, 720. The docking tube 1740 can include an internally threaded hub for coupling to the coaptation assistance element 500, 600, 700. In some methods of use, the docking tube 1740 is removed for tether mode. FIG. 24 shows the coaptation assistance element 500, 600, 700 going to tether mode by retracting the docking tube 1740.

FIG. 24 illustrates a method involving an anchor driver 1745. The anchor driver 1745 can be disposed within the docking tube 1740. The anchor driver 1745 can include any of the features described herein, including those shown in FIGS. 42A-45K. The anchor driver 1745 can rotate the anchor 800 during the method shown in FIG. 21. The anchor driver 1745 can rotate the anchor 800 through the annular hub 520, 620, 720. In some methods of use, the anchor driver 1745 is removed for tether mode. FIG. 24 shows the coaptation assistance element 500, 600, 700 going to tether mode by retracting the anchor driver 1745.

The anchor driver 1745 can include a tether rail 1750. The tether rail 1750 can include any of the features described herein, including those shown in FIGS. 42A-45K. The tether rail 1750 can be secured to the anchor 800. The tether rail 1750 can allow for a minimal force evaluation of the effective of the coaptation assistance element 500, 600, 700 prior to releasing the coaptation assistance element 500, 600, 700. As one example, the user can verify that the coaptation assistance element 500, 600, 700 is functional. As one example, the user can verify that the native leaflet is coapting against the coaptation assistance element 500, 600, 700. As one example, the user can verify that the force exerted on the coaptation assistance element 500, 600, 700 is within an acceptable range. As one example, the user can verify that the coaptation assistance element 500, 600, 700 is not deforming under the force of the native leaflet. As one example, the user can verify that the coaptation assistance element 500, 600, 700 is deployed. As one example, the user can verify that the coaptation assistance element 500, 600, 700 spans the mitral valve. The docking tube 1740 can be retracted as shown. As shown in FIG. 24, the tether rail 1750 can remain coupled to the anchor 800 during tether mode.

Figure 25:
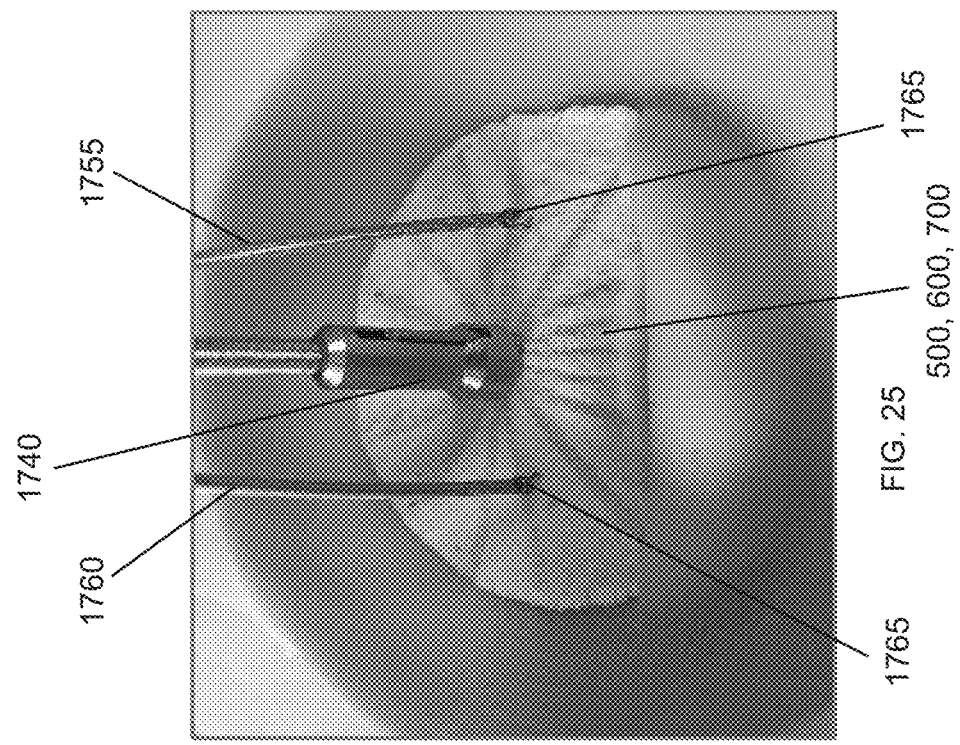
FIG. 25 illustrates a method for advancing secondary anchor guiderails.

FIG. 25 illustrates a method for advancing secondary anchor guiderails. In the illustrated embodiment, the method can include the first guiderail 1755 and the second guidewire 1760. In some embodiments, the coaptation assistance element 500, 600, 700 can include any number of secondary anchor guiderails (e.g., one, two, three, four, five, etc.). In some embodiments, the number of secondary anchor guiderails corresponds to the number of secondary guidewires (e.g., one guiderail for one secondary guidewire, two guiderails for two secondary guidewires, etc.). The first guiderail 1755 can be advance along the first guidewire 1730. The second guiderail 1760 can be advanced along the second guidewire 1735. The method can involve advancing both secondary anchor guiderails 1755, 1760. The secondary anchor guiderails 1755, 1760 are over the guidewires 1730, 1735 in FIG. 25.

The distal end 1765 of each secondary anchor guiderail 1755, 1760 can be threaded. In some embodiments, the distal end 1765 of each secondary anchor guiderail 1755, 1760 engages tissue in the annulus. The distal end 1765 can be threaded to temporarily secure the secondary anchor to the guiderail 1755, 1760 during delivery. In some embodiments, the distal end 1765 of each secondary anchor guiderail 1755, 1760 can reduce the likelihood that the secondary anchor inadvertently comes off the secondary anchor guiderail 1755, 1760. The secondary anchor guiderails 1755, 1760 can reduce the likelihood that the secondary anchors get tangled with the guide wires 1730, 1735. In some embodiments, the diameter of the secondary anchor guiderails 1755, 1760 is greater than or equal to the secondary anchor pitch.

In some methods of use, the docking tube 1740 can be coupled to the coaptation assistance element 500, 600, 700. The attachment can allow for recess of the anchor 800 during delivery of the coaptation assistance element 500, 600, 700. In some embodiments, the secondary anchor guiderails 1755, 1760 are advanced over guidewires 1730, 1735 prior to deploying the anchor 800. In some embodiments, the secondary anchor guiderails 1755, 1760 are advanced over guidewires 1730, 1735 after deploying the anchor 800. FIG. 25 shows the coaptation assistance element 500, 600, 700 secured to the annulus with the anchor 800 with secondary anchor guiderails advanced to the surface of the coaptation assistance element 500, 600, 700.

Figure 26:
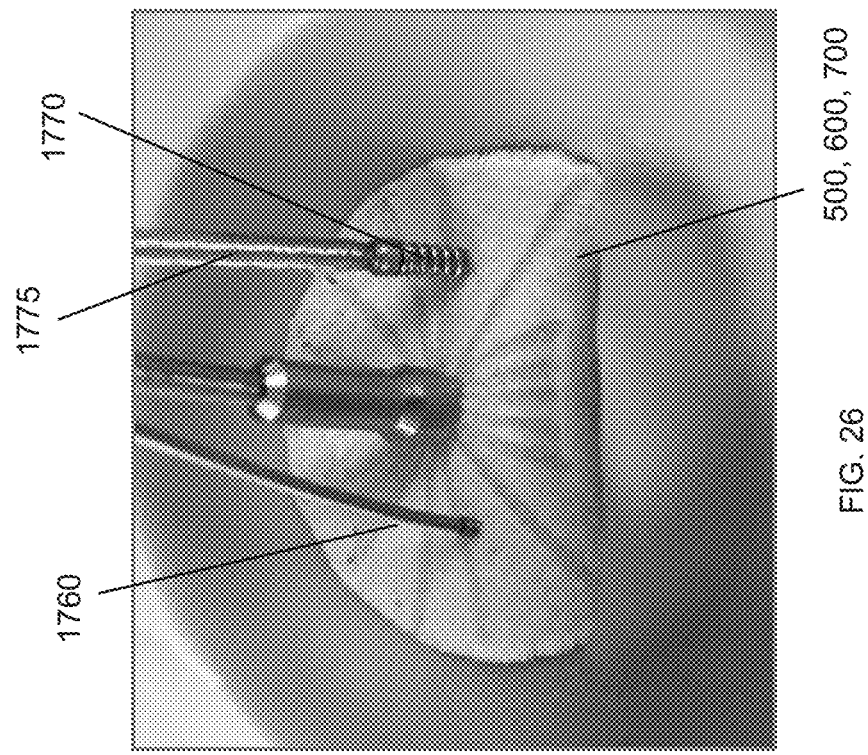
FIG. 26 illustrates a method for delivering a secondary anchor.

FIG. 26 illustrates a method for delivering a secondary anchor 1770. The secondary anchor 1770 is advanced over the first guiderail 1755. The secondary anchor 1770 can be advanced toward the coaptation assistance element 500, 600, 700. The secondary anchor 1770 can be installed with a driver 1775. The driver 1775 can translate the secondary anchor 1770 along the first guiderail 1755.

Figure 27:
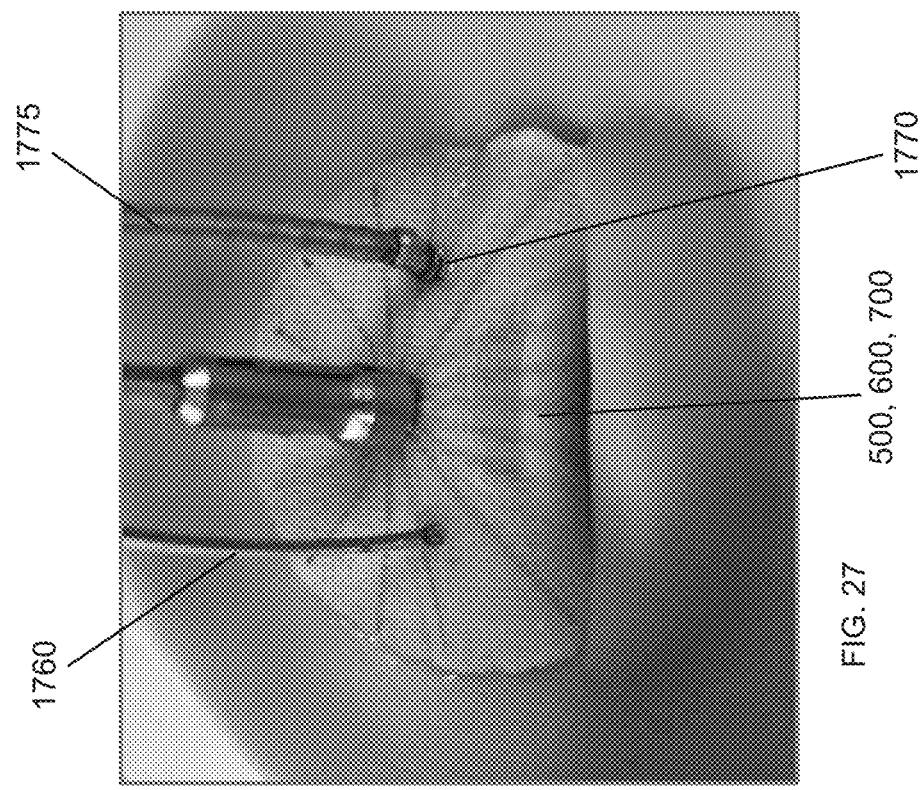
FIG. 27 illustrates a method for inserting a secondary anchor.
Figure 31A:
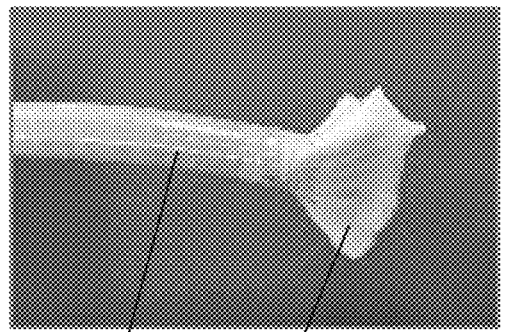
FIGS. 31A-31F illustrate a method for retrieving the implant.
Figure 31B:
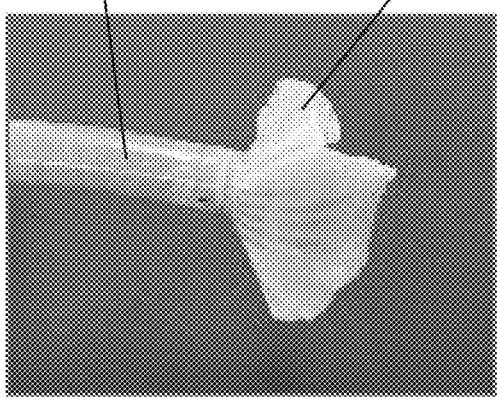
Figure 31C:
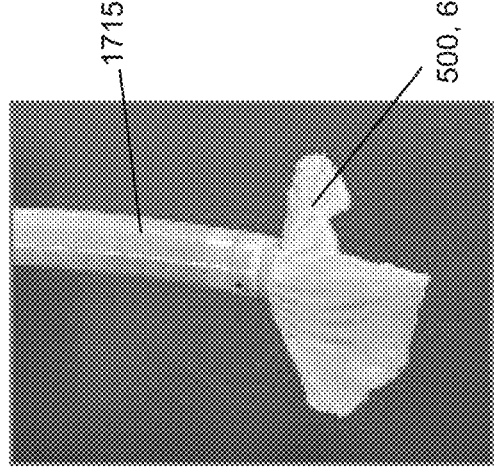
Figure 31D:
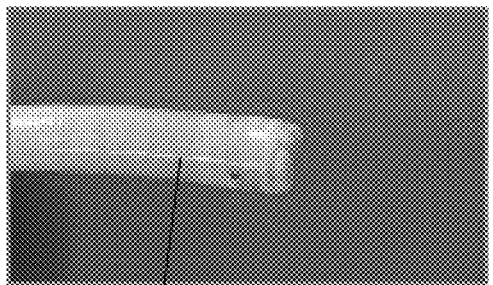
Figure 31E:
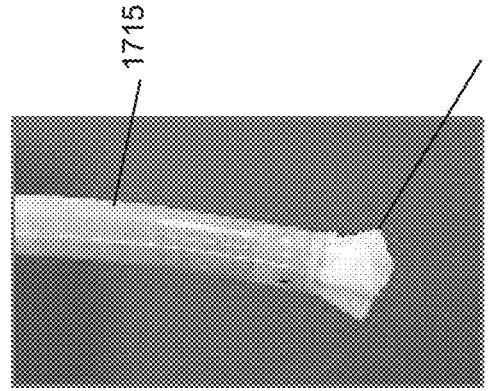
Figure 31F:
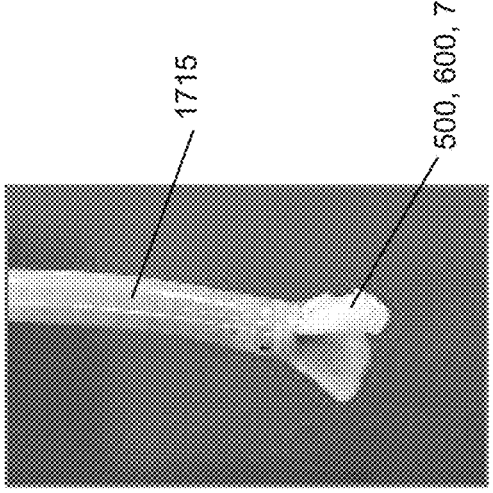

FIG. 27 illustrates a method for inserting the secondary anchor 1770. The driver 1775 can rotate the secondary anchor 1770 along the first guiderail 1755. The secondary anchor 1770 can be threaded through the coaptation assistance element 500, 600, 700. The secondary anchor 1770 can be rotated to engage tissue underneath the coaptation assistance element 500, 600, 700. FIG. 26 shows the coaptation assistance element 500, 600, 700 secured to the annulus with the anchor 800 when the secondary anchor 1770 is delivered. FIG. 26 shows the coaptation assistance element 500, 600, 700 secured to the annulus with the anchor 800 when the secondary anchor 1770 is inserted into tissue. The driver 1775 is still attached as shown in FIG. 27 The secondary anchor 1770 can be a medial anchor. The secondary anchor 1770 can be positioned on a medial side of the anchor 800.

Figure 28:
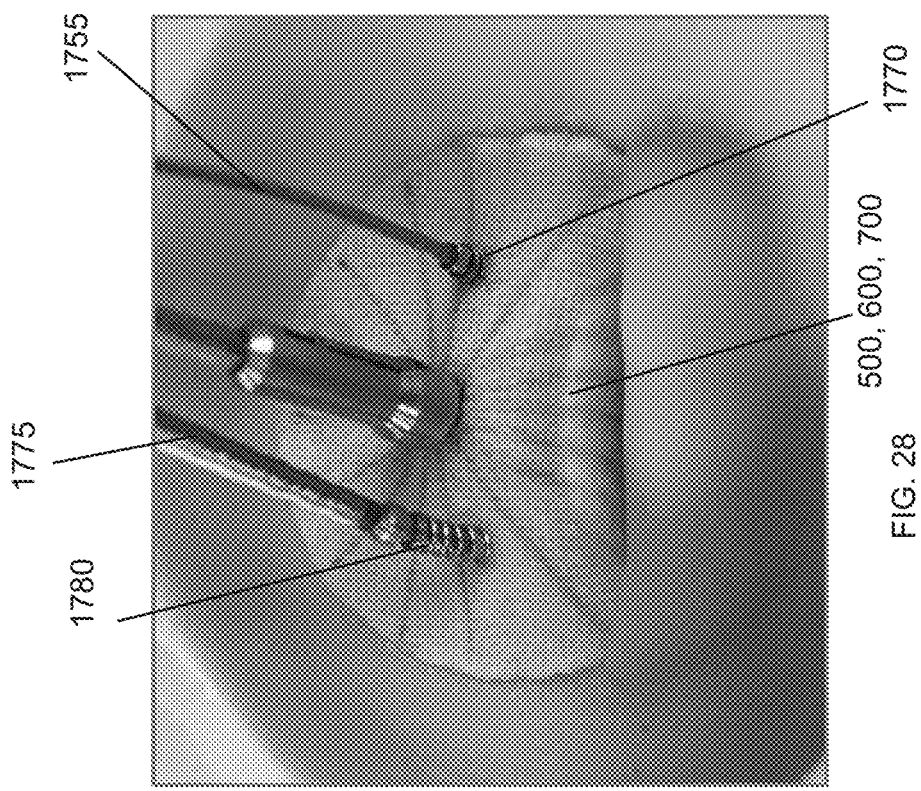
FIG. 28 illustrates a method for delivering another secondary anchor.

FIG. 28 illustrates a method for delivering a secondary anchor 1780. The secondary anchor 1780 is advanced over the second guiderail 1760. The secondary anchor 1780 can be advanced toward the coaptation assistance element 500, 600, 700. In some methods of use, the secondary anchor 1780 can be installed with a driver 1775. In some methods of use, the driver 1775 can be retracted along the first guide rail 1755 prior to being advanced along the second guiderail 1760. In other methods of use, the secondary anchor 1780 is installed with a different driver than the secondary anchor 1770. The driver 1775 can translate the secondary anchor 1780 along the first guiderail 1760. In some methods of use, the secondary anchor 1770 can be previously inserted into the tissue.

The driver 1775 can rotate the secondary anchor 1780 along the second guiderail 1760. The secondary anchor 1780 can be threaded through the coaptation assistance element 500, 600, 700. The secondary anchor 1780 can be rotated to engage tissue underneath the coaptation assistance element 500, 600, 700. FIG. 28 shows the coaptation assistance element 500, 600, 700 secured to the annulus with the anchor 800 and the secondary anchor 1770 when the secondary anchor 1780 is delivered. FIG. 26 shows the coaptation assistance element 500, 600, 700 secured to the annulus with the anchor 800 and the secondary anchor 1770 when the secondary anchor 1780 is inserted into tissue. The secondary anchor 1780 can be a lateral anchor. The secondary anchor 1780 can be positioned on a lateral side of the anchor 800.

Figures 29, 30:
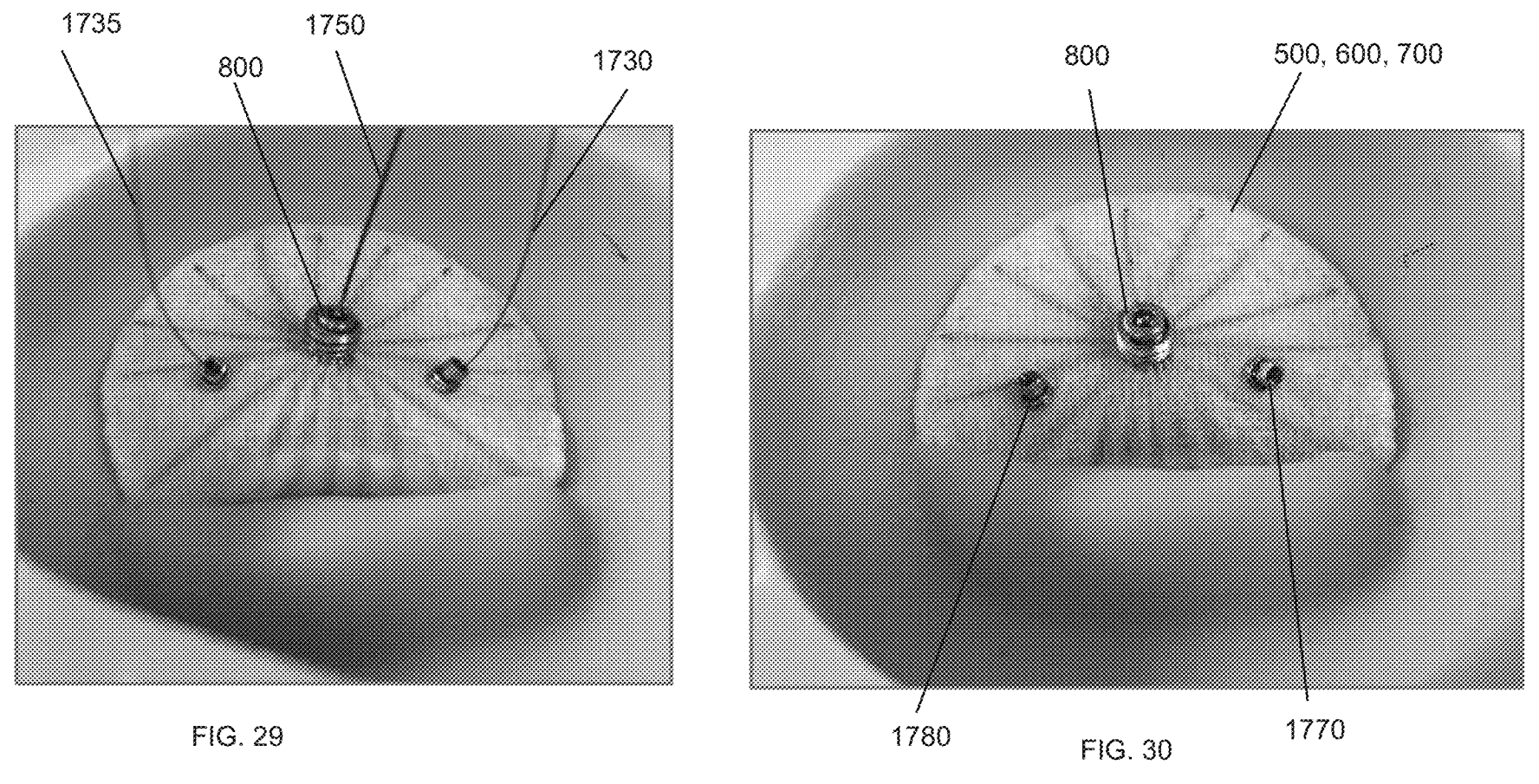

FIG. 29 illustrates the coaptation assistance element 500, 600, 700 with secondary anchor guidewires 1730, 1735. The tether rail 1750 can remain coupled to the anchor 800. The secondary anchor guidewires 1730, 1735 remain connected. The delivery system can be re-attached. In some methods of use, one or more guiderails 1755, 1760 can be re-attached. In some methods of use, the driver 1775 is re-attached. One or more secondary anchors 1770, 1780 can be removed. One or more secondary anchors 1770, 1780 can be repositioned. In some methods of use, the docking tube 1740 can be re-attached. In some methods of use, the anchor driver 1745 can be re-attached. The anchor 800 can be removed. The anchor 800 can be repositioned. The anchor 800 and the secondary anchors 1770, 1780 can be removed. The coaptation assistance element 500, 600, 700 can be retrieved. FIG. 29 shows the deployed and anchored coaptation assistance element 500, 600, 700 with the secondary anchor guidewires 1730, 1735 and the tether rail 1750 remaining, allowing for retrieval.

FIG. 30 illustrates the anchored coaptation assistance element 500, 600, 700. The secondary anchor guidewires 1730, 1735 are removed. The tether rail 1750 is removed. In some embodiments, the tether rail 1750 is rotated and retracted. The coaptation assistance element 500, 600, 700 is shown completely deployed and anchored. In some methods of use, retrieval is no longer possible. In some methods of use, retrieval through the method described in FIGS. 31A-31F is no longer possible.

FIGS. 31A-31F illustrate methods for retrieving the coaptation assistance element 500, 600, 700. The coaptation assistance element 500, 600, 700 can be retrieved through the transseptal sheath 1715. In some methods of use, without secondary anchors 1770, 1780, the coaptation assistance element 500, 600, 700 can be retrieved after the anchor 800 is removed. In some methods of use, the coaptation assistance element 500, 600, 700 can be retrieved after the anchor 800 and all the secondary anchors 1770, 1780 are removed. The coaptation assistance element 500, 600, 700 is being retrieved through the transseptal sheath 1715 in FIGS. 31A-31F. In some methods of use, the retrieval is optional. In some methods of use, the retrieval occurs after the method shown in FIG. 29 and before the method shown in FIG. 30.

FIGS. 32-35 illustrate a method for installing one or more secondary anchors. One or more methods can be used in conjunction with methods described herein. One or more methods can be as an alternative to methods described herein. As one example, one or more methods shown in FIGS. 32-35 can replace one or more methods shown in FIGS. 23-30. The secondary anchors described herein can be delivered using guidewires and/or guiderails with a variety of designs. In some embodiments, each secondary anchor can have a dedicated lumen (e.g., two secondary anchors use two lumens; four secondary anchors use four lumens, etc.). In some embodiments, each secondary anchor can have a dedicated guidewire (e.g., two secondary anchors use two guidewires, four secondary anchor use four guidewires, etc.). In some embodiments, two secondary anchors share a lumen (e.g., two secondary anchors in one lumen, four secondary anchors in two lumens; two guidewires in one lumen, four guidewires in two lumens, etc.) In some embodiments, each of the two guidewires in the shared lumen is covered by a guiderail. The guiderail can reduce secondary anchor entanglement. The guiderail can reduce secondary anchor entanglement with the two or more guidewires in the lumen.

Figure 32:
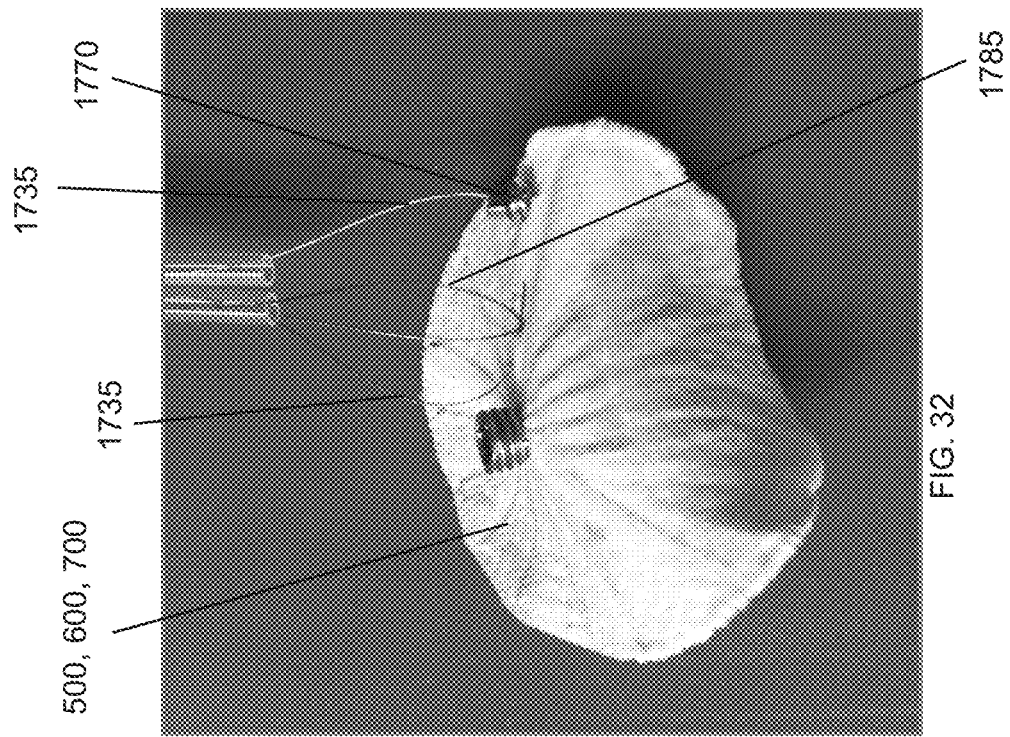
FIG. 32 illustrates a method for inserting a secondary anchor.

FIG. 32 illustrates a method for inserting a secondary anchor. In some methods of use, the secondary anchor 1770 is inserted as described herein. The guidewire 1735 can extend from the secondary anchor 1770. The guidewire 1735 can extend into a lumen or a shared lumen. In some methods of use, the secondary anchor 1770 is inserted as described herein. One or more secondary anchors 1170, 1780 can be inserted.

In some embodiments, one guidewire 1735 can be used for two secondary anchors. In some methods of sue, to facilitate removal of the guidewire 1735 after delivery of the first secondary anchor 1770, the guidewire 1735 can be snared and removed. In some embodiments, the guidewire 1735 forms a loop. In some embodiments, a portion of the loop of the guidewire 1735 is contained within the coaptation assistance element 500, 600, 700. In some embodiments, the loop threads through the coaptation assistance element 500, 600, 700. In some embodiments, a snare 1785 can be positioned along the guidewire 1735. In some embodiments, the snare 1785 forms a loop. In some embodiments, a portion of the loop of the guidewire 1735 is contained within loop of the snare 1785. The method can include using the snare 1785. The snare 1785 can be for unthreading the guidewire 1735. The snare 1785 can be retracted. The snare 1785 can be pulled proximally through a lumen.

Figure 33:
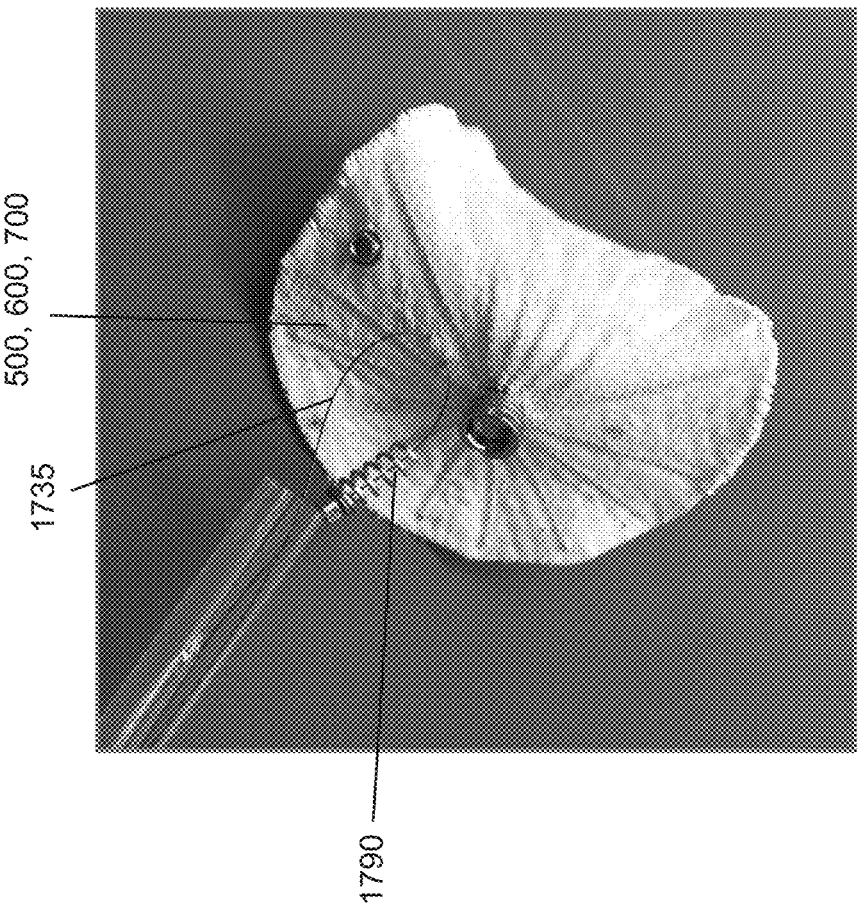
FIG. 33 illustrates a method for delivering another secondary anchor.

FIG. 33 illustrates a method for delivering a secondary anchor 1790. The snare 1785 has been retracted within the lumen. The snare 1785 has pulled the guidewire 1735 proximally. In some embodiments, the driver 1775 or another driver can advance the secondary anchor 1790 along the guidewire 1735. In some embodiments the secondary anchor 1790 is to be delivered with the guidewire 1735 removed using the snare 1785 from the anchor 1770.

Figure 34:
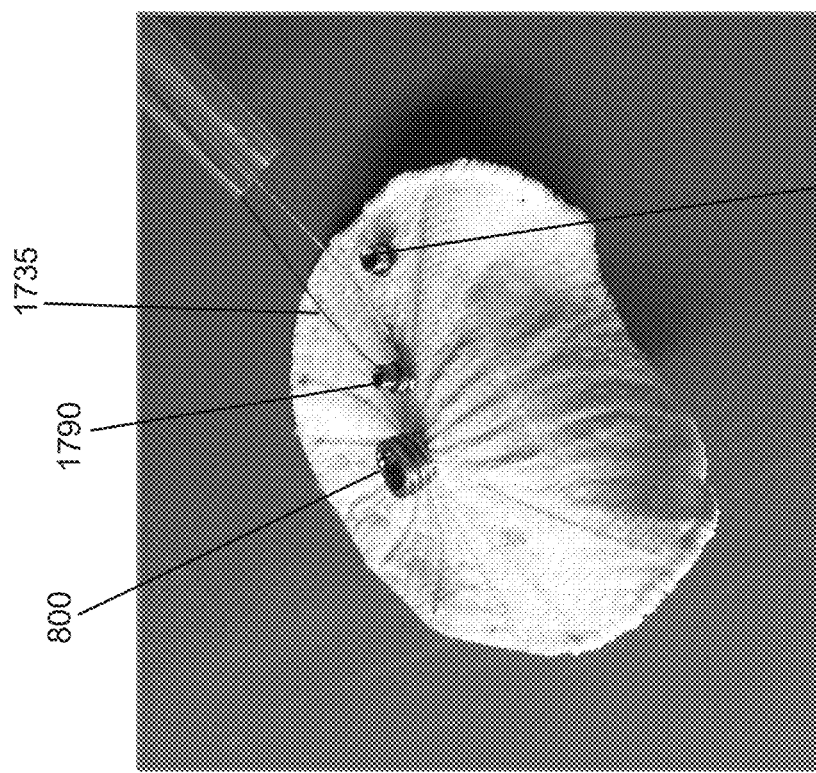
FIG. 34 illustrates a method for inserting another secondary anchor.

FIG. 34 illustrates a method for inserting the secondary anchor 1790. The secondary anchor 1790 can be rotated. The secondary anchor 1790 can be threaded through the coaptation assistance element 500, 600, 700. The secondary anchor 1790 can be rotated to engage tissue underneath the coaptation assistance element 500, 600, 700. FIG. 34 shows the coaptation assistance element 500, 600, 700 secured to the annulus with the anchor 800 and the secondary anchor 1770 when the secondary anchor 1790 is delivered. The secondary anchor 1790 can be a medial anchor. The secondary anchor 1790 can be positioned on a medial side of the anchor 800. The secondary anchor 1790 can be positioned between the anchor 800 and the secondary anchor 1770.

Figure 35:
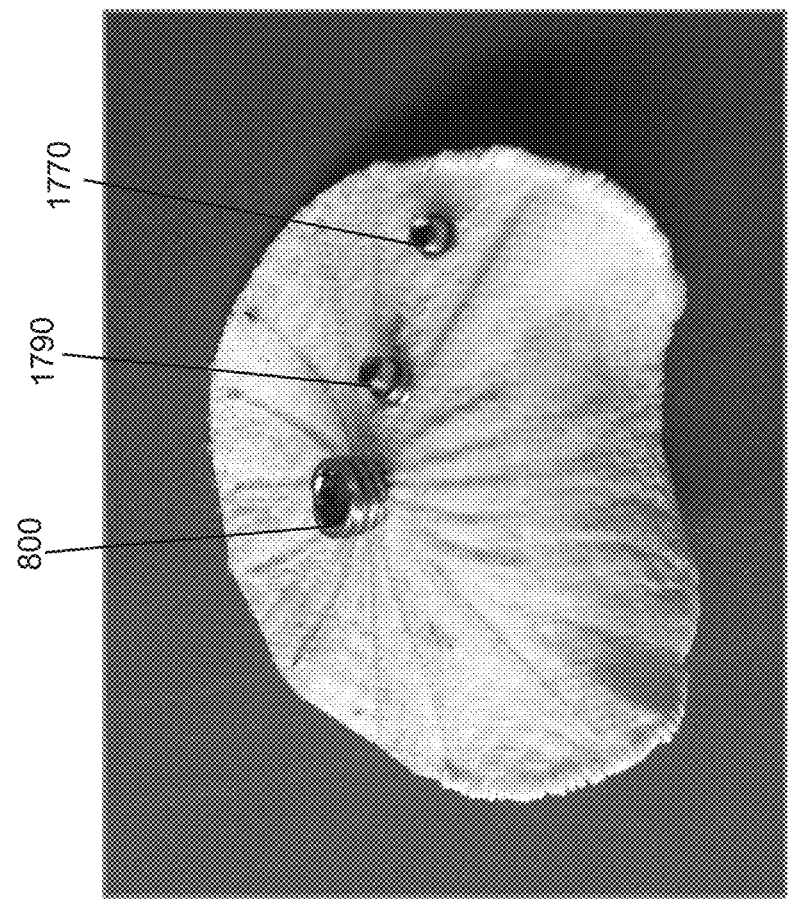
FIG. 35 illustrates the anchored implant.

FIG. 35 illustrates the anchored coaptation assistance element 500, 600, 700. The methods can be repeated to install one or more additional secondary anchors. For instance, one or more additional secondary anchors can be positioned between the secondary anchor 1780 and the anchor 800 as shown in FIG. 30. For instance, one or more additional secondary anchors can be positioned between the secondary anchor 1770 and the anchor 800 as shown in FIG. 30. For instance, one or more additional secondary anchors can be positioned anywhere on the annular portion of the coaptation assistance element 500, 600, 700.

Figure 36:
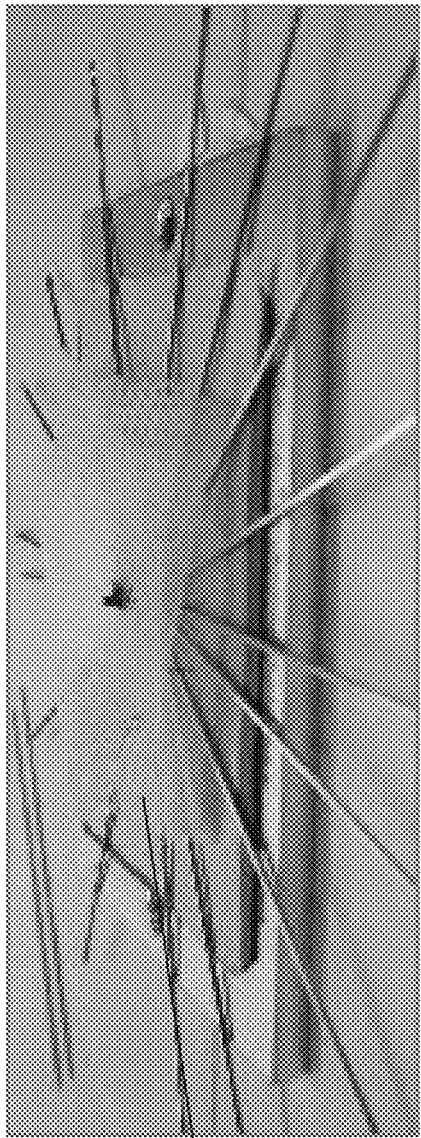
FIG. 36 illustrates an embodiment of lamination.
Figure 37:
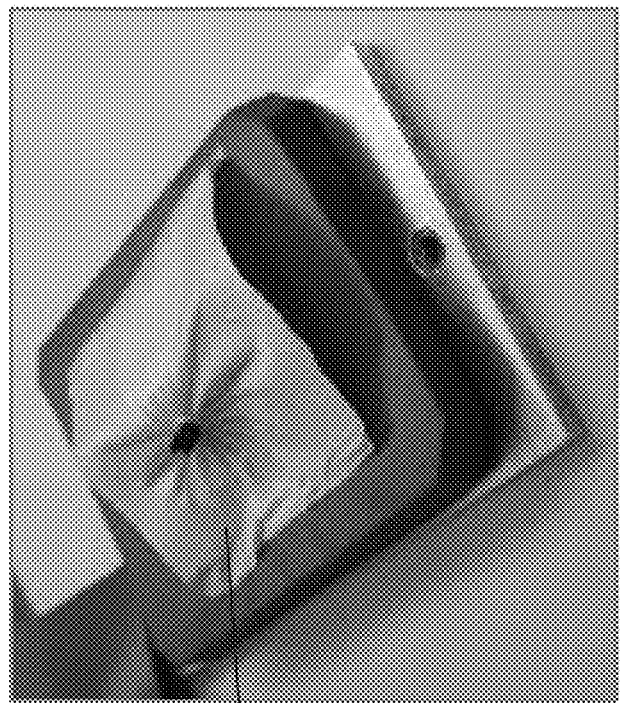
FIG. 37 illustrates an embodiment of lamination.
Figure 39:
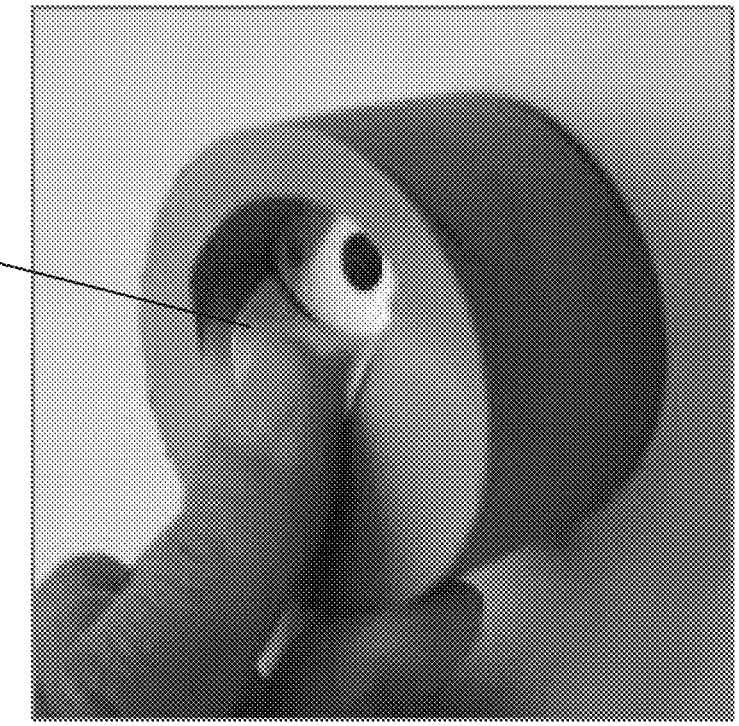
FIG. 39 illustrates an embodiment of 3D forming.
Figure 38:
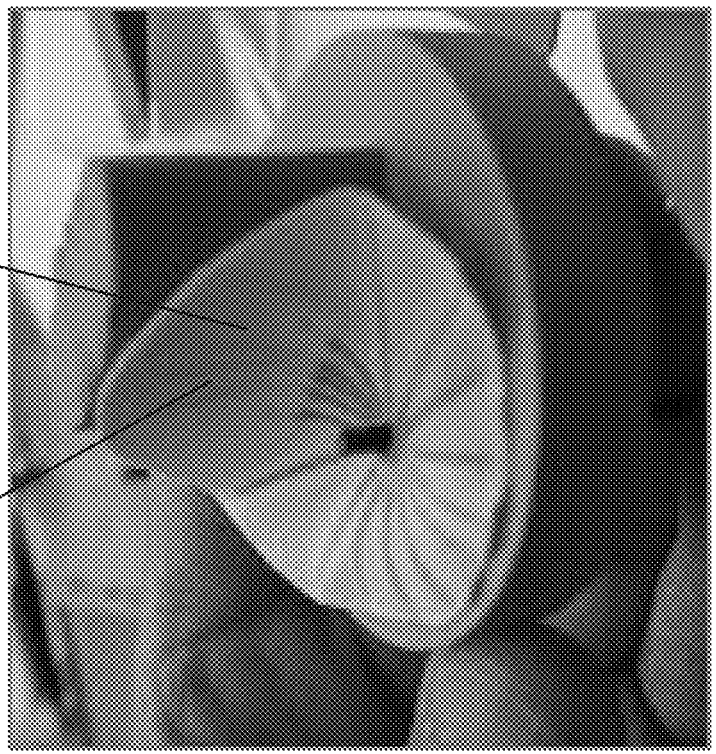
FIG. 38 illustrates an embodiment of 3D forming.

FIGS. 36 and 37 illustrates embodiments of 2D lamination. FIGS. 38 and 39 illustrate embodiments of 3D forming. In some embodiments, the coaptation assistance element 500, 600, 700 comprises a multi-layer laminate on the entire, or only a portion of the coaptation assistance element. In some embodiments, the multi-layer laminate can comprise two or more layers of laminate (e.g., two, three, four, five, etc.). Two or more layers of the multi-layer laminate can comprise the same material. Two or more layers of the multi-layer laminate can comprise different materials. Two or more layers of the multi-layer laminate can comprise the same dimensions (e.g., length, width, thickness, diameter, etc.). Two or more layers of the multi-layer laminate can comprise one or more different dimensions. The laminate can be variable, depending on the zone of the coaptation assistance element 500, 600, 700. In some embodiments, the cooptation zone can have additional protective layers. In some embodiments, the coaptation surface 560, 660, 760 includes one or more additional layers than another portion of the coaptation assistance element 500, 600, 700. FIG. 38 shows the additional layer 1795 only in the coaptation zone (e.g., inferior zone) of the coaptation assistance element 500, 600, 700. As such the inferior coaptation zone can be thicker than that of the superior zone of the coaptation assistance element residing proximate the heart valve annulus, such at least about 10%, 25%, 50%, 75%, 100%, 150%, 200%, 250%, 300%, or more thicker than that of the superior zone, or ranges incorporating any two of the aforementioned values.

The multi-layer laminate can be fabricated in 2D lamination methods. In some methods of use, two or more layers are bonded together. The layers can be bonded by heat. The layers can be bonded by adhesive. The layers can be bonded together through any mechanical or chemical change. The coaptation assistance element 500, 600, 700 can have a generally 2D shape. The coaptation assistance element 500, 600, 700 can be flat or generally flat. In some embodiments, one or more layers comprise high density polyethylene (PE), polypropylene Dacron, acellular collagen matrix such as SIS, or other plastics.

The multi-layer laminate can be fabricated in 3D shape forming methods. The coaptation assistance element 500, 600, 700 can be shaped. As described herein, the coaptation assistance element 500, 600, 700 can comprise struts 530, 630, 730. In some embodiments, the struts 530, 630, 730 are composed of resiliently deformable materials such as a shape memory metal, e.g., Nitinol or a shape memory polymer. In some embodiments, the material is Elgiloy. In some embodiments, the struts 530 may be composed of other materials to include stainless steel, polypropylene, high density polyethylene (PE), Dacron, acellular collagen matrix such as SIS, or other plastics, etc. The 3D forming can involve molding the shape of the struts 530, 630, 730. The 3D forming can include adjusting the shape memory metal into the appropriate shape. The shape can be set with appropriate molds which bend the struts 530, 630, 730 into the desired shape. Shape setting or shape training may include constraining the coaptation assistance element 500, 600, 700 on a fixture or within a mold. In some methods of use, an appropriate heat treatment is applied to the coaptation assistance element 500, 600, 700 while on the fixture or within the mold. In some embodiments, the temperature, time and/or other parameters are adjusted to heat set the coaptation assistance element 500, 600, 700. In some embodiments, the temperature for heat setting is greater than 300° C., greater than 400° C., greater than 500° C., greater than 600° C., etc. In some embodiments, the time for heat setting is 1 minute, 2 minutes, 3 minutes, 4 minutes, 5 minutes, 6 minutes, 7 minutes, 8 minutes, 9 minutes, 10 minutes, more than 2 minutes, more than 5 minutes, more than 10 minutes, etc. In some embodiments, the method can include rapid cooling. In some embodiments, the method can include rapid cooling via water or air.

Figure 40:
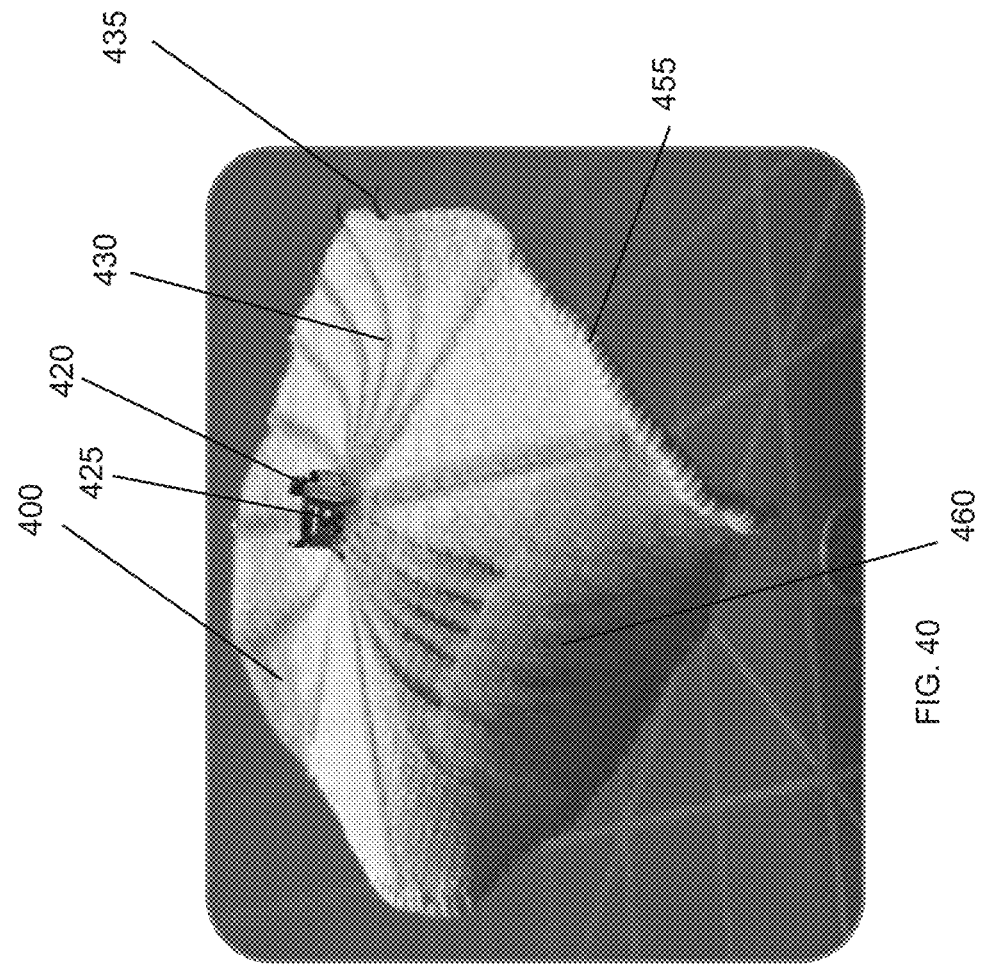
FIG. 40 illustrates an implant.

FIG. 40 illustrates a coaptation assistance element 400. The coaptation assistance element 400 can include any of the features of the coaptation assistance elements described herein. The coaptation assistance element 400 can include an annular hub 420 to facilitate attachment to a delivery system, similar to the annular hubs described herein. The annular hub 425 can include an externally threaded portion 425. The coaptation assistance element 400 can include struts 430. The struts 430 can be atrial arms that may be bend in the superior and/or inferior direction.

Figure 41:
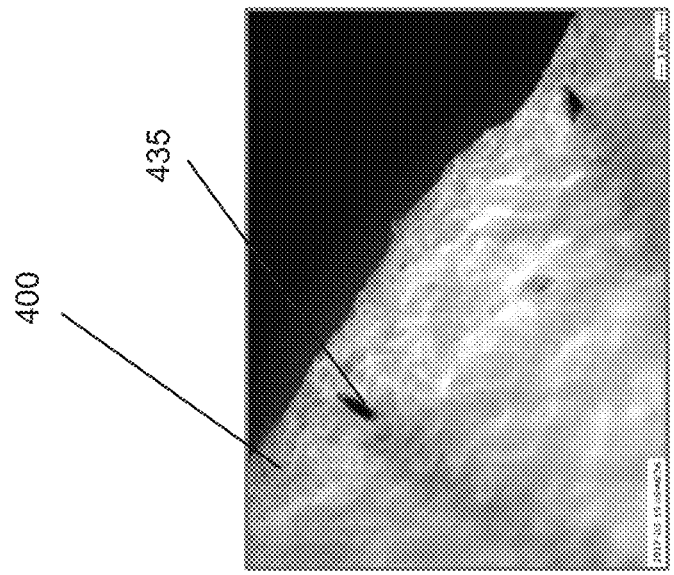
FIG. 41 illustrates an embodiment of a barb.

The coaptation assistance element 400 can include an annular anchor site 435. The annular anchor site 435 can be a portion of the struts 430. In some embodiments, the annular anchor site 435 comprises one or more barbs having a sharpened tip. The annular anchor site 435 can be a passive anchor. The barbs can be exposed fully and shaped as shown in FIG. 40. In some embodiments, the barbs extend from the multi-layer laminate. The barbs can be the free ends of the struts 430. In some embodiments, the barbs can lay on the surface of the coaptation assistance element 400. In some embodiments, the barbs can engage tissue with push-back of laminate. For instance, the multi-layer laminate can be pushed back as shown in FIG. 41. FIG. 41 illustrates an embodiment of a barb. In some methods of use, engagement of the barb with tissue may cause the multi-layer laminate to push back.

The coaptation assistance element 400 can include a knotless sutured edge 455. The edge may reduce trauma to the native tissue. The coaptation assistance element 400 can include one or more rounded edges that reduce trauma. In some embodiment, the lateral edges of the coaptation assistance element 400 are rounded. In some embodiment, the superior edge of the coaptation assistance element 400 is rounded. In some embodiment, the inferior edge of the coaptation assistance element 400 is rounded.

The coaptation assistance element 400 can include a coaptation surface 460. The coaptation surface 460 can include additional protective layers. In some embodiments, the coaptation surface 460 can include one or more additional layers of the multi-layer laminate. In some embodiments, the coaptation surface 460 can include one or more different layers of the multi-layer laminate. The one or more layers of the coaptation surface 460 can be designed to facilitate longevity of the coaptation assistance element 400. The one or more layers of the coaptation surface 460 can be designed to facilitate coaptation with the native leaflet.

FIGS. 42A-45K illustrate embodiments of implant delivery systems. The implant delivery systems can include any coaptation assistance element described herein. The implant delivery systems can be designed to position the coaptation assistance element within the heart. The implant delivery systems can include any anchor described herein. The implant delivery systems can be designed to engage the anchor with tissue. The implant delivery systems can be designed to rotate the anchor.

FIGS. 42A-42i illustrate an embodiment of implant delivery system 1800. The implant delivery system 1800 can include a docking tube 1805. The docking tube 1805 is connected to an implant torque shaft 1810. In some embodiments, the implant torque shaft 1810 can be rigidly coupled to the docking tube 1805. In some embodiments, the implant torque shaft 1810 is welded or soldered to the docking tube 1805. The implant torque shaft 1810 can transmit torque to the docking tube 1805, as described herein. The docking tube 1805 can be coupled to the coaptation assistance element 400, 500, 600, 700. In the illustrated embodiment, only a portion of the struts 430, 530, 630, 730 are shown.

Figure 42B:
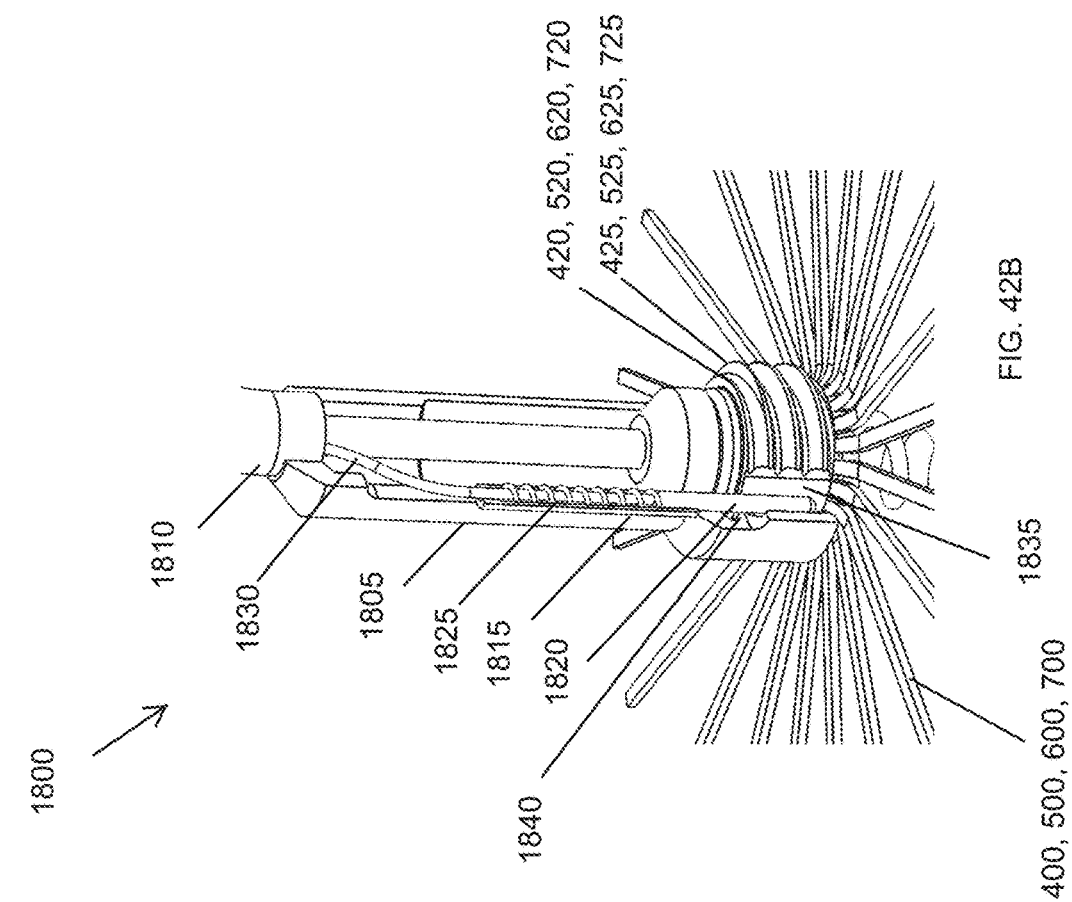
Figure 42A:
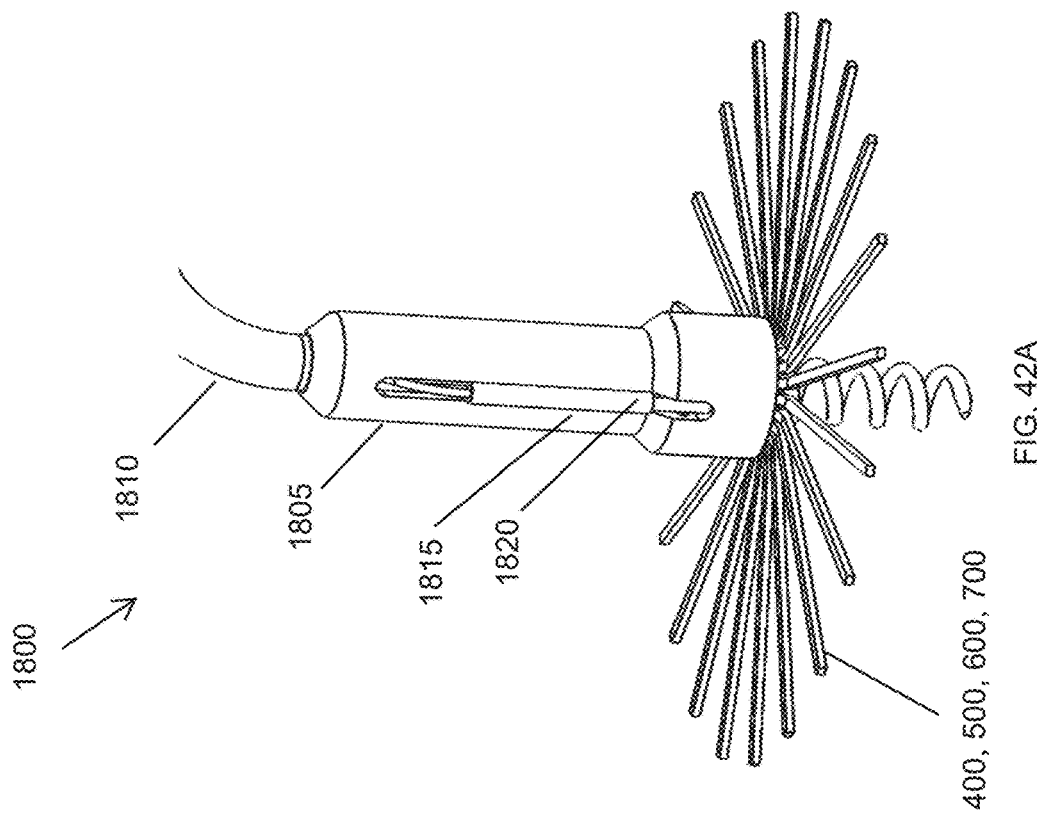

Referring now to FIGS. 42A-42B, the docking tube 1805 can include one or more slots 1815. In the illustrated embodiment, the docking tube 1805 can include one slot 1815, but other configurations are contemplated (e.g., two slots, three slots, four slots, two diametrically opposed slots, four radially spaced slots, etc.). The slot 1815 can extend through the docking tube 1815. In some embodiments, the docking tube 1805 can include one or more grooves, which do not extend through the docking tube. The slots 1815 can extend along the length of the docking tube 1805, or a portion thereof. The slots 1815 can extend between a distal end and a proximal end of the docking tube 1805.

The docking tube 1805 can include a pin 1820 disposed within the slot 1815. In some embodiments, the docking tube 1805 can include a spring 1825 disposed within the slot 1815. The pin 1820 can be coupled to a pullwire 1830. The pullwire 1830 can cause the pin 1820 to move within the slot 1815, as described herein. The annular hub 420, 520, 620, 720 can include a groove 1835. The groove 1835 in the annular hub 420, 520, 620, 720 can align with the slot 1815 in the docking tube 1805. The pin 1820 can be disposed within the groove 1835.

The annular hub 420, 520, 620, 720 can include an externally threaded portion 425, 525, 625, 725. The docking tube 1805 can include an internally threaded portion 1840. In some methods of use, the docking tube 1805 is rotated to engage the docking tube 1805 to the annular hub 420, 520, 620, 720. The internally threaded portion 1840 engages the externally threaded portion 425, 525, 625, 725. The groove 1835 can be cut on the outer diameter of the threads on the externally threaded portion 425, 525, 625, 725. The slot 1815 can be cut on the inner diameter of the internally threaded portion 1840 of the docking tube 1805. The slot 1815 can align with the groove 1835. In some embodiments, the slot 1815 can align with the groove 1835 when the docking tube 1805 is bottomed out against the coaptation assistance element 400, 500, 600, 700.

FIGS. 42A-42B illustrate a neutral position of the pin 1820. The spring 1825 biases the pin 1820 downward and into engagement with the groove 1835. The pin 1835 spans between the docking tube 1805 and the annular hub 420, 520, 620, 720. The natural state is with the pin 1820 forward. In this state, the pin 1820 is locking the threaded connection between the internally threaded portion 1840 of the docking tube 1805 and the externally threaded portion 425, 525, 625, 725 of the annular hub 420, 520, 620, 720. The pin 1820 allows the user to torque the coaptation assistance element 400, 500, 600, 700 in both directions via the docking tube 1805 and the implant torque shaft 1810. The pin 1820 allows the user to rotate the coaptation assistance element 400, 500, 600, 700 clockwise or counterclockwise by rotating the docking tube 1805. In some methods of use, the pin 1820 can facilitate movement of the coaptation assistance element 400, 500, 600, 700 via the docking tube 1805. When the slot 1815 and the groove 1835 are aligned, the spring-loaded pin 1820 can slip into the groove 1835 and essentially jam the threads. FIG. 42A shows the pin 1820 forward such that the docking tube 1805 and the coaptation assistance element 400, 500, 600, 700 are locked together. FIG. 42B shows a cross-sectional view of the locking pin 1820 in its natural forward position.

FIG. 42C-42D show the release of the pin 1820. The pin 1820 can be pulled back via the pullwire 1830. The pin 1820 can compress the spring 1825. The pin 1820 can be removed from the groove 1835. The pin 1820 slides along the slot 1815. In this position, the docking tube 1805 can be unscrewed from the coaptation assistance element 400, 500, 600, 700. The internally threaded portion 1840 can be disengaged from the externally threaded portion 425, 525, 625, 725 by rotation of the docking tube 1805. FIG. 42C shows a cross-sectional view of the retracted pin 1820. With the pin 1820 retracted, the docking tube 1805 can be unscrewed from the annular hub 420, 520, 620, 720. FIG. 42A-42D illustrate that the docking hub 1805 can be coupled to the coaptation assistance element 400, 500, 600, 700 in order to position the coaptation assistance element 400, 500, 600, 700. FIG. 42A-42D illustrate that the docking hub 1805 can be coupled to the coaptation assistance element 400, 500, 600, 700 in order to rotate the coaptation assistance element 400, 500, 600, 700.

FIG. 42E-42i illustrate the use of the anchor 800 with the implant delivery system 1800. The anchor 800 is located within the docking hub 1805 as shown in FIG. 42E. The anchor 800 is in a retracted state within the docking hub 1805. The anchor 800 is internal to the locking mechanism or pin 1820. The docking hub 1805 is shown in line form, or penciled in. The docking hub 1805 and the implant torque shaft 1810 shown in FIG. 42E are removed in FIG. 42F for clarity.

The anchor 800 can be screwed in at the anatomical P2 position on the posterior leaflet, as described herein. The anchor 800 can be considered the P2 anchor. The anchor 800 can be driven by a driver 1845. FIG. 42G shows a close-up view of the driver 1845. The driver 1845 has driven the anchor 800 fully into the issue and down onto the annular hub 420, 520, 620, 720 of the coaptation assistance element 400, 500, 600, 700. The driver 1845 is connected to an internal torque shaft 1850. The driver 1845 and the anchor 800 are fully housed within the docking hub 1805 as described herein. The internal torque shaft 1850 can extend through the implant torque shaft 1810, see FIG. 42E.

FIG. 42H shows an internal, cross-sectional view of the anchor 800. To ensure a secure connection to the driver 1845, the anchor 800 can be tensioned against the driver 1845 by a tether rail 1855. The tether rail 1855 can include a guidewire with a small screw or externally threaded portion 1860 at the distal tip. The externally threaded portion 1860 of the tether rail 1855 is configured to engage an internally threaded portion 1865 of the anchor 800. The internal view of the tether rail 1855 as well as the connection between the anchor 800 and the annular hub 420, 520, 620, 720 is shown in FIG. 42H

FIG. 42H also shows a square recess 1870 of the head of the anchor 800. The driver 1845 can include a square portion (not shown) configured to engage the square recess 1870 in the head of the anchor 800. Other designs for mating the anchor 800 and the driver 1845 are contemplated (e.g., any non-round shape, polygonal, hex, Philips, elliptical, etc.).

Figure 42I:
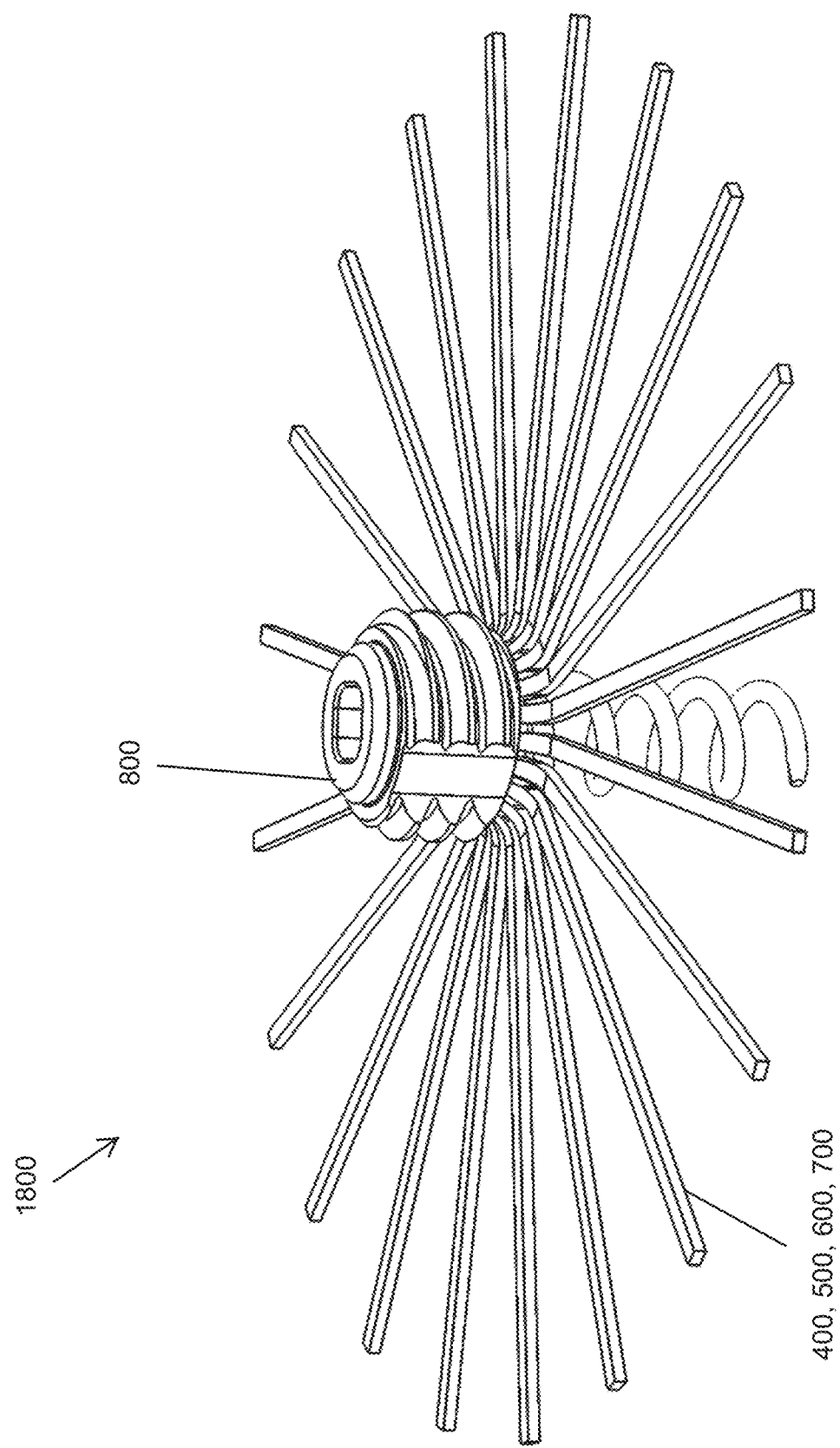

The anchor 800 can include a shoulder 1875. Once the anchor 800 is completely driven into the tissue, the shoulder 1875 of the anchor 800 pushes the annular hub 420, 520, 620, 720 down to secure the coaptation assistance element 400, 500, 600, 700. FIG. 42i shows the view of the anchored coaptation assistance element 400, 500, 600, 700.

FIGS. 43A-43E illustrate an embodiment of an implant delivery system 1900. The implant delivery system 1900 can include a docking tube 1905. The docking tube 1905 can be cylindrical. The docking tube 1905 is connected to an implant torque shaft 1910. In some embodiments, the implant torque shaft 1910 can be rigidly coupled to the docking tube 1905. In some embodiments, the implant torque shaft 1910 is welded or soldered to the docking tube

1905. The implant torque shaft 1910 can transmit torque to the docking tube 1905, as described herein. The docking tube 1905 can be coupled to the coaptation assistance element 400, 500, 600, 700. In the illustrated embodiment, only a portion of the struts 430, 530, 630, 730 are shown.

The docking tube 1905 can include two or more hypotubes 1915 embedded in the wall. The hypotubes 1915 can include a lumen. The hypotubes 1915 can be diametrically opposed. The hypotubes 1915 can be spaced 180° apart. The hypotubes 1915 can extend within a slot. The hypotubes 1915 can extend along a portion of the length of the docking tube 1905. In some embodiments, the docking tube 1905 comprises two or more lumens. In some embodiments, the lumens are monolithically or integrally formed with the docking tube 1905. In the illustrated embodiment, the docking tube 1905 can include two hypotubes 1915, but other configurations are contemplated (e.g., four hypotubes, etc.).

The docking tube 1905 can include tether 1920 disposed within the hypotubes 1915. In some embodiments, the tether 1920 can be looped through opposing gaps in the coaptation assistance element 400, 500, 600, 700. In some embodiments, the tether 1920 can be threaded between struts 430, 530, 630, 730 in the coaptation assistance element 400, 500, 600, 700. The tether 1920 can extend through one hypotube 1915, through the coaptation assistance element 400, 500, 600, 700, underneath the annular hub 420, 520, 620, 720, through the coaptation assistance element 400, 500, 600, 700, and through the other hypotube 1915. The tether 1920 can loop through the coaptation assistance element 400, 500, 600, 700. The tether 1920 can loop through the coaptation assistance element 400, 500, 600, 700 and back up to the proximal or handle end of the system.

FIGS. 43A-43B illustrate an initial position of the tether 1920. In this state, the tether 1920 holds the docking tube 1905 and coaptation assistance element 400, 500, 600, 700 together. The tether 1920 allows the user to torque the coaptation assistance element 400, 500, 600, 700 in both directions via the docking tube 1905 and the implant torque shaft 1910. The tether 1920 allows the user to rotate the coaptation assistance element 400, 500, 600, 700 clockwise or counterclockwise by rotating the docking tube 1905. In some methods of use, the tether 1920 can facilitate movement of the coaptation assistance element 400, 500, 600, 700 via the docking tube 1905. The tether 1920 can be released. With the tether 1920 released, the docking tube 1905 can be uncoupled from the annular hub 420, 520, 620, 720. FIG. 43A-43B illustrates that the docking hub 1905 can be coupled to the coaptation assistance element 400, 500, 600, 700 in order to position the coaptation assistance element 400, 500, 600, 700. FIG. 43A-43B illustrate that the docking hub 1805 can be coupled to the coaptation assistance element 400, 500, 600, 700 in order to rotate the coaptation assistance element 400, 500, 600, 700.

FIG. 43C-43E illustrate the use of the anchor 800 with the implant delivery system 1900. The anchor 800 is located within the docking hub 1905 as shown in FIG. 43C. The anchor 800 is in a retracted state within the docking hub 1905. The anchor 800 is internal to the locking mechanism or tether 1920. The docking hub 1905 is shown in line form in FIG. 43B.

The anchor 800 can be screwed in at the anatomical P2 position on the posterior leaflet, as described herein. The anchor 800 can be considered the P2 anchor. The anchor 800 can be driven by a driver 1945. FIG. 43D shows a close-up view of the driver 1945. The driver has driven the anchor 800 fully into the tissue and down onto the annular hub 420, 520, 620, 720 of the coaptation assistance element 400, 500, 600, 700. The driver 1945 is connected to an internal torque shaft 1950. In some embodiments, the internal torque shaft 1950 is welded or soldered to the driver 1945. The driver 1945 and the anchor 800 are fully housed within the docking hub 1905. The internal torque shaft 1950 can extend through the implant torque shaft 1910. FIG. 43C illustrates advancement of the anchor 800 prior to full seating of the anchor 800. FIG. 43D shows the anchor 800 screwed down into tissue.

FIG. 43C also shows an internal, cross-sectional view of the anchor 800. To ensure a secure connection to the driver 1945, the anchor 800 can be tensioned against the driver 1945 by a tether rail 1955. The tether rail 1955 can include a guidewire with a small screw or externally threaded portion 1960 at the distal tip. The externally threaded portion 1960 of the tether rail 1955 is configured to engage an internally threaded portion 1965 of the anchor 800. The internal view of the tether rail 1955 as well as the connection between the anchor 800 and the annular hub 420, 520, 620, 720 is shown in FIG. 42C. The tether rail 1955 can allow for minimal force evaluation of the effectiveness of the coaptation assistance element 400, 500, 600, 700 prior to release of the coaptation assistance element 400, 500, 600, 700. The tether rail 1955 can allow for minimal force evaluation of the effectiveness of the coaptation assistance element 400, 500, 600, 700 prior to release of tether 1920. FIG. 43C illustrates a cross-sectional view showing the path of the tether 1920.

FIG. 43E shows the view of the implanted anchor 800. FIG. 42E also shows a square recess 1970 of the head of the anchor 800. The driver 1945 can include a square portion (not shown) configured to engage the square recess 1970 in the head of the anchor 800. Other designs for mating the anchor 800 and the driver 1945 are contemplated (e.g., any non-round shape, polygonal, hex, Philips, elliptical, etc.). The anchor 800 can comprise an anchor hub. The hub can include the internally threaded portion 1965 of the anchor 800 to allow for a connection to the tether rail 1955. The anchor 800 can include an anchor helix. The anchor helix can include a ground tip for optimal tissue penetration.

The coaptation assistance element 400, 500, 600, 700 can include some cutouts to minimize the sliding friction of the tether 1920. The anchor 800 can be screwed into the tissue and bottomed out on the hub 420, 520, 620, 720. The user can retract the docking tube 1905 leaving behind the two ends of the tether 1920. The tether can be connected via a connecting inner torque shaft. If the user is satisfied with the performance of the coaptation assistance element 400, 500, 600, 700, the user can remove the tether 1920. If the user is unsatisfied with the performance of the coaptation assistance element 400, 500, 600, 700, the user can re-dock the implant delivery system 1900 with the tether 1920. If the user is unsatisfied with the performance of the coaptation assistance element 400, 500, 600, 700, the user can thread the tether 1920 through the hypotubes 1915. If the user is unsatisfied with the performance of the coaptation assistance element 400, 500, 600, 700, the user can remove the anchor 800 and/or remove the coaptation assistance element 400, 500, 600, 700 entirely.

FIGS. 44A-44E illustrate an embodiment of an implant delivery system 2000. The implant delivery system 2000 can include a docking tube 2005. The docking tube 2005 can be a desired shape, such as cylindrical for example. The docking tube 2005 is connected to an implant torque shaft 2010. In some embodiments, the implant torque shaft 2010 can be rigidly coupled to the docking tube 2005. In some embodiments, the implant torque shaft 2010 is welded or soldered to the docking tube 2005. The implant torque shaft 2010 can transmit torque to the docking tube 2005, as described herein. The docking tube 2005 can include a docking endcap 2015.

The docking tube 2005 can include one, two, or more retention arms 2020 cut out at the distal end. The one, two, or more retention arms 2020 can allow for the transfer of torque as well as push/push to the coaptation assistance element 400, 500, 600, 700 via the implant torque shaft 2010. The docking tube 2005 can include three retention arms 2020. The retention arms 2020 can be equally spaced around the docking tube 2005. The retention arms 2020 can be spaced about, at least about, or no more than about 120° apart or another desired angle. The retention arms 2020 can extend along a portion of the length of the docking tube 2005. In some embodiments, the retention arms 2020 are monolithically or integrally formed with the docking tube 2005. In the illustrated embodiment, the docking tube 2005 can include three retention arms 2020, but other configurations are contemplated (e.g., one retention arm, two retention arms, four retention arms, five retention arms, etc.). The retention arms 2020 can be formed from a U-shaped cut in the docking tube 2005.

Figure 44A:
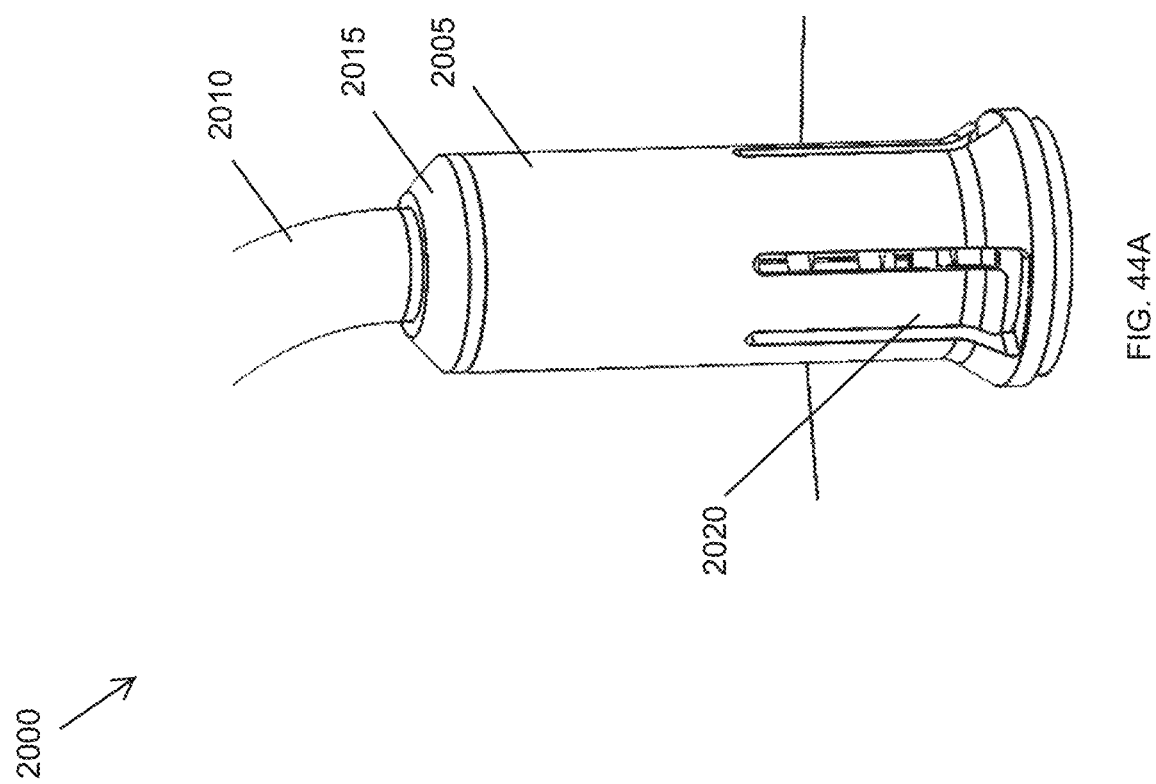
FIGS. 44A-44E illustrate an embodiment of an implant delivery system.
Figure 44C:
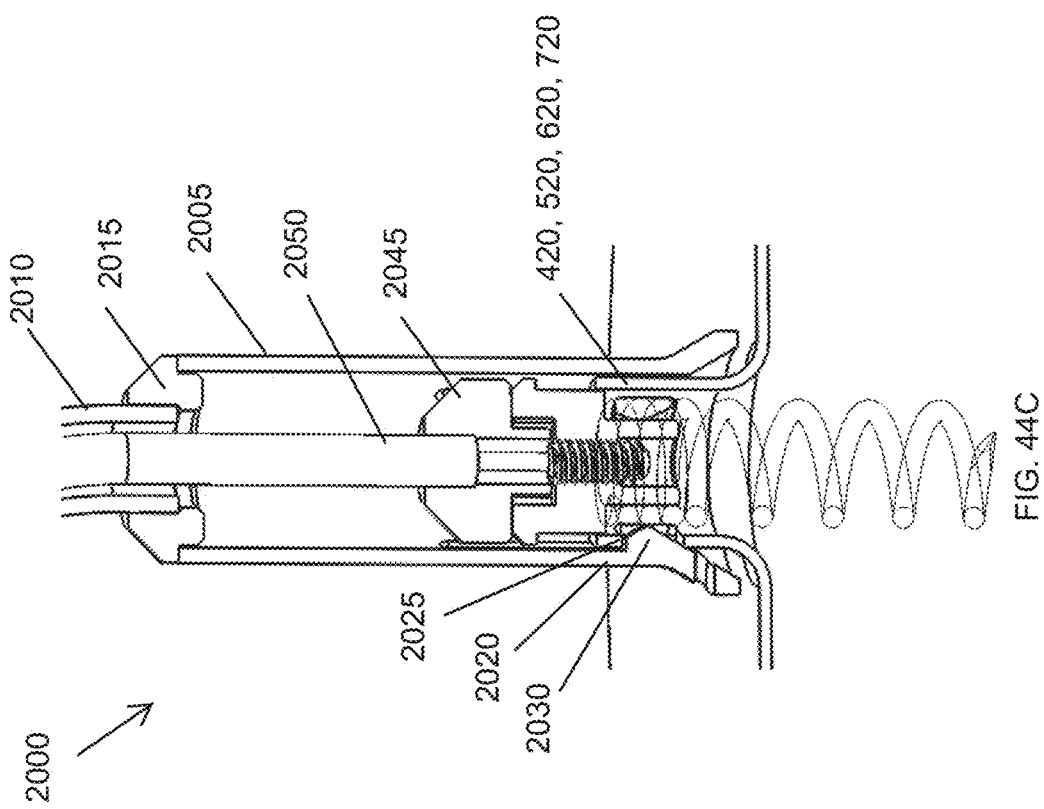
Figure 44B:
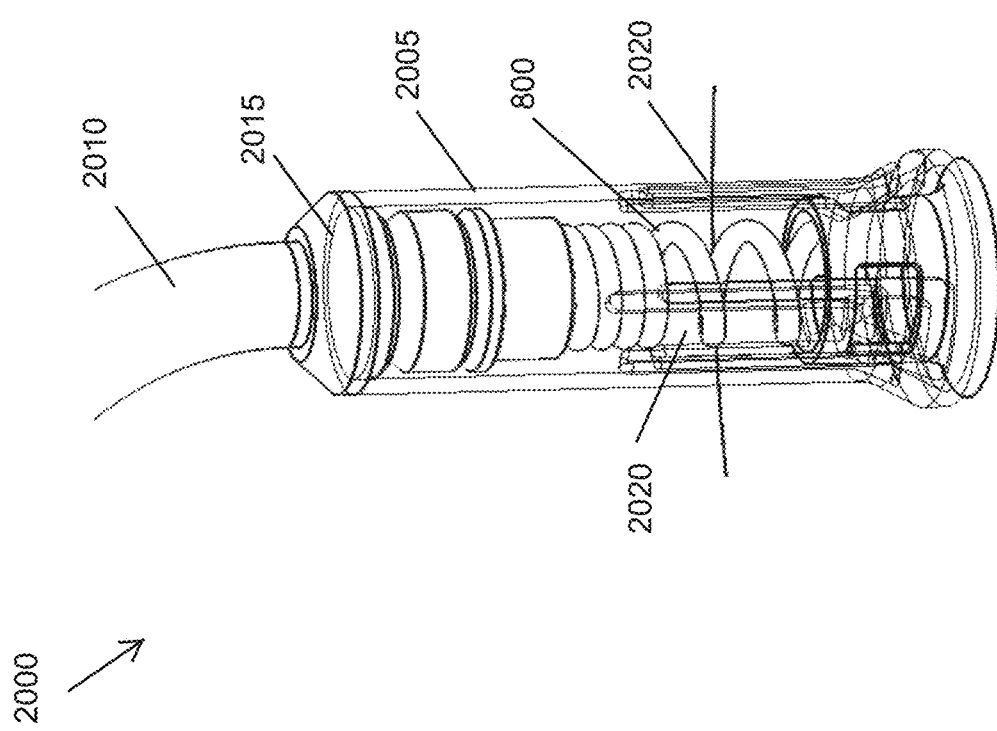

FIGS. 44B-44C illustrate an initial position of the retention arms 2020. In this state, the retention arms 2020 hold the docking tube 2005 and coaptation assistance element 400, 500, 600, 700 together. The retention arms 2020 allow the user to torque the coaptation assistance element 400, 500, 600, 700 in both directions via the docking tube 2005 and the implant torque shaft 2010. The retention arms 2020 allow the user to rotate the coaptation assistance element 400, 500, 600, 700 clockwise or counterclockwise by rotating the docking tube 2005. In some methods of use, the retention arms 2020 can facilitate movement of the coaptation assistance element 400, 500, 600, 700 via the docking tube 2005.

Figure 44D:
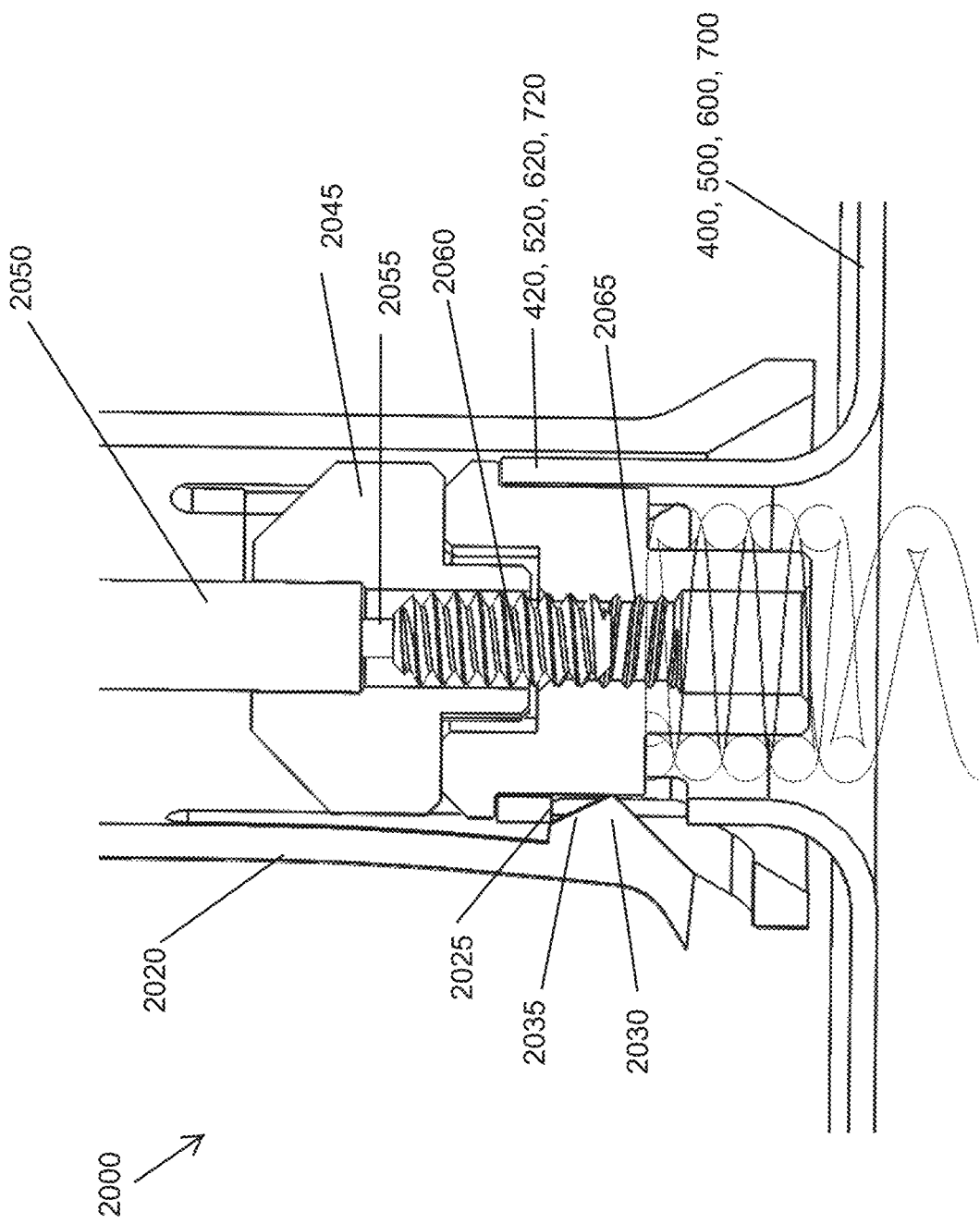
Figure 44E:
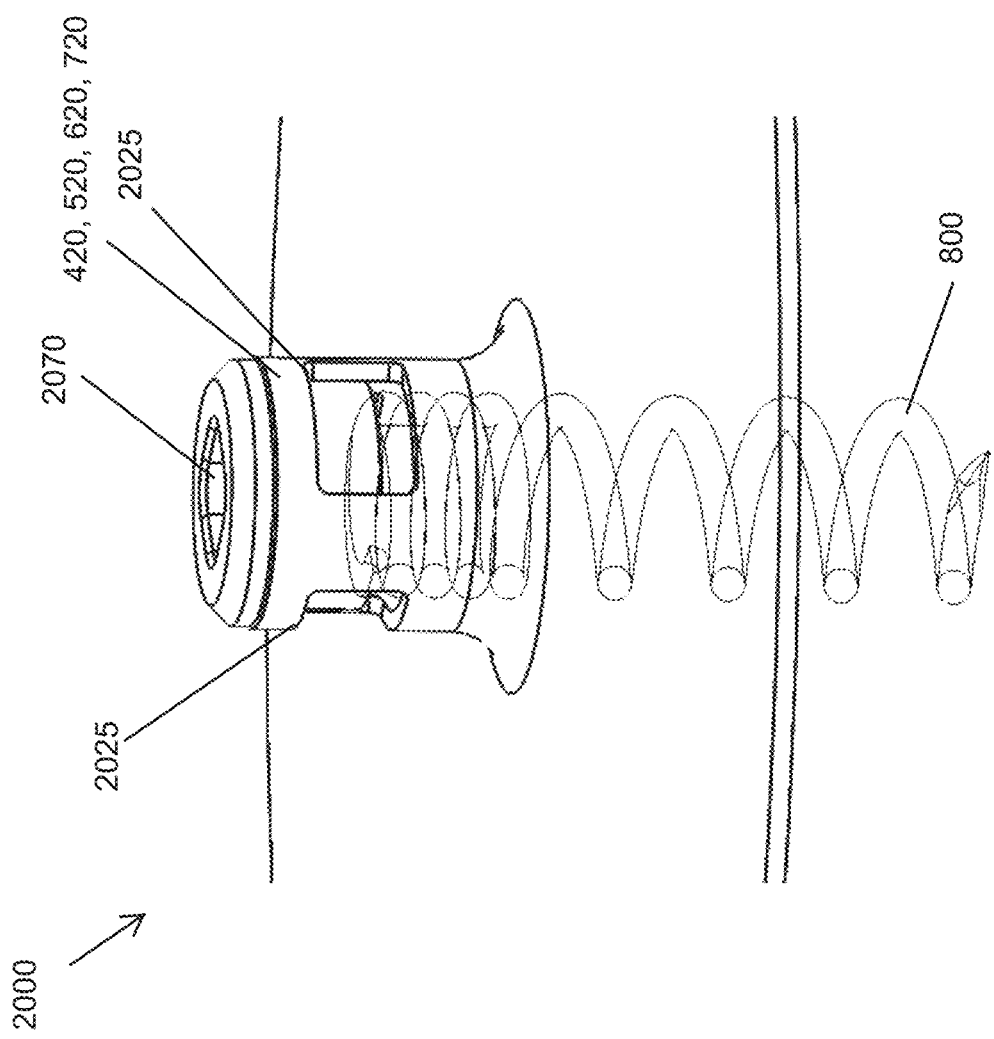

Referring to FIG. 44E, the retention arms 2020 engage windows 2025 in the head of the anchor 800. In some embodiments, the windows 2025 are laser cut windows. In some embodiments, the windows 2025 extend through the annular hub 420, 520, 620, 720. In some embodiments, the windows 2025 are slots or grooves. The number of windows 2025 can correspond to the number of retention arms 2020. In some embodiments, each retention arms 2020 engages a window 2025. The windows 2025 can be shaped to accept a portion of a retention arm 2020 such as a tab 2030. In some embodiments, each retention arm 2020 can include an inwardly facing tab 2030. The tab 2030 can have an increased thickness relative to the retention arm 2020. The tab 2030 can be shaped to engage the window 2025. The tab 2030 can be a distal inner section of the retention arm 2020.

FIG. 44B-44D illustrate the use of the anchor 800 with the implant delivery system 2000. The anchor 800 is located within the docking hub 2005 as shown in FIG. 44B. The anchor 800 is in a retracted state within the docking hub 2005. The anchor 800 is internal to the locking mechanism or tabs 2030 of the retention arms 2020. The docking hub 2005 is shown in line form in FIG. 44B. FIG. 44C shows advance of the anchor 800. FIG. 44C illustrate anchor 800 advancement prior to full seating of the anchor 800 and prior to flexing of the retention arms 2020.

The anchor 800 can be screwed in, for example, at the anatomical P2 position on the posterior leaflet, as described herein. The anchor 800 can be considered the P2 anchor. The anchor 800 can be driven by a driver 2045. FIG. 44D shows a close-up view of the driver 2045. The driver 2045 has driven the anchor 800 fully into the issue and down onto the annular hub 420, 520, 620, 720 of the coaptation assistance element 400, 500, 600, 700. The driver 2045 is connected to an internal torque shaft 2050. In some embodiments, the internal torque shaft 2050 is welded or soldered to the driver 2045. The driver 2045 and the anchor 800 are fully housed within the docking hub 2005 as shown in FIG. 44B. The internal torque shaft 2050 can extend through the implant torque shaft 2010.

FIG. 44D shows an internal, cross-sectional view of the anchor 800. To ensure a secure connection to the driver 2045, the anchor 800 can be tensioned against the driver 2045 by a tether rail 2055. The tether rail 2055 can include a guidewire with a small screw or externally threaded portion 2060 at the distal tip. The externally threaded portion 2060 of the tether rail 2055 is configured to engage an internally threaded portion 2065 of the anchor 800. The internal view of the tether rail 2055 as well as the connection between the anchor 800 and the annular hub 420, 520, 620, 720 is shown in FIG. 44D. The tether rail 2055 can allow for minimal force evaluation of the effectiveness of the coaptation assistance element 400, 500, 600, 700 prior to release of the coaptation assistance element 400, 500, 600, 700. The tether rail 2055 can allow for minimal force evaluation of the effectiveness of the coaptation assistance element 400, 500, 600, 700 prior to release of retention arms 2020.

FIG. 44D illustrates a cross-sectional view showing the release of the retention arms 2020. When the anchor 800 is screwed into tissue, the annular hub 420, 520, 620, 720 makes contact with the tabs 2030 of the retention arms 2020. The retention arms 2020 can bend outward from the windows 2025 of the anchor 800 due to the distal movement of the annular hub 420, 520, 620, 720. The tabs 2030 can include angled faces 2035 which allow for easy removal of the docking tube 2005 from the annular hub 420, 520, 620, 720 when the retention arms 2020 are bent outward. FIG. 44D illustrate anchor 800 advancement wherein the retention arms 2020 bend outward as the anchor 800 is fully driven in.

With the retention arms 2020 bent outward, the docking tube 2005 can be uncoupled from the annular hub 420, 520, 620, 720. FIG. 44D illustrates that the docking hub 2005 can be uncoupled to the coaptation assistance element 400, 500, 600, 700. FIGS. 44A-44C illustrates that the docking hub 2005 can be coupled to the coaptation assistance element 400, 500, 600, 700 in order to position the coaptation assistance element 400, 500, 600, 700. FIGS. 44A-44C illustrate that the docking hub 2005 can be coupled to the coaptation assistance element 400, 500, 600, 700 in order to rotate the coaptation assistance element 400, 500, 600, 700.

FIG. 44E shows the view of the implanted anchor 800. FIG. 44E also shows a square recess 2070 of the head of the anchor 800. The driver 2045 can include a square portion (not shown) configured to engage the square recess 2070 in the head of the anchor 800. Other designs for mating the anchor 800 and the driver 2045 are contemplated (e.g., any non-round shape, polygonal, hex, Philips, elliptical, etc.). The anchor 800 can comprise an anchor hub. The hub can include the internally threaded portion 2065 of the anchor 800 to allow for a connection to the tether rail 2055. The anchor 800 can include an anchor helix. The anchor 800 can include the windows 2025. The windows 2025 allow the retention arms 2020 to snap in and hold onto the annular hub 420, 520, 620, 720. The windows 2025 allow the retention arms 2020 hold onto the annular hub 420, 520, 620, 720 in compression, tension and torsion.

FIGS. 45A-45K illustrate an embodiment of an implant delivery system 2100. The implant delivery system 2100 can include a docking tube 2105. The docking tube 2105 can be cylindrical. The docking tube 2105 is connected to an implant torque shaft 2110. In some embodiments, the implant torque shaft 2110 can be rigidly coupled to the docking tube 2105. In some embodiments, the implant torque shaft 2110 is welded or soldered to the docking tube 2105. The implant torque shaft 2110 can transmit torque to the docking tube 2105, as described herein. The docking tube 2105 can include a docking endcap 2115.

The docking tube 2105 can include one or more slots 2120 cut out at the distal end. The slot 2120 can be a bayonet slot. The slot 2120 can have a bayonet configuration. The one or more slots 2120 can allow for the transfer of torque as well as push/push to the coaptation assistance element 400, 500, 600, 700 via the implant torque shaft 2110. The docking tube 2105 can include three slots 2120. The slots 2120 can be equally spaced around the docking tube 2105. The slots 2120 can be spaced 120° apart. The slots 2120 can extend along a portion of the length of the docking tube 2105. In some embodiments, the slots 2120 are monolithically or integrally formed with the docking tube 2105. In the illustrated embodiment, the docking tube 2105 can include three slots 2120, but other configurations are contemplated (e.g., one slot, two slots, four slots, five slots, etc.). The slots 2120 can be formed from a J-shaped cut in the docking tube 2105.

The docking tube 2105 can include a flared ring 2125 shown in FIG. 45B. The flared ring 2125 can ensure that the slots 2120 do not weaken the distal end of the docking tube 2105. The flared ring 2125 can ensure the ease of re-docking. The flared ring 2125 can be welded or soldered to the distal end of the docking tube 2105.

Referring to FIG. 45F, the slots 2120 engage retention pins 2030 in the head of the anchor 800. In some embodiments, the retention pins 2030 protrude a sufficient amount to ensure proper interface with the slots 2120 at the tip of the docking tube 2105. In some embodiments, the retention pins 2030 extend radially outward from the annular hub 420, 520, 620, 720. In some embodiments, the retention pins 2030 are cylindrical. The number of retention pins 2030 can correspond to the number of slots 2120. In some embodiments, each slot 2120 engages a retention pin 2025. The slots 2120 can be shaped to accept and guide the retention pins 2030.

FIGS. 45B-45C illustrate an initial position of the slots 2120 relative to retention pins 2030. In this state, the slots 2120 and retention pins 2030 hold the docking tube 2005 and coaptation assistance element 400, 500, 600, 700 together. The slots 2120 and retention pins 2030 allows the user to torque the coaptation assistance element 400, 500, 600, 700 in both directions via the docking tube 2005 and the implant torque shaft 2010. The slots 2120 and retention pins 2030 allow the user to rotate the coaptation assistance element 400, 500, 600, 700 clockwise or counterclockwise by rotating the docking tube 2005. In some methods of use, the slots 2120 and retention pins 2030 can facilitate movement of the coaptation assistance element 400, 500, 600, 700 via the docking tube 2105.

FIG. 45B-45E illustrate the use of the anchor 800 with the implant delivery system 2100. The anchor 800 is located within the docking hub 2105 as shown in FIG. 45B. The anchor 800 is in a retracted state within the docking hub 2105. The anchor 800 is internal to the locking mechanism or the slots 2120. The docking hub 2105 is shown in line form in FIG. 45B. FIG. 45C shows advancement of the anchor 800.

The anchor 800 can be screwed in at the anatomical P2 position on the posterior leaflet, as described herein. The anchor 800 can be considered the P2 anchor. The anchor 800 can be driven by a driver 2145. FIG. 45D shows a close-up view of the driver 2145. The driver 2145 has driven the anchor 800 fully into the tissue and down onto the annular hub 420, 520, 620, 720 of the coaptation assistance element 400, 500, 600, 700. The driver 2145 is connected to an internal torque shaft 2150. In some embodiments, the internal torque shaft 2150 is welded or soldered to the driver 2145. The driver 2145 and the anchor 800 are fully housed within the docking hub 2105 as shown in FIG. 45B. The internal torque shaft 2150 can extend through the implant torque shaft 2110.

FIG. 45E shows an internal, cross-sectional view of the anchor 800. To ensure a secure connection to the driver 2145, the anchor 800 can be tensioned against the driver 2145 by a tether rail 2155. The tether rail 2155 can include a guidewire with a small screw or externally threaded portion 2160 at the distal tip. The externally threaded portion 2160 of the tether rail 2155 is configured to engage an internally threaded portion 2165 of the anchor 800. The internal view of the tether rail 2055 as well as the connection between the anchor 800 and the annular hub 420, 520, 620, 720 is shown in FIG. 45E. The tether rail 2155 can allow for minimal force evaluation of the effectiveness of the coaptation assistance element 400, 500, 600, 700 prior to release of the coaptation assistance element 400, 500, 600, 700. The tether rail 2155 can allow for minimal force evaluation of the effectiveness of the coaptation assistance element 400, 500, 600, 700 prior to release of retention pins 2030.

When the anchor 800 is screwed into tissue, the retention pins 2030 of the annular hub 420, 520, 620, 720 moves proximally within the slots 2120. The docking tube 2005 can be rotated, thereby moving the retention pins 2030 of the annular hub 420, 520, 620, 720 laterally within the slots 2120. The docking tube 2005 can be moved proximally, thereby moving the retention pins 2030 of the annular hub 420, 520, 620, 720 distally within the slots 2120. Further movement of the docking tube 2005 proximally can release the docking tube 2105 from the annular hub 420, 520, 620, 720. FIGS. 45A-45C illustrates that the docking hub 2005 can be coupled to the coaptation assistance element 400, 500, 600, 700 in order to position the coaptation assistance element 400, 500, 600, 700. FIGS. 45A-45C illustrate that the docking hub 2105 can be coupled to the coaptation assistance element 400, 500, 600, 700 in order to rotate the coaptation assistance element 400, 500, 600, 700.

Figure 45H:
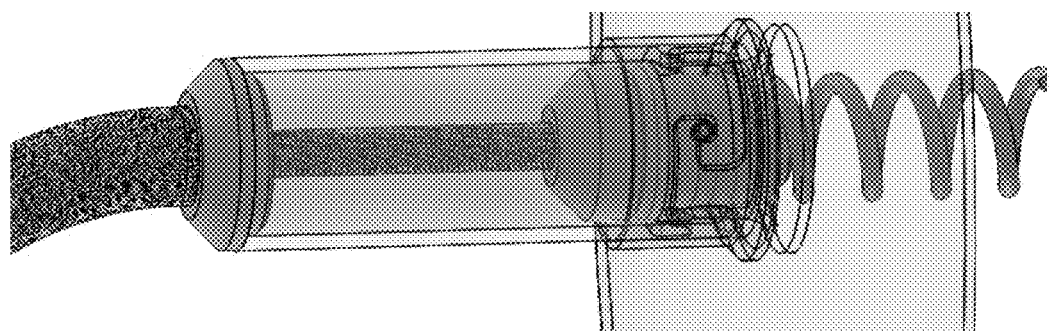
Figure 45G:
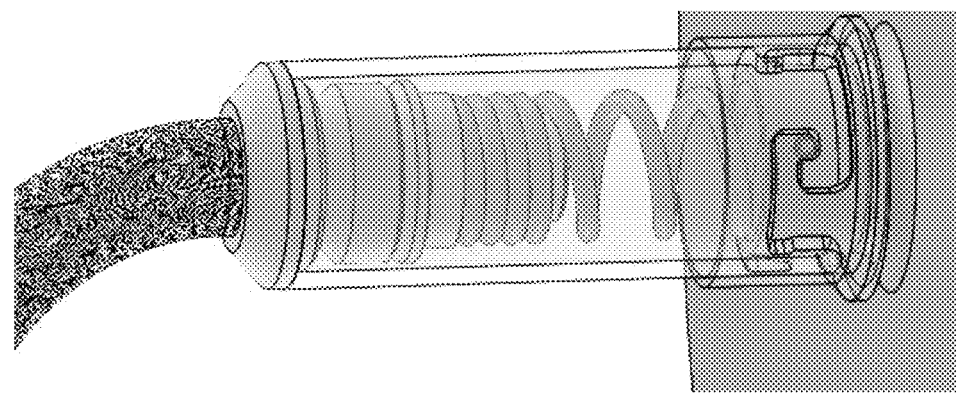
Figure 45K:
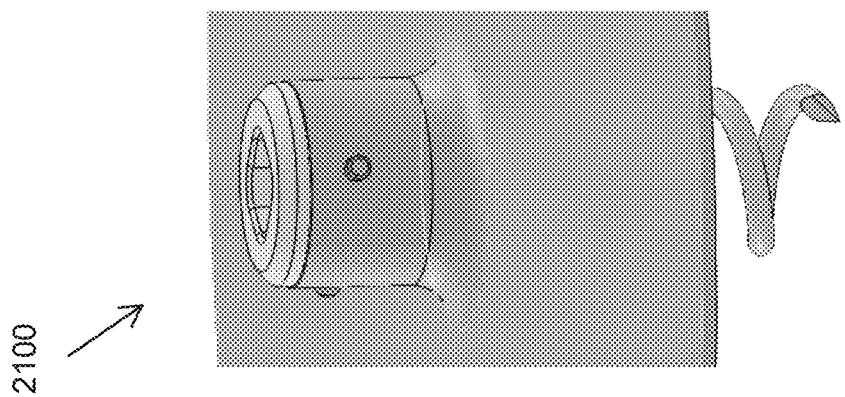
Figure 45J:
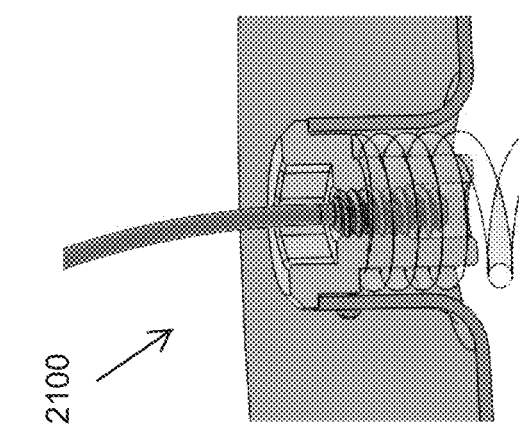
Figure 45I:
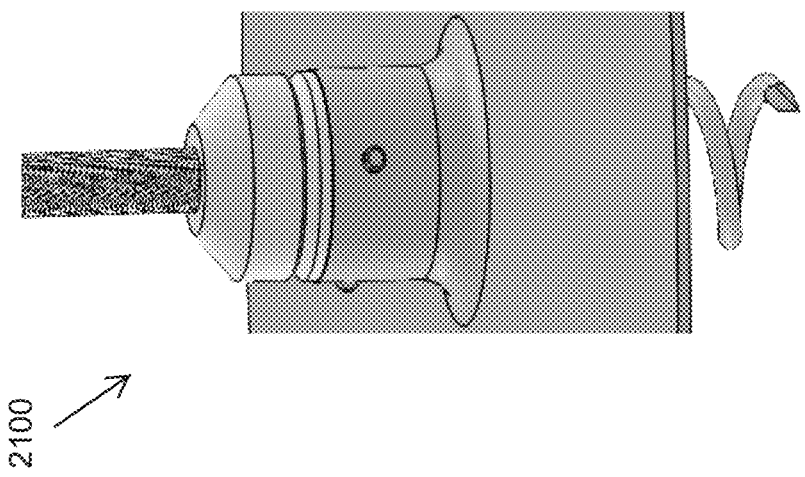

FIG. 45E-45F show the view of the implanted anchor 800. FIG. 45E also shows a square recess 2170 of the head of the anchor 800. The driver 2145 can include a square portion (not shown) configured to engage the square recess 2170 in the head of the anchor 800. Other designs for mating the anchor 800 and the driver 2145 are contemplated (e.g., any non-round shape, polygonal, hex, Philips, elliptical, etc.). The anchor 800 can comprise an anchor hub. The hub can include the internally threaded portion 2165 of the anchor 800 to allow for a connection to the tether rail 2155. The anchor 800 can include an anchor helix. In some embodiments, the annular hub 420, 520, 620, 720 can include three laser cut holes to accept the three retention pins 2130. The retention pins 2130 can be welded to the holes. In some embodiments, the retention pins 2130 are nitinol. FIGS. 45G-45K show additional views.

FIGS. 45A-45C illustrate deploying one or more secondary anchors 850, 1770, 1780. The secondary anchor 850, 1770, 1780 can include any of the features of the anchor 800. The secondary anchor 850, 1770, 1780 can comprise a helix or helical structure 852. The secondary anchor 850, 1770, 1780 can be designed to engage the tissue of heart, such as the tissue of the annulus. The secondary anchor 850, 1770,

1780 can include a tip 854 designed to engage tissue. The tip 854 can be sharpened. The tip 854 can be ground for optimal penetration. The secondary anchor 850, 1770, 1780 can include a hub 856. The hub 856 can be an annular hub having any of the features of annular hub 420, 520, 620, 720 described herein. The hub 856 can include one or more mating features 858. The mating feature 858 can be a cutout. The mating feature 858 can create two semi-circular portions at different heights. The mating feature 858 can include a first circular portion and a second circular portion. The first and second circular portions can be separated by a perpendicular cut. The mating feature 858 can include any configuration which allows torque to be transmitted to the secondary anchor 850, 1770, 1780.

Figure 46A:
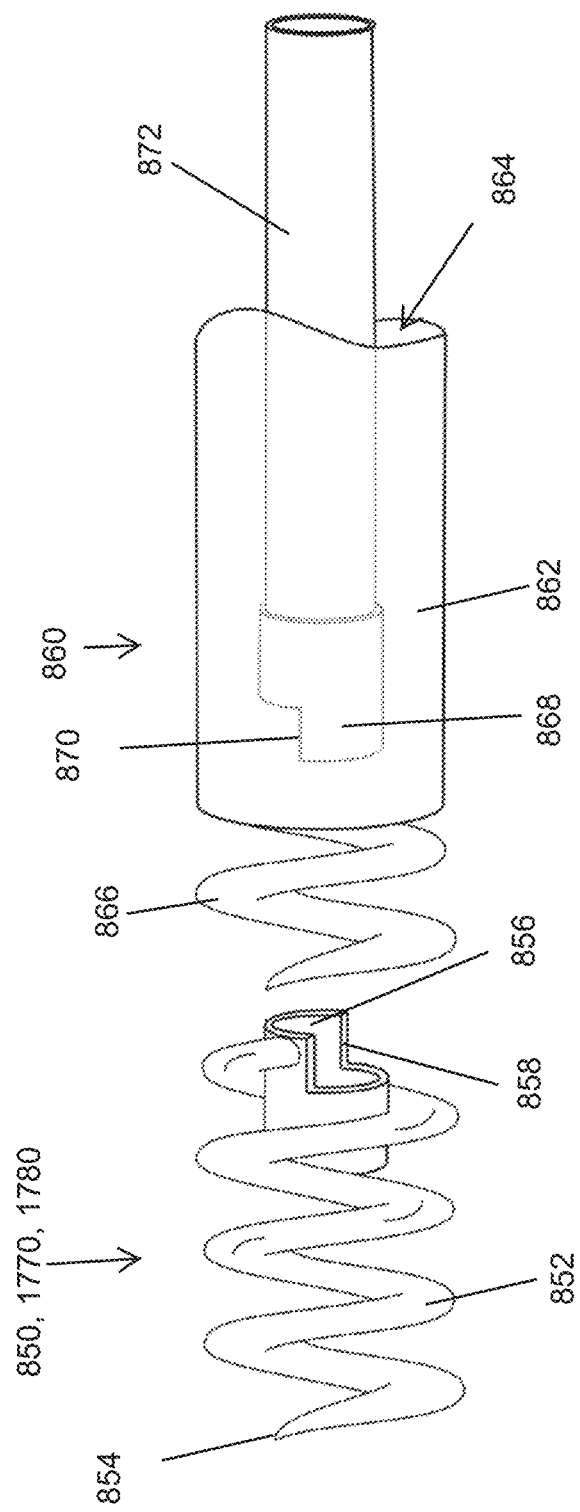

FIGS. 46A-46C illustrate a delivery catheter 860 designed for deploying one or more secondary anchors 850, 1770, 1780. The distal end of the delivery catheter 860 is shown in the figures. The delivery catheter 860 can include a proximal end outside the body of the patient. The proximal end can include one or more controls to manipulate the delivery catheter 860. The delivery catheter 860 can include a torque shaft 862. In some embodiments, the torque shaft 862 can rotate the secondary anchors 850, 1770, 1780 in either direction. The torque shaft 862 can include a lumen 864. The torque shaft 862 can include a helix or helical structure 866. The helix or helical structure 866 of the torque shaft 862 can have the same or similar features as the helix or helical structure 852 of the one or more secondary anchors 850, 1770, 1780. The helix or helical structure 866 of the torque shaft 862 can have the same pitch as the helix or helical structure 852 of the one or more secondary anchors 850, 1770, 1780. The helix or helical structure 866 of the torque shaft 862 can have the same diameter as the helix or helical structure 852 of the one or more secondary anchors 850, 1770, 1780. The helix or helical structure 866 of the torque shaft 862 can have the same wire diameter as the helix or helical structure 852 of the one or more secondary anchors 850, 1770, 1780.

The delivery catheter 860 can include a locking hub 868. The locking hub 868 can be an annular hub. The locking hub 868 can include one or more mating features 870. The mating feature 870 can be designed to lock with the mating feature 858 of the hub 856. The mating feature 870 can create two semi-circular portions at different heights. The mating feature 870 can include a first circular portion and a second circular portion. The first and second circular portions can be separated by a perpendicular cut. The mating feature 870 can include any configuration which allows torque to be transmitted to the hub 856 of the one or more secondary anchors 850, 1770, 1780. The locking hub 868 can be coupled to a locking shaft 872.

FIG. 46A shows a configuration in which the delivery catheter 860 is not engaged with the secondary anchor 850, 1770, 1780. FIG. 46B shows a configuration in which the delivery catheter 860 is engaged with the secondary anchor 850, 1770, 1780. In some embodiments, the helix or helical structure 866 can engage the helix or helical structure 852 of the secondary anchor 850, 1770, 1780. In some embodiments, both helices can have the same pitch and diameter. Because both helices have same pitch and diameter, the combined profile will be the same as the profile of the secondary anchor 850, 1770, 1780. The helix or helical structure 866 can interlock with the helix or helical structure 852 of the secondary anchor 850, 1770, 1780. The helix or helical structure 866 can fit within the voids of the helix or helical structure 852 of the secondary anchor 850, 1770, 1780. The diameter of the combined structure can be the same as the diameter of the helix or helical structure 852 of the secondary anchor 850, 1770, 1780. In some embodiments, the torque shaft 862 can be rotated to engage the helix or helical structure 866 with the helix or helical structure 852 of the secondary anchor 850, 1770, 1780. In some embodiments, the secondary anchor 850, 1770, 1780 can be rotated to engage the helix or helical structure 852 of the secondary anchor 850, 1770, 1780 with the helix or helical structure 866. FIG. 46B shows the engaged helices.

In some embodiments, the locking hub 868 is engaged with the hub 856 of the secondary anchor 850, 1770, 1780. In some embodiments, the locking hub 868 can be translated within the lumen 864 of the torque shaft 862 toward the secondary anchor 850, 1770, 1780. The mating feature 870 of the locking hub 868 can interlock with the mating feature 858 of the hub 565 of the secondary anchor 850, 1770, 1780. The locking hub 868 can engage the secondary anchor 850, 1770, 1780. The hub 856 of the secondary anchor 850, 1770, 1780 and the locking hub 868 are engaged to connect the secondary anchor 850, 1770, 1780 to the delivery catheter 860. In some embodiments, the locking shaft 872 can advance or withdraw the locking hub 868.

FIG. 46C shows the locking hub 868 engaged with the hub 856 of the secondary anchor 850, 1770, 1780. The locking hub 868 engaged with the hub 856 allow rotation of the secondary anchor 850, 1770, 1780. In some embodiments, the locking hub 868 engaged with the hub 856 can reduce the likelihood of disengagement of the delivery catheter 860 from the secondary anchor 850, 1770, 1780 during delivery. In some embodiments, the locking hub 868 engaged with the hub 856 allow counter-clockwise rotation of the secondary anchor 850, 1770, 1780 without disengaging from the delivery catheter 860. The secondary anchor 850, 1770, 1780 can be rotated counter-clockwise to be driven into tissue.

Once the secondary anchor 850, 1770, 1780 is driven into tissue, the delivery catheter 860 can be disengaged from the secondary anchor 850, 1770, 1780. In some embodiments, the locking hub 868 can be disengaged with the hub 856 of the secondary anchor 850, 1770, 1780. The locking hub 868 can be translated within the lumen 864 of the torque shaft 862 away from the secondary anchor 850, 1770, 1780. The locking shaft 872 can withdraw the locking hub 868. In some embodiments, the torque shaft 862 can be rotated to disengage the helices. In some embodiments, the torque shaft 862 can be rotated to disengage the helix or helical structure 866 with the helix or helical structure 852 of the secondary anchor 850, 1770, 1780.

In some embodiments, the coaptation assistance element 400, 500, 600, 700 can include an annular section configured to be implanted within a heart superior to a valve annulus. In some embodiments, the coaptation assistance element 400, 500, 600, 700 can include a plurality of struts comprising at least a first strut residing within the annular section and a second strut having a total length that is longer than that of the first strut. In some embodiments, the coaptation assistance element 400, 500, 600, 700 can include a superior edge which is cupped and carried by annular section. In some embodiments, the coaptation assistance element 400, 500, 600, 700 can improve the entire length coaptation without disrupting the anatomy. In some embodiments, the coaptation assistance element 400, 500, 600, 700 can include a plurality of radial struts. In some embodiments, the coaptation assistance element 400, 500, 600, 700 can include a plurality of radial struts comprising first struts residing within the annular section and second struts having a total length that is longer than that of the first struts. In some embodiments, the coaptation assistance element 400, 500, 600, 700 includes a superior edge which is cupped. In some embodiments, the coaptation assistance element 400, 500, 600, 700 can include a hub positioned near the annulus. In some embodiments, the coaptation assistance element 400, 500, 600, 700 can include struts which are radially expanding. In some embodiments, the coaptation assistance element 400, 500, 600, 700 can include improving coaptation of struts over the entire length without disrupting the anatomy. In some embodiments, the coaptation assistance element 400, 500, 600, 700 can be expanded via the struts.

In some methods, the method can include positioning the hub near the annulus. In some methods, the struts are radially expanding. In some methods, the method can include improving coaptation of struts over the entire length without disrupting anatomy. In some methods, the method can include expansion of the coaptation element carried via the struts extending radially outward. In some methods, the method can include expansion of the coaptation element carried via the struts extending radially outward to form an annulus section. In some methods, the method can include expansion of the coaptation element carried via the struts forming an annulus section.

In some embodiments, the annular hub 420, 520, 620, 720 is spaced inward from the lateral edges of the coaptation assistance element 400, 500, 600, 700. In some embodiments, the annular hub 420, 520, 620, 720 is spaced inward from the superior edge of the coaptation assistance element 400, 500, 600, 700. In some embodiments, the annular hub 420, 520, 620, 720 is spaced inward from the inferior edge of the coaptation assistance element 400, 500, 600, 700. In some embodiments, the annular hub 420, 520, 620, 720 is not expandable. In some embodiments, the annular hub 420, 520, 620, 720 has a fixed circumference. In some embodiments, the annular hub 420, 520, 620, 720 retains the shape during expansion of the coaptation assistance element 400, 500, 600, 700. In some embodiments, the annular hub 420, 520, 620, 720 is formed from a tube. The struts 430, 530, 630, 730 can be laser cut from the tube. The cuts can extend from one end of the tubing toward the second end. The uncut portion of the tubing can be annular hub 420, 520, 620, 720. In some embodiments, the coaptation assistance element 400, 500, 600, 700 can be formed from a sheet of material. The sheet can be laser cut to include the struts 430, 530, 630, 730. The sheet can be rolled to form a tube. The tube can be welded or otherwise held together. The uncut portion of the sheet can form the annular hub 420, 520, 620, 720.

In some embodiments, the anchor 800 is an active anchor. The anchor 800 can be coupled to the annular hub 420, 520, 620, 720. The anchor 800 can be coupled to the annular hub 420, 520, 620, 720 by interlocking the helix of the anchor 800 with a structure of the annular hub 420, 520, 620, 720. The anchor 800 can be configured to be rotated relative to the annular hub 420, 520, 620, 720. The anchor 800 can be configured to be rotated relative to the annular hub 420, 520, 620, 720 when coupled to the annular hub 420, 520, 620, 720. The anchor 800 is configured to be rotated to be selectively deployed. The anchor 800 is configured to be rotated to engage tissue. The anchor 800 is configured to be rotated to engage the annulus. The anchor 800 is configured to be rotated through the annulus. The anchor 800 is configured to be rotated in a first direction relative the annular hub 420, 520, 620, 720. The anchor 800 is configured to be rotated in a first direction to selectively deploy the anchor 800. The anchor 800 is configured to be rotated to deploy the anchor 800 at a first target location. The anchor 800 is configured to be rotated to engage tissue in the annulus. The anchor 800 can be selectively deployed in the annulus. The annular hub 420, 520, 620, 720 can remain stationary as the anchor 800 is rotated to engage tissue. The non-expandable, annular hub 420, 520, 620, 720 can remain stationary as the anchor 800 is rotated to engage tissue.

In some embodiments, the anchor 800 is configured to be rotated in a second direction relative the annular hub 420, 520, 620, 720. The anchor 800 is configured to be rotated in a second direction to selectively disengage the anchor 800. The anchor 800 is configured to be rotated to disengage the anchor 800 from the first target location. The anchor 800 is configured to be rotated to disengage tissue in the annulus. The annular hub 420, 520, 620, 720 can remain stationary as the anchor 800 is rotated to disengage tissue. The non-expandable, annular hub 420, 520, 620, 720 can remain stationary as the anchor 800 is rotated to disengage tissue. The second direction can be opposite the first direction. In some embodiments, the first direction can be clockwise and the second direction can be counter-clockwise. In some embodiments, the first direction can be counter-clockwise and the second direction can be clockwise.

In some embodiments, the plurality of struts 430, 530, 630, 730 are spaced circumferentially around the annular hub 420, 520, 620, 720. In some embodiments, the plurality of struts 430, 530, 630, 730 are evenly spaced around the annular hub 420, 520, 620, 720. In some embodiments, the plurality of struts 430, 530, 630, 730 are unevenly spaced around the annular hub 420, 520, 620, 720. In some embodiments, the struts 430, 530, 630, 730 comprising the annular section are evenly spaced around the annular hub 420, 520, 620, 720. In some embodiments, the struts 430, 530, 630, 730 comprising the annular section are unevenly spaced around the annular hub 420, 520, 620, 720. In some embodiments, the struts 430, 530, 630, 730 forming the superior edge are evenly spaced around the annular hub 420, 520, 620, 720. In some embodiments, the struts 430, 530, 630, 730 forming the superior edge are unevenly spaced around the annular hub 420, 520, 620, 720. In some embodiments, the struts 430, 530, 630, 730 comprising the ventricular section are evenly spaced around the annular hub 420, 520, 620, 720. In some embodiments, the struts 430, 530, 630, 730 comprising the ventricular section are unevenly spaced around the annular hub 420, 520, 620, 720. In some embodiments, the struts 430, 530, 630, 730 forming the inferior edge are evenly spaced around the annular hub 420, 520, 620, 720. In some embodiments, the struts 430, 530, 630, 730 forming the inferior edge are unevenly spaced around the annular hub 420, 520, 620, 720. In some embodiments, two or more struts 430, 530, 630, 730 are evenly spaced around the annular hub 420, 520, 620, 720. In some embodiments, two or more 430, 530, 630, 730 are unevenly spaced around the annular hub 420, 520, 620, 720.

In some embodiments, the plurality of struts 430, 530, 630, 730 extend outward from the annular hub 420, 520, 620, 720. In some embodiments, the plurality of struts 430, 530, 630, 730 have a portion near the annular hub 420, 520, 620, 720 which is radial. In some embodiments, the plurality of struts 430, 530, 630, 730 are placed along a radius. In some embodiments, the plurality of struts 430, 530, 630, 730 diverge from a center. In some embodiments, the plurality of struts 430, 530, 630, 730 diverge from the annular hub 420, 520, 620, 720. In some embodiments, the plurality of struts 430, 530, 630, 730 develop uniformly around a central axis. In some embodiments, the plurality of struts 430, 530, 630, 730 develop uniformly around the annular hub 420, 520, 620, 720. In some embodiments, the plurality of struts 430, 530, 630, 730 develop uniformly around the anchor 800. In some embodiments, the plurality of struts 430, 530, 630, 730 can form spokes. In some embodiments, the plurality of struts 430, 530, 630, 730 extend from the center outward. In some embodiments, the plurality of struts 430, 530, 630, 730 extend from the edge of the coaptation assistance element 400, 500, 600, 700 inward. In some embodiments, the plurality of struts 430, 530, 630, 730 are branched. In some embodiments, the plurality of struts 430, 530, 630, 730 are outspread. In some embodiments, the plurality of struts 430, 530, 630, 730 are radiating. In some embodiments, the plurality of struts 430, 530, 630, 730 spread outward. In some embodiments, the plurality of struts 430, 530, 630, 730 can include an inflection point. In some embodiments, a strut 430, 530, 630, 730 can include an inflection point. In some embodiments, the plurality of struts 430, 530, 630, 730 can include a curved shape. In some embodiments, a strut 430, 530, 630, 730 can include a curved shape. In some embodiments, a strut 430, 530, 630, 730 can include a U-shaped curve. In some embodiments, a strut 430, 530, 630, 730 can include a C-shaped curve. In some embodiments, a strut 430, 530, 630, 730 can include an S-shaped curve. In some embodiments, a strut 430, 530, 630, 730 can include an L-shaped curve.

In some embodiments, the plurality of struts 430, 530, 630, 730 increase the volume of the coaptation assistance element 400, 500, 600, 700 when deployed. In some embodiments, the plurality of struts 430, 530, 630, 730 increase the thickness of the coaptation assistance element 400, 500, 600, 700 when deployed. In some embodiments, the plurality of struts 430, 530, 630, 730 increase the length of the coaptation assistance element 400, 500, 600, 700 when deployed. In some embodiments, the plurality of struts 430, 530, 630, 730 increase the height of the coaptation assistance element 400, 500, 600, 700 when deployed. In some embodiments, the plurality of struts 430, 530, 630, 730 increase the width of the coaptation assistance element 400, 500, 600, 700 when deployed.

In some embodiments, the plurality of struts 430, 530, 630, 730 can include a first strut. The first strut can be configured to be implanted within a heart superior to a valve annulus. The first strut can be an annular strut. In some embodiments, the plurality of struts 430, 530, 630, 730 can include a second strut. The second strut can be configured to be implanted within a heart inferior to a valve annulus. The second strut can be a ventricular strut. The second strut can traverse the mitral valve. The second strut can traverse a plane of the valve annulus. In some embodiments, the first strut and the second strut have different lengths. In some embodiments, the second strut is longer than the first strut.

In some embodiments, the superior edge of the coaptation assistance element 400, 500, 600, 700 forms a curve. In some embodiments, the superior edge forms a lip. In some embodiments, the superior edge is cupped downward toward the inferior edge. In some embodiments, the superior edge is cupped upward from the inferior edge. In some embodiments, the annular hub 420, 520, 620, 720 extends upward from the inferior edge. In some embodiments, the annular hub 420, 520, 620, 720 extends upward from the superior edge. In some embodiments, the annular hub 420, 520, 620, 720 extends upward from the annular portion of the coaptation assistance element 400, 500, 600, 700. In some embodiments, the annular hub 420, 520, 620, 720 extends upward from the coaptation surface of the coaptation assistance element 400, 500, 600, 700. In some embodiments, the annular hub 420, 520, 620, 720 is tubular. In some embodiments, the annular hub 420, 520, 620, 720 forms a circle. In some embodiments, the annular hub 420, 520, 620, 720 has the form of a ring. In some embodiments, the hub 420, 520, 620, 720 is non-annular. In some embodiments, the hub 420, 520, 620, 720 forms a polygon (e.g., triangular, square, rectangular, hexagonal, octagonal, etc.). In some embodiments, the hub 420, 520, 620, 720 forms a non-round shape. In some embodiments, the hub 420, 520, 620, 720 forms an elliptical shape.

FIGS. 47A-47E illustrates embodiments of implant features. FIGS. 47A-47E illustrate some nonlimiting potentially clinically relevant aspects of the implant. While the coaptation assistance element 400 is illustrated, any of the coaptation assistance elements described herein can include the features described herein. In addition, the coaptation assistance element 400 can include any of the features of the coaptation assistance elements described herein with respect to other embodiments, for example.

As described herein, the coaptation assistance element 400 can include the annular hub 420 which can be relatively centrally located. The coaptation assistance element 400 can have a generally elongate shape, but other shapes are contemplated, for example, polygonal, circular, elliptical, rounded, rectangular, triangular, etc. The coaptation assistance element 400 can have a superior edge 440, lateral edges 470 and 475, and inferior edge 480. In some embodiments, the superior edge 440 has a length greater than that of inferior edge 480, such that the transverse distance between lateral edges 470 and 475 generally decreases from superior to inferior on the coaptation assistance element 400. The superior edge 440 of the coaptation assistance element 400 can be curved to match the general shape of the annulus or adjoining atrial wall.

The coaptation assistance element 400 can include a first surface 405 configured to be disposed toward a mal-coapting native leaflet, in use, and a second surface 415 configured to be disposed toward the anterior leaflet. The second surface 415 can include a coaptation surface 460. The coaptation assistance element 400 can include one or more struts 430. The plurality of struts 430 can provide structural support for the coaptation assistance element 400. The plurality of struts 430 can provide the deployed shape for the coaptation assistance element 400. As described herein, the plurality of struts can comprise a shape memory material, such as a shape memory metal or plastic.

In some embodiments, a first strut 430 of the plurality of struts extends from the annular hub 420 to or toward the superior edge 440. In some embodiments, a second strut 430 of the plurality of struts extends from the annular hub 420 to or toward the inferior edge 480. In some embodiments, a third strut 430 of the plurality of struts extends from the annular hub 420 to or toward the lateral edge 470. In some embodiments, a fourth strut 430 of the plurality of struts extends from the annular hub 420 to or toward the lateral edge 475. Any two or more of the first strut, the second strut, the third strut, or the fourth strut can include the same features, including material, length, width, thickness, configuration, pre-formed bend, curvature, etc. Any two or more of the first strut, the second strut, the third strut, or the fourth strut can include different features, including material, length, width, thickness, configuration, pre-formed bend, curvature, etc. In some embodiments, at least one of the struts, e.g., in the superior zone of the implant can extend radially outwardly of, and protrude from the covering 450 of the implant 400 to act as spaced-apart barbs and can assist with anchoring and/or tissue ingrowth in the valve annulus. In some embodiments, the barbs extend only in the annular zone (e.g., superior zone) of the implant but are not present in the inferior (leaflet) copation zone which is atraumatic in some embodiments. In some embodiments, the entire peripheral edge of the implant can be atraumatic.

In some embodiments, the struts 430 can be covered with one, two, or more layers of coaptation assistance element body covering 450. The coaptation assistance element body covering 450 can include a layer or a plurality of layers (e.g., one layer, two layers, three layers, four layers, five layers, or more, or ranges incorporating any two of the foregoing values). In some embodiments, the first surface 405 can include one or more layers. In some embodiments, the second surface 415 can include one or more layers. Any two or more layers of the plurality of layers can include the same or different features, including material, length, width, thickness, etc. In some embodiments, one or more layers extend along the entire, or only a portion of the first surface 405. In some embodiments, one or more layers extend along the entire, or only a portion of the second surface 415. The layers can be formed from any process described herein.

The coaptation assistance element body covering 450 may be comprised of a material such as a polymer, e.g., ePTFE. Other materials for the coaptation assistance element body covering 450 include polyester, polyurethane foam, polycarbonate foam, biologic tissue such as porcine pericardium, processed bovine pericardium, pleura, peritoneum, silicone, Dacron, acellular collagen matrix, combinations thereof, etc. In some embodiments, the coaptation assistance element body covering 450 can include a foam material surrounded by ePTFE.

In some embodiments, the struts 430 can be formed with or embedded one or more layers of coaptation assistance element body covering 450. In some embodiments, the struts 430 can be encased or at least partially encased by the coaptation assistance element body covering 450. In some embodiments, a portion of the strut 430 can extend from the coaptation assistance element body covering 450 to engage tissue as described elsewhere herein. FIGS. 47A-47E illustrate features which may facilitate interaction between the coaptation assistance element 400, or a portion thereof, and the native anatomy.

Figure 47B:
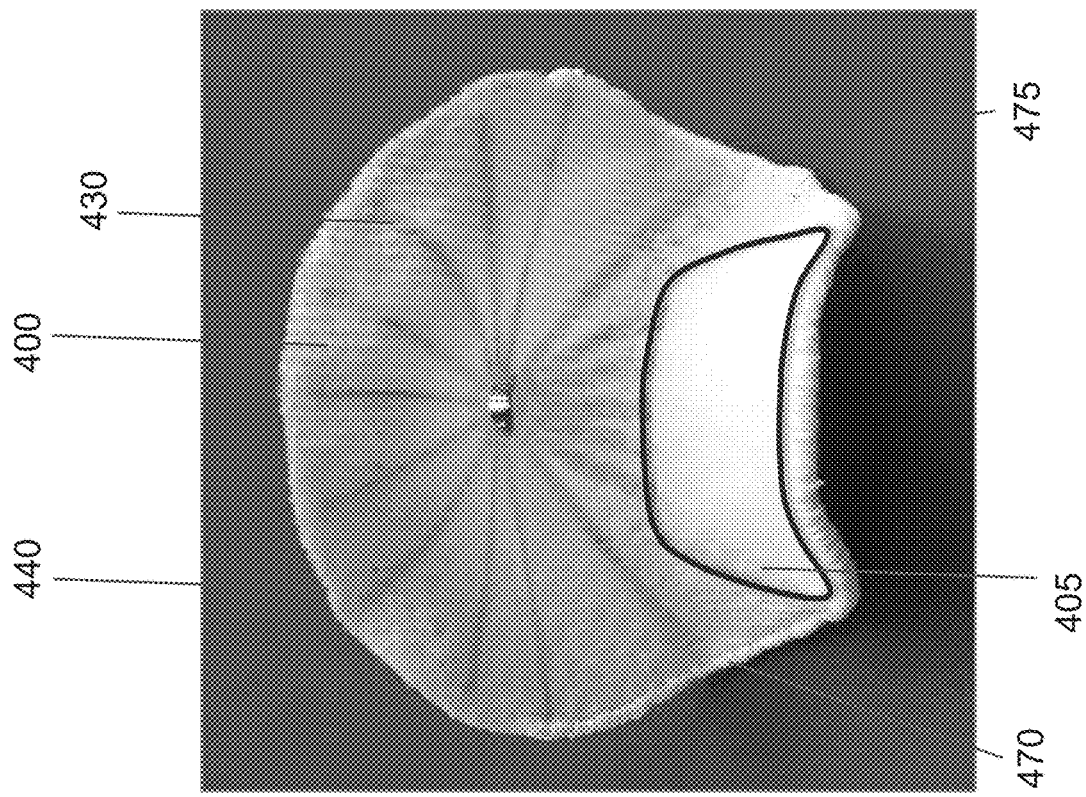
FIGS. 47A-47E illustrate views of an embodiment of a coaptation assistance element.
Figure 47A:
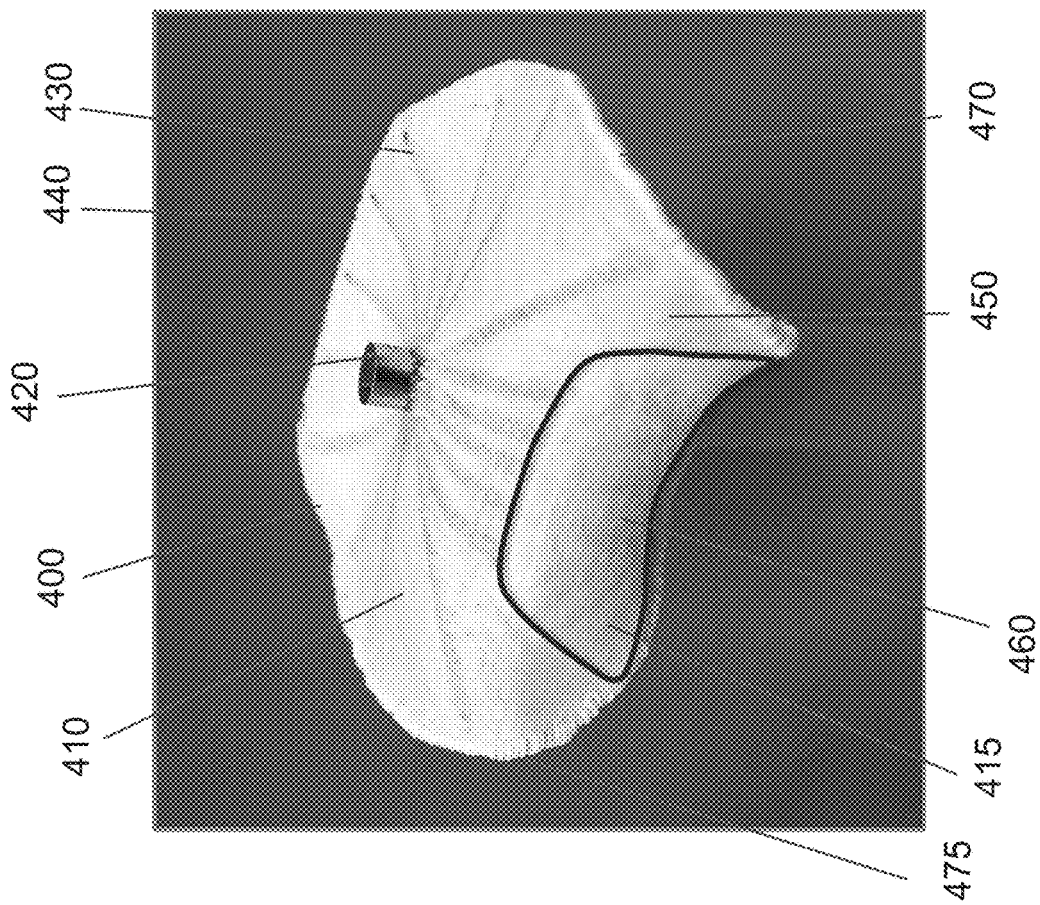

FIG. 47A illustrates the coaptation surface 460, which can define a relatively inferior zone of the implant. The anterior ventricular coaption surface can be reinforced. As described herein, the coaptation surface 460 can contact a leaflet of the patient. The coaptation assistance element 400, after placement, can entirely cover the posterior leaflet so that the anterior leaflet coapts with the coaptation surface 460 during systole. The coaptation assistance element 400 and anterior leaflet can maintain the valve seal at the annular ring.

In some embodiments, the second surface 415, or a portion thereof, is reinforced. In some embodiments, the coaptation surface 460 is reinforced. The second surface 415 including but not limited to the coaptation surface 460 can be reinforced with one or more additional layers. The one or more additional layers can extend over the second surface 415 or a portion thereof. The one or more additional layers can extend over the coaptation surface 460 or a portion thereof. The one or more additional layers can extend over a portion of the second surface 415 including the coaptation surface 460. The one or more additional layers can extend over a portion of the second surface 415 larger than the coaptation surface 460.

The coaptation surface 460 can be reinforced with any material described herein. The coaptation surface 460 can be reinforced with ePTFE. The coaptation surface 460 can be reinforced any material of the coaptation assistance element body covering 450, such as ePTFE, Dacron, and/or polypropylene.

FIG. 47B illustrates the first surface 405. The posterior ventricular coaption surface can be reinforced. As described herein, the first surface 405 can contact a leaflet of the patient. The coaptation assistance element 400, after placement, can entirely cover the posterior leaflet with the first surface 405. The first surface 405 can be opposite the second surface 415 which includes the coaptation surface 460.

In some embodiments, the first surface 405, or a portion thereof, is reinforced. The first surface 405 can be reinforced with one or more additional layers. The one or more additional layers can extend over the first surface 405 or a portion thereof. The one or more additional layers can be diametrically opposed to the one or more additional layers that extend over the second surface 415. The one or more additional layers can extend over a portion of the first surface 405 opposite the coaptation surface 460. The one or more additional layers can extend over a portion of the first surface 405 larger than the contact area with the posterior leaflet.

The first surface 405 can be reinforced with any material described herein. The first surface 405, or a portion thereof, can be reinforced with ePTFE. The first surface 405 can be reinforced with any material of the coaptation assistance element body covering 450, such as ePTFE, Dacron, and/or polypropylene, which can advantageously create an atraumatic surface to reduce the risk of native leaflet damage from repeated coaptation against the coaptation surface of the coaptation assist body.

Figure 47D:
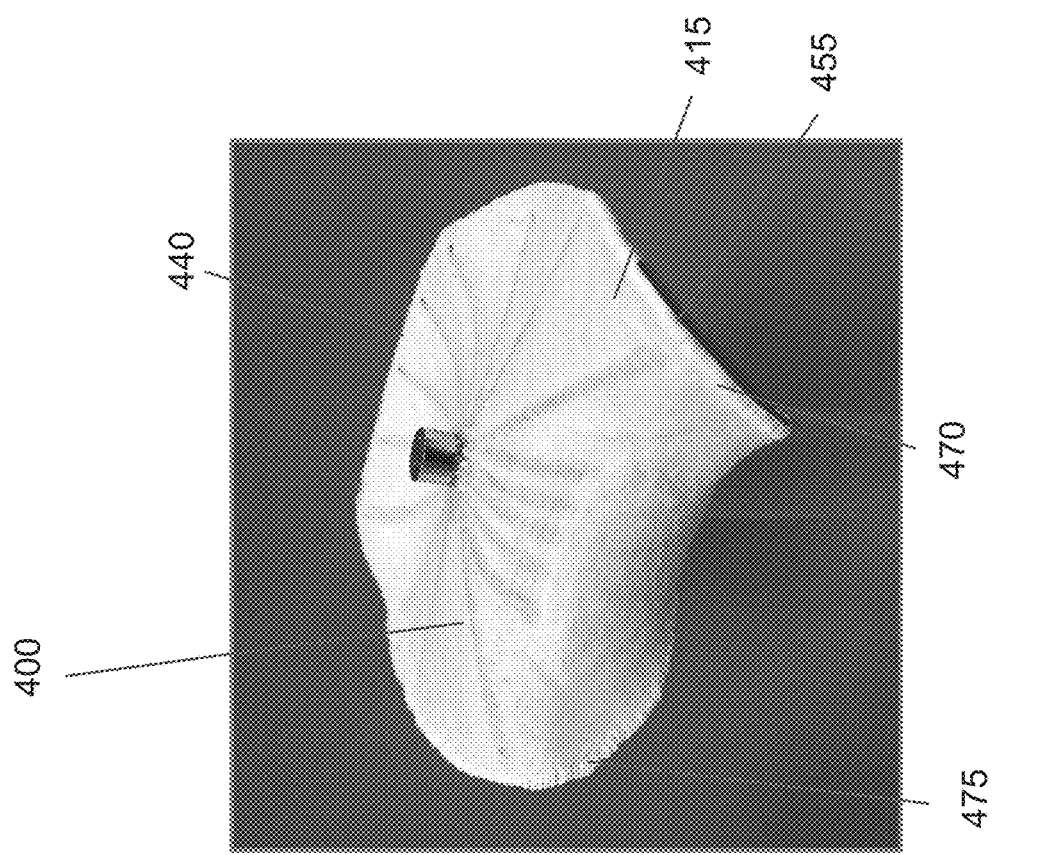
Figure 47C:
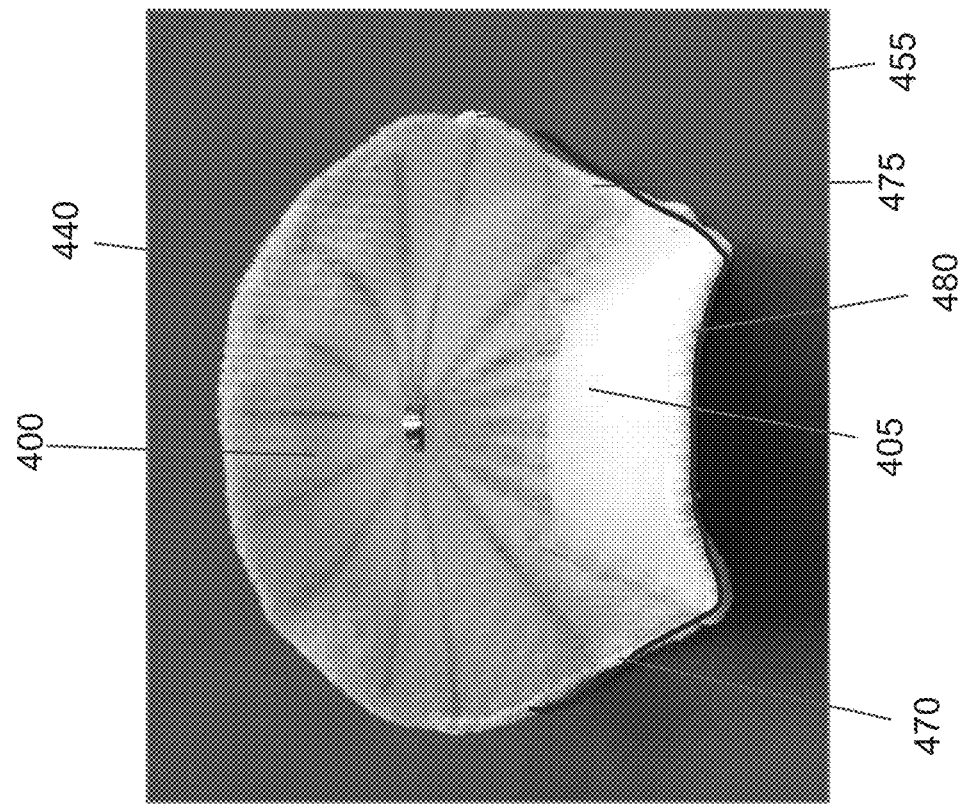

FIGS. 47C-47D illustrate an edge of the coaptation assistance element 400. As described herein, the coaptation assistance element 400 can include a reinforced edge with increased thickness, e.g., the knotless sutured edge 455. The superior edge 440, the lateral edges 470 and 475, and/or the inferior edge 480 of the coaptation assistance element 400 can include a raised edge or bumper. In some embodiments, only one, two, or more edges of the superior edge 440, the lateral edges 470 and 475, or the inferior edge 480 can include a raised edge or bumper. In some embodiments, the raised edge or bumper can comprise Gore-Tex. In some embodiments, the raised edge or bumper is circumferential or at least partially circumferential around the peripheral edge of the inferior zone, or the entire coaptation assist body.

The raised edge or bumper can be formed from a suture. The suture can be wrapped around the edge to form a raised edge or bumper. The raised edge or bumper may have features, such as increased thickness and/or softness for example reduce trauma to the native tissue. The raised edge or bumper can reduce contact between the coaptation assistance element 400 and the anatomy of the patient. The raised edge or bumper can reduce contact between the coaptation assistance element 400 and posterior leaflet, in the case of the mitral valve. In some embodiments, only the first surface 405 includes the raised edge. In some embodiments, both the first surface 405 and the second surface 415 include the raised edge. The raised edge or bumper can be at or near the edge of the first surface 405 or the second surface 415. The raised edge or bumper can be spaced inward from the first surface 405 or the second surface 415. FIG. 47C illustrates the posterior surface. FIG. 47D illustrates the anterior surface.

The raised edge or bumper can include one or more rounded edges that reduce contact between the coaptation assistance element 400 and the underlying anatomy of the patient. In some embodiments, contact is reduced between the coaptation assistance element 400 and the posterior leaflet. In some embodiments, contact is not reduced between the coaptation assistance element 400 and the annulus. In some embodiments, the coaptation assistance element 400 is configured to minimize contact with the posterior leaflet but maximize contact with the annulus. Other configurations are contemplated.

Figure 47E:
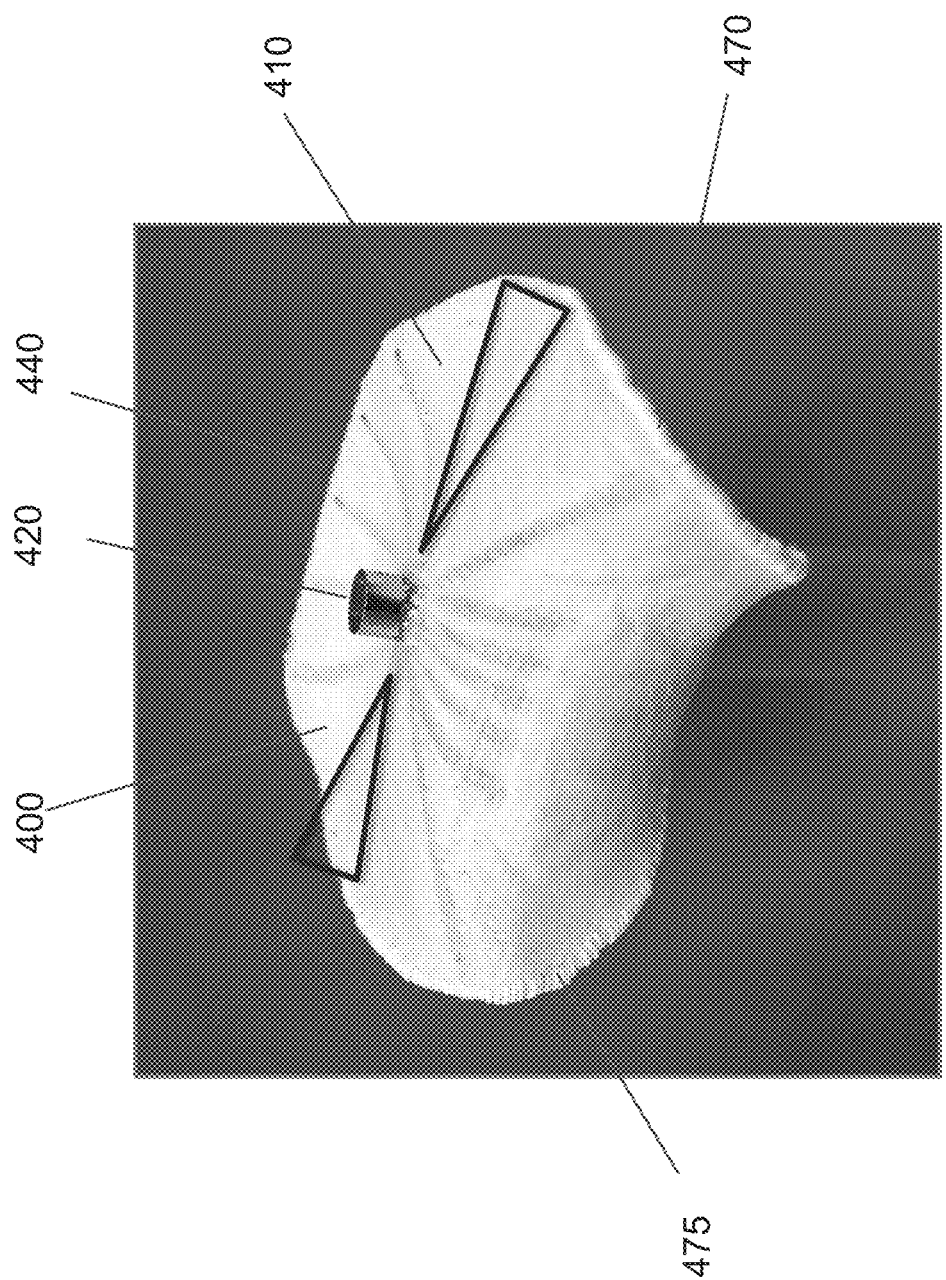

FIG. 47E illustrates an anchor zone. The coaptation assistance element 400 can include a generally annular superior section 410. The anchor zone can be located within the annular section 410, and can comprise two sections spaced apart from and extending laterally from the hub 420. The annular section 410 can be positioned relative to the annulus when the coaptation assistance element 400 is deployed. In some embodiments, the annular section 410 may be curved toward the annulus or curved away from the annulus. In other embodiments, the annular section 410 may be substantially flat with respect to the annulus. The annular section 410 can be configured to accept one or more secondary anchors. The secondary anchors can be advanced over a guide rail which can be coupled to the coaptation assistance element 400 as described herein. The secondary anchors can be rotated to penetrate the annular section 410. The secondary anchor can engage the tissue disposed under the coaptation assistance element 400.

The annular section 410 such as an anchor zone can be reinforced to have an increased thickness with respect to the rest of the superior zone, and more than, equal to, or less than the thickness of the inferior coaptation zone of the implant. The annular section 410 can be reinforced in the area configured to accept one, two, three, four, or more secondary anchors. As described herein, the first surface 405 of the coaptation assistance element 400 can lie against the annulus after placement with the heart of the patient. The second surface 415 can face upward from the annulus. In some embodiments, the annular section 410 or a portion thereof is reinforced. The annular section 410 can be reinforced with one or more additional layers. The one or more additional layers can extend over the annular section 410 or a portion thereof. The one or more additional layers can be diametrically opposed relative to the annular hub 420. The one or more additional layers can extend over a portion of the first surface 405. The one or more additional layers can extend over a portion of the second surface 415. The anchor zone can be near the annular hub 420. The anchor zone can include one or more separate zones.

The annular section 410 can be reinforced with any material described herein. The annular section 410, or a portion thereof, can be reinforced with ePTFE. The annular section 410, or a portion thereof, can be reinforced with velour. The annular section 410 can be reinforced any material of the coaptation assistance element body covering 450, such as ePTFE, Dacron, and/or polypropylene. The one or more additionally layers can extend outward from the annular hub 420. The one or more additionally layers be any shape sufficient to cover an area larger than the area engaged by the one or more secondary anchors.

In some embodiments, the annular portion 410 can include a sharper edge than another edge of the coaptation assistance element 400. In some embodiments, the superior edge 440 is thinner and/or sharper than another edge of the coaptation assistance element 400 (e.g., the lateral edge 470, the lateral edge 474, or the inferior edge 480). In some embodiments, the annular portion 410 and/or the superior edge 440 can be irritating to or engaging with the tissue. In some embodiments, the annular portion 410 is configured to be implanted near the annulus. In some embodiments, the annular portion 410 is configured to promote an immune response. In some embodiments, the annular portion 410 is configured to promote tissue ingrowth.

FIG. 48 illustrates an exploded view of an embodiment of a covering surrounding part of the implant, and includes the laminate. While the coaptation assistance element 400 is illustrated, any of the coaptation assistance elements described herein can include any number of the features described herein, can exclude/omit any of the features as described herein, or be placed in a different order relative to each other. In addition, the coaptation assistance element 400 can include or exclude/omit any of the features of the coaptation assistance elements described herein. The exploded view illustrates the thick reinforcement layer for the anterior and posterior ventricular portions. The exploded view illustrates the single velour anchor zone. The raised edge or bumper is not shown. The raised edge or bumper can be added in the final stage of assembly. The laminate 1100 described herein can form the coaptation assistance element body covering 450. The laminate 1100 can include one or more layers as described herein. The laminate 1100 can include one or more layers in any order.

The coaptation assistance element 400 can include a posterior layer 1102. The posterior layer can form the first surface 405. In some embodiments, the posterior layer 1102 is thin relative to other layers. In some embodiments, the posterior layer 1102 is ePTFE. In some embodiments, the posterior layer 1102 has a thickness (e.g., about 0.001", about 0.0015", about 0.002", about 0.0025", about 0.003", or any range including two of the foregoing values). The posterior layer 1102 can include an opening for the anchor 800 to extend there through. The posterior layer 1102 can be any shape including rectangular, polygonal, triangular, circular, and elliptical. In some embodiments, the posterior layer 1102 is not the final shape of the coaptation assistance element 400.

The coaptation assistance element 400 can include a first supporting structure layer 1104. The first supporting structure 1104 can be a mesh. In some embodiments, the first supporting structure layer 1104 comprises UHMPE. The first supporting structure 1104 can be disposed over the posterior layer 1102. The first supporting structure layer 1104 can be disposed on the posterior side of the struts 430. The first supporting structure layer 1104 can include an opening for the anchor 800 to extend there through.

The coaptation assistance element 400 can include a first fabric layer 1106. The first fabric layer 1106 can be relatively thin, and in some cases has a thickness (e.g., about 0.001", about 0.0015", about 0.002", about 0.0025", about 0.003", about 0.004", about 0.005", about 0.01" or any range including two of the foregoing values). In some embodiments, the first fabric layer 1106 comprises a polyester fabric. The first fabric layer 1106 can be disposed over the first supporting structure layer 1104. The first fabric layer 1106 can be disposed on the posterior side of the struts 430. The first fabric layer 1106 can include an opening for the anchor 800 to extend there through. In some embodiments, the first fabric layer 1106 extends only along a portion of the coaptation assistance element 400. In some embodiments, the first fabric layer 1106 includes a cut out portion.

The coaptation assistance element 400 can include a first ventricular layer 1108. The ventricular surface layer 1108 can be the reinforcement layer for the first surface 405. In some embodiments, the first ventricular layer 1108 is thick relative to other layers. In some embodiments, the first ventricular layer 1108 is ePTFE. In some embodiments, the first ventricular layer 1108 has a thickness (e.g., about 0.01", 0.02" 0.03", about 0.035", about 0.040", about 0.045", about 0.05", about 0.07", about 0.10" or any range including two of the foregoing values). The first ventricular layer 1108 can be any shape including rectangular, polygonal, triangular, circular, elliptical, etc. The first ventricular layer 1108 can be disposed on the posterior side of the struts 430.

The coaptation assistance element 400 can include an anchor layer 1110. The anchor layer 1110 can be the reinforcement layer for the one or more secondary anchor. In some embodiments, the anchor layer 1110 is thick relative to other layers. In some embodiments, the anchor layer 1110 is ePTFE. In some embodiments, the anchor layer 1110 is velour. In some embodiments, the anchor layer 1110 has a thickness (e.g., about 0.01", 0.02", 0.03", about 0.035", about 0.040", about 0.045", about 0.05", about 0.07", about 0.10" or any range including two of the foregoing values). The anchor layer 1110 can be any shape including rectangular, polygonal, triangular, circular, elliptical, etc. In some embodiments, the coaptation assistance element 400 includes a single anchor zone which forms the anchor layer 1110. In some embodiments, the coaptation assistance element 400 includes two or more separate anchor zones which form the anchor layer 1110. The anchor layer 1110 can be disposed on the posterior side of the struts 430 as shown. In the illustrate embodiment, the ventricular surface layer 1108 and the anchor layer 1110 can be sandwiched between the same two adjoining layers. In some embodiments, the ventricular surface layer 1108 and the anchor layer 1110 are separated by one or more layers.

The coaptation assistance element 400 can include a second supporting structure layer 1112. The second supporting structure layer 1112 can be a mesh. In some embodiments, the second supporting structure layer 1112 comprises UHMPE. The second supporting structure layer 1112 can be disposed over the ventricular surface layer 1108. The second supporting structure layer 1112 can be disposed on the posterior side of the struts 430. In some embodiments, the second supporting structure layer 1112 extends only along a portion of the coaptation assistance element 400. In some embodiments, the second supporting structure layer 1112 extends only along the ventricular portion of the coaptation assistance element 400.

The coaptation assistance element 400 can include a frame 465. In some embodiments, the frame 465 is cut from a tubular stock. The frame 465 can include one or more struts 430. The frame 465 can be constructed from a single, unitary piece of material. The frame 465 including the struts 430 thereof can be formed using any method described herein including a water jet, laser etching or similar technology. The details of the struts 430, including barbs, can be machined into the struts 430. The frame 465 can be bent and/or shape set to achieve the desired geometry. The frame 465 including the struts 430 thereof can comprise a resiliently deformable material such as a shape memory metal, e.g., Nitinol or a shape memory polymer. In some embodiments, the material is Elgiloy. In some embodiments, the frame 465 can comprise of other materials including stainless steel, polypropylene, high density polyethylene (PE), Dacron, acellular collagen matrix such as SIS, or other plastics, etc. In some embodiments, the struts 430 can include shape memory material and a strut covering. The strut covering can be any material described herein and can cover the entire strut 430 or a portion thereof. In some embodiments, the struts 430 can comprise Nitinol and a LDPE tubing or covering over each strut 430. In some embodiments, the frame 465 can be considered a layer.

The coaptation assistance element 400 can include a second ventricular layer 1114. The second ventricular layer 1114 can be the reinforcement layer for the second surface 415. In some embodiments, the second ventricular layer 1114 is thick relative to other layers. In some embodiments, the second ventricular layer 1114 is ePTFE. In some embodiments, the second ventricular layer 1114 has a thickness (e.g., about 0.03", about 0.035", about 0.040", about 0.045", about 0.05", or any range including two of the foregoing values or other thickness values as described with respect to other layers herein). second ventricular layer 1114 can be any shape including rectangular, polygonal, triangular, circular, elliptical, etc. The second ventricular layer 1114 can be disposed on the anterior side of the struts 430. In some embodiments, the second ventricular layer 1114 extends only along a portion of the coaptation assistance element 400. In some embodiments, the second ventricular layer 1114 extends only along the ventricular portion of the coaptation assistance element 400. In some embodiments, the first ventricular layer 1108 and second ventricular layer 1114 are the same shape.

The coaptation assistance element 400 can include a third supporting structure layer 1116. The a third supporting structure layer 1116 can be a mesh. In some embodiments, the a third supporting structure layer 1116 can comprise UHMPE. The third supporting structure layer 1116 can be disposed over the second ventricular layer 1114. The third supporting structure layer 1116 can be disposed on the anterior side of the struts 430. In some embodiments, the third supporting structure layer 1116 extends only along a portion of the coaptation assistance element 400. In some embodiments, the third supporting structure layer 1116 extends only along the ventricular portion of the coaptation assistance element 400.

The coaptation assistance element 400 can include a second fabric layer 1118. The second fabric layer 1118 can be thin relative to other layers. In some embodiments, the second fabric layer 1118 has a thickness (e.g., about 0.001", about 0.0015", about 0.002", about 0.0025", about 0.003", or any range including two of the foregoing values). In some embodiments, the second fabric layer 1118 comprises a polyester fabric. The second fabric layer 1118 can be disposed over the third supporting structure layer 1116. The second fabric layer 1118 can be disposed on the anterior side of the struts 430. The second fabric layer 1118 can include an opening for the anchor 800 to extend there through.

The coaptation assistance element 400 can include a fourth supporting structure layer 1120. The fourth supporting structure layer 1120 can be a mesh. In some embodiments, the fourth supporting structure layer 1120 can comprise UHMPE. The fourth supporting structure layer 1120 can be disposed over the second fabric layer 1118. The fourth supporting structure layer 1120 can be disposed on the anterior side of the struts 430. The fourth supporting structure layer 1120 can include an opening for the anchor 800 to extend there through. In some embodiments, the first supporting structure layer 1104 and the fourth supporting structure layer 1120 are the same shape.

The coaptation assistance element 400 can include an anterior layer 1122. The anterior layer 1122 can form the second surface 415. In some embodiments, the anterior layer 1122 is thin relative to other layers. In some embodiments, the anterior layer 1122 is ePTFE. In some embodiments, the anterior layer 1122 has a thickness (e.g., about 0.001", about 0.0015", about 0.002", about 0.0025", about 0.003", or any range including two of the foregoing values, or other thickness values as described with respect to other layers herein). The anterior layer 1122 can include an opening for the anchor 800 to extend there through. The anterior layer 1122 can be any shape including rectangular, polygonal, triangular, circular, and elliptical. In some embodiments, the anterior layer 1122 is not the final shape of the coaptation assistance element 400. In some embodiments, the posterior layer 1102 and the anterior layer 1122 are the same shape.

Figure 49:
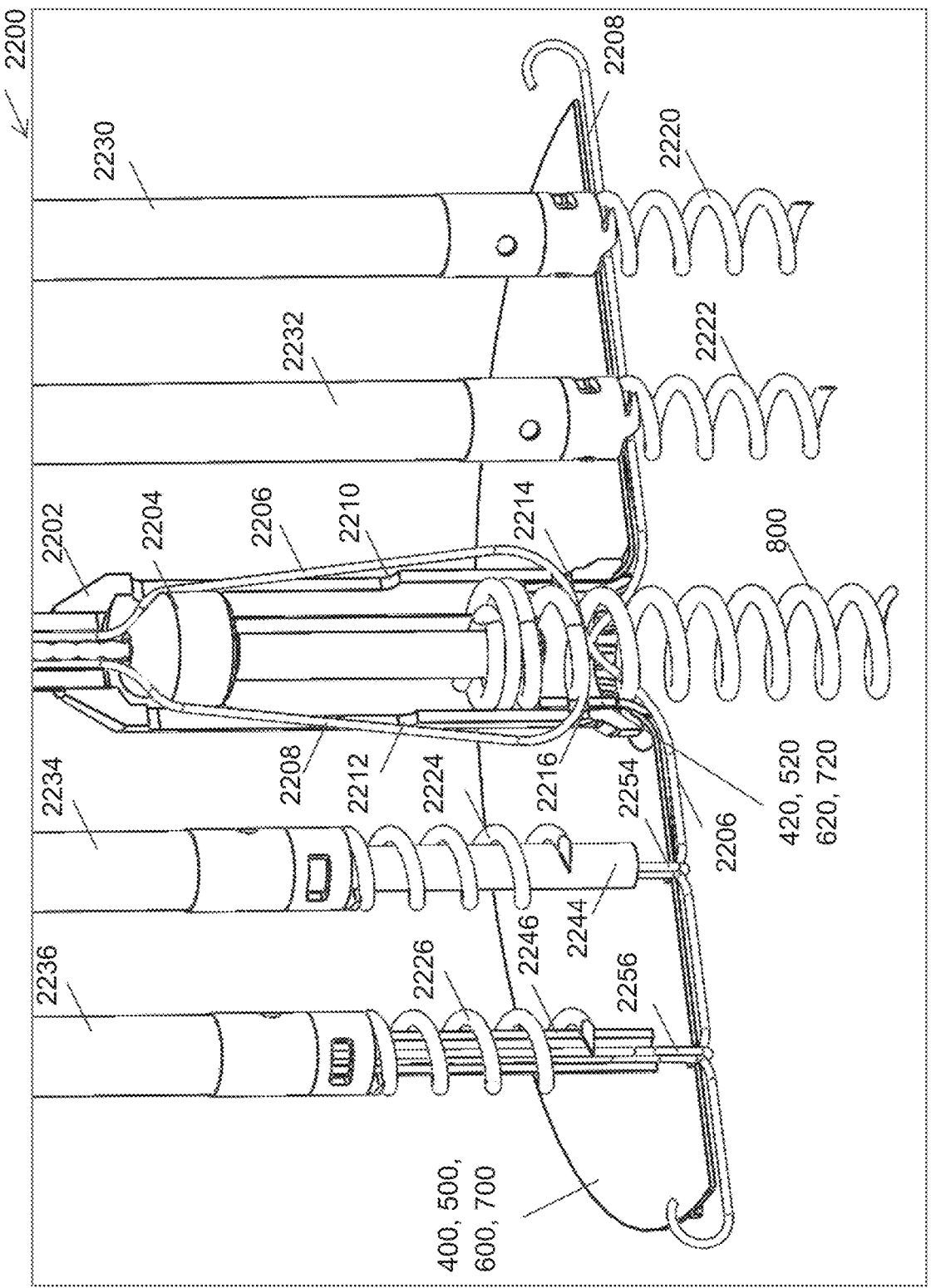
FIG. 49 illustrates an embodiment of an implant delivery system.

FIG. 49 illustrate an embodiment of implant delivery system 2200. The implant delivery system 2200 can include any of the features of implant delivery systems described herein. The implant delivery system 2200 can include a primary anchor housing 2202. In some embodiments, the primary anchor housing 2202 is a docking tube. The primary anchor housing 2202 can be cylindrical. The primary anchor housing 2202 can include a central lumen. The primary anchor housing 2202 can be disposed around the annular hub 420, 520, 620, 720 of the coaptation assistance element 400, 500, 600, 700.

The implant delivery system 2200 can include a primary anchor driver 2204. The primary anchor housing 2202 can be dimensioned to fit the primary anchor driver 2204. In some embodiments, the primary anchor driver 2204 is a torque shaft. In some embodiments, the primary anchor driver 2204 is configured to rotate relative to the primary anchor housing 2202. In some embodiments, the primary anchor driver 2204 is not configured to translate relative to the primary anchor housing 2202. The primary anchor driver 2204 can be considered a primary anchor fork driver, as described herein. The primary anchor driver 2204 can designed to engage and rotate the anchor 800. The anchor 800 can be considered a primary anchor 800 to distinguish from one or more secondary anchors.

The implant delivery system 2200 can include one or more release wires 2206, 2208. In the illustrated embodiment, the implant delivery system 2200 can include two release wires 2206, 2208, but other configurations are contemplated (e.g., one release wire, two release wires, three release wires, four release wires, five release wires, six release wires, etc.). The release wires 2206, 2208 can extend proximally from the primary anchor housing 2202. In some embodiments, the release wires 2206, 2208 can extend beyond the implant surface. The release wires 2206, 2208 can extend through at least a portion of the primary anchor housing 2202. The release wires 2206, 2208 can extend through one or more channels or tubes within the primary anchor housing 2202. The release wires 2206, 2208 can be diametrically opposed within the primary anchor housing 2202.

The release wires 2206, 2208 can extend outside of the primary anchor housing 2202. The primary anchor housing 2202 can include slots 2210, 2212 that allow the release wires 2206, 2208 to extend there through. The release wires 2206, 2208 can extend from inside the primary anchor housing 2202 to outside of the primary anchor housing 2202 through the slots 2210, 2212 (e.g., the release wire 2206 can extend through slot 2210, the release wire 2208 can extend through slot 2212).

The release wires 2206, 2208 can extend back inside the primary anchor housing 2202. The primary anchor housing 2202 can include slots 2214, 2216 that allow the release wires 2206, 2208 to extend there through. The release wires 2206, 2208 can extend from outside the primary anchor housing 2202 to inside of the primary anchor housing 2202 through the slots 2214, 2216 (e.g., the release wire 2206 can extend through slot 2214, the release wire 2208 can extend through slot 2216). The release wires 2206, 2208 can weave in and out of the primary anchor housing 2202. The release wires 2206, 2208 can couple to the primary anchor housing 2202. The release wires 2206, 2208 can extend through the anchor 800. The release wires 2206, 2208 can cross.

The release wires 2206, 2208 can extend along the coaptation assistance element 400, 500, 600, 700. The release wires 2206, 2208 can extend along the annular surface 410, 510, 610, 710. The release wires 2206, 2208 can extend underneath the coaptation assistance element 400, 500, 600, 700. The release wires 2206, 2208 can extend in opposite directions. The release wires 2206, 2208 can be diametrically opposed. The release wires 2206, 2208 can be coaxial. The release wires 2206, 2208 can be generally along a line. The release wires 2206, 2208 can be adjacent to the annulus. The release wires 2206, 2208 can contact the annulus. The release wires 2206, 2208 can facilitate coupling between the implant delivery system 2200 and the coaptation assistance element 400, 500, 600, 700. The release wires 2206, 2208 can rigidly hold the primary anchor housing 2202 against the annular hub 420, 520, 620, 720 of the coaptation assistance element 400, 500, 600, 700. The release wires 2206, 2208 can extend from the anterior side to the posterior side of the coaptation assistance element 400, 500, 600, 700. In some embodiments, the ends of the release wires 2206, 2208 wrap around the coaptation assistance element 400, 500, 600, 700. In some embodiments, the ends of the release wires 2206, 2208 are curved or form a c-shaped configuration.

The implant delivery system 2200 can include one or more secondary anchors 2220, 2222, 2224, 2226 (e.g., one secondary anchor, two secondary anchors, three secondary anchors, four secondary anchors (as shown), five secondary anchors, six secondary anchors, seven secondary anchors, eight secondary anchors, etc.). In some embodiments, two or more secondary anchors 2220, 2222, 2224, 2226 are the same. In some embodiments, two or more secondary anchors 2220, 2222, 2224, 2226 are different (e.g., different pitch, different diameter, different material, different shoulder, different window, etc.). In some embodiments, the secondary anchor 2220, 2222, 2224, 2226 can be helical anchors. The secondary anchor 2220, 2222, 2224, 2226 can have a smaller diameter than the primary anchor 800. The secondary anchor 2220, 2222, 2224, 2226 can have a smaller pitch than the primary anchor 800. The secondary anchor 2220, 2222, 2224, 2226 can be configured to rotate to engage tissue in the annulus.

The implant delivery system 2200 can include one or more secondary anchor drivers 2230, 2232, 2234, 2236 (e.g., one secondary anchor driver, two secondary anchor drivers, three secondary anchor drivers, four secondary anchor drivers (as shown), five secondary anchor drivers, six secondary anchor drivers, seven secondary anchor drivers, eight secondary anchor drivers, etc.). In some embodiments, two or more secondary anchor drivers 2230, 2232, 2234, 2236 are the same. In some embodiments, two or more secondary anchor drivers 2230, 2232, 2234, 2236 are different (e.g., different configuration, mirror image, different anchor coupled therewith, etc.). In some embodiments, the secondary anchor driver 2230, 2232, 2234, 2236 is a torque shaft. In some embodiments, the secondary anchor driver 2230, 2232, 2234, 2236 is configured to rotate the respective secondary anchor 2220, 2222, 2224, 2226. In some embodiments, the secondary anchor driver 2230, 2232, 2234, 2236 is configured to translate the respective secondary anchor 2220, 2222, 2224, 2226.

In some embodiments, the secondary anchor driver 2230, 2232, 2234, 2236 can be coupled to the respective secondary anchor 2220, 2222, 2224, 2226 according to any embodiment described herein. In some embodiments, each secondary anchor drivers 2230, 2232, 2234, 2236 couples to a respective secondary anchor 2220, 2222, 2224, 2226. In some embodiments, each secondary anchor drivers 2230, 2232, 2234, 2236 couples to two or more secondary anchors 2220, 2222, 2224, 2226. In some embodiments, a single secondary anchor driver, for example 2230, couples to all of the secondary anchors 2220, 2222, 2224, 2226.

The implant delivery system 2200 can include one or more secondary anchor guide rails 2240, 2242, 2244, 2246 (e.g., one secondary anchor guide rail, two secondary anchor guide rails, three secondary anchor guide rails, four secondary anchor guide rails (as shown), five secondary anchor guide rails, six secondary anchor guide rails, seven secondary anchor guide rails, eight secondary anchor guide rails, etc.). The number of secondary anchor guide rails 2240, 2242, 2244, 2246 can correspond to the number of secondary anchors 2220, 2222, 2224, 2226. The secondary anchor 2220, 2222, 2224, 2226 can include a passageway there through. The passageway can extend through the middle of the helical wire of the secondary anchor 2220, 2222, 2224, 2226. The secondary anchor guide rail 2240, 2242, 2244, 2246 can be configured to extend through the respective passageway.

The implant delivery system 2200 can include one or more secondary anchor tethers 2250, 2252, 2254, 2256 (e.g., one secondary anchor tether, two secondary anchor tethers, three secondary anchor tethers, four secondary anchor tethers (as shown), five secondary anchor tethers, six secondary anchor tethers, seven secondary anchor tethers, eight secondary anchor tethers, etc.). The number of secondary anchor tethers 2250, 2252, 2254, 2256 can correspond to the number of secondary anchors 2220, 2222, 2224, 2226. The secondary anchor tethers 2250, 2252, 2254, 2256 can form a loop. Each secondary anchor tether 2250, 2252, 2254, 2256 can include a first strand, a second strand, and an arc there between. Each secondary anchor tether 2250, 2252, 2254, 2256 can loop around a respective release wire 2206, 2208 as described herein. The secondary anchor tethers 2250, 2252, 2254, 2256 can extend through the coaptation assistance element 400, 500, 600, 700. The coaptation assistance element 400, 500, 600, 700 can include one or more passageways to facilitate passage of the secondary anchor tether 2250, 2252, 2254, 2256 there through.

The secondary anchor guide rails 2240, 2242, 2244, 2246 can include a passageway there through. The passageway can extend through the middle of the secondary anchor guide rails 2240, 2242, 2244, 2246. The secondary anchor tethers 2250, 2252, 2254, 2256 can be configured to extend through the passageway of the secondary anchor guide rails 2240, 2242, 2244, 2246. In some embodiments, each secondary anchor tethers 2250, 2252, 2254, 2256 extends through a respective secondary anchor guide rails 2240, 2242, 2244, 2246. The secondary anchor drivers 2230, 2232, 2234, 2236 can include a passageway there through. The passageway can extend through the middle of the secondary anchor drivers 2230, 2232, 2234, 2236. The secondary anchor tethers 2250, 2252, 2254, 2256 can be configured to extend through the passageway of the secondary anchor drivers 2230, 2232, 2234, 2236.

The release wires 2206, 2208 can maintain the connection to the coaptation assistance element 400, 500, 600, 700. The release wires 2206, 2208 can maintain the connection between the coaptation assistance element 400, 500, 600, 700 and the primary anchor 800. The release wires 2206, 2208 can maintain the connection between the coaptation assistance element 400, 500, 600, 700 and the primary anchor driver 2204. The release wires 2206, 2208 can maintain the connection between the coaptation assistance element 400, 500, 600, 700 and the secondary anchor tethers 2250, 2252, 2254, 2256.

Figure 50:
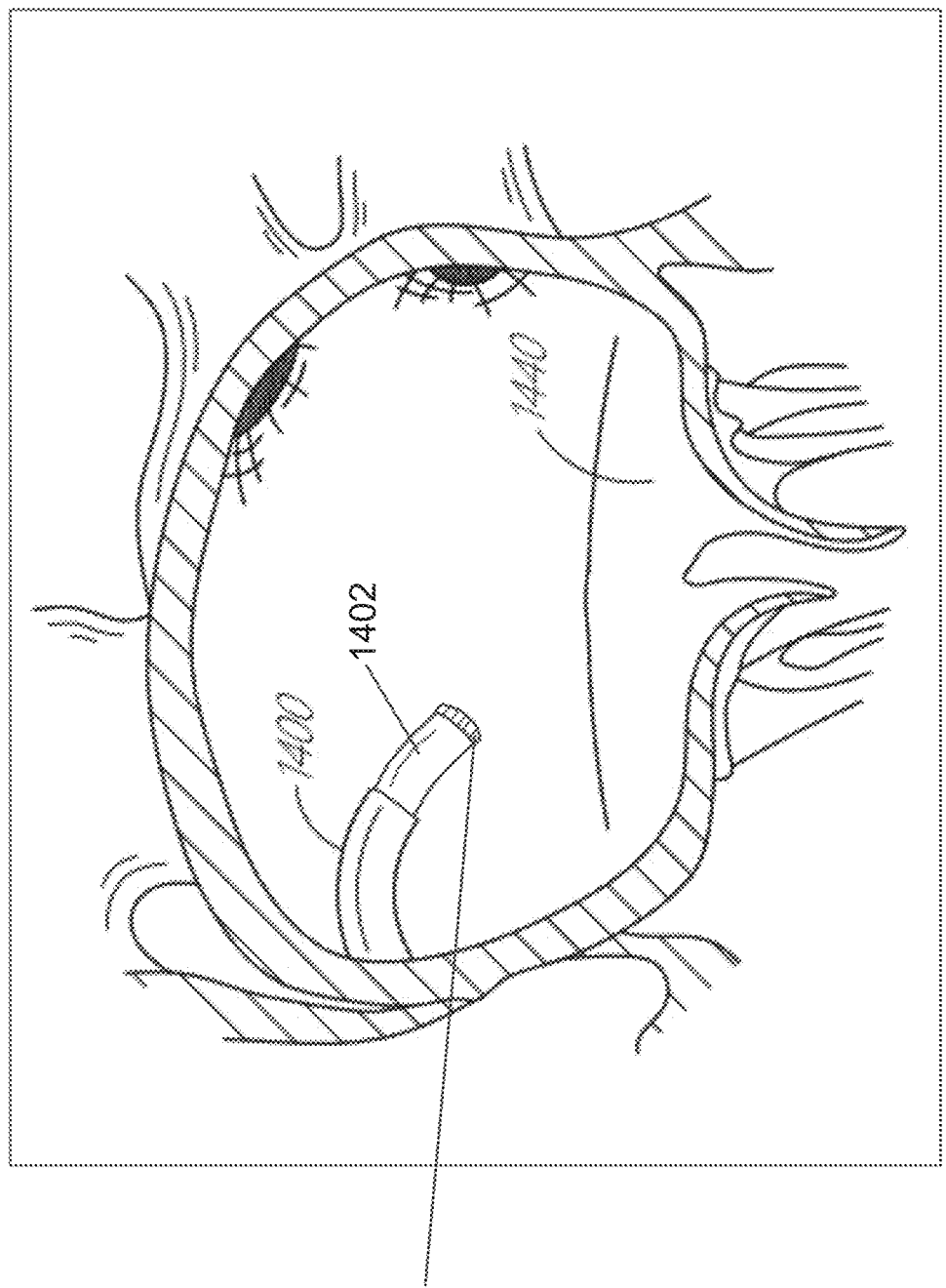
FIG. 50 illustrates a method of delivery.

FIG. 50 illustrates the telescoping action to access the primary anchor location according to some embodiments of the invention. The primary anchor 800 can be positioned near the leaflets. The primary anchor 800 can be positioned near the annulus. In some methods, access is achieved with the transseptal sheath 1400. The transseptal sheath 1400 can include a lumen for the passage of one or more additional catheters. The coaptation assistance element 400, 500, 600, 700 described herein can be delivered via a delivery catheter 1402. The coaptation assistance element 400, 500, 600, 700 can be within the delivery catheter 1402. The delivery catheter 1402 can telescope relative to the transseptal sheath 1400. The delivery catheter 1402 can telescope relative to the transseptal sheath 1400 to extend outward relative to the transseptal sheath 1400 for delivery of the coaptation assistance element 400, 500, 600, 700. The coaptation assistance element 400, 500, 600, 700 can telescope relative to the delivery catheter 1402 to extend outward relative to the delivery catheter 1402 for delivery of the coaptation assistance element 400, 500, 600, 700.

Figure 51:
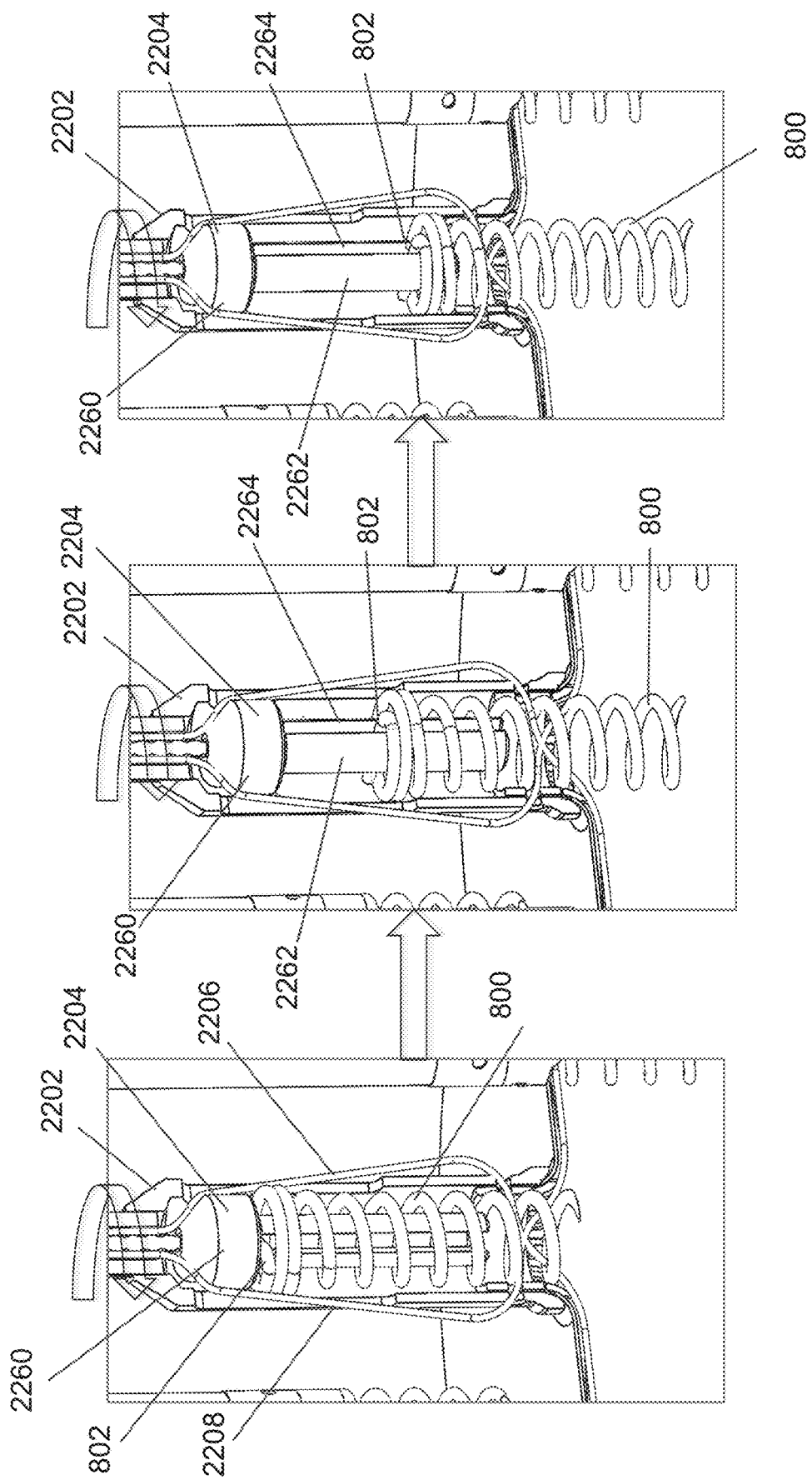
FIG. 51 illustrates an embodiment of a primary anchor driver.

FIG. 51 illustrates the rotation of the primary anchor driver 2204 according to some embodiments of the invention. FIG. 51 illustrates a progression of engaging the primary anchor 800. On the left, the initial position of the primary anchor driver 2204 and the primary anchor 800 are illustrated. The primary anchor 800 can be proximal the tissue in a proximal position. In the middle, the primary anchor driver 2204 is rotated to rotate the primary anchor 800. The primary anchor 800 rotates and translates relative to the primary anchor driver 2204. The primary anchor 800 engages the tissue. On the right, the primary anchor 800 is further rotated to engage tissue. The primary anchor 800 can be reversible. The primary anchor 800 can be rotated in one direction to engage tissue, and rotated in a second, opposite direction to disengage tissue.

The primary anchor driver 2204 can engage and rotate the primary anchor 800. The primary anchor driver 2204 can be disposed within the primary anchor housing 2202. The primary anchor 800 can be disposed within the primary anchor housing 2202. The release wires 2206, 2208 can extend through at least a portion of the primary anchor housing 2202. As the primary anchor 800 is rotates, the helixes of the primary anchor pass around the release wires 2206, 2208. The release wires 2206, 2208 maintain their position as the primary anchor 800 rotates. The primary anchor 800 can be advanced to engage tissue when the coaptation assistance element 400, 500, 600, 700 is adjacent to the annulus. The primary anchor driver 2204 can include a hub 2260 and one or more extensions 2262, 2264. The primary anchor driver 2204 can include two extensions 2262, 2264, but other configurations are contemplated. The extensions 2262, 2264 can be perpendicular to the hub 2560 or extend at other angles. The primary anchor driver 2204 can be a fork driver. The primary anchor 800 can include a cross-bar 802. The cross-bar 802 can form the proximal part of the primary anchor 800. The cross-bar 802 can be formed from a helix of the helical anchor. The two extensions 2262, 2264 can be configured to slide within the passageway of the primary anchor 800 on either side of the cross-bar 802. The cross-bar 802 can be disposed between the extensions 2262, 2264. Other configurations of coupling the primary anchor driver 2204 to the primary anchor 800 are contemplated including any of the mating configurations described herein.

In some embodiments, the primary anchor driver 2204 rotates but does not move in the axial direction. In some embodiments, the primary anchor driver 2204 rotates but does not translate relative to the primary anchor housing 2202. The fork of the primary anchor driver 2204 rotates to drive the primary anchor 800. In some embodiments, the primary anchor driver 2204 does not advance axially. In some embodiments, the primary anchor driver 2204 is retained within the primary anchor housing 2202. In some embodiments, an advantage is to limit translation of the primary anchor driver 2204. The limit related to axial movement of the primary anchor driver 2204 can reduce or prevent inadvertent interaction of the primary anchor driver 2204 with the tissue. The limit related to axial movement of the primary anchor driver 2204 can reduce or prevent inadvertent interaction of the primary anchor driver 2204 with the release wires 2206, 2208.

Figure 52:
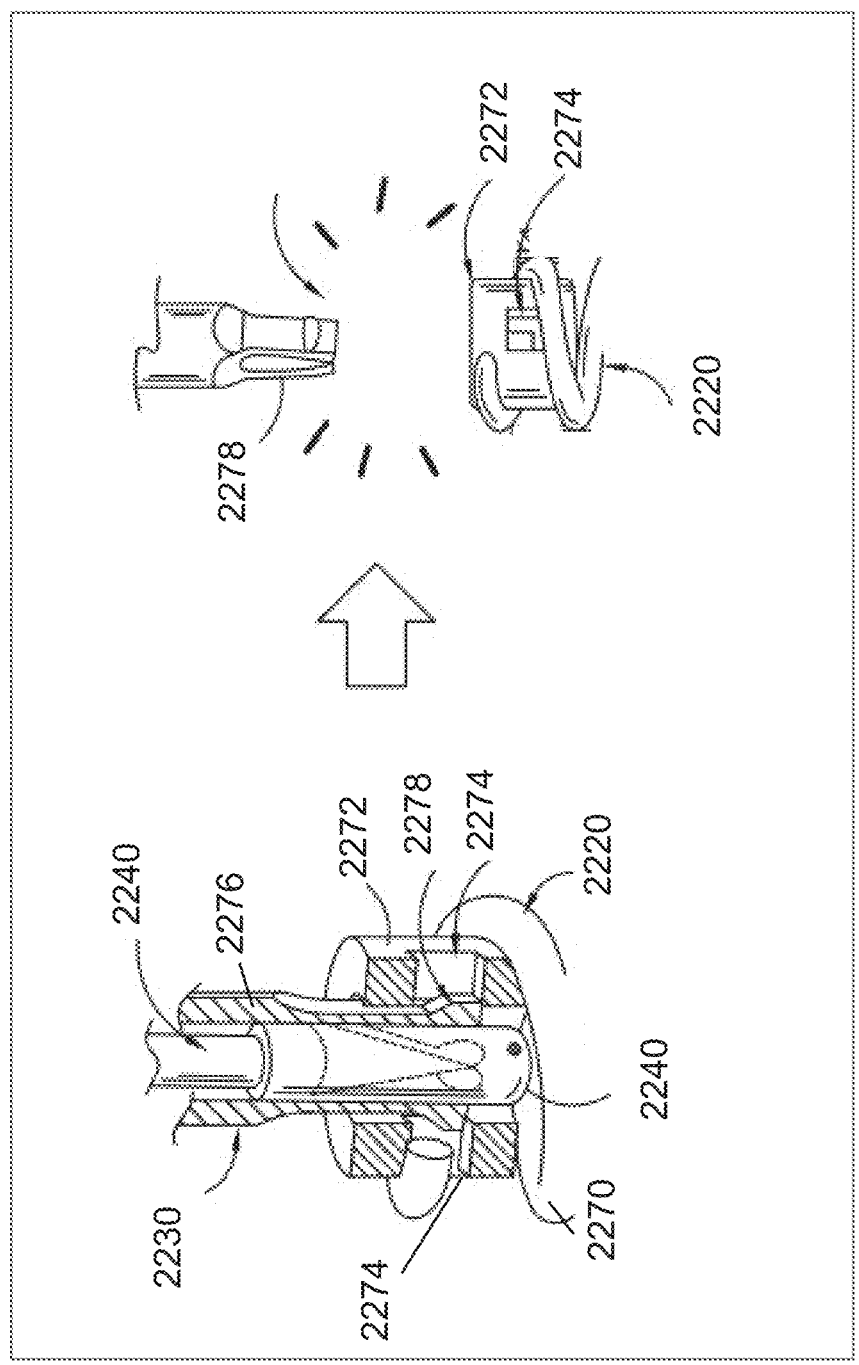
FIG. 52 illustrates an embodiment of a secondary anchor guide rail.

FIG. 52 illustrates the connection between the secondary anchor driver 2230 and the respective secondary anchor 2220 according to some embodiments. While the secondary anchor driver 2230 and the secondary anchor 2220 are illustrated, each secondary anchor drivers 2230, 2232, 2234, 2236 can couple to a respective secondary anchor 2220, 2222, 2224, 2226.

The secondary anchor 2220 can include a helical body 2270. The secondary anchor 2220 can include a shoulder 2272. The shoulder 2272 can be configured to engage the secondary anchor driver 2230. The shoulder 2272 can have features such as one or more windows 2274. The windows 2274 can be diametrically opposed, equally spaced, or otherwise spaced apart. While two windows 2274 are shown, other configurations of windows are contemplated (e.g., one window, two windows (shown), three windows, four windows, five windows, six windows, etc.).

The secondary anchor driver 2230 can include an elongated shaft 2276. The elongated shaft can include a lumen for passage of the secondary anchor guide rail 2240 there through. The secondary anchor driver 2230 can include one or more locking tabs 2278. The locking tabs 2278 can be diametrically opposed, equally spaced, or otherwise spaced apart. While two locking tabs 2278 are shown, other configurations of locking tabs are contemplated (e.g., one locking tab, two locking tabs (shown), three locking tabs, four locking tabs, five locking tabs, six locking tabs, etc.). The number and configuration of the locking tabs can correspond to the number of windows. The locking tabs 2278 can include a shape memory or springy material. The locking tabs 2278 can be designed to flex outward into engagement with the windows 2274.

The secondary anchor guide rail 2240 can activate the lock mechanism between the secondary anchor driver 2230 and the respective secondary anchor 2220. The lock mechanism can be an axial-torsional lock. Once coupled, the axial movement of the secondary anchor driver 2230 can cause axial movement of the secondary anchor 2220. Once coupled, the torsional movement of the secondary anchor driver 2230 can cause torsional movement of the secondary anchor 2220. The secondary anchor guide rail 2240 can lock the secondary anchor driver 2230 to the secondary anchor 2220. This lock can be temporary. This lock can be reversible. The secondary anchor guide rail 2240 can push outward the locking tabs 2278. The locking tabs 2278 can be pushed outward into the windows 2274 by the secondary anchor guide rail 2240.

The secondary anchor guide rail 2240 can maintain the locking tabs 2278 in the open position to keep the locking tabs 2278 engaged with the windows 2274 in the secondary anchor 2230. In some embodiments, the longitudinal movement of the secondary anchor guide rail 2240 toward the secondary anchor 2220 can push the locking tabs 2278 outward toward the windows 2274. In some embodiments, the longitudinal movement of the secondary anchor guide rail 2240 away from the secondary anchor 2220 can allow the locking tabs 2278 to regain a neutral configuration and disengage from the windows 2274. The locking tabs 2278 engaged with the windows 2274 of the secondary anchor 2220 can allow the transmission of axial movement between the secondary anchor driver 2230 and the secondary anchor 2220. The locking tabs 2278 engaged with the windows 2274 of the secondary anchor 2220 can allow the transmission of torque between the secondary anchor driver 2230 and the secondary anchor 2220. In some embodiments, an advantage is the secondary anchor 2220 can be rotated independently of the rotation of the primary anchor 800. In some embodiments, an advantage is the secondary anchor 2220 can be rotated independently of the rotation of one or more other secondary anchors 2232, 2234, 2236.

Figure 53A:
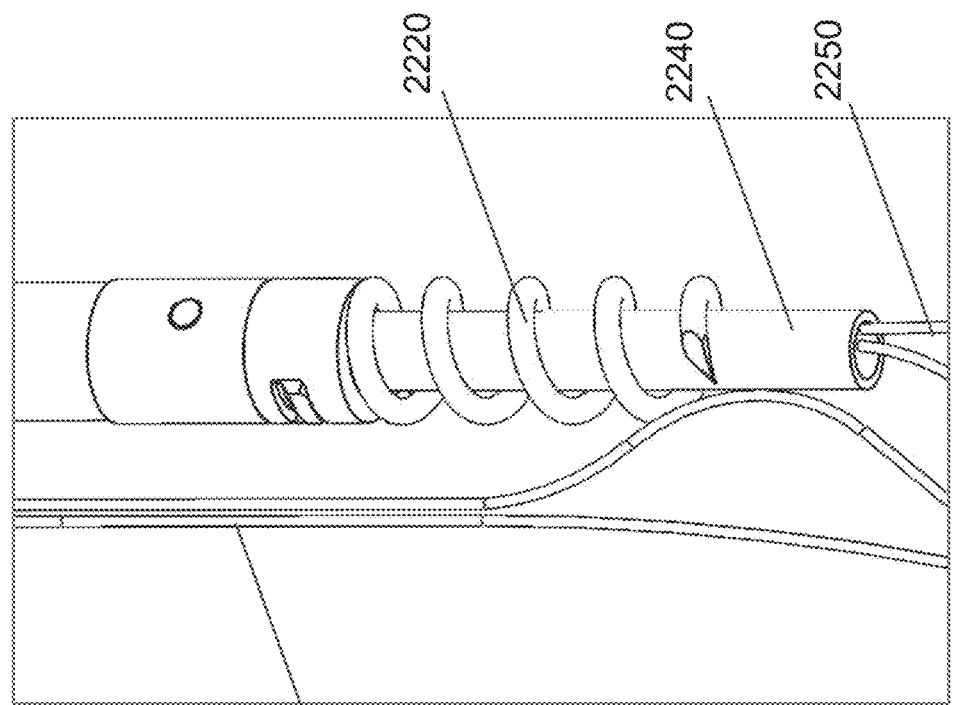
FIGS. 53A-53B illustrate an embodiment of a secondary anchor guide rail to prevent entanglement.
Figure 53B:
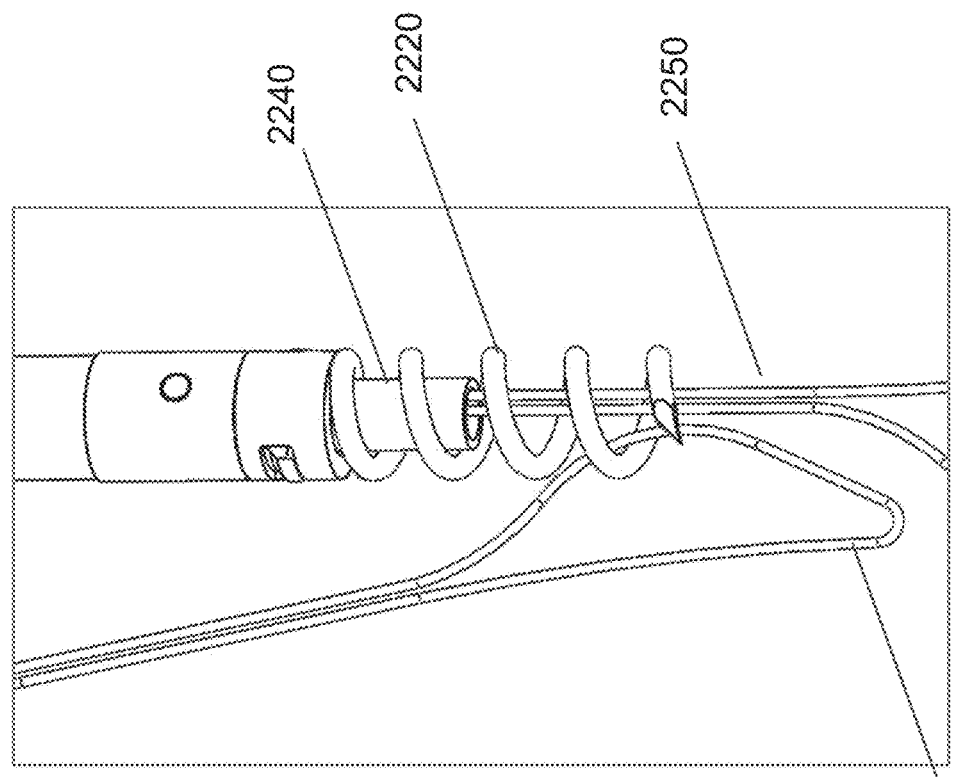

FIGS. 53A-53B illustrates the relationship between the secondary anchor guide rail 2240, secondary anchor tether 2250, and the respective secondary anchor 2220 according to some embodiments. While the secondary anchor guide rail 2240, secondary anchor tether 2250, and the secondary anchor 2220 are illustrated, each secondary anchor guide rail 2240, 2242, 2244, 2246 can engage a respective secondary anchor 2220, 2222, 2224, 2226. The secondary anchor guide rail 2240 can limit or prevent anchor and tether engagement. FIGS. 53A-53B illustrate the secondary anchor tether 2250 and an adjacent secondary anchor tether 2252. Each secondary anchor tether can include two strands and an arc there between, see secondary anchor tether 2252.

The secondary anchor 2220 can be a helical anchor. The helical anchor can include a pitch and a diameter. The helical anchor can include an open distal end. The pitch of the secondary anchor 2220 can be larger than a strand of the secondary anchor tether (e.g., secondary anchor tether 2252). The open end of the secondary anchor 2220 can be larger than a strand of the secondary anchor tether (e.g., secondary anchor tether 2252). The dimension of the open end can be defined by the pitch. This configuration may allow the secondary anchor 2220 and the secondary anchor tether 2252 to become tangled as shown in FIG. 53A. In this figure, the secondary anchor tether 2252 and the secondary anchor 2220 can become entangled because the secondary anchor guide rail 2240 is proximal, exposing the open end of the secondary anchor 2220.

FIG. 53B illustrates the secondary anchor guide rail 2240 extending through the open end of the pitch the secondary anchor 2220, according to some embodiments of the invention. The pitch of the secondary anchor 2220 can be smaller than a strand of the secondary anchor tether (e.g., secondary anchor tether 2252). The open end of the secondary anchor 2220 can be smaller than a strand of the secondary anchor tether (e.g., secondary anchor tether 2252). The space between the secondary anchor guide rail 2240 and the secondary anchor 2220 can be advantageously too small to allow the entanglement of the secondary anchor tether 2252. This configuration may prevent the secondary anchor 2220 and the secondary anchor tether 2252 from becoming tangled. In FIG. 53B, the open end of the secondary anchor is protected from entanglement.

Figure 54:
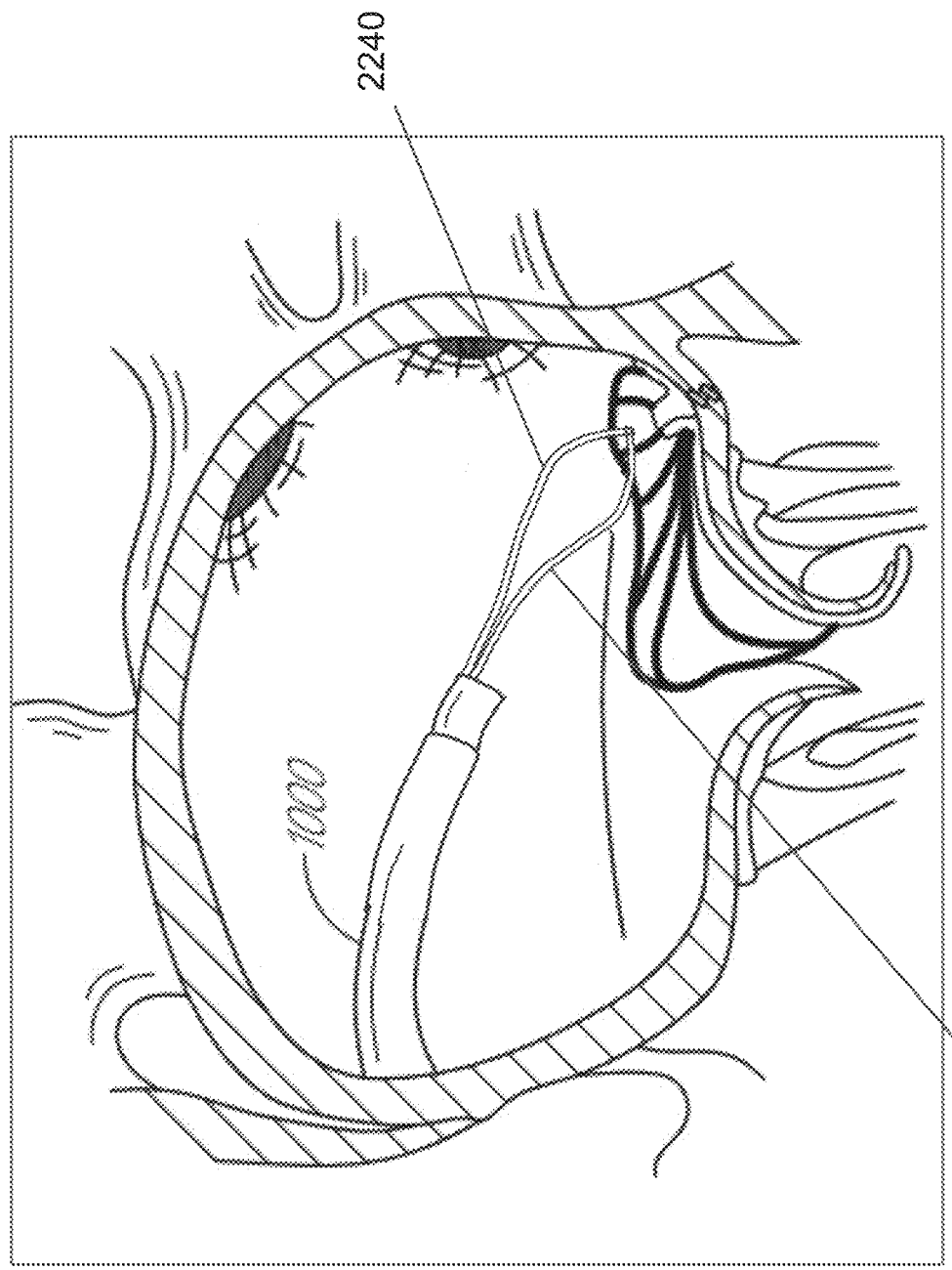
FIG. 54 illustrates an embodiment of a secondary anchor guide rail to facilitate the trajectory for a secondary anchor.

FIG. 54 illustrates the secondary anchor guide rail 2240, according to some embodiments of the invention. While the secondary anchor guide rail 2240 is illustrated, one or more secondary anchor guide rails 2240, 2242, 2244, 2246 can be deployed. The secondary anchor guide rail 2240, 2242, 2244, 2246 can include a pre-shaped material. The secondary anchor guide rail 2240, 2242, 2244, 2246 can include a shape memory material such as a shape memory metal or plastic. The secondary anchor guide rail 2240, 2242, 2244, 2246 can include any shape including one or more linear segments and one or more non-linear segments such as one or more curved segments. The pre-shape of the secondary anchor guide rail 2240, 2242, 2244, 2246 can facilitate the trajectory for the respective secondary anchor 2220, 2222, 2224, 2226. The pre-shaped distal end of the secondary anchor guide rail 2240, 2242, 2244, 2246 can influence the anchoring trajectory for the secondary anchor 2220. In FIG. 54, the secondary anchor guide rail 2240 is pre-shaped to include a distal curve. The secondary anchor guide rail 2240 is shown in two different orientations. The orientation of the secondary anchor guide rail 2240 can allow the ability to define different secondary anchor trajectories. In some embodiments, two or more trajectories can be defined by secondary anchor guide rail 2240.

FIGS. 55A-55C illustrates the proximal assembly for secondary anchors, according to some embodiments of the invention. The proximal assembly can include one or more guide rail locks. The secondary anchor guide rails 2240, 2242, 2244, 2246 can be locked to limit or prevent axial movement. Locking of the secondary anchor guide rails 2240, 2242, 2244, 2246 can ensure that the secondary anchor guide rails 2240, 2242, 2244, 2246 will be distal to the secondary anchor 2220, 2222, 2224, 2226, see FIG. 53B. The secondary anchor guide rails 2240, 2242, 2244, 2246 can be locked in a position wherein at least a portion is distal to the open end of the secondary anchor 2220, 2222, 2224, 2226. The secondary anchor guide rails 2240, 2242, 2244, 2246 can be locked to ensure that the secondary anchor 2220, 2222, 2224, 2226 does not become entangled with the secondary anchor tethers 2250, 2252, 2254, 2256. The secondary anchor guide rails 2240, 2242, 2244, 2246 can be locked to ensure that the secondary anchor 2220, 2222, 2224, 2226 remains coupled to a respective secondary anchor drivers 2230, 2232, 2234, 2236. The secondary anchor guide rails 2240, 2242, 2244, 2246 can be locked to ensure that the secondary anchor 2220, 2222, 2224, 2226 does not become prematurely released.

The proximal assembly can include one or more tether locks. The secondary anchor tethers 2250, 2252, 2254, 2256 can be locked to ensure appropriate tension is maintained. In some embodiments, applying appropriate tension to the secondary anchor tethers 2250, 2252, 2254, 2256 defines the desired trajectory for the secondary anchor 2220, 2222, 2224, 2226. Locking the secondary anchor tethers 2250, 2252, 2254, 2256 after tension is applied can ensure that the tension is reliably maintained during the delivery of the secondary anchor 2220, 2222, 2224, 2226.

FIG. 55A illustrates the proximal assembly coupled to the secondary anchor driver 2230. While secondary anchor driver 2230 is illustrated, each secondary anchor driver 2230, 2232, 2234, 2236 can be coupled to a proximal assembly. In some embodiments, two or more secondary anchor drivers 2230, 2232, 2234, 2236 can be coupled to the same proximal assembly in order to lock two or more respective secondary anchor guide rails or two or more respective secondary anchor tethers. The proximal assembly can include the secondary anchor guide rail lock 2280. The proximal assembly can include the secondary anchor tether lock 2282. FIG. 55B illustrates the secondary anchor guide rail lock 2280 in a locked position wherein the secondary anchor guide rails 2240 is prevented or limited from moving proximally. The secondary anchor guide rail lock 2280 can include a threaded bolt configured to engage a threaded nut. The secondary anchor guide rail lock 2280 can limit proximal motion by functioning as a stop when locked. The secondary anchor guide rail lock 2280 can allow proximal motion when unlocked. In some embodiments, the secondary anchor guide rails 2240 can be removed in the unlocked position. The secondary anchor guide rails 2240 can be removed to release the secondary anchor driver 2230 from the secondary anchor 2220.

FIG. 55C illustrates the secondary anchor tether lock 2282 in an unlocked position wherein the secondary anchor tether 2250 can move proximally. The secondary anchor tether lock 2282 can include a threaded bolt configured to engage a threaded nut. The secondary anchor tether lock 2282 can limit any proximal motion by functioning as a stop when locked. In some embodiments, the secondary anchor tether 2250 can be removed in the unlocked position. The secondary anchor tether 2250 can be removed after the secondary anchor 2220 is delivered. The secondary anchor tether 2250 can be pulled from outside of the body of the patient. The secondary anchor tether 2250 can allow the user to perform a suture count.

Figure 56:
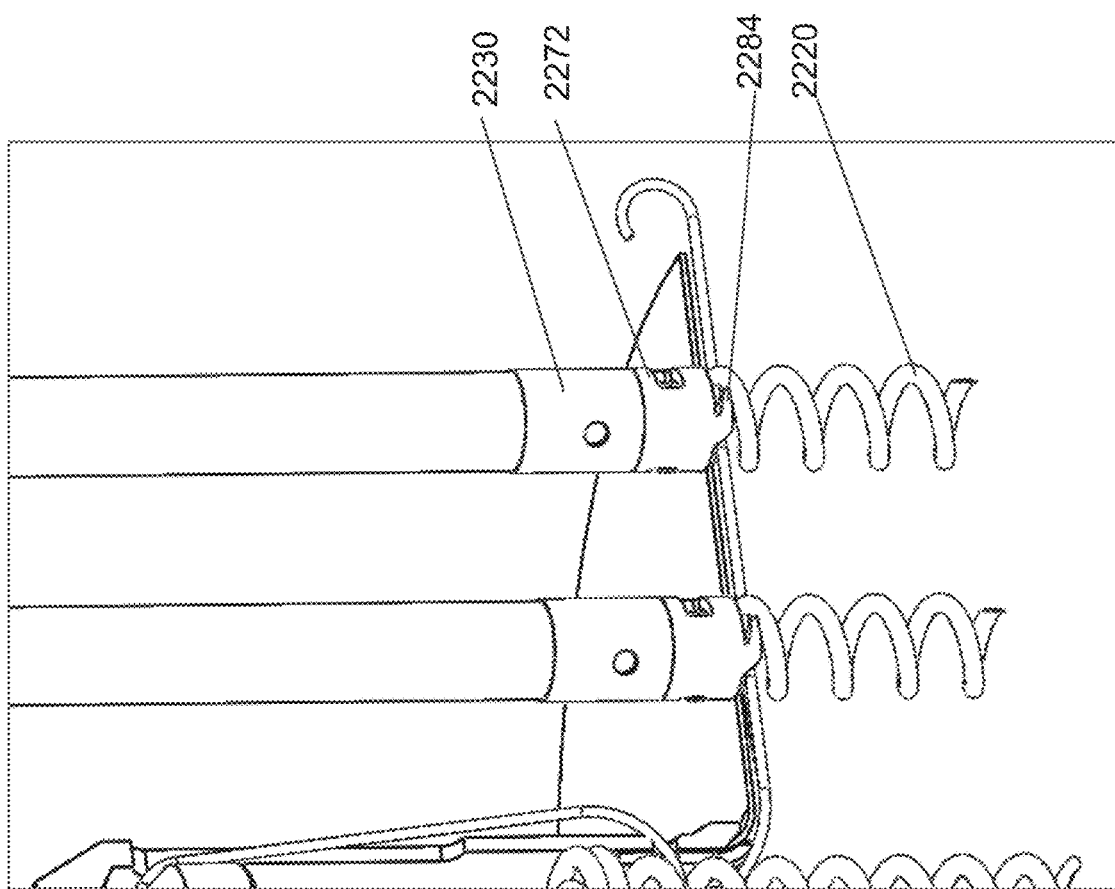
FIG. 56 illustrates an embodiment of an anti-rotation feature.

FIG. 56 illustrates an anti-rotation feature on the secondary anchor 2220, 2222, 2224, 2226. The secondary anchor 2220 can include the shoulder 2272. The shoulder 2272 can be configured to engage the secondary anchor driver 2230 as described herein. The shoulder 2272 can have features such as one or more anti-rotation features 2284. The anti-rotation feature 2284 can include one or more barbs configured to engage tissue. While one anti-rotation feature 2284 is shown, other configurations of anti-rotation features are contemplated (e.g., one anti-rotation feature (shown), two anti-rotation features, three anti-rotation features, four anti-rotation features, five anti-rotation features, six anti-rotation features, etc.). Two or more anti-rotation features 2284 can be diametrically opposed, equally spaced, or otherwise spaced apart. In some embodiments, the anti-rotation feature 2284 prevents further rotation of the secondary anchor 2220, 2222, 2224, 2226. In some embodiments, the secondary anchor 2220, 2222, 2224, 2226 is configured for left-handed rotation. In some embodiments, the secondary anchor 2220, 2222, 2224, 2226 is configured for right-handed rotation. In some embodiments, the anti-rotation feature 2284 is configured for reduce or limit left-handed rotation. In some embodiments, the anti-rotation feature 2284 is configured for reduce or limit right-handed rotation.

Figure 57B:
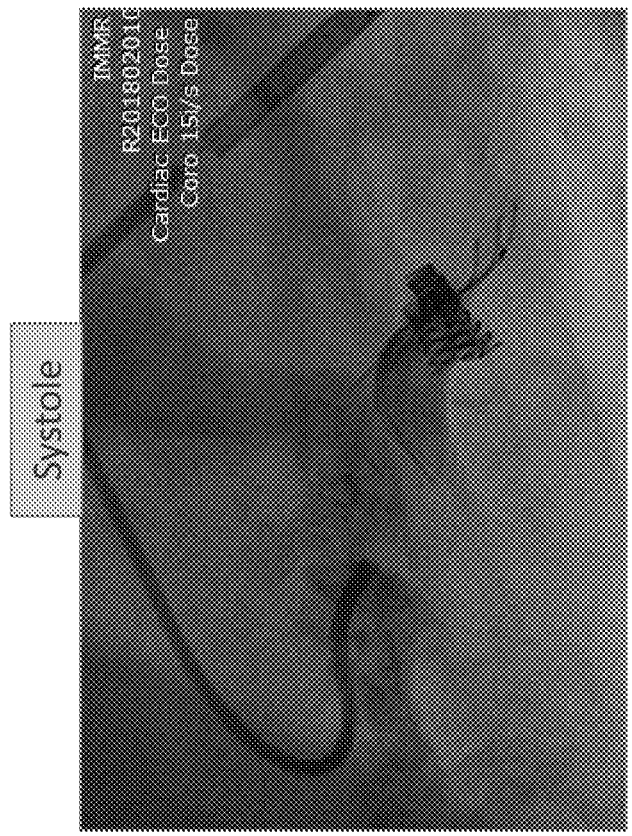
FIGS. 57A-57B illustrates an embodiment of posterior leaflet augmentation and restoration.
Figure 57A:
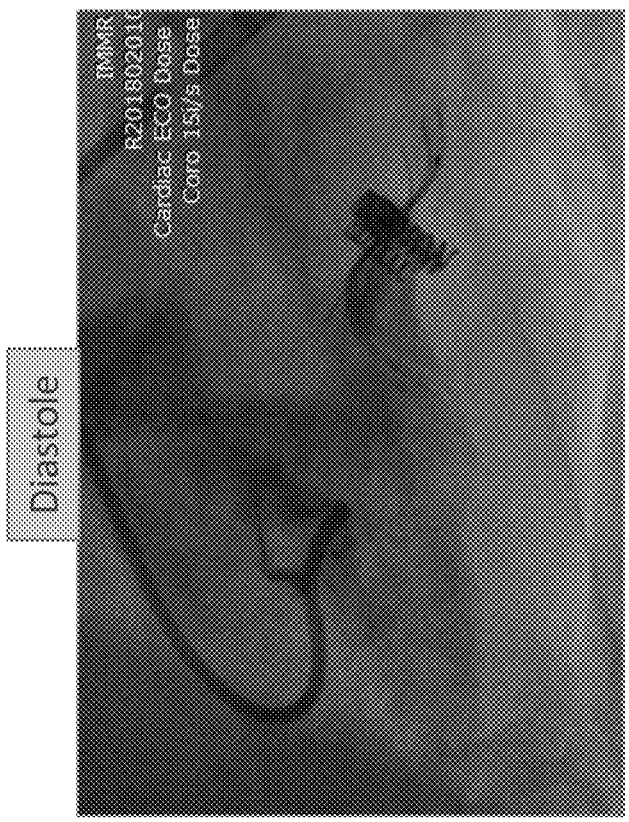

FIG. 57 illustrates posterior leaflet augmentation and restoration in diastole. FIG. 57 illustrates posterior leaflet augmentation and restoration in systole.

Referring back to FIG. 49, the coaptation assistance element 400, 500, 600, 700 can be delivered to the valve annulus. The primary anchor 800 can be disposed within the primary anchor housing 2202. The primary anchor driver 2204 can be disposed within the primary anchor housing 2202. The one or more release wires 2206, 2208 can engage the primary anchor housing 2202. The release wires 2206, 2208 can engage the primary anchor 800. The release wires 2206, 2208 can be disposed on the annular side of the coaptation assistance element 400, 500, 600, 700. The secondary anchor tethers 2250, 2252, 2254, 2256 can extend through the coaptation assistance element 400, 500, 600, 700. The secondary anchor tethers 2250, 2252, 2254, 2256 can form a loop around the release wires 2206, 2208. The secondary anchor tethers 2250, 2252, 2254, 2256 can extend proximally. The secondary anchor tethers 2250, 2252 can extend around release wire 2208. The secondary anchor tethers 2250, 2252 can be spaced apart along the release wire 2208. The secondary anchor tethers 2254, 2256 can extend around release wire 2206. The secondary anchor tethers 2254, 2256 can be spaced apart along the release wire 2206.

The coaptation assistance element 400, 500, 600, 700 can be delivered in a low profile configuration. The coaptation assistance element 400, 500, 600, 700 can rolled, compressed, folded, or otherwise reduced in size for delivery. In some embodiments, the release wires 2206, 2208 help to maintain the position of the primary anchor driver 2204 relative to the coaptation assistance element 400, 500, 600, 700. In some embodiments, the release wires 2206, 2208 help to maintain the position of the primary anchor 800 relative to the coaptation assistance element 400, 500, 600, 700. In some embodiments, the release wires 2206, 2208 help to maintain the position of the secondary anchor tethers 2250, 2252, 2254, 2256 relative to the coaptation assistance element 400, 500, 600, 700. In some embodiments, the ends of the release wires 2206, 2208 wrap around the coaptation assistance element 400, 500, 600, 700 to maintain the position of the release wires 2206, 2208 relative to the coaptation assistance element 400, 500, 600, 700.

The coaptation assistance element 400, 500, 600, 700 can be delivered via the delivery catheter 1402 as shown in FIG. 50. The telescoping action can position the coaptation assistance element 400, 500, 600, 700 relative to a location to engage the primary anchor 800 with tissue. The coaptation assistance element 400, 500, 600, 700 can be expanded, or partially expanded within the heart valve.

The primary anchor 800 can be rotated to engage tissue as shown in FIG. 51. The primary anchor driver 2204 can rotate to rotate the primary anchor 800. The primary anchor driver 2204 can rotate, but in some embodiments, does not translate. The primary anchor driver 2204 can engage the cross-bar 802 of the primary anchor 800. The primary anchor driver 2204 can include forked configuration to engage either side of the cross-bar 802. The primary anchor 800 can be removed by rotating the primary anchor driver 2204 in the opposite direction. The coaptation assistance element 400, 500, 600, 700 can be functionally tested prior to engaging one or more secondary anchors 2220, 2222, 2224, 2226. In some embodiments, only the primary anchor 800 is utilized. In some embodiments, only one or more secondary anchors 2220, 2222, 2224, 2226 are utilized. In some embodiments, one or more secondary anchors 2220, 2222, 2224, 2226 engage tissue after the primary anchor 800 engages tissue.

Referring back to FIG. 49, in some methods, the secondary anchor assembly is moved toward the annulus. The secondary anchor drivers 2230, 2232, 2234, 2236 can engage a respective secondary anchor 2220, 2222, 2224, 2226. Referring to FIG. 52, the secondary anchor guide rails 2240, 2242, 2244, 2246 can maintain the engagement between the secondary anchor drivers 2230, 2232, 2234, 2236 and the respective secondary anchors 2220, 2222, 2224, 2226. The secondary anchor guide rails 2240, 2242, 2244, 2246 can keep the locking tabs 2278 engaged with the windows 2274. Referring to FIG. 53, the secondary anchor guide rails 2240, 2242, 2244, 2246 can extend beyond the open end of the secondary anchor 2220, 2222, 2224, 2226. The secondary anchor guide rail 2240, 2242, 2244, 2246 can prevent entanglement between the secondary anchor 2220, 2222, 2224, 2226 and an adjacent tether. Referring to FIG. 55B, the guide rail lock 2280 can reduce or prevent proximal movement of the secondary anchor guide rails 2240, 2242, 2244, 2246.

FIG. 48 illustrates the delivery of the secondary anchor 2224. The secondary anchor driver 2234 can be coupled with the secondary anchor 2224. The secondary anchor guide rail 2244 can extend beyond the open end of the secondary anchor 2224. The secondary anchor guide rail 2244 can facilitate the coupling between the secondary anchor driver 2234 and the secondary anchor 2224. The secondary anchor guide rail 2244 can reduce or prevent tangling between the secondary anchor 2224 and the adjacent secondary anchor tethers 2256. The secondary anchor guide rail 2244 can slide along the secondary anchor tethers 2254 toward the annulus. The secondary anchor guide rail 2244 can be partially retracted when the secondary anchor 2224 is near the coaptation assistance element 400, 500, 600, 700. The secondary anchor guide rail 2244 can facilitate the coupling between the secondary anchor driver 2234 and the secondary anchor 2224 when partially retracted. The secondary anchor guide rail 2244 can be partially retracted along the helical length of the secondary anchor 2224, however, the secondary anchor guide rail 2244 can still be positioned to interact with the locking tabs 2278 (see position in FIG. 52).

The secondary anchor driver 2234 can rotate to engage the secondary anchor 2224 with tissue. The secondary anchor 2224 can penetrate the coaptation assistance element 400, 500, 600, 700. The secondary anchor 2224 can include one or more anti-rotation feature 2284. The secondary anchor 2224 can be rotated until the anti-rotation feature 2284 is adjacent or engages tissue. The secondary anchor 2224 can be rotated until the anti-rotation feature 2284 is adjacent or engages the coaptation assistance element 400, 500, 600, 700.

After deploying the secondary anchor 2224, the secondary anchor guide rail 2244 can be removed which can allow the secondary anchor driver 2234 to decouple from the secondary anchor 2224. The secondary anchor driver 2234 can be removed. The anchor tether 2254 can be removed by pulling on an extracorporeal end of a strand of the tether 2254. The secondary anchors 2220, 2222, 2224, 2226 can be similarly deployed using the respective secondary anchor drivers 2230, 2232, 2234, 2236, secondary anchor guide rails 2240, 2242, 2244, 2246, and secondary anchor tethers 2250, 2252, 2254, 2256. The secondary anchors 2220, 2222, 2224, 2226 can be independently rotated to engage tissue. The secondary anchors 2220, 2222, 2224, 2226 can be simultaneously rotated to engage tissue. The secondary anchors 2220, 2222, 2224, 2226 can be sequentially rotated to engage tissue.

After deployment of the primary anchor 800 and/or one or more secondary anchors 2220, 2222, 2224, 2226, the release wires 2206, 2208 can be removed. The release wires 2206, 2208 can be removed by pulling on the extracorporeal end of the release wire 2206, 2208. The primary anchor housing 2202 can be removed with the primary anchor driver 2204 disposed therein.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "inserting a coaptation assist body proximate the mitral valve" includes "instructing the inserting of a coaptation assist body proximate the mitral valve." The ranges disclosed herein also encompass any and all overlap, subranges, and combinations thereof. Language such as "up to," "at least," "greater than," "less than," "between," and the like includes the number recited. Numbers preceded by a term such as "approximately", "about", and "substantially" as used herein include the recited numbers, and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A coaptation assistance element for treating mal-coaptation of a heart valve, the heart valve having an annulus, the coaptation assistance element comprising:
   a first surface and an opposed second surface, each surface bounded by a first lateral edge, a second lateral edge, an inferior edge, and a superior edge;
   a hub; and
   a plurality of struts spaced around the hub and extending outward from the hub, the plurality of struts comprising at least a first strut configured to be implanted within a heart and a second strut configured to be implanted within the heart,
   wherein the coaptation assistance element comprises lamination configured to surround one or more struts of the plurality of struts.

2. The coaptation assistance element of claim 1, wherein the coaptation assistance element is configured to provide an atraumatic surface to reduce the risk of native leaflet damage.

3. The coaptation assistance element of claim 1, wherein the lamination comprises ePTFE.

4. The coaptation assistance element of claim 1, wherein the first surface comprises ePTFE.

5. The coaptation assistance element of claim 1, wherein the second surface comprises ePTFE.

6. A coaptation assistance element for treating mal-coaptation of a heart valve, the heart valve having an annulus, the coaptation assistance element comprising:
   a first surface and an opposed second surface, each surface bounded by a first lateral edge, a second lateral edge, an inferior edge, and a superior edge, wherein the first surface comprises a first coaptation surface configured for an anterior leaflet to coapt against;
   a hub;
   a plurality of struts spaced around the hub and extending outward from the hub, the plurality of struts comprising at least a first strut configured to be implanted within a heart and a second strut configured to be implanted within the heart,
   wherein the coaptation assistance element comprises a reinforced edge with increased thickness.

7. The coaptation assistance element of claim 6, wherein the reinforced edge is configured to reduce trauma to native tissue.

8. The coaptation assistance element of claim 6, wherein the reinforced edge is configured to reduce contact between the coaptation assistance element and a posterior leaflet.

9. The coaptation assistance element of claim 6, wherein the first surface comprises the reinforced edge.

10. The coaptation assistance element of claim 6, wherein the second surface comprises the reinforced edge.

11. The coaptation assistance element of claim 6, wherein the first lateral edge comprises the reinforced edge.

12. The coaptation assistance element of claim 6, wherein the inferior edge comprises the reinforced edge.

13. The coaptation assistance element of claim 6, wherein the reinforced edge is at least partially circumferential.

14. A coaptation assistance element for treating mal-coaptation of a heart valve, the heart valve having an annulus, the coaptation assistance element comprising:
   a first surface and an opposed second surface, each surface bounded by a first lateral edge, a second lateral edge, an inferior edge, and a superior edge, wherein the first surface comprises a first coaptation surface configured for the anterior leaflet to coapt against;
   a hub;
   a plurality of struts spaced around the hub and extending outward from the hub,
   wherein the coaptation assistance element comprises a layer of pericardium.

15. The coaptation assistance element of claim 14, wherein the plurality of struts comprise nitinol.

16. The coaptation assistance element of claim 14, wherein the hub and the plurality of struts are integrally formed.

17. The coaptation assistance element of claim 14, wherein the coaptation assistance element comprises the same material on the first surface and the second surface.

18. The coaptation assistance element of claim 14, wherein the coaptation assistance element comprises different materials on the first surface, or a portion thereof, and the second surface, or a portion thereof.

19. The coaptation assistance element of claim 14, wherein the layer of pericardium comprises porcine pericardium.

20. The coaptation assistance element of claim 14, wherein the layer of pericardium comprises bovine pericardium.

* * * * *